US011648128B2

(12) United States Patent
Tanaka et al.

(10) Patent No.: US 11,648,128 B2
(45) Date of Patent: May 16, 2023

(54) FACET SCREW AND DELIVERY DEVICE

(71) Applicant: Providence Medical Technology, Inc., Pleasanton, CA (US)

(72) Inventors: Shigeru Tanaka, Half Moon Bay, CA (US); Christopher U. Phan, Dublin, CA (US); Christopher Lambert, Oakland, CA (US); Bon Champ, Campbell, CA (US); Edward Liou, Pleasanton, CA (US); Jeffrey D. Smith, Clayton, CA (US); Nicholas Domek, Oakland, CA (US)

(73) Assignee: Providence Medical Technology, Inc., Pleasanton, CA (US)

( * ) Notice: Subject to any disclaimer, the term of this patent is extended or adjusted under 35 U.S.C. 154(b) by 169 days.

(21) Appl. No.: 16/959,522

(22) PCT Filed: Jan. 4, 2019

(86) PCT No.: PCT/US2019/012367
§ 371 (c)(1),
(2) Date: Jul. 1, 2020

(87) PCT Pub. No.: WO2019/136263
PCT Pub. Date: Jul. 11, 2019

(65) Prior Publication Data
US 2021/0059833 A1    Mar. 4, 2021

Related U.S. Application Data

(60) Provisional application No. 62/734,568, filed on Sep. 21, 2018, provisional application No. 62/667,951, (Continued)

(51) Int. Cl.
*A61F 2/44*    (2006.01)
*A61F 2/30*    (2006.01)
(Continued)

(52) U.S. Cl.
CPC ........ *A61F 2/4405* (2013.01); *A61F 2/30749* (2013.01); *A61F 2/446* (2013.01);
(Continued)

(58) Field of Classification Search
None
See application file for complete search history.

(56) References Cited

U.S. PATENT DOCUMENTS 1,934,962 A    11/1933    Barry
2,708,376 A    5/1955    Booth
(Continued)

FOREIGN PATENT DOCUMENTS

DE    G9304368.6 U1    5/2003
FR    2722980 A1    2/1996
(Continued)

OTHER PUBLICATIONS

US 7,063,700 B2, 06/2006, Michelson (withdrawn)
(Continued)

*Primary Examiner* — Tessa M Matthews
(74) *Attorney, Agent, or Firm* — Dorsey & Whitney LLP

(57) ABSTRACT

Disclosed is a system for delivering a facet screw assembly to a facet joint. The system includes a facet screw assembly and a delivery device. The distal end of the delivery device includes a facet screw engagement feature, which is keyed to a corresponding delivery device engagement feature. In other embodiments, the system may include a facet screw assembly, a facet access guide, a washer sizer tool removably engaged with the facet access guide, a lateral mass decorticator guide slidably and removably engaged with the washer size tool, a washer implant delivery tool removably engaged with the facet access guide and detachably coupled to the facet screw assembly, and optionally an impact handle
(Continued)

detachably coupled to the facet access guide, washer sizer tool, and washer implant delivery tool.

13 Claims, 76 Drawing Sheets

Related U.S. Application Data filed on May 7, 2018, provisional application No. 62/613,547, filed on Jan. 4, 2018.

(51) Int. Cl.
*A61B 17/16* (2006.01)
*A61B 17/70* (2006.01)
*A61B 17/02* (2006.01)
*A61F 2/46* (2006.01)

(52) U.S. Cl.
CPC ......... *A61F 2/4611* (2013.01); *A61B 17/1671* (2013.01); *A61B 17/7035* (2013.01); *A61B 2017/0256* (2013.01); *A61F 2002/3085* (2013.01); *A61F 2002/30433* (2013.01); *A61F 2002/30616* (2013.01); *A61F 2002/4627* (2013.01); *A61F 2002/4658* (2013.01); *A61F 2002/4681* (2013.01)

(56) References Cited

U.S. PATENT DOCUMENTS

| | | |
|---|---|---|
| 2,984,241 A | 5/1961 | Carlson |
| 3,486,505 A | 12/1969 | Morrison |
| 4,479,491 A | 10/1984 | Martin |
| 4,530,355 A | 7/1985 | Griggs |
| 4,604,995 A | 8/1986 | Stephens et al. |
| 4,772,287 A | 9/1988 | Ray et al. |
| 4,877,020 A | 10/1989 | Vich |
| 4,878,915 A | 11/1989 | Brantigan |
| 5,015,247 A | 5/1991 | Michelson |
| 5,026,373 A | 6/1991 | Ray et al. |
| 5,100,405 A | 3/1992 | McLaren |
| 5,135,528 A | 8/1992 | Winston |
| 5,192,327 A | 3/1993 | Brantigan |
| 5,236,460 A | 8/1993 | Barber |
| 5,443,514 A | 8/1995 | Steffee |
| 5,484,437 A | 1/1996 | Michelson |
| 5,489,307 A | 2/1996 | Kuslich et al. |
| 5,505,732 A | 4/1996 | Michelson |
| 5,527,312 A | 6/1996 | Ray |
| 5,549,679 A | 8/1996 | Kuslich et al. |
| 5,554,191 A | 9/1996 | Lahille et al. |
| 5,571,109 A | 11/1996 | Bertagnoli |
| 5,571,191 A | 11/1996 | Fitz |
| 5,584,832 A | 12/1996 | Schlapfer et al. |
| 5,593,409 A | 1/1997 | Michelson |
| 5,632,747 A | 5/1997 | Scarborough et al. |
| 5,649,945 A | 7/1997 | Ray et al. |
| 5,653,763 A | 8/1997 | Errico et al. |
| 5,665,122 A | 9/1997 | Kambin |
| 5,674,295 A | 10/1997 | Ray et al. |
| 5,720,748 A | 2/1998 | Kuslich et al. |
| 5,741,253 A | 4/1998 | Michelson |
| 5,772,661 A | 6/1998 | Michelson |
| 5,792,044 A | 8/1998 | Foley et al. |
| 5,797,909 A | 8/1998 | Michelson |
| 5,836,948 A | 11/1998 | Zucherman et al. |
| 5,879,353 A | 3/1999 | Terry |
| 5,885,299 A | 3/1999 | Winslow et al. |
| 5,891,147 A | 4/1999 | Moskovitz |
| 5,895,426 A | 4/1999 | Scarborough et al. |
| 5,899,908 A | 5/1999 | Kuslich et al. |
| 5,928,238 A | 7/1999 | Scarborough et al. |
| 5,953,820 A | 9/1999 | Vasudeva |
| 5,961,522 A | 10/1999 | Mehdizadeh |
| 5,976,146 A | 11/1999 | Ogawa et al. |
| 6,008,433 A | 12/1999 | Stone |
| 6,033,405 A | 3/2000 | Winslow et al. |
| 6,045,580 A | 4/2000 | Scarborough et al. |
| 6,063,088 A | 5/2000 | Winslow |
| RE36,758 E | 6/2000 | Fitz |
| 6,080,155 A | 6/2000 | Michelson |
| 6,090,143 A | 7/2000 | Meriwether et al. |
| 6,096,038 A | 8/2000 | Michelson |
| 6,099,531 A | 8/2000 | Bonutti |
| 6,102,950 A | 8/2000 | Vaccaro |
| 6,113,602 A | 9/2000 | Sand |
| 6,149,650 A | 11/2000 | Michelson |
| RE37,005 E | 12/2000 | Michelson et al. |
| 6,159,245 A | 12/2000 | Meriwether et al. |
| 6,174,311 B1 | 1/2001 | Branch et al. |
| 6,176,882 B1 | 1/2001 | Biedermann et al. |
| 6,179,873 B1 | 1/2001 | Zientek |
| 6,190,388 B1 | 2/2001 | Michelson et al. |
| 6,190,414 B1 | 2/2001 | Young et al. |
| 6,193,757 B1 | 2/2001 | Foley et al. |
| 6,200,322 B1 | 3/2001 | Branch et al. |
| 6,210,412 B1 | 4/2001 | Michelson |
| RE37,161 E | 5/2001 | Michelson et al. |
| 6,224,595 B1 | 5/2001 | Michelson |
| 6,224,607 B1 | 5/2001 | Michelson |
| 6,224,630 B1 | 5/2001 | Bao et al. |
| 6,245,108 B1 | 6/2001 | Biscup |
| 6,248,110 B1 | 6/2001 | Reiley et al. |
| D444,878 S | 7/2001 | Walter |
| D445,188 S | 7/2001 | Walter |
| 6,264,656 B1 | 7/2001 | Michelson |
| 6,267,763 B1 | 7/2001 | Castro |
| 6,270,498 B1 | 8/2001 | Michelson |
| 6,283,966 B1 | 9/2001 | Boufburg |
| 6,315,795 B1 | 11/2001 | Scarborough et al. |
| 6,325,827 B1 | 12/2001 | Lin |
| 6,371,984 B1 | 4/2002 | Van Dyke et al. |
| 6,371,988 B1 | 4/2002 | Pafford et al. |
| 6,402,784 B1 | 6/2002 | Wardlaw |
| 6,423,063 B1 | 7/2002 | Bonutti |
| 6,423,083 B2 | 7/2002 | Reiley et al. |
| 6,425,919 B1 | 7/2002 | Lambrecht |
| 6,436,098 B1 | 8/2002 | Michelson |
| 6,436,142 B1 | 8/2002 | Paes et al. |
| 6,443,988 B2 | 9/2002 | Felt et al. |
| 6,451,023 B1 | 9/2002 | Salazar et al. |
| 6,454,807 B1 | 9/2002 | Jackson |
| 6,478,796 B2 | 11/2002 | Zucherman et al. |
| 6,500,206 B1 | 12/2002 | Bryan |
| 6,514,256 B2 | 2/2003 | Zucherman et al. |
| 6,524,312 B2 | 2/2003 | Landry et al. |
| 6,530,955 B2 | 3/2003 | Boyle et al. |
| 6,537,279 B1 | 3/2003 | Michelson |
| 6,558,390 B2 | 5/2003 | Cragg |
| 6,565,574 B2 | 5/2003 | Michelson |
| 6,565,605 B2 | 5/2003 | Fallin et al. |
| 6,569,186 B1 | 5/2003 | Winters et al. |
| 6,575,899 B1 | 6/2003 | Foley et al. |
| 6,575,919 B1 | 6/2003 | Reiley et al. |
| 6,575,979 B1 | 6/2003 | Cragg |
| 6,579,319 B2 | 6/2003 | Goble et al. |
| 6,582,432 B1 | 6/2003 | Michelson |
| 6,582,467 B1 | 6/2003 | Teitelbaum et al. |
| 6,607,530 B1 | 8/2003 | Carl et al. |
| 6,610,091 B1 | 8/2003 | Reiley |
| 6,626,905 B1 | 9/2003 | Schmiel et al. |
| 6,632,235 B2 | 10/2003 | Weikel et al. |
| 6,635,060 B2 | 10/2003 | Hanson et al. |
| 6,641,582 B1 | 11/2003 | Hanson et al. |
| 6,648,893 B2 | 11/2003 | Dudasik |
| 6,652,584 B2 | 11/2003 | Michelson |
| 6,663,647 B2 | 12/2003 | Reiley et al. |
| 6,666,866 B2 | 12/2003 | Martz et al. |
| 6,679,886 B2 | 1/2004 | Weikel et al. |
| 6,682,535 B2 | 1/2004 | Hoogland |
| 6,685,742 B1 | 2/2004 | Jackson |
| 6,709,458 B2 | 3/2004 | Michelson |
| 6,712,853 B2 | 3/2004 | Kuslich |

(56) References Cited

U.S. PATENT DOCUMENTS

| | | |
|---|---|---|
| 6,719,773 B1 | 4/2004 | Boucher et al. |
| 6,719,794 B2 | 4/2004 | Gerber et al. |
| 6,723,095 B2 | 4/2004 | Hammerslag |
| 6,733,534 B2 | 5/2004 | Sherman |
| 6,740,093 B2 | 5/2004 | Hochschuler et al. |
| 6,751,875 B2 | 6/2004 | Jones |
| 6,770,074 B2 | 8/2004 | Michelson |
| 6,793,679 B2 | 9/2004 | Michelson |
| 6,805,715 B2 | 10/2004 | Reuter et al. |
| 6,808,537 B2 | 10/2004 | Michelson |
| 6,814,738 B2 | 11/2004 | Naughton et al. |
| 6,823,871 B2 | 11/2004 | Schmieding |
| 6,840,941 B2 | 1/2005 | Rogers et al. |
| 6,851,430 B2 | 2/2005 | Tsou |
| 6,875,213 B2 | 4/2005 | Michelson |
| 6,899,719 B2 | 5/2005 | Reiley et al. |
| 6,921,403 B2 | 7/2005 | Cragg et al. |
| 6,923,813 B2 | 8/2005 | Phillips et al. |
| 6,958,077 B2 | 10/2005 | Suddaby |
| 6,962,606 B2 | 11/2005 | Michelson |
| 6,964,686 B2 | 11/2005 | Gordon |
| 6,966,930 B2 | 11/2005 | Arnin et al. |
| 6,972,035 B2 | 12/2005 | Michelson |
| 6,974,478 B2 | 12/2005 | Reiley et al. |
| 6,979,333 B2 | 12/2005 | Hammerslag |
| 6,986,772 B2 | 1/2006 | Michelson |
| 7,001,385 B2 | 2/2006 | Bonutti |
| 7,008,453 B1 | 3/2006 | Michelson |
| 7,033,362 B2 | 4/2006 | McGahan et al. |
| 7,033,392 B2 | 4/2006 | Schmiel et al. |
| 7,033,394 B2 | 4/2006 | Michelson |
| 7,066,961 B2 | 6/2006 | Michelson |
| D524,443 S | 7/2006 | Blain |
| 7,083,623 B2 | 8/2006 | Michelson |
| 7,090,698 B2 | 8/2006 | Fallin et al. |
| 7,096,972 B2 | 8/2006 | Orozco, Jr. |
| 7,101,398 B2 | 9/2006 | Dooris et al. |
| 7,115,128 B2 | 10/2006 | Michelson |
| 7,118,598 B2 | 10/2006 | Michelson |
| 7,128,760 B2 | 10/2006 | Michelson |
| 7,156,877 B2 | 1/2007 | Lotz et al. |
| 7,166,110 B2 | 1/2007 | Yundt |
| 7,175,023 B2 | 2/2007 | Martin |
| 7,179,263 B2 | 2/2007 | Zdeblick et al. |
| 7,207,991 B2 | 4/2007 | Michelson |
| D541,940 S | 5/2007 | Blain |
| 7,220,280 B2 | 5/2007 | Kast et al. |
| 7,255,703 B2 | 8/2007 | Mujwid et al. |
| 7,261,739 B2 | 8/2007 | Ralph et al. |
| 7,264,622 B2 | 9/2007 | Michelson |
| 7,273,498 B2 | 9/2007 | Bianchi et al. |
| 7,288,093 B2 | 10/2007 | Michelson |
| 7,291,149 B1 | 11/2007 | Michelson |
| 7,300,440 B2 | 11/2007 | Zdeblick et al. |
| 7,326,211 B2 | 2/2008 | Padget et al. |
| 7,326,214 B2 | 2/2008 | Michelson |
| 7,371,238 B2 | 5/2008 | Soboleski et al. |
| 7,399,303 B2 | 7/2008 | Michelson |
| 7,410,501 B2 | 8/2008 | Michelson |
| 7,431,722 B1 | 10/2008 | Michelson |
| 7,445,636 B2 | 11/2008 | Michelson |
| 7,452,359 B1 | 11/2008 | Michelson |
| 7,452,369 B2 | 11/2008 | Barry |
| 7,465,304 B1 | 12/2008 | Haufe et al. |
| 7,476,226 B2 | 1/2009 | Weikel et al. |
| 7,476,251 B2 | 1/2009 | Zucherman et al. |
| 7,479,160 B2 | 1/2009 | Branch et al. |
| 7,491,205 B1 | 2/2009 | Michelson |
| 7,491,240 B1 | 2/2009 | Carver et al. |
| 7,500,992 B2 | 3/2009 | Li |
| 7,517,358 B2 | 4/2009 | Peterson |
| 7,524,333 B2 | 4/2009 | Lambrecht et al. |
| 7,569,054 B2 | 8/2009 | Michelson |
| 7,569,057 B2 | 8/2009 | Liu et al. |
| 7,580,743 B2 | 8/2009 | Bourlion et al. |
| 7,591,851 B2 | 9/2009 | Winslow et al. |
| 7,601,170 B2 | 10/2009 | Winslow et al. |
| 7,608,077 B2 | 10/2009 | Cragg et al. |
| 7,608,107 B2 | 10/2009 | Michelson |
| 7,615,079 B2 | 11/2009 | Flickinger et al. |
| 7,618,451 B2 | 11/2009 | Berez et al. |
| 7,632,291 B2 | 12/2009 | Stephens et al. |
| 7,641,664 B2 | 1/2010 | Pagano |
| 7,648,509 B2 | 1/2010 | Stark |
| 7,648,523 B2 | 1/2010 | Mirkovic et al. |
| 7,655,027 B2 | 2/2010 | Michelson |
| 7,655,043 B2 | 2/2010 | Peterman et al. |
| 7,662,173 B2 | 2/2010 | Cragg et al. |
| D611,147 S | 3/2010 | Hanson et al. |
| 7,682,378 B2 | 3/2010 | Truckai et al. |
| 7,686,805 B2 | 3/2010 | Michelson |
| 7,686,807 B2 | 3/2010 | Padget et al. |
| 7,699,878 B2 | 4/2010 | Pavlov et al. |
| D615,653 S | 5/2010 | Horton |
| 7,708,761 B2 | 5/2010 | Petersen |
| 7,722,619 B2 | 5/2010 | Michelson |
| D619,719 S | 7/2010 | Pannu |
| D620,113 S | 7/2010 | Courtney et al. |
| 7,763,024 B2 | 7/2010 | Bertagnoli et al. |
| 7,763,050 B2 | 7/2010 | Winslow et al. |
| 7,776,090 B2 | 8/2010 | Winslow et al. |
| D623,748 S | 9/2010 | Horton et al. |
| D623,749 S | 9/2010 | Horton et al. |
| 7,789,898 B2 | 9/2010 | Peterman |
| D627,468 S | 11/2010 | Richter et al. |
| 7,824,431 B2 | 11/2010 | McCormack |
| 7,837,713 B2 | 11/2010 | Peterson |
| 7,846,183 B2 | 12/2010 | Blain |
| 7,846,184 B2 | 12/2010 | Sasso et al. |
| 7,850,733 B2 | 12/2010 | Baynham et al. |
| 7,862,589 B2 | 1/2011 | Thramann |
| 7,867,277 B1 | 1/2011 | Tohmeh |
| D631,967 S | 2/2011 | Horton |
| 7,879,098 B1 | 2/2011 | Simmons, Jr. |
| 7,887,565 B2 | 2/2011 | Michelson |
| 7,892,261 B2 | 2/2011 | Bonutti |
| 7,892,286 B2 | 2/2011 | Michelson |
| 7,896,803 B2 | 3/2011 | Schara et al. |
| 7,896,903 B2 | 3/2011 | Link |
| 7,901,439 B2 | 3/2011 | Horton |
| 7,914,530 B2 | 3/2011 | Michelson |
| 7,918,891 B1 | 4/2011 | Curran et al. |
| 7,922,729 B2 | 4/2011 | Michelson |
| 7,922,766 B2 | 4/2011 | Grob et al. |
| 7,935,136 B2 | 5/2011 | Alamin et al. |
| 7,938,857 B2 | 5/2011 | Krueger et al. |
| 7,942,903 B2 | 5/2011 | Moskowitz et al. |
| 7,988,712 B2 | 8/2011 | Hale et al. |
| 7,988,714 B2 | 8/2011 | Puekert et al. |
| 7,998,174 B2 | 8/2011 | Malandain et al. |
| 8,007,534 B2 | 8/2011 | Michelson |
| 8,029,540 B2 | 10/2011 | Winslow et al. |
| 8,043,334 B2 | 10/2011 | Fisher et al. |
| 8,052,728 B2 | 11/2011 | Hestad |
| 8,062,303 B2 | 11/2011 | Berry et al. |
| 8,066,705 B2 | 11/2011 | Michelson |
| D650,481 S | 12/2011 | Gottlieb et al. |
| 8,097,034 B2 | 1/2012 | Michelson |
| 8,100,944 B2 | 1/2012 | Lauryssen et al. |
| D653,757 S | 2/2012 | Binder |
| 8,114,158 B2 | 2/2012 | Carl et al. |
| 8,118,838 B2 | 2/2012 | Winslow et al. |
| 8,128,660 B2 | 3/2012 | Mitchel et al. |
| 8,133,261 B2 | 3/2012 | Fisher et al. |
| 8,142,503 B2 | 3/2012 | Malone |
| 8,147,553 B2 | 4/2012 | Vresilovic et al. |
| 8,162,981 B2 | 4/2012 | Vestgaarden |
| 8,172,877 B2 | 5/2012 | Winslow et al. |
| 8,177,872 B2 | 5/2012 | Nelson et al. |
| 8,197,513 B2 | 6/2012 | Fisher et al. |
| 8,206,418 B2 | 6/2012 | Triplett et al. |
| 8,267,966 B2 | 9/2012 | McCormack et al. |
| D674,900 S | 1/2013 | Janice et al. |
| 8,348,979 B2 | 1/2013 | McCormack |

(56) References Cited

U.S. PATENT DOCUMENTS

| | | |
|---|---|---|
| 8,361,152 B2 | 1/2013 | McCormack et al. |
| 8,366,748 B2 | 2/2013 | Kleiner |
| 8,382,767 B2 | 2/2013 | Wassinger et al. |
| D677,791 S | 3/2013 | Danacioglu et al. |
| 8,394,107 B2 | 3/2013 | Fanger et al. |
| 8,394,129 B2 | 3/2013 | Morgenstern et al. |
| D681,205 S | 4/2013 | Farris et al. |
| 8,425,558 B2 | 4/2013 | McCormack et al. |
| 8,439,922 B1 | 5/2013 | Arnold et al. |
| 8,512,347 B2 | 8/2013 | McCormack et al. |
| 8,523,908 B2 | 9/2013 | Malone |
| 8,529,609 B2 | 9/2013 | Helgerson et al. |
| 8,623,054 B2 | 1/2014 | McCormack et al. |
| 8,668,722 B2 | 3/2014 | Pavlov et al. |
| 8,753,345 B2 | 6/2014 | McCormack et al. |
| 8,753,347 B2 | 6/2014 | McCormack et al. |
| 8,764,755 B2 | 7/2014 | Michelson |
| 8,828,062 B2 | 9/2014 | McCormack et al. |
| 8,834,530 B2 | 9/2014 | McCormack |
| 8,845,727 B2 | 9/2014 | Gottlieb et al. |
| 8,870,882 B2 | 10/2014 | Kleiner |
| D723,690 S | 3/2015 | McCormack et al. |
| D723,691 S | 3/2015 | McCormack et al. |
| 8,998,905 B2 | 4/2015 | Marik et al. |
| 9,005,288 B2 | 4/2015 | McCormack et al. |
| 9,011,492 B2 | 4/2015 | McCormack et al. |
| D732,667 S | 6/2015 | McCormack et al. |
| 9,186,193 B2 | 11/2015 | Kleiner et al. |
| D745,156 S | 12/2015 | McCormack et al. |
| 9,211,198 B2 | 12/2015 | Michelson |
| 9,220,608 B2 | 12/2015 | McKay |
| D750,249 S | 2/2016 | Grimberg, Jr. et al. |
| 9,271,765 B2 | 3/2016 | Blain |
| 9,333,086 B2 | 5/2016 | McCormack et al. |
| 9,358,127 B2 | 6/2016 | Duffield et al. |
| 9,381,049 B2 | 7/2016 | McCormack et al. |
| 9,427,264 B2 | 8/2016 | Kleiner et al. |
| 9,504,583 B2 | 11/2016 | Blain |
| 9,622,791 B2 | 4/2017 | McCormack et al. |
| 9,622,873 B2 | 4/2017 | McCormack et al. |
| 9,622,874 B2 | 4/2017 | McCormack et al. |
| 9,629,665 B2 | 4/2017 | McCormack et al. |
| 9,717,403 B2 | 8/2017 | Kleiner et al. |
| 9,937,053 B2 | 4/2018 | Melkent et al. |
| 10,039,649 B2 | 8/2018 | McCormack et al. |
| 10,149,673 B2 | 12/2018 | McCormack et al. |
| 10,172,721 B2 | 1/2019 | McCormack et al. |
| D841,165 S | 2/2019 | McCormack et al. |
| D841,167 S | 2/2019 | Ricca et al. |
| 10,201,375 B2 | 2/2019 | McCormack et al. |
| 10,206,787 B2 | 2/2019 | Voellmicke |
| 10,219,910 B2 | 3/2019 | McCormack et al. |
| 10,226,285 B2 | 3/2019 | McCormack et al. |
| 10,238,501 B2 | 3/2019 | McCormack et al. |
| 10,327,913 B2 | 6/2019 | Palmatier et al. |
| 10,456,175 B2 | 10/2019 | McCormack et al. |
| 10,568,666 B2 | 2/2020 | McCormack et al. |
| 10,588,672 B2 | 3/2020 | McCormack et al. |
| D884,895 S | 5/2020 | McCormack et al. |
| D887,552 S | 6/2020 | Tanaka et al. |
| 10,682,243 B2 | 6/2020 | Phan et al. |
| D911,525 S | 2/2021 | Tanaka et al. |
| RE48,501 E | 4/2021 | McCormack et al. |
| 11,272,964 B2 | 3/2022 | Mccormack et al. |
| 11,285,010 B2 | 3/2022 | Mccormack |
| 2001/0004710 A1 | 6/2001 | Felt et al. |
| 2001/0047208 A1 | 11/2001 | Michelson |
| 2001/0053914 A1 | 12/2001 | Landry et al. |
| 2002/0026195 A1 | 2/2002 | Layne et al. |
| 2002/0068941 A1 | 6/2002 | Hanson et al. |
| 2002/0077641 A1 | 6/2002 | Michelson |
| 2002/0107519 A1 | 8/2002 | Dixon et al. |
| 2002/0143343 A1 | 10/2002 | Castro |
| 2002/0147496 A1 | 10/2002 | Belef et al. |
| 2002/0165612 A1 | 11/2002 | Gerber et al. |
| 2002/0169471 A1 | 11/2002 | Ferdinand |
| 2002/0177866 A1 | 11/2002 | Weikel et al. |
| 2003/0023312 A1 | 1/2003 | Thalgott |
| 2003/0028251 A1 | 2/2003 | Mathews |
| 2003/0032962 A1 | 2/2003 | McGahan et al. |
| 2003/0033017 A1 | 2/2003 | Lotz et al. |
| 2003/0083668 A1 | 5/2003 | Rogers et al. |
| 2003/0105526 A1 | 6/2003 | Bryant et al. |
| 2003/0109928 A1 | 6/2003 | Pasquet et al. |
| 2003/0139816 A1 | 7/2003 | Michelson |
| 2003/0144737 A1 | 7/2003 | Sherman |
| 2003/0149438 A1 | 8/2003 | Nichols et al. |
| 2003/0158553 A1 | 8/2003 | Michelson |
| 2003/0225416 A1 | 12/2003 | Bonvallet et al. |
| 2004/0010259 A1 | 1/2004 | Keller et al. |
| 2004/0059337 A1 | 3/2004 | Hanson et al. |
| 2004/0073217 A1 | 4/2004 | Michelson |
| 2004/0087948 A1 | 5/2004 | Suddaby |
| 2004/0087956 A1 | 5/2004 | Weikel et al. |
| 2004/0106999 A1 | 6/2004 | Mathews |
| 2004/0133277 A1 | 7/2004 | Michelson |
| 2004/0133280 A1 | 7/2004 | Trieu |
| 2004/0162562 A1 | 8/2004 | Martz |
| 2004/0215344 A1 | 10/2004 | Hochshculer et al. |
| 2005/0010294 A1 | 1/2005 | Michelson |
| 2005/0015097 A1 | 1/2005 | Mujwid et al. |
| 2005/0015149 A1 | 1/2005 | Michelson |
| 2005/0021042 A1 | 1/2005 | Marnay et al. |
| 2005/0027358 A1 | 2/2005 | Suddaby |
| 2005/0033432 A1 | 2/2005 | Gordon et al. |
| 2005/0038511 A1 | 2/2005 | Martz et al. |
| 2005/0049623 A1 | 3/2005 | Moore et al. |
| 2005/0049705 A1 | 3/2005 | Hale et al. |
| 2005/0055096 A1 | 3/2005 | Serhan et al. |
| 2005/0065518 A1 | 3/2005 | Michelson |
| 2005/0065519 A1 | 3/2005 | Michelson |
| 2005/0065608 A1 | 3/2005 | Michelson |
| 2005/0065609 A1 | 3/2005 | Wardlaw |
| 2005/0080422 A1 | 4/2005 | Otte et al. |
| 2005/0090829 A1 | 4/2005 | Martz et al. |
| 2005/0090901 A1 | 4/2005 | Studer |
| 2005/0113842 A1 | 5/2005 | Bertagnoli et al. |
| 2005/0119680 A1 | 6/2005 | Dykes |
| 2005/0124993 A1 | 6/2005 | Chappuis |
| 2005/0149192 A1 | 7/2005 | Zucherman et al. |
| 2005/0159650 A1 | 7/2005 | Raymond et al. |
| 2005/0159746 A1 | 7/2005 | Grob et al. |
| 2005/0177240 A1 | 8/2005 | Blain |
| 2005/0182417 A1 | 8/2005 | Pagano |
| 2005/0209698 A1 | 9/2005 | Gordon et al. |
| 2005/0216018 A1 | 9/2005 | Sennett |
| 2005/0234455 A1 | 10/2005 | Binder et al. |
| 2005/0240188 A1 | 10/2005 | Chow et al. |
| 2005/0251146 A1 | 11/2005 | Martz et al. |
| 2005/0251257 A1 | 11/2005 | Mitchell et al. |
| 2005/0267480 A1 | 12/2005 | Suddaby |
| 2006/0004367 A1 | 1/2006 | Alamin et al. |
| 2006/0015184 A1 | 1/2006 | Winterbottom et al. |
| 2006/0036243 A1 | 2/2006 | Sasso et al. |
| 2006/0036247 A1 | 2/2006 | Michelson |
| 2006/0036323 A1 | 2/2006 | Carl et al. |
| 2006/0041311 A1 | 2/2006 | McLeer |
| 2006/0058790 A1 | 3/2006 | Carl et al. |
| 2006/0058793 A1 | 3/2006 | Michelson |
| 2006/0058878 A1 | 3/2006 | Michelson |
| 2006/0069442 A1 | 3/2006 | Michelson |
| 2006/0079905 A1 | 4/2006 | Beyar et al. |
| 2006/0079962 A1 | 4/2006 | Michelson |
| 2006/0085068 A1 | 4/2006 | Barry |
| 2006/0085074 A1 | 4/2006 | Raiszadeh |
| 2006/0095028 A1 | 5/2006 | Bleich |
| 2006/0095036 A1 | 5/2006 | Hammerslag |
| 2006/0111779 A1 | 5/2006 | Peterson |
| 2006/0111780 A1 | 5/2006 | Petersen |
| 2006/0111781 A1 | 5/2006 | Petersen |
| 2006/0142762 A1 | 6/2006 | Michelson |
| 2006/0149279 A1 | 7/2006 | Mathews |
| 2006/0149289 A1 | 7/2006 | Winslow et al. |
| 2006/0184172 A1 | 8/2006 | Michelson |

(56) References Cited

U.S. PATENT DOCUMENTS

| | | |
|---|---|---|
| 2006/0189991 A1 | 8/2006 | Bickley |
| 2006/0190081 A1 | 8/2006 | Kraus et al. |
| 2006/0195109 A1 | 8/2006 | McGahan et al. |
| 2006/0200137 A1 | 9/2006 | Soboleski et al. |
| 2006/0200138 A1 | 9/2006 | Michelson |
| 2006/0200139 A1 | 9/2006 | Michelson |
| 2006/0206118 A1 | 9/2006 | Kim et al. |
| 2006/0217812 A1 | 9/2006 | Lambrecht et al. |
| 2006/0229627 A1 | 10/2006 | Hunt et al. |
| 2006/0235391 A1 | 10/2006 | Sutterlin |
| 2006/0241597 A1 | 10/2006 | Mitchell et al. |
| 2006/0241626 A1 | 10/2006 | McGahan et al. |
| 2006/0241758 A1 | 10/2006 | Peterman et al. |
| 2006/0247632 A1 | 11/2006 | Winslow et al. |
| 2006/0247633 A1 | 11/2006 | Winslow et al. |
| 2006/0247650 A1 | 11/2006 | Yerby et al. |
| 2006/0259142 A1 | 11/2006 | Dooris et al. |
| 2006/0271195 A1 | 11/2006 | Thramann |
| 2006/0276790 A1 | 12/2006 | Dawson et al. |
| 2006/0276801 A1 | 12/2006 | Yerby et al. |
| 2006/0276897 A1 | 12/2006 | Winslow et al. |
| 2006/0293663 A1 | 12/2006 | Walkenhorst et al. |
| 2007/0016195 A1 | 1/2007 | Winslow et al. |
| 2007/0016196 A1 | 1/2007 | Winslow et al. |
| 2007/0016218 A1 | 1/2007 | Winslow et al. |
| 2007/0032871 A1 | 2/2007 | Michelson |
| 2007/0043362 A1 | 2/2007 | Malandain et al. |
| 2007/0050031 A1 | 3/2007 | Khosrowshahi |
| 2007/0055245 A1 | 3/2007 | Sasso et al. |
| 2007/0055263 A1 | 3/2007 | Way et al. |
| 2007/0073402 A1 | 3/2007 | Vresilovic et al. |
| 2007/0083265 A1 | 4/2007 | Malone |
| 2007/0123863 A1 | 5/2007 | Winslow et al. |
| 2007/0123888 A1 | 5/2007 | Bleich et al. |
| 2007/0135814 A1 | 6/2007 | Farris |
| 2007/0135921 A1 | 6/2007 | Park |
| 2007/0149976 A1 | 6/2007 | Hale et al. |
| 2007/0149983 A1 | 6/2007 | Link |
| 2007/0150061 A1 | 6/2007 | Trieu |
| 2007/0161991 A1 | 7/2007 | Altarac et al. |
| 2007/0162138 A1 | 7/2007 | Heinz |
| 2007/0179617 A1 | 8/2007 | Brown et al. |
| 2007/0179619 A1 | 8/2007 | Grob et al. |
| 2007/0191861 A1 | 8/2007 | Allard et al. |
| 2007/0225721 A1 | 9/2007 | Thelen et al. |
| 2007/0225812 A1 | 9/2007 | Gill |
| 2007/0244483 A9 | 10/2007 | Winslow et al. |
| 2007/0250167 A1 | 10/2007 | Bray et al. |
| 2007/0276491 A1 | 11/2007 | Ahrens |
| 2007/0282441 A1 | 12/2007 | Stream et al. |
| 2007/0288014 A1 | 12/2007 | Shadduck et al. |
| 2007/0293949 A1 | 12/2007 | Salerni et al. |
| 2007/0299451 A1 | 12/2007 | Tulkis |
| 2008/0015581 A1 | 1/2008 | Eckman |
| 2008/0021457 A1 | 1/2008 | Anderson et al. |
| 2008/0021464 A1 | 1/2008 | Morin et al. |
| 2008/0058954 A1 | 3/2008 | Trieu |
| 2008/0065219 A1 | 3/2008 | Dye |
| 2008/0077245 A1 | 3/2008 | Lee |
| 2008/0097436 A1 | 4/2008 | Culbert et al. |
| 2008/0108996 A1 | 5/2008 | Padget et al. |
| 2008/0140207 A1 | 6/2008 | Olmos et al. |
| 2008/0154377 A1 | 6/2008 | Voellmicke |
| 2008/0161810 A1 | 7/2008 | Melkent |
| 2008/0161929 A1 | 7/2008 | McCormack et al. |
| 2008/0167657 A1 | 7/2008 | Greenhaigh |
| 2008/0177311 A1 | 7/2008 | Winslow et al. |
| 2008/0183209 A1 | 7/2008 | Robinson et al. |
| 2008/0195206 A1 | 8/2008 | Chee et al. |
| 2008/0208341 A1 | 8/2008 | McCormack et al. |
| 2008/0216846 A1 | 9/2008 | Levin |
| 2008/0234677 A1 | 9/2008 | Dahners et al. |
| 2008/0234758 A1 | 9/2008 | Fisher et al. |
| 2008/0249571 A1 | 10/2008 | Sasso et al. |
| 2008/0255564 A1 | 10/2008 | Michelson |
| 2008/0255618 A1 | 10/2008 | Fisher et al. |
| 2008/0255622 A1 | 10/2008 | Mickiewicz et al. |
| 2008/0255666 A1 | 10/2008 | Fisher et al. |
| 2008/0255667 A1 | 10/2008 | Horton |
| 2008/0275455 A1 | 11/2008 | Berry et al. |
| 2008/0287955 A1 | 11/2008 | Michelson |
| 2008/0300685 A1 | 12/2008 | Carls et al. |
| 2008/0306537 A1 | 12/2008 | Culbert |
| 2008/0312744 A1 | 12/2008 | Vresilovic et al. |
| 2009/0131986 A1 | 5/2009 | Lee et al. |
| 2009/0138053 A1 | 5/2009 | Assell et al. |
| 2009/0177205 A1 | 7/2009 | McCormack et al. |
| 2009/0177215 A1 | 7/2009 | Stack et al. |
| 2009/0177237 A1 | 7/2009 | Zucherman et al. |
| 2009/0182429 A1 | 7/2009 | Humphreys et al. |
| 2009/0234397 A1 | 9/2009 | Petersen |
| 2009/0248076 A1 | 10/2009 | Reynolds et al. |
| 2009/0263461 A1 | 10/2009 | McKay |
| 2009/0270929 A1 | 10/2009 | Suddaby et al. |
| 2009/0275994 A1 | 11/2009 | Phan et al. |
| 2009/0297603 A1 | 12/2009 | Joshi |
| 2009/0306671 A1 | 12/2009 | McCormack et al. |
| 2009/0312763 A1 | 12/2009 | McCormack et al. |
| 2010/0036418 A1 | 2/2010 | Siemionow et al. |
| 2010/0069912 A1 | 3/2010 | McCormack et al. |
| 2010/0082065 A1 | 4/2010 | Butler et al. |
| 2010/0086185 A1 | 4/2010 | Weiss |
| 2010/0093829 A1 | 4/2010 | Gorman |
| 2010/0111829 A1 | 5/2010 | Drapeau et al. |
| 2010/0114318 A1 | 5/2010 | Gittings et al. |
| 2010/0145391 A1 | 6/2010 | Kleiner |
| 2010/0145459 A1 | 6/2010 | Mcdonough et al. |
| 2010/0191241 A1 | 7/2010 | McCormack et al. |
| 2010/0211104 A1 | 8/2010 | Moumene et al. |
| 2010/0286783 A1 | 11/2010 | Lechmann et al. |
| 2011/0004247 A1 | 1/2011 | Lechmann et al. |
| 2011/0022089 A1 | 1/2011 | Assell et al. |
| 2011/0054613 A1 | 3/2011 | Hansen |
| 2011/0077686 A1 | 3/2011 | Mishra et al. |
| 2011/0082548 A1 | 4/2011 | Assell et al. |
| 2011/0144755 A1 | 6/2011 | Baynham et al. |
| 2011/0184470 A1 | 7/2011 | Gorek et al. |
| 2011/0190821 A1 | 8/2011 | Chin et al. |
| 2011/0245930 A1 | 10/2011 | Alley et al. |
| 2011/0295327 A1 | 12/2011 | Moskowitz et al. |
| 2011/0307061 A1 | 12/2011 | Assell et al. |
| 2012/0010659 A1 | 1/2012 | Angert et al. |
| 2012/0010662 A1 | 1/2012 | O'Neil et al. |
| 2012/0010669 A1 | 1/2012 | O'Neil et al. |
| 2012/0029545 A1 | 2/2012 | Nelson et al. |
| 2012/0065613 A1 | 3/2012 | Pepper et al. |
| 2012/0130496 A1 | 5/2012 | Duffield et al. |
| 2012/0143334 A1 | 6/2012 | Boyce et al. |
| 2012/0179259 A1 | 7/2012 | Mcdonough et al. |
| 2012/0215259 A1 | 8/2012 | Cannestra |
| 2012/0245689 A1 | 9/2012 | Gimbel et al. |
| 2012/0265250 A1 | 10/2012 | Ali |
| 2012/0277801 A1 | 11/2012 | Marik et al. |
| 2012/0283776 A1 | 11/2012 | Mishra |
| 2012/0323242 A1 | 12/2012 | Tsuang et al. |
| 2013/0006364 A1 | 1/2013 | McCormack et al. |
| 2013/0012994 A1 | 1/2013 | McCormack et al. |
| 2013/0013070 A1 | 1/2013 | McCormack et al. |
| 2013/0018474 A1 | 1/2013 | McCormack et al. |
| 2013/0023889 A1 | 1/2013 | Blain et al. |
| 2013/0023995 A1 | 1/2013 | McCormack et al. |
| 2013/0023996 A1 | 1/2013 | McCormack et al. |
| 2013/0030440 A1 | 1/2013 | McCormack et al. |
| 2013/0030532 A1 | 1/2013 | McCormack et al. |
| 2013/0110168 A1 | 5/2013 | McCormack et al. |
| 2013/0110243 A1 | 5/2013 | Patterson et al. |
| 2013/0123922 A1 | 5/2013 | McCormack et al. |
| 2013/0144389 A1 | 6/2013 | Bonutti |
| 2013/0226239 A1 | 8/2013 | Altarac et al. |
| 2013/0238095 A1 | 9/2013 | Pavento et al. |
| 2013/0253649 A1 | 9/2013 | Davis |
| 2013/0274763 A1 | 10/2013 | Drapeau et al. |
| 2013/0310839 A1 | 11/2013 | McCormack et al. |
| 2013/0310878 A1 | 11/2013 | McCormack et al. |

(56) References Cited

U.S. PATENT DOCUMENTS

| | | |
|---|---|---|
| 2013/0310943 A1 | 11/2013 | McCormack et al. |
| 2013/0317548 A1 | 11/2013 | Malone |
| 2013/0338720 A1 | 12/2013 | Kleiner |
| 2014/0012318 A1 | 1/2014 | Goel |
| 2014/0025113 A1 | 1/2014 | McCormack et al. |
| 2014/0100657 A1 | 4/2014 | McCormack et al. |
| 2014/0114415 A1 | 4/2014 | Tyber |
| 2014/0135930 A1 | 5/2014 | Georges |
| 2014/0172103 A1 | 6/2014 | O'neil et al. |
| 2014/0228959 A1 | 8/2014 | Niemiec et al. |
| 2014/0296916 A1 | 10/2014 | Mccormack et al. |
| 2014/0379087 A1 | 12/2014 | McCormack |
| 2015/0025635 A1 | 1/2015 | Laubert |
| 2015/0100129 A1 | 4/2015 | Waugh et al. |
| 2015/0201977 A1 | 7/2015 | Mccormack et al. |
| 2015/0230834 A1 | 8/2015 | Cannestra |
| 2015/0297357 A1 | 10/2015 | McCormack et al. |
| 2015/0328005 A1 | 11/2015 | Padovani et al. |
| 2015/0328010 A1 | 11/2015 | Martynova et al. |
| 2015/0342648 A1 | 12/2015 | Mccormack et al. |
| 2015/0342649 A1 | 12/2015 | Mccormack et al. |
| 2016/0008040 A1 | 1/2016 | Mccormack et al. |
| 2016/0242754 A1 | 8/2016 | Mccormack et al. |
| 2016/0250035 A1 | 9/2016 | De Villiers et al. |
| 2016/0317316 A1 | 11/2016 | Mccormack et al. |
| 2016/0331553 A1* | 11/2016 | Tanaka .................. A61F 2/4611 |
| 2017/0027713 A1 | 2/2017 | Kleiner |
| 2017/0135733 A1 | 5/2017 | Donner et al. |
| 2017/0189199 A1 | 7/2017 | Maier et al. |
| 2017/0216044 A1 | 8/2017 | McCormack et al. |
| 2017/0281360 A1 | 10/2017 | Seifert |
| 2017/0348027 A1 | 12/2017 | McCormack et al. |
| 2017/0354444 A1 | 12/2017 | McCormack et al. |
| 2017/0360571 A1 | 12/2017 | Mesiwala |
| 2018/0161077 A1 | 6/2018 | McCormack et al. |
| 2018/0303631 A1 | 10/2018 | Phan et al. |
| 2019/0083271 A1* | 3/2019 | Donner .............. A61B 17/1662 |
| 2019/0209151 A1 | 7/2019 | McCormack et al. |
| 2019/0239932 A1 | 8/2019 | McCormack et al. |
| 2019/0240041 A1 | 8/2019 | McCormack et al. |
| 2019/0247099 A1 | 8/2019 | McCormack et al. |
| 2019/0307571 A1 | 10/2019 | McCormack et al. |
| 2019/0307572 A1 | 10/2019 | McCormack et al. |
| 2019/0350626 A1 | 11/2019 | McCormack et al. |
| 2020/0085475 A1 | 3/2020 | McCormack et al. |
| 2020/0155205 A1 | 5/2020 | Tanaka et al. |
| 2020/0289285 A1 | 9/2020 | Siemionow et al. |
| 2020/0375633 A1 | 12/2020 | McCormack et al. |
| 2020/0405502 A1* | 12/2020 | Gephart ................ A61F 2/4455 |
| 2021/0022881 A1 | 1/2021 | McCormack et al. |
| 2021/0378720 A1 | 12/2021 | Mccormack et al. |
| 2021/0386434 A1 | 12/2021 | Tanaka et al. |
| 2022/0031297 A1 | 2/2022 | Mccormack et al. |
| 2022/0151663 A1 | 5/2022 | Mccormack et al. |
| 2022/0211513 A1 | 7/2022 | Mccormack et al. |

FOREIGN PATENT DOCUMENTS

| | | |
|---|---|---|
| JP | H11508781 A | 8/1999 |
| JP | 2004523288 A | 8/2004 |
| JP | 2008509735 A | 4/2008 |
| JP | 2008522787 A | 7/2008 |
| JP | 2012501234 A | 1/2012 |
| JP | 2014516268 A | 7/2014 |
| WO | 9641582 A1 | 12/1996 |
| WO | 99/49818 A1 | 10/1999 |
| WO | 00/035388 A1 | 6/2000 |
| WO | 00/53126 A1 | 9/2000 |
| WO | 01/01895 A1 | 1/2001 |
| WO | 02/34120 A2 | 5/2002 |
| WO | 02/038062 A2 | 5/2002 |
| WO | 02/076335 A2 | 10/2002 |
| WO | 2005032358 A2 | 4/2005 |
| WO | 2006058221 A2 | 6/2006 |
| WO | 2006130791 A2 | 12/2006 |
| WO | 2007120903 A2 | 10/2007 |
| WO | 2008083349 A1 | 7/2008 |
| WO | 2008127978 A2 | 10/2008 |
| WO | 2008153732 A1 | 12/2008 |
| WO | 2009089367 A2 | 7/2009 |
| WO | 2009148619 A2 | 12/2009 |
| WO | 2010030994 A2 | 3/2010 |
| WO | 2010074714 A2 | 7/2010 |
| WO | 2010107692 A1 | 9/2010 |
| WO | 2011050140 A1 | 4/2011 |
| WO | 2013043584 A2 | 3/2013 |
| WO | 2014188280 A2 | 11/2014 |
| WO | 2016049784 A1 | 4/2016 |

OTHER PUBLICATIONS

Spinal News International, "FDA clears Renovis Surgical 3D-printed titanium standalone cervical cage", first available Apr. 11, 2016. https://spinalnewsinternational.com/fda-clears-renovis-surgical-3d-printed-titanium-standalone-cervical-cage/.
Research Gate, "DTRAX Posterior Cervical Cage", first available Jul. 2016. (hllps://www.researchgate.net/figure/ DTRAX-Posterior-Cervical-Cage-Note-The-cervical-cages-are-manufactured-from-implant_fig3_305314436).
Providence Medical Technology, "Cavux Cervical Cages", first available Oct. 5, 2016. (hllps://web.archive.org/web/20161005063842/ https:/providencemt.com/cavux-cervical-cages/).
Providence Medical Technology, "Posterior Cervical Stabilization System (PCSS)", first available Jun. 21, 2020. (hllps://web.archive.org/web/20200621181620/hllps:/providencemt.com/pcss/).
Atul Goel, Facetal distraction as treatment for single- and multilevel cervical spondylotic radiculopathy and myelopathy: a preliminary report, J Neurosurg Spine, Jun. 2011, pp. 689-696.
Press Release, Interventional Spine, Inc., Interventional Spine, Inc. Introduces the PERPOS Fusion Facet Prep Kit, Oct. 14, 2008, 1 Page.
Press Release, minSURG Corp., Orthopedic Development Corporation's TruFUSE Procedure Tops 1,750 Patients in First Year, Sep. 24, 2007, 1 Page.
Press Release, Interventional Spine, Inc., FDA Grants Conditional Approval to Interventional Spine's PercuDyn System IDE Application, Jul. 1, 2008, 1 Page.
Stein, et al., "Percutaneous Facet Joint Fusion: Preliminary Experience," Journal of Vascular and Interventional Radiology, Jan.-Feb. 1993, pp. 69-74, vol. 4, No. 1.

\* cited by examiner

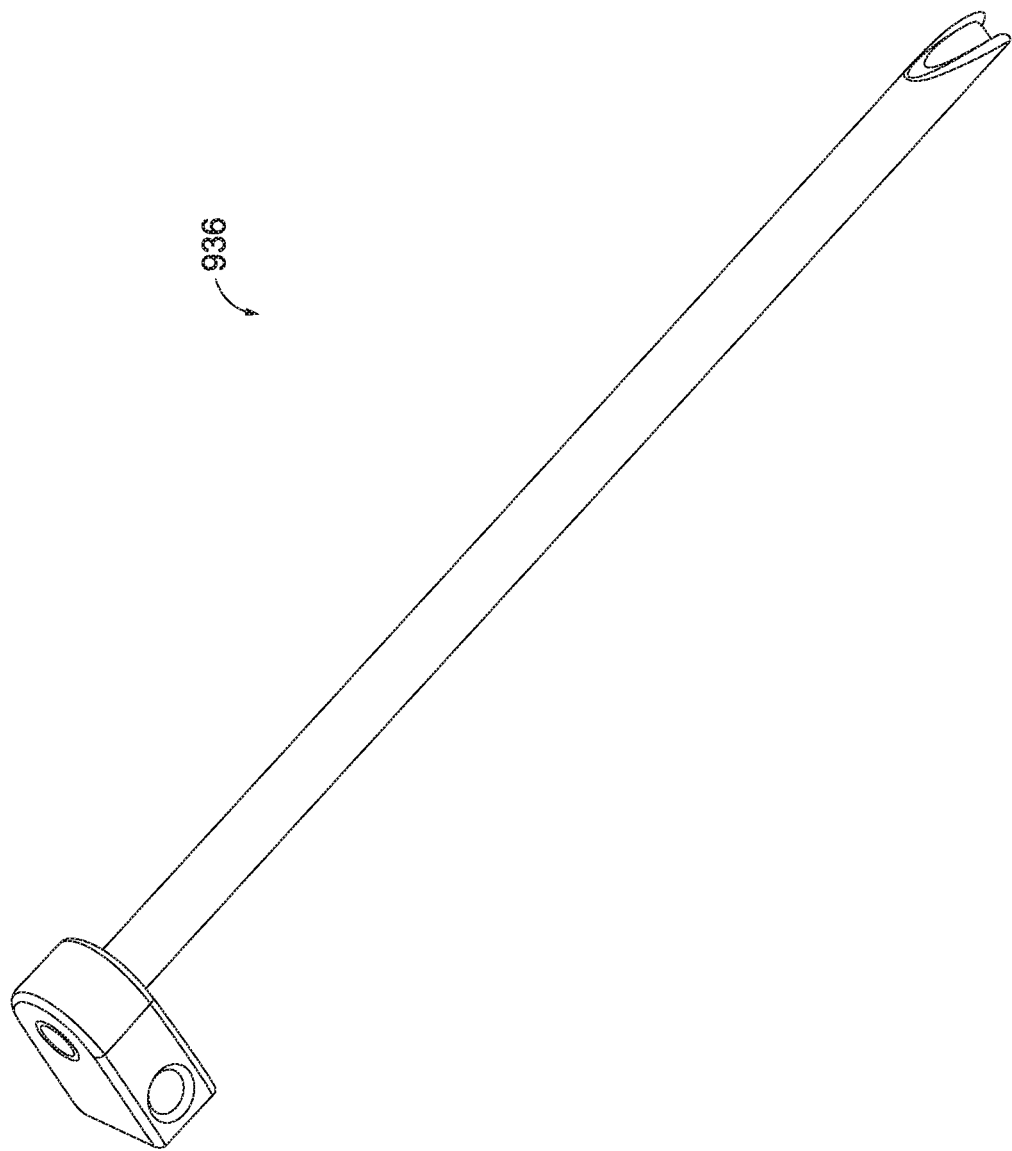

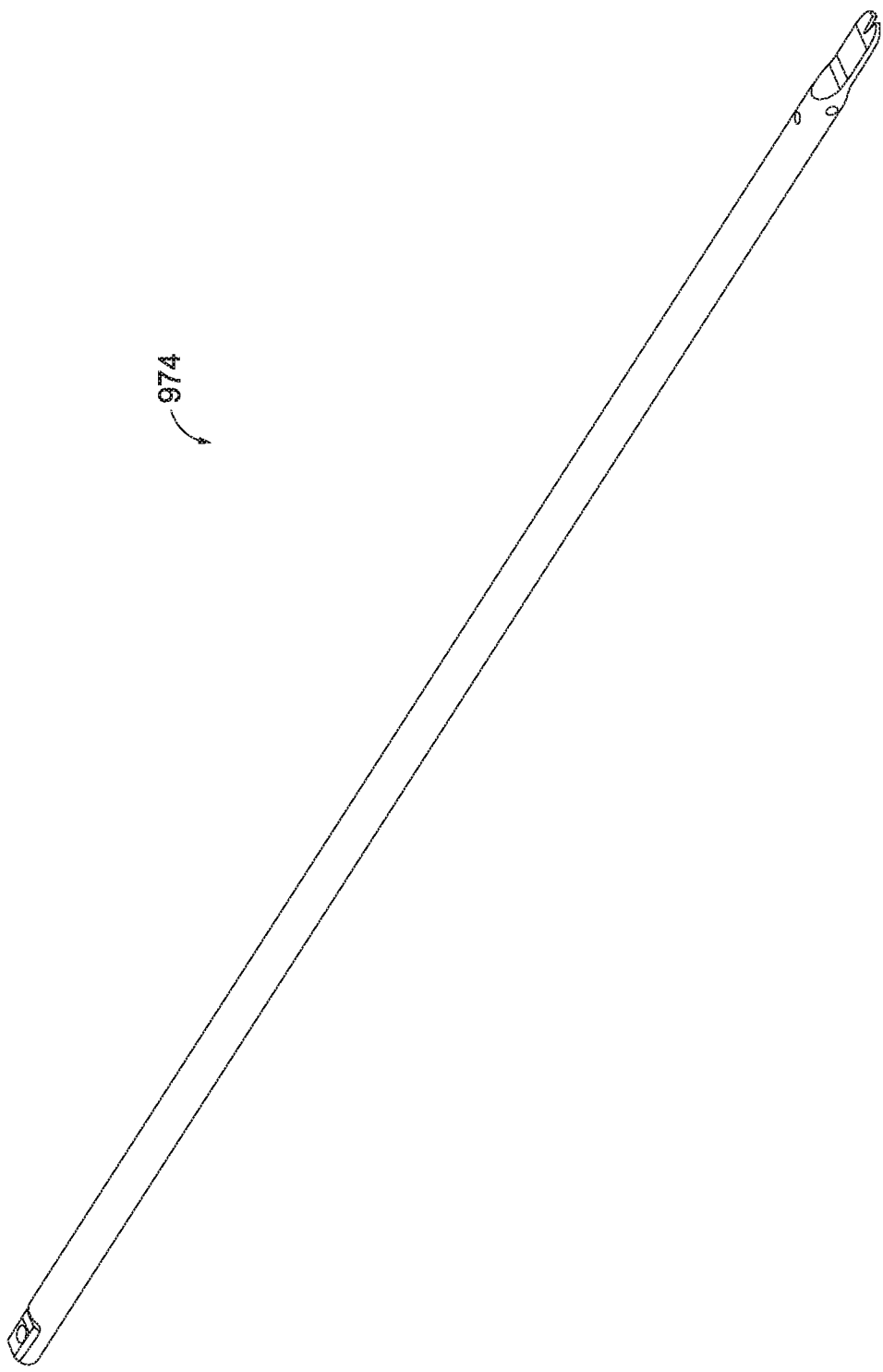

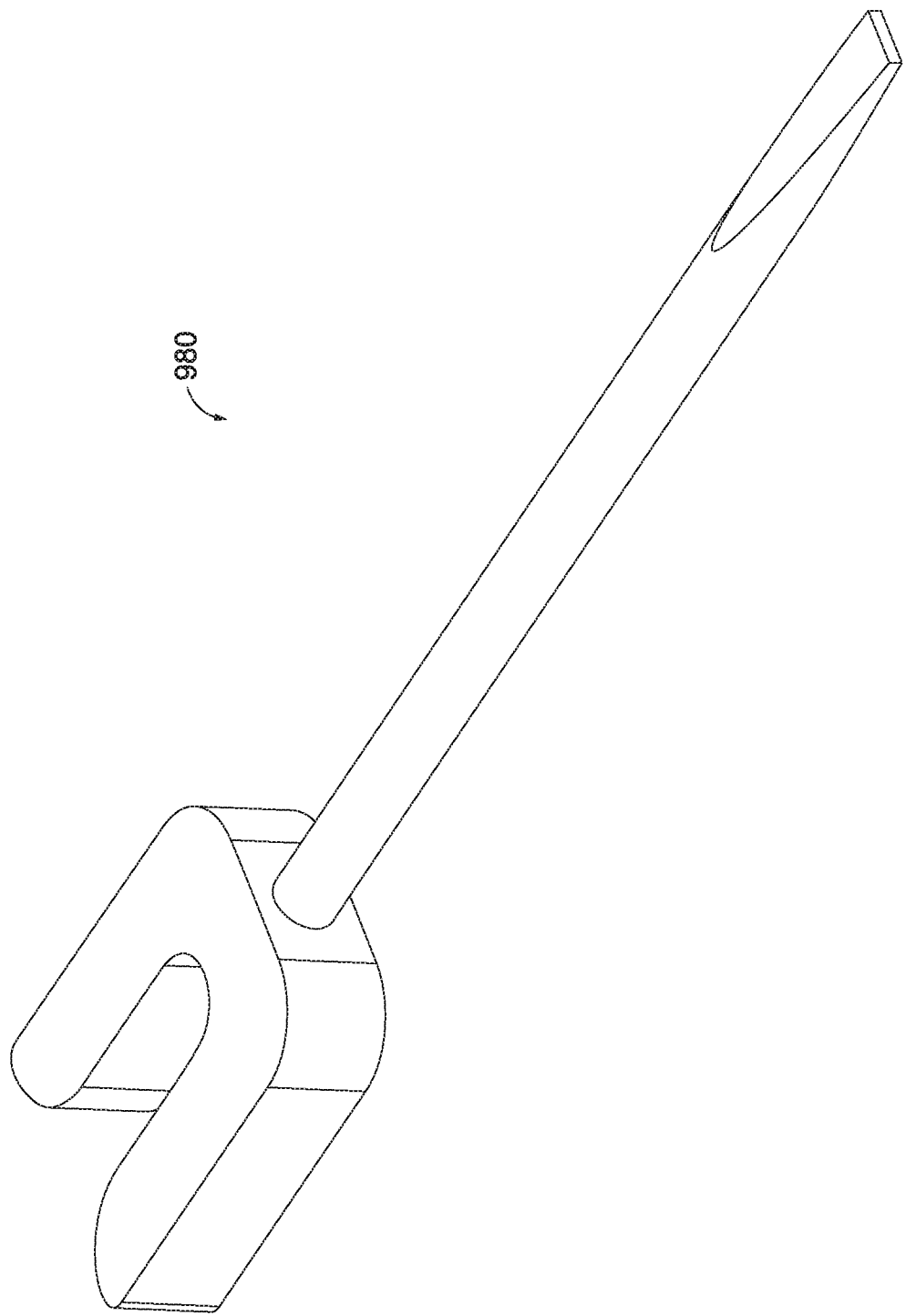

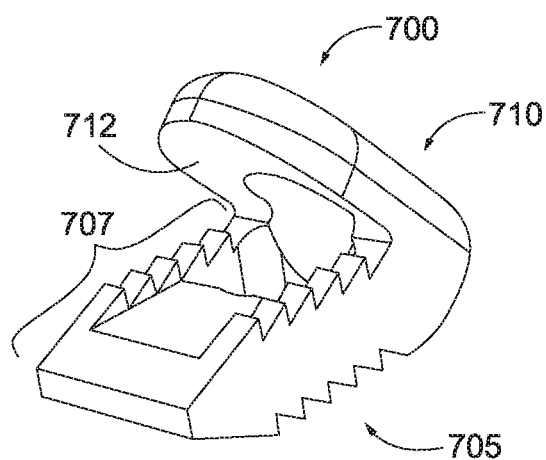
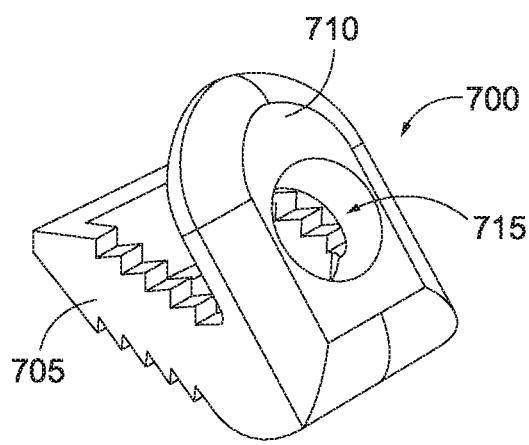
FIG. 15A    FIG. 15B
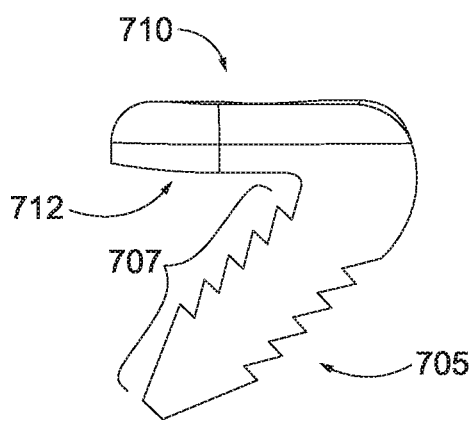
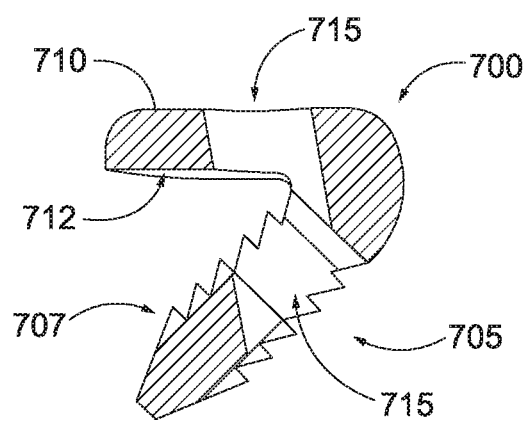
FIG. 15C    FIG. 15D
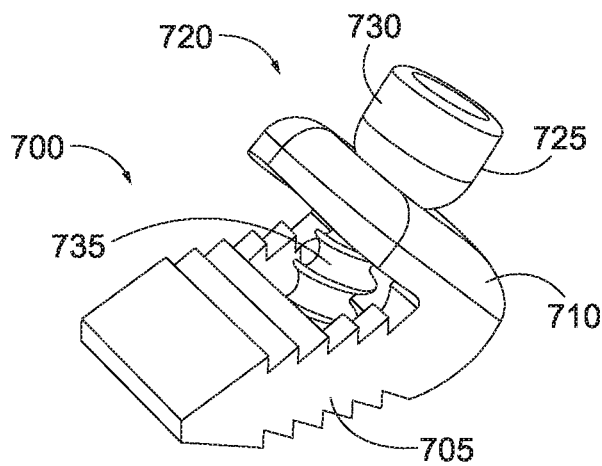
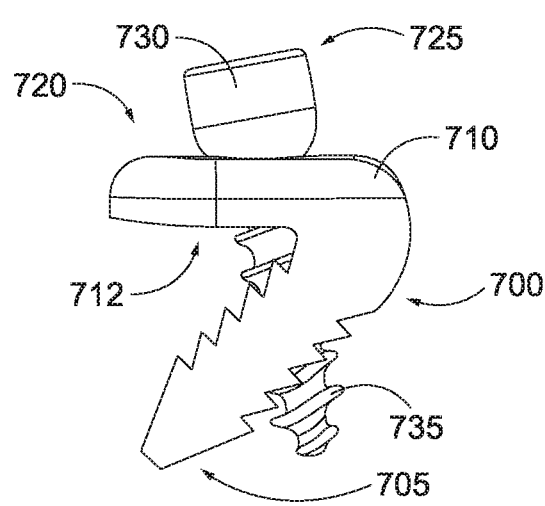
FIG. 15E    FIG. 15F

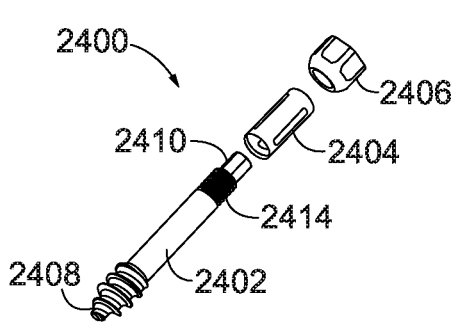 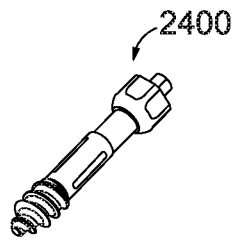 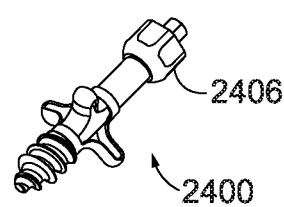
FIG. 39A  FIG. 39B  FIG. 39C
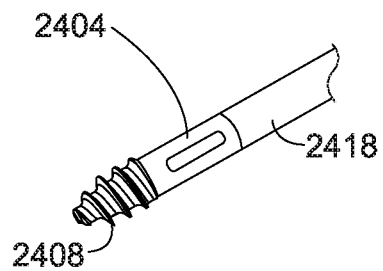 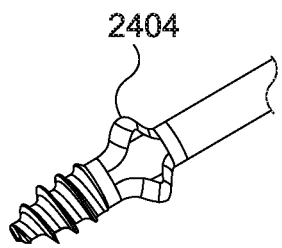 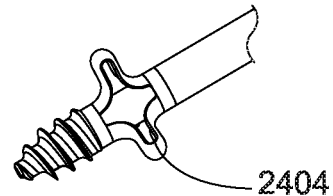
FIG. 40A  FIG. 40B  FIG. 40C
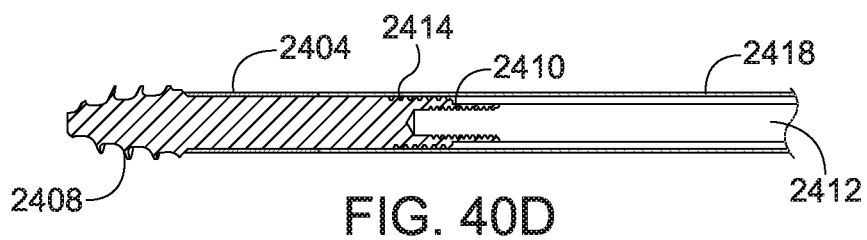
FIG. 40D
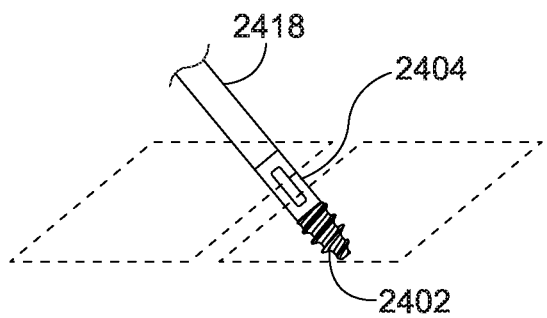 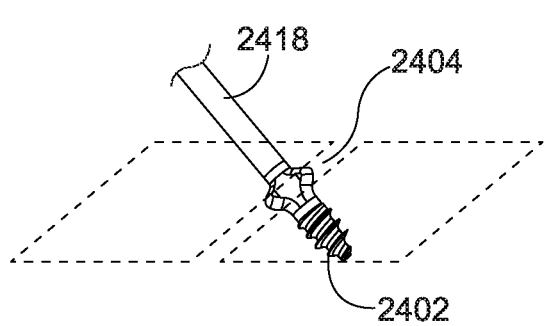
FIG. 41A  FIG. 41B

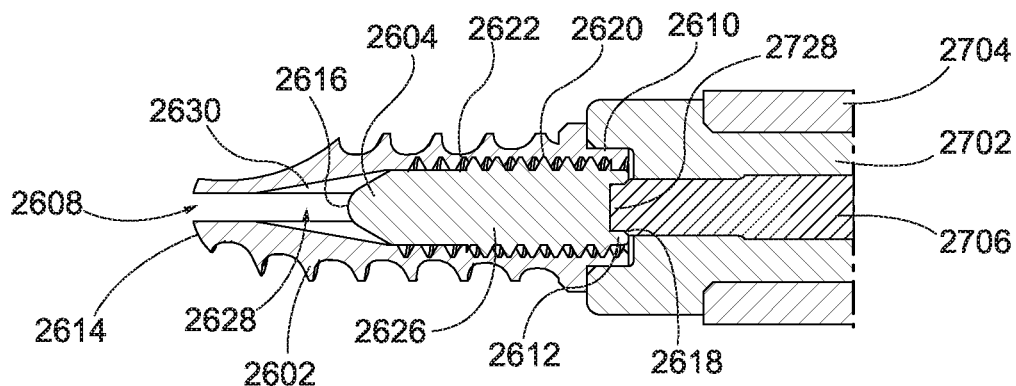
FIG. 45E
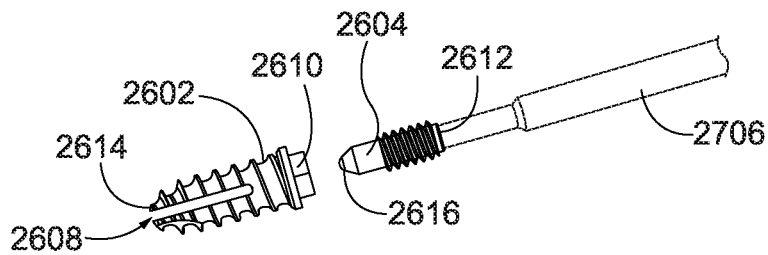
FIG. 45F
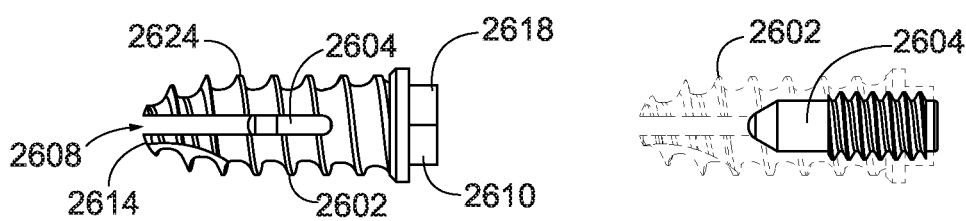
FIG. 46A
FIG. 46B
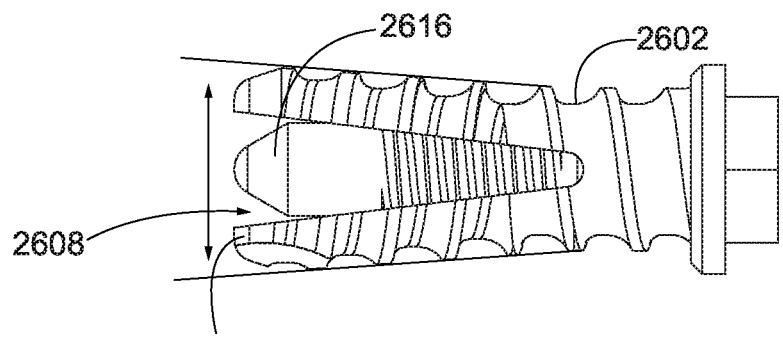
FIG. 46C

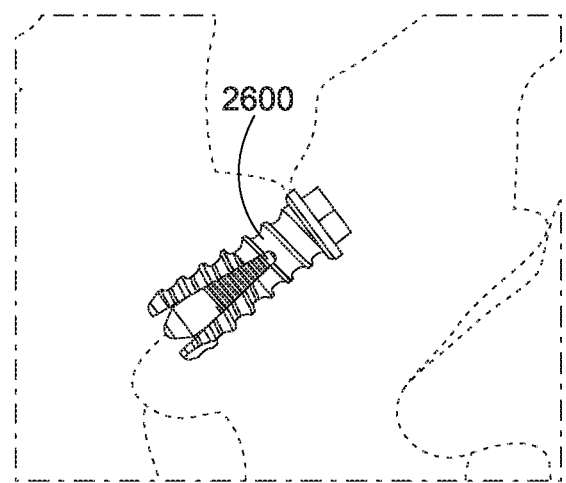
FIG. 50C
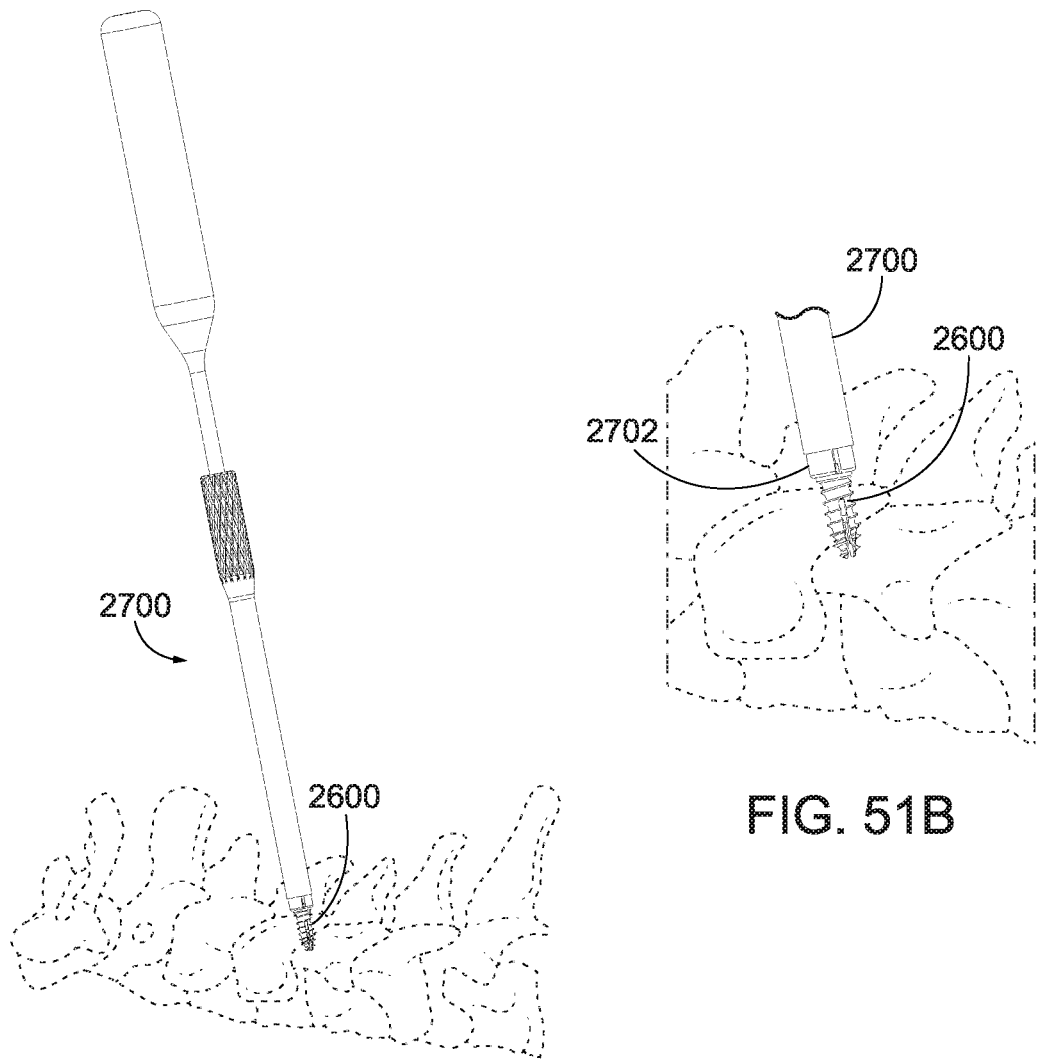
FIG. 51B
FIG. 51A

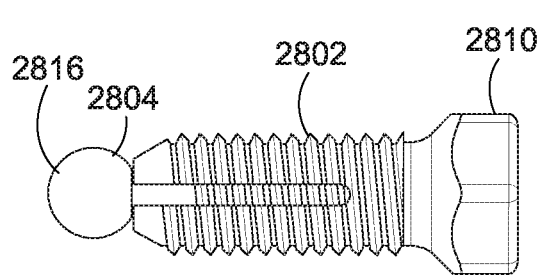
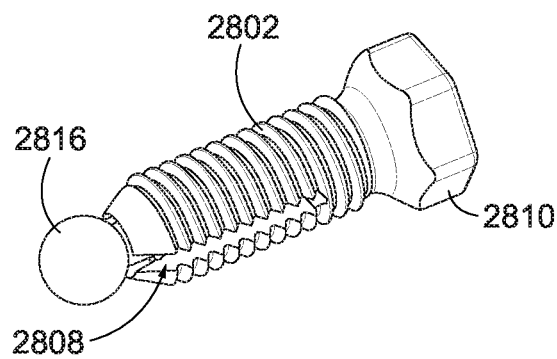
FIG. 53A          FIG. 53B
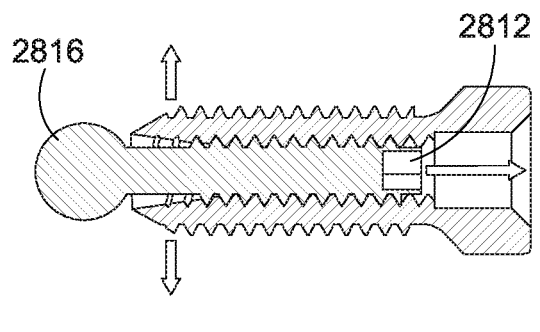
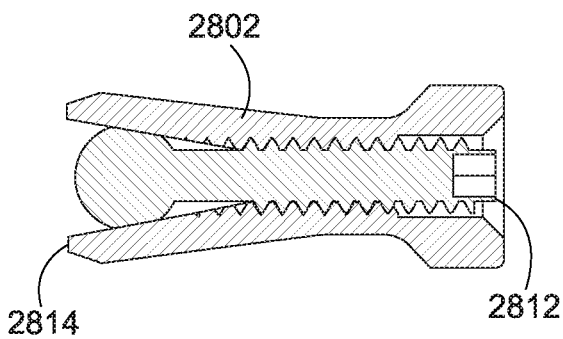
FIG. 53C          FIG. 53D
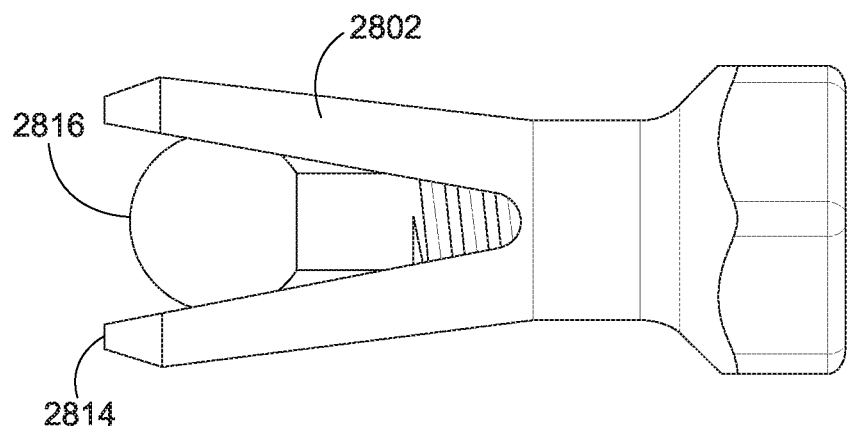
FIG. 53E

FACET SCREW AND DELIVERY DEVICE

CROSS REFERENCE TO RELATED APPLICATIONS

This application is a U.S. National Stage Patent Application of International Patent Application No. PCT/US2019/012367, filed Jan. 4, 2019, which is related to and claims priority to U.S. Pat. Appl. No. 62/613,547 filed on Jan. 4, 2018; U.S. Pat. Appl. No. 62/667,951 filed on May 7, 2018; and U.S. Pat. Appl. No. 62/734,568 filed on Sep. 21, 2018; all of which are hereby incorporated by reference herein for any purpose.

FIELD

This application is directed to medical devices and methods. More specifically, the application is directed to devices and methods related to use of a facet screw in various spine surgery procedures.

BACKGROUND

Chronic back problems are one of the most common causes of pain and disability in the United States and other developed countries, and they account for enormous economic costs. According to at least one estimate, spinal fusion procedures, in which two adjacent vertebrae are fused together using plates, screws and other implants, are the most commonly performed surgical procedures in the United States. Spinal fusion is often performed in conjunction with an attempt to increase space between the two adjacent vertebrae being operated on (spinal distraction) and to thus prevent impingement of the spinal cord or nerve roots branching from the spinal cord and passing through openings in the vertebral column (radiculopathy). Unfortunately, most techniques and devices used for performing spinal fusion are relatively invasive and involve a number of risks and difficult recovery and rehabilitation.

One of the reasons that spinal fusion surgery is often very invasive is that, due to the position of the spinal cord in back of (posterior to) the central vertebral bodies of spine, many of the procedures require entering the patient through the front of the body (an "anterior approach") and dissecting through various tissues to gain access to the spine. Fusion procedures are often performed on the cervical spine (neck region), which requires dissecting through the neck, or the lumbar spine (lower back region), which requires dissecting through the abdomen. In either case, cutting through the anterior tissues of the patient to reach the spine is not without risk. Fusion procedures may also involve relatively large plates and screws, which require a relatively large surgical access field and thus more dissection of tissue than would be ideal. Not only are these invasive spinal fusion techniques potentially risky, but they are also expensive and typically require lengthy recovery and rehabilitation times.

Therefore, a need exists for alternative devices and methods for treating spinal instability and spinal stenosis, particularly via fusion of adjacent vertebrae. Such devices and methods may be minimally invasive or less invasive than many of the currently available techniques. For example, it may be advantageous to have devices and methods that use a posterior approach for accessing the spine. At least some of these objectives will be met by the embodiments described below.

BRIEF SUMMARY

Embodiments described herein address the challenges described above by providing a system for implanting facet screw assembly through a vertebra of a vertebral column of a patient.

Embodiments described herein address the challenges described above by providing a system for implanting a locking screw through a vertebra of a vertebral column of a patient, the locking screw extending near or through a facet screw in the vertebral column. In some embodiments, the locking screw is advanced through an opening in a facet screw that has been placed in a facet joint between two vertebrae, so that the locking screw attaches to one of the two vertebrae and thus helps secure the facet screw in place within the facet joint. In one embodiment, a system for implanting a locking screw includes a facet screw, a locking screw, a locking screw delivery mechanism detachably connected to the locking screw, and a guide tube configured to receive, at a proximal end of the guide tube, the locking screw and locking screw delivery mechanism and, at a distal end, the facet screw. The guide tube includes one or more bends, and as the locking screw is advanced through the guide tube along a first trajectory, the bend in the guide tube (or multiple bends) causes the locking screw to exit a distal end of the guide tube along a second trajectory. The angle of the second trajectory is generally such that the locking screw enters the facet screw and the vertebra at a desired angle for its intended purpose.

In one aspect, a system may be provided for implanting a locking screw into a vertebra of a vertebral column of a patient to help secure a facet screw within a joint between the vertebra and an adjacent vertebra. The system may include a facet screw, a locking screw, a locking screw delivery mechanism detachably connected to the locking screw, and a guide tube. The guide tube may include a proximal end, a distal end, a lumen configured to receive the locking screw and the locking screw delivery mechanism, and at least one bend disposed nearer the distal end than the proximal end. The bend (or bends) in the guide tube are designed to change a trajectory of the locking screw and the locking screw delivery mechanism advancing through the lumen from a first trajectory along a longitudinal axis of the guide tube to a second trajectory that is angled relative to the longitudinal axis. The second trajectory is designed to direct the locking screw out of the distal end of the guide tube and into the vertebra at a desired angle offset from the longitudinal axis of the facet screw to help secure the facet screw.

In some embodiments, the joint in which the system is used is a facet joint, and the implant is a facet screw. In such embodiments, the locking screw, the locking screw delivery mechanism and the guide tube may be designed to advance the locking screw through an opening in the facet screw and into the vertebra. In some embodiments, the bend in the guide tube changes the trajectory from the first trajectory to the second trajectory without assistance from a user of the system. In some embodiments, the locking screw delivery mechanism may be detachable from the locking screw by breaking the locking screw delivery mechanism off of the locking screw at a breakable junction. For example, the locking screw delivery mechanism may break off of the locking screw when a predetermined amount of force is applied to the locking screw delivery mechanism and a break in the junction occurs.

In some embodiments, the locking screw delivery mechanism includes a flexible region configured to flex when the delivery mechanism is advanced through the bend in the guide tube. In such embodiments, when the locking screw is engaged with the vertebra and the flexible region is flexed, a load may be concentrated at a breakable junction between the locking screw and the locking screw delivery mechanism. In some embodiments, the locking screw delivery mechanism detaches from the locking screw upon the breakable junction experiencing a predetermined load. Furthermore, in some embodiments, the locking screw and the locking screw delivery mechanism are a one-piece device with a breakable section between the locking screw and the locking screw delivery mechanism. In such embodiments, the locking screw detaches from the locking screw delivery mechanism when the locking screw breaks off of the locking screw delivery mechanism at the breakable section.

In another aspect, a device for securing an implant within a joint formed by two adjacent vertebrae may include an elongate locking screw delivery mechanism extending along a longitudinal axis from a proximal end to a distal end and a locking screw detachably connected to the distal end of the locking screw delivery mechanism. In some embodiments, the device may also include a breakable junction between the locking screw delivery mechanism and the locking screw, and the locking screw delivery mechanism is detachable from the locking screw by breaking the locking screw delivery mechanism off of the locking screw at the breakable junction. In some embodiments, the locking screw delivery mechanism breaks off of the locking screw when a predetermined amount of force is applied to the locking screw delivery mechanism and a break in the junction occurs. In some embodiments, the locking screw delivery mechanism includes a flexible region.

The locking screw may include a shaft extending from a screw head, the screw head being monolithically formed with the distal end of the delivery mechanism. In some embodiments, for example, the shaft extends from the screw head along the longitudinal axis. In some embodiments, the locking screw and the locking screw delivery mechanism are a one-piece device with a breakable section between the locking screw and the locking screw delivery mechanism.

In some aspects, a system for delivering a facet screw to a vertebra is disclosed. The system includes a facet screw and a guide tube having a proximal end, a distal end configured to receive the facet screw, and a lumen comprising a bend disposed nearer the distal end than the proximal end. The bend in the guide tube is configured to change a trajectory of a screw device advancing through the lumen from a first trajectory along a longitudinal axis of the guide tube to a second trajectory that is angled relative to the longitudinal axis. The second trajectory is configured to direct the screw device out of the distal end of the guide tube and into the facet screw and the vertebra at an angle offset from a longitudinal axis of the facet screw. In some aspects, the facet screw includes a proximal end and a distal end and a guide tube engagement feature positioned proximate the proximal end of the facet screw. The guide tube engagement feature includes one or more notches. The distal end of the guide tube includes one or more protrusions. The one or more notches are complementary to and receive the one or more protrusions such that the guide tube engagement feature and the distal end of the guide tube are releasably coupled together.

In some aspects, a system for delivering a facet screw assembly to a joint between a vertebra and an adjacent vertebra is disclosed. The system includes a facet screw assembly and a delivery device. The delivery device may include an actuator shaft having a distal threaded end configured to receive at least a portion of the facet screw assembly, a central sleeve defining a first longitudinally extending lumen, the central sleeve configured to receive the actuator shaft, and an outer sleeve having one or more notches at a distal end and further defining a second longitudinally extending lumen, the outer sleeve configured to receive the central sleeve. The one or more notches of the outer sleeve engage at least a second portion of the facet screw assembly to aid in delivery of the facet screw assembly. In some aspects, the facet screw assembly includes a facet screw having an elongated shaft with a proximal end and a distal end, a washer including: a base having an opening for engagement with the proximal end of the elongated shaft of the facet screw, and one or more protrusions extending longitudinally from the base, the protrusions having teeth extending therefrom. The facet screw assembly may also include a locking ring configured to secure the washer to the proximal end of the facet screw. In some aspects, the joint is a facet joint. In some aspects, the proximal end of the elongated shaft of the facet screw comprises internal threads configured for engagement with the actuator shaft of the delivery device. The distal end of the elongated shaft of the facet screw may include external threads configured for engagement with the facet joint. In some aspects, a channel is defined at least partially in the external threads of the facet screw and the channel may hinder rotation of the screw in the facet joint. In some aspects, the central sleeve has a hex shape to rotationally drive the facet screw. In some aspects, the proximal portion of the one or more protrusions of the washer are complementary to and received by the one or more notches at the distal end of the outer sleeve.

In some aspects, an intra-facet screw assembly is disclosed. The assembly includes a facet screw having an elongated shaft with a proximal end and a distal end. The assembly further includes a washer including a base having an opening for engagement with the proximal end of the elongated shaft of the facet screw and one or more protrusions extending longitudinally from the base, the protrusions having teeth extending therefrom. The assembly further includes a locking ring configured to secure the washer to the proximal end of the facet screw. In some aspects, a method of treating radiculopathy is disclosed. The method may include delivering the intra-facet screw assembly to a narrowed facet joint between a vertebra and an adjacent vertebra, and inserting the intra-facet screw assembly into the narrowed facet joint to expand the facet joint and increase foraminal height to decompress a nerve root, in addition to stabilizing and fixating the joint.

In some aspects, a trans-facet screw assembly is disclosed. The assembly includes a facet screw having an elongated shaft with a proximal end and a distal end. The assembly further includes a washer including a base having an opening for engagement with the proximal end of the elongated shaft of the facet screw and one or more protrusions extending longitudinally from the base, the protrusions having teeth extending therefrom. The assembly further includes a locking ring configured to secure the washer to the proximal end of the facet screw. In some aspects, a method of treating spinal instability is disclosed. The method may include delivering the trans-facet screw assembly through a facet joint between a vertebra and an adjacent vertebra, to stabilize an fixate the facet joint.

In another aspect, a system for delivering a facet screw assembly to a joint between a vertebra and an adjacent vertebra is disclosed. The system includes a facet screw assembly comprising a facet screw having a proximal portion and a distal portion and a delivery device including a proximal and distal end and defining a longitudinally extending lumen therethrough. The distal end of the delivery device may include a facet screw engagement feature. The facet screw engagement feature is keyed to a corresponding delivery device engagement feature located at or near the proximal portion of the facet screw.

In another aspect, a method for implanting a locking screw and a facet screw in a vertebra may involve inserting the locking screw and a locking screw delivery mechanism through a proximal end of a guide tube along a first trajectory, where a proximal end of the locking screw is attached to a distal end of the locking screw delivery mechanism, and a distal end of the guide tube, including a facet screw, is positioned adjacent the vertebra. The method may further involve advancing the locking screw and the locking screw delivery mechanism through a bend in the guide tube to cause the locking screw to exit the distal end of the guide tube along a second trajectory, through the facet screw and contact the vertebra. The method may also involve rotating the delivery mechanism to cause the locking screw to screw into the vertebra and detaching the locking screw delivery mechanism from the locking screw.

In some embodiments, the locking screw delivery mechanism is advanced through the guide tube in a straight direction along the first trajectory, and the bend in the guide tube automatically adjusts a path of travel of the locking screw delivery mechanism from the first trajectory to the second trajectory. In some embodiments, detaching the locking screw delivery mechanism from the locking screw comprises breaking the locking screw delivery mechanism off of the locking screw at a breakable junction. For example, breaking the locking screw delivery mechanism off of the locking screw may involve screwing the locking screw into the vertebra until a break in the junction occurs. More generally, breaking the locking screw delivery mechanism off of the locking screw may involve applying force to the locking screw delivery mechanism until a break in the junction occurs. In some embodiments, the locking screw and the locking screw delivery mechanism are a one-piece device with a breakable section between the locking screw and the locking screw delivery mechanism. In such embodiments, detaching the locking screw delivery mechanism from the locking screw may involve breaking the locking screw delivery mechanism off of the locking screw at the breakable section.

The method may further involve advancing the guide tube into the patient to position the distal end of the guide tube adjacent the vertebra. In some embodiments, this advancing of the guide tube involves advancing it through a larger guide tube previously placed in the patient proximate the vertebra.

In some embodiments, the step of advancing the locking screw may involve advancing the locking screw through an opening in a facet screw located in a facet joint formed by the vertebra and an adjacent vertebra. Optionally, the method may further involve, prior to the inserting step: advancing a larger guide tube into the patient from a posterior approach, to position a distal end of the larger guide tube in the facet joint; implanting the facet screw in the facet joint through the larger guide tube; and positioning the guide tube in a desired position for advancing the locking screw through the facet screw. In some embodiments, when the locking screw is engaged with the vertebra and the flexible region is flexed, a load is concentrated at a breakable junction. In some embodiments, the locking screw delivery mechanism detaches from the locking screw upon the breakable junction experiencing a predetermined load.

In another aspect, a method for implanting a locking screw through a facet screw to attach to a vertebra may involve: advancing a guide tube into the patient to position a distal end of the guide tube adjacent the facet joint; inserting a distal end of a locking screw delivery mechanism through the guide tube along a first trajectory; advancing the locking screw delivery mechanism through a bend in the guide tube to cause a distal locking screw portion of the locking screw delivery mechanism to exit the distal end of the guide tube along a second trajectory and advance through an opening in the facet screw at an angle; rotating the locking screw delivery mechanism to cause the distal locking screw portion to screw into the vertebra to secure the facet screw to the vertebra; and breaking a proximal elongate shaft portion of the locking screw delivery mechanism off of the distal locking screw portion at a breakable junction between the two portions.

Advancing the locking screw delivery mechanism may involve advancing the locking screw delivery mechanism in a straight direction along the first trajectory, where the bend in the guide tube automatically adjusts a path of travel of the locking screw delivery mechanism from the first trajectory to the second trajectory. In some embodiments, breaking the proximal elongate shaft portion off of the distal locking screw portion involves screwing the distal locking screw portion into the vertebra until a break in the breakable junction occurs. In other embodiments, breaking the proximal elongate shaft portion off of the distal locking screw portion comprises applying force to the proximal elongate shaft portion until a break in the breakable junction occurs. In some embodiments, the proximal elongate shaft portion and the distal locking screw portion are a one-piece device with the breakable junction between them.

In another aspect, a method is provided for implanting a locking screw in a vertebra at or immediately adjacent a facet screw disposed in a spinal joint formed by the vertebra and an adjacent vertebra. The method may first involve inserting a locking screw delivery mechanism through a proximal end of a guide tube along a first trajectory, where a distal end of the locking screw delivery mechanism is attached to a proximal end of the locking screw, and where a distal end of the guide tube is positioned proximate the facet screw. The method may next involve advancing the facet screw delivery mechanism through one or more bends in the guide tube to cause the facet screw to exit the distal end of the guide tube along a second trajectory and contact the vertebra. The method may further involve rotating the delivery mechanism to cause the locking screw to screw into the vertebra to help secure the facet screw within the spinal joint and separating the locking screw delivery mechanism from the locking screw. In some embodiments, the locking screw may be advanced through an opening in the facet screw to contact the vertebra. In some embodiments, the spinal joint is a facet joint.

In another aspect, a facet screw assembly delivery system is disclosed. The system comprises a facet screw assembly and an articulating delivery device. The delivery device includes a facet screw delivery lumen, a spacer delivery lumen and an actuator rod having a knob and a spacer engagement member configured for receipt in the spacer delivery lumen.

In another aspect, a system for delivering a facet screw assembly to a joint between a vertebra and an adjacent vertebra is disclosed. The system comprises a facet screw assembly and a delivery device. The delivery device includes a first lumen configured for delivery of a facet screw, a second lumen configured for delivery of a rotatable spacer, the lumens coupled together in a coplanar orientation, and an actuator rod having a knob and a spacer engagement member configured for receipt in the spacer delivery lumen.

In either or both systems, the facet screw assembly comprises a facet screw having an elongated shaft with a proximal end and a distal end, and a rotatable spacer. The rotatable spacer includes a base having a rotatable member including a rod opening, the rod opening configured to receive the actuator rod and one or more protrusions extending longitudinally from the base, the protrusions having teeth extending therefrom. The actuator rod engages the rod opening to rotate the rotatable member. Either or both systems may further comprise a connecting member coupling the lumens together.

In some aspects, the spacer delivery lumen has a length and the facet screw delivery lumen extends less than a full length of the spacer delivery lumen.

In some aspects, the second lumen has a length and the first lumen extends less than a full length of the second lumen.

In some aspects, the joint is a facet joint.

In some aspects, an intra-facet screw assembly is disclosed. The assembly includes a facet screw having an elongated shaft with a proximal portion and a distal portion and a spacer. The spacer includes a base having a rotatable member including a rod opening, the rod opening configured to receive an actuator rod, and one or more protrusions extending longitudinally from the base, the protrusions having teeth extending therefrom.

In some aspects, a method of treating radiculopathy is disclosed. The method comprises delivering the intra-facet screw assembly as disclosed herein to a narrowed facet joint between a vertebra and an adjacent vertebra and inserting the intra-facet screw assembly into the narrowed facet joint to expand the facet joint and increase foraminal height to decompress a nerve root.

In some aspects, an intra-facet screw assembly is disclosed. The assembly comprises a facet screw having an elongated shaft with a proximal portion having a head and a distal portion including threads and a spacer. The spacer comprises a first portion having an intrafacet engagement portion and a second portion having a lateral mass engagement portion, each portion further including a facet screw opening configured to receive at least a portion of the facet screw.

In some aspects of the assembly, the first portion comprises one or more surfaces having teeth extending therefrom. In some aspects, the second portion comprises one or more surfaces configured for engagement with at least a portion of a lateral mass of a vertebra.

In some aspects, a facet screw assembly delivery system is disclosed. The system comprises a facet screw assembly and a delivery device. The delivery device comprises a facet screw delivery lumen coupled to and positioned in parallel to a spacer delivery lumen and an actuator rod having a knob and a spacer engagement member configured for receipt in the spacer delivery lumen.

In some aspects, the facet screw assembly comprises a facet screw having an elongated shaft with a proximal portion having a head and a distal portion including threads and a spacer comprising a first portion having an intrafacet engagement portion and a second portion at an angle relative to the first portion, the second portion having a lateral mass engagement portion, each portion further including a facet screw opening configured to receive at least a portion of the facet screw. In some aspects of the system, the angle between the first portion and the second portion is an acute angle or less than 90 degrees, preferably approximately 45-60 degrees.

A method of treating radiculopathy is disclosed. In some aspects, the method comprises delivering the intra-facet screw assembly as disclosed herein or the facet screw assembly delivery system as disclosed herein to a narrowed facet joint between a vertebra and an adjacent vertebra and inserting the assembly or delivery device into the narrowed facet joint to expand the facet joint and increase foraminal height to decompress a nerve root.

In some embodiments, a facet screw assembly delivery system may include a facet screw assembly, a facet access guide, a washer sizer tool configured to removably engage with the facet access guide, a lateral mass decorticator guide configured to slidably and removably engage with the washer size tool, a washer implant delivery tool configured to removably engage with the facet access guide and detachably couple to the facet screw assembly, and an impact handle configured to detachably couple to the facet access guide, the washer sizer tool, and the washer implant delivery tool.

In some embodiments, the facet screw assembly includes facet screw having an elongated shaft with a proximal end and a distal end, a washer implant including a lateral mass engagement portion, an intrafacet engagement portion, a facet screw opening extending through the lateral mass engagement portion and the intrafacet engagement portion, the facet screw opening configured to accept the distal end of the facet screw, a keyway configured to align with a keyed feature on the washer implant delivery tool to maintain a position of the washer implant during delivery, and a coupling member configured to detachably couple the washer implant to the washer implant delivery tool.

In some embodiments, the facet access guide includes a proximal end including an instrument guide handle portal that is parallel to an impact handle socket, a ramped distal end including an intra-facet distractor and depth stop adjacent the intra-facet distractor, and an instrument guide portal formed an open channel and extending between the proximal end and the distal end.

In some embodiments, the washer sizer tool includes an access guide interface configured to engage with a facet access guide, a joint spacer positioned at a distal end of the washer size tool, the joint spacer angled with respect to a central portion of the washer sizer tool, a pin positioned adjacent the joint spacer and configured to engage with the facet access guide, an alignment feature extending from a posterior side of the washer sizer tool and configured to slidably engage with the lateral mass decorticator guide, and a washer size marker configured to provide a user with information regarding a recommended size of the facet screw assembly.

In some embodiments, the washer implant delivery tool includes a shaft, a rotatable washer release knob adjacent a proximal end of the shaft, an actuation rod coupled to the rotatable washer release knob and extending through at least a portion of the shaft, the actuation rod including a distal end configured to engage the facet screw assembly, a facet screw guide positioned at an angle with respect to the shaft and including a facet screw portal extending through the facet screw guide, and a key feature configured to align with a keyway feature on facet screw assembly to maintain a position of the face screw assembly during delivery.

In some embodiments, a system for delivering a facet screw assembly to a joint between a vertebra and an adjacent vertebra includes a facet screw assembly, a delivery device including a facet access guide, a washer implant delivery tool configured to removably engage with the facet access guide and detachably couple to the facet screw assembly, an impact handle configured to detachably connect to the facet access guide and the washer implant delivery tool.

In some embodiments, a method of delivering a facet screw assembly to a facet joint using a facet screw assembly delivery system includes placing a facet access guide into the facet joint, detachably coupling a washer sizer tool with the facet access guide, disconnecting an impact handle from the facet access guide and detachably coupling the impact handle to the washer sizer tool, impacting the impact handle to position the washer sizer tool in an appropriate location with respect to the facet joint, coupling a lateral mass decorticator guide with the washer sizer tool, contacting a lateral mass of the facet joint with the lateral mass decorticator tool, advancing a decorticator through a tool guide of the lateral mass decorticator guide and decorticating the lateral mass, determining a recommended facet screw assembly size for the facet joint, selecting a facet screw assembly size and coupling a component of the facet screw assembly to a washer implant delivery tool, decoupling the lateral mass decorticator guide and washer sizer tool from the facet access guide, coupling the impact handle to the washer implant delivery tool, coupling the washer implant delivery tool to the facet access guide and impacting the impact handle to position the component of a facet screw assembly into the facet joint, drilling a pilot hole across the facet joint, advancing a facet screw through the pilot hole and placing the facet screw across the facet joint, tightening the facet screw onto the component of a facet screw assembly and compressing the facet joint, decoupling the washer implant delivery tool from the facet screw assembly, and removing the washer implant delivery tool and facet access guide from the facet joint. In some embodiments, the method includes accessing the surgical site using angled instruments configured to reduce tissue incision size or instrument footprint.

In some embodiments, a facet screw assembly includes a facet screw having an elongated shaft with a proximal end and a distal end, a washer implant including a lateral mass engagement portion, an intrafacet engagement portion, a facet screw opening extending through the lateral mass engagement portion and the intrafacet engagement portion, the facet screw opening configured to accept the distal end of the facet screw, a keyway configured to align with a keyed feature on a washer implant delivery tool to maintain a position of the washer implant during delivery, and a coupling member configured to detachably couple the washer implant to the washer implant delivery tool.

In some embodiments, a facet access guide includes a proximal end including an instrument guide handle portal that is parallel to an impact handle socket, a ramped distal end including an intra-facet distractor and depth stop adjacent the intra-facet distractor, and an instrument guide portal formed an open channel and extending between the proximal end and the distal end.

In some embodiments, a washer sizer tool includes an access guide interface configured to engage with a facet access guide, a joint spacer positioned at a distal end of the washer size tool, the joint spacer angled with respect to a central portion of the washer sizer tool, a pin positioned adjacent the joint spacer and configured to engage with the facet access guide, an alignment feature extending from a posterior side of the washer sizer tool and configured to slidably engage with the lateral mass decorticator guide, and a washer size marker configured to provide a user with information regarding a recommended size of a facet screw assembly.

In some embodiments, a washer implant delivery tool includes a shaft, a rotatable washer release knob adjacent a proximal end of the shaft, an actuation rod coupled to the rotatable washer release knob and extending through at least a portion of the shaft, the actuation rod including a distal end configured to engage a facet screw assembly, a facet screw guide positioned at an angle with respect to the shaft and including a facet screw portal extending through the facet screw guide, and a key feature configured to align with a keyway feature on the facet screw assembly to maintain a position of the facet screw assembly during delivery.

In some embodiments, a system for delivering a facet screw assembly to a joint between a vertebra and an adjacent vertebra while reducing tissue incision size includes a facet screw assembly, an angled delivery device including an angled facet access guide, a washer implant delivery tool configured to removably engage with the facet access guide and detachably couple to the facet screw assembly, and an impact handle configured to detachably connect to the facet access guide and the washer implant delivery tool.

In some embodiments, a system for delivering a facet screw assembly to a joint between a vertebra and an adjacent vertebra includes a facet screw assembly, a non-linear delivery device including a non-linear facet access guide, a washer implant delivery tool configured to removably engage with the facet access guide and detachably couple to the facet screw assembly, and an impact handle configured to detachably connect to the facet access guide and the washer implant delivery tool.

In some embodiments, a facet screw assembly includes a trans-facet screw having an elongated shaft with a proximal portion and a distal portion; an intra-facet screw having an elongated shaft with a proximal portion and a distal portion; a washer including an intra-facet threaded aperture extending through a length of or along a longitudinal axis of the washer; and a trans-facet aperture extending through a width of or along a transverse axis of the washer. When assembled, the trans-facet screw is positioned within the trans-facet aperture and the intra-facet screw is positioned within the intra-facet aperture, and the washer is configured to be positioned in a facet joint.

In some aspects, the washer includes a reduced thickness, with the height of the washer at a first end being larger than a height of a second end of the washer along the length of the intra-facet threaded aperture. In some aspects, the second end of the washer is configured to expand in a width-direction as the intra-facet screw is inserted. In some embodiments, the assembly further includes a pivoting plate rotatably coupled to the first end of the washer, wherein the pivoting plate is configured to pivot about the first end of the washer.

In some embodiments, a facet implant assembly includes a facet screw with a first end and a tapered, threaded end opposite the first end; a cylindrical expandable spacer coupled to the first end of the facet screw, wherein the expandable spacer is configured to rotate in unison with the facet screw when coupled to the face screw, and a compression nut; wherein in a deployed position, the spacer is configured to expand to distract the facet joint and maintain the distracted aspect; and wherein the compression nut is threadably coupled to the first end of the facet screw to fixate the facet screw across the facet joint.

In some embodiments, a facet implant assembly includes a first facet implant comprising a screw and a polyaxial head with a rod receiving feature; a second facet implant comprising a screw and a polyaxial head with a rod receiving feature; and a rod; wherein in a deployed position, the first facet implant is configured to be deployed across a first facet joint and the second facet implant is configured to be deployed across a second facet joint, and a portion of the rod is positioned within each of the rod receiving features of the first facet implant and the second facet implant to couple the first facet implant with the second facet implant.

In some aspects, the first facet implant is deployed across the first facet joint in a trans-facet manner and the second facet implant is deployed across the second facet join in a trans-facet manner. In some aspects. the first facet implant is deployed across the first facet joint in an intra-facet manner and the second facet implant is deployed across the second facet join in an intra-facet manner.

In some embodiments, a facet implant assembly includes a first facet implant comprising a polyaxial head with a rod receiving feature; a second facet implant comprising a polyaxial head with a rod receiving feature; a first cage implant; and a rod; wherein in a deployed position, the first facet implant and optionally, the first cage implant, are configured to be deployed in an intra-facet manner adjacent one another between a first vertebra and a second vertebra; the second facet implant and optionally, a second cage implant, are configured to be deployed in an intra-facet manner adjacent one another between a second vertebra and a third vertebra; and wherein a portion of the rod is positioned within each of the rod receiving features of the first facet implant and the second facet implant to couple the first facet implant with the second facet implant.

In some embodiments, a system for delivering a facet screw assembly to a joint between a vertebra and an adjacent vertebra includes a facet screw assembly; and a delivery device including a screw driver configured to drive a facet screw into the joint; a screw driver locking collar positioned about a portion of the screw driver shaft and configured to engage the screw driver to engage with the facet screw assembly; and a screw expander driver positioned within a lumen of the screw driver configured to expand the facet screw assembly into a deployed configuration once the facet screw assembly is driven into the facet joint.

In some aspects, the facet screw assembly includes a screw and a screw expander, and wherein the screw expander is configured to splay an end of the screw when the facet screw assembly is in a deployed configuration. In some aspects, the screw expander is a retracting ball expander. In some aspects, the ball expander is positioned adjacent a first end of the screw expander so that threaded portions of the screw expander extend from both sides of the ball expander, and the first end of the screw expander is configured to remain within the facet joint space when the facet screw assembly is in a deployed configuration.

In some embodiments, a system for delivering a facet screw assembly to a joint between a vertebra and an adjacent vertebra includes a facet screw including a screw body including self-tapping threads; and a head including a first keyway and a second keyway, wherein an outer circumference of the head includes teeth; wherein the teeth have alternating teeth angles and are positioned on two sides of the head; a delivery device comprising a driver including a shaft with a keyed first end and a handle opposite the first end; and a holder including a tapered end with at least one arm extending from the taper end, wherein the keyed first end of the driver is configured to engage with the first keyway of the facet screw, and the arm of the holder is configured to engage with the second keyway of the facet screw.

These and other aspects and embodiments will be described in further detail below, in reference to the attached drawing figures.

BRIEF DESCRIPTION OF DRAWINGS

FIGS. 12A-12G depict various tools of a distraction system that may be used according to certain embodiments.

FIGS. 15A-15F depict various views of a facet assembly, according to certain embodiments.

FIGS. 39A-41D depict views of an implant and delivery device that may be used with embodiments according to the present disclosure.

FIGS. 50A-50C depict views of the implant and delivery tool of FIGS. 45A-49F in use in an intra-facet deployment.

FIGS. 51A-51C depict views of the implant and delivery tool of FIGS. 45A-49C in use in a trans-facet deployment.

FIGS. 52A-53E depict views of an implant and delivery device that may be used with embodiments according to the present disclosure.

DETAILED DESCRIPTION

Figure 1A:
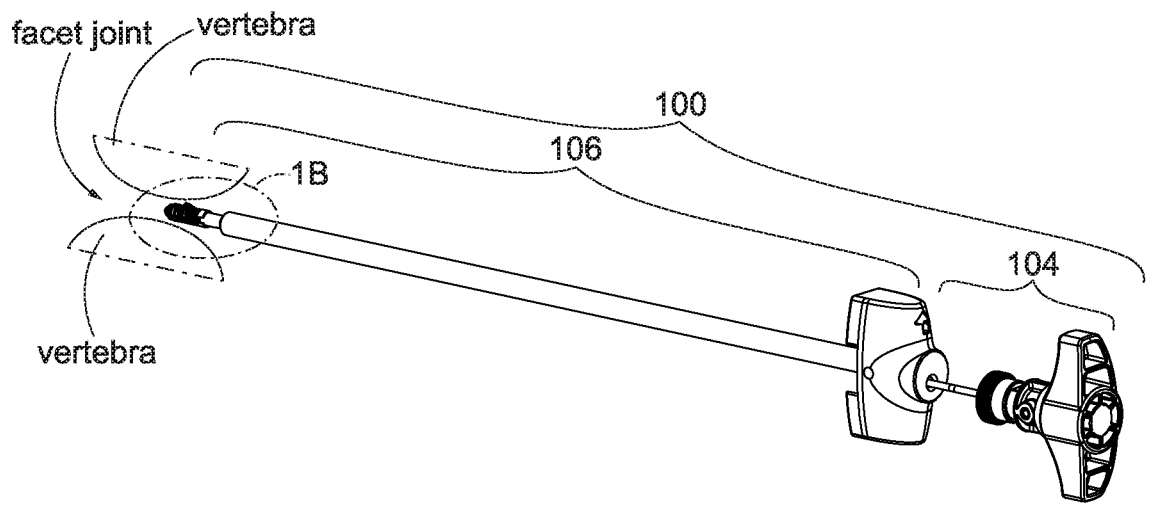
FIG. 1A is a perspective view of a system including a locking screw device and an implant delivery device, depicted for intra-facet placement, according to certain embodiments.

Aspects of the present disclosure generally involve devices and methods for treating spinal instability, spinal stenosis and radiculopathy. Spinal stenosis reflects a narrowing of one or more areas of the spine, often in the upper or lower back. This narrowing can put pressure on the spinal cord or on the nerves that branch out from the compressed areas (radiculopathy). Individual vertebrae of the spine are positioned relative to each other, and their separation is maintained by discs separating main vertebral bodies and by capsules positioned within facet joints. The discs and capsules are separated from the bone of their respective joints by cartilage. Spinal stenosis is often indicative of degeneration of a disc, a capsule, or the cartilage in a joint, which leads to a compression of the joints and the narrowing mentioned.

Various embodiments of a device, system and method are described herein for posterior fixation of two adjacent vertebrae of a spine, in an effort to ameliorate spinal instability, spinal stenosis and radiculopathy. Some embodiments involve delivery of the fixation device from a posterior approach.

Facet screws are commonly used in spine surgery as a means for posterior fixation. The screw consists of either a cannulated or solid screw and with or without a head washer. Typically, a facet screw is placed across the facet joint to provide posterior fixation. The concern with placing a screw across the facet joint is that it may potentially compress the joint and narrow the foraminal space where the nerve root resides causing foraminal stenosis.

In addition, there are challenges in placing the facet screw in the posterior spine, such as the cervical, thoracic, and/or lumbar spine, such as ensuring proper trajectory across the facet joint, preventing bone breach which may cause nerve or tissue damage, and properly anchoring the screw in bone to prevent screw backout.

In some cases, it may be possible to insert a fixation device, such as a facet screw or facet screw assembly, into a facet joint by itself and, due to the design of the facet screw, do nothing further to secure the facet screw within the joint. In other words, the shape, size, surface features and overall configuration of the facet screw may cause it to remain securely within the facet joint without further attachment devices required. In some cases however, and in general for overall safety of a facet joint distraction procedure, it may be advantageous to use one or more additional devices to help secure the facet screw to one or both of the adjacent vertebrae that form the joint. Such an additional device may include a screw, anchor, washer or similar securement device, and it may help to maintain the facet screw in a desired position within the joint and to prevent it from "backing out" of the joint—i.e., slipping posteriorly out of the joint. In such embodiments, a locking screw may be delivered through an opening in a facet screw or adjacent the facet screw, so that the locking screw is attached to one of the vertebrae that form the facet joint, to help secure the facet screw within the joint. Thus, although this detailed description focuses on embodiments in which the locking screw is advanced through an opening in a facet screw to secure the facet screw in a facet joint, alternative embodiments may use the locking screw system, device and method in other ways within the spine.

In one embodiment, a system for delivering a facet screw assembly to a joint between a vertebra and an adjacent vertebra may include the facet screw assembly. The facet screw assembly includes a facet screw having a proximal portion and a distal portion. The system also includes a delivery device, which may include a proximal end and a distal end and the delivery device defines a longitudinally extending lumen therethrough. In one aspect, the distal end of the delivery device may include a facet screw engagement feature. The facet screw engagement feature may be keyed to a corresponding delivery device engagement feature located at or near the proximal portion of the facet screw.

In some embodiments, the system may include a locking screw and a locking screw delivery mechanism for anchoring an implant, such as a facet screw, into a facet joint, and for distracting and maintaining the distracted position of the joint. In one embodiment, the locking screw is detachably connected to a locking screw delivery mechanism. The system may also include a guide tube for delivering the implant and to guide the locking screw to the implant. The locking screw is caused to detach from the delivery mechanism upon the locking screw becoming sufficiently secured to the implant and facet joint. This approach may ensure that the implant is securely affixed to the facet joint, for maintaining the distraction of the joint, thereby relieving symptoms associated with spinal stenosis.

In one particular aspect, the system includes a locking screw detachably connected to a delivery mechanism at a breakable junction, and a guide tube configured to receive the locking screw and delivery mechanism. The guide tube may include a bend, and as the locking screw and delivery mechanism is advanced through the guide tube along a first trajectory, the bend causes the locking screw to exit a distal end of the guide tube along a second trajectory. The delivery mechanism may include a flexible region, which flexes as it advances through the bend in the guide tube. In some embodiments, the guide tube may include multiple bends. The bend (or bends) in the guide tube are configured to direct the locking screw out of the distal end of the guide tube at a desired angle, such as an angle that will direct the locking screw through an opening in an implant and into one of two adjacent vertebrae. As the locking screw is screwed into vertebral bone, the flexible region of the delivery mechanism continues to flex, and a load is concentrated at the breakable junction. Upon the locking screw becoming sufficiently secured to the vertebral bone, the breakable junction experiences a predetermined load to cause the locking screw to detach from the delivery mechanism.

Figure 1B:
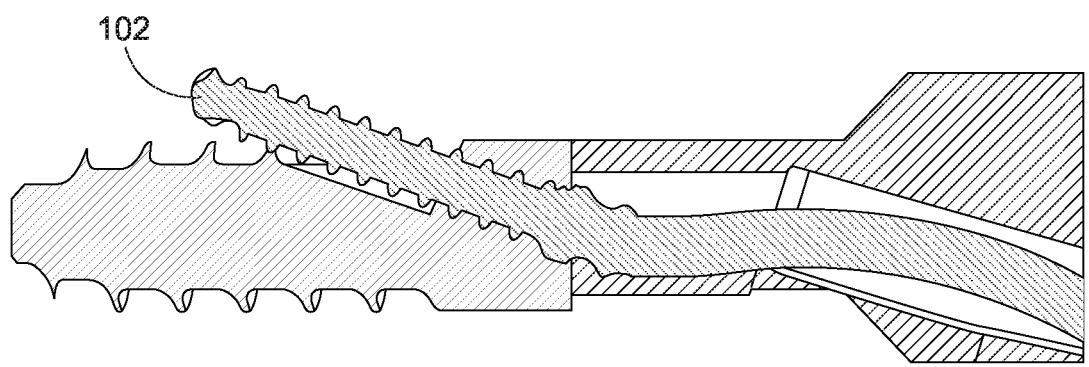
FIG. 1B is a cross-section view of a distal end of the devices of FIG. 1A, shown without the vertebra for clarity.
Figure 1C:
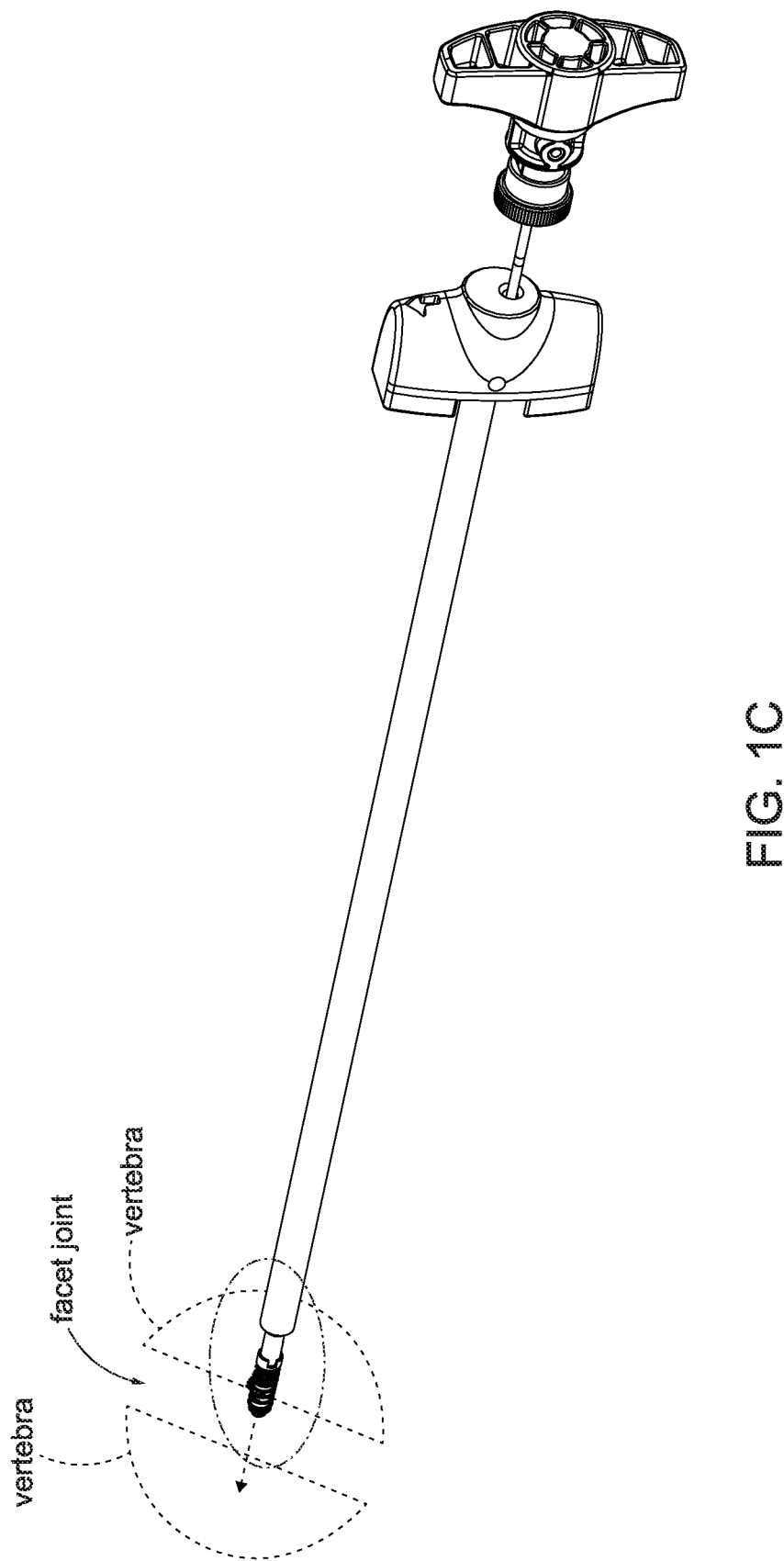
FIG. 1C is a perspective view of the system including a locking screw device and an implant delivery device of FIG. 1A, depicted for trans-facet placement, according to certain embodiments.

FIG. 1A shows a perspective view of a fixation system 100 including a locking screw device 101 including a locking screw 102 and a locking screw delivery mechanism 104, the fixation system also including a guide tube assembly 106, according to certain embodiments. FIG. 1B is an exploded view of a distal portion of the system 100. The locking screw 102 is detachably connected to the delivery mechanism 104. In some embodiments, the locking screw 102 and delivery mechanism 104 are separate components that couple together for delivery of the locking screw 102 and then separate when the locking screw 102 is secured to a vertebra, similar to the way a conventional screw and screwdriver work. In other embodiments, the locking screw 102 and delivery mechanism 104 are separate components, which are attached to one another at a breakable junction during manufacturing, and the breakable junction is configured to break upon experiencing a predetermined load. In yet other embodiments, the locking screw 102 and delivery mechanism 104 are manufactured as a one-piece, monolithically formed unit, having a breakable junction, which breaks upon experiencing a predetermined load. Therefore, although the following description focuses on the embodiment in which the locking screw 102 and the delivery mechanism 104 are a one-piece unit, other embodiments are possible and are encompassed within the scope of the disclosure. FIG. 1A depicts a portion of the fixation system for an intra-facet placement. FIG. 1C depicts a portion of the fixation system for a trans-facet placement.

Figure 2A:
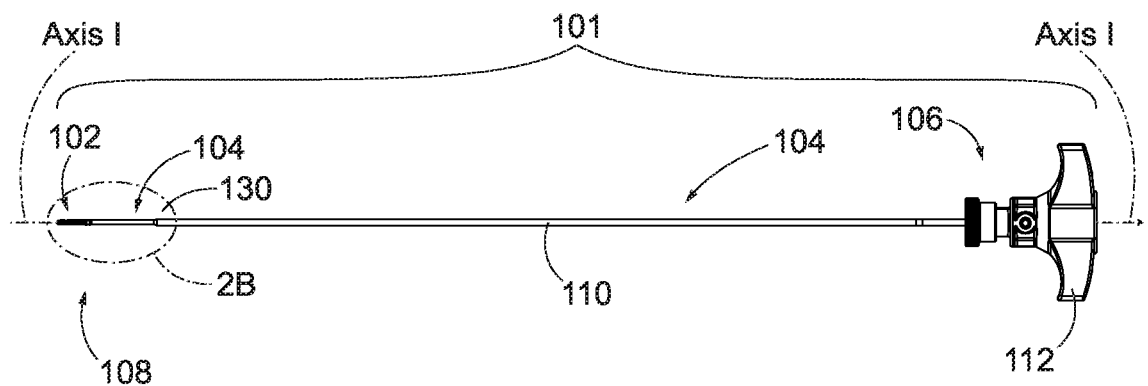
FIG. 2A is a detailed side view of the locking screw device of FIG. 1A.
Figure 2B:
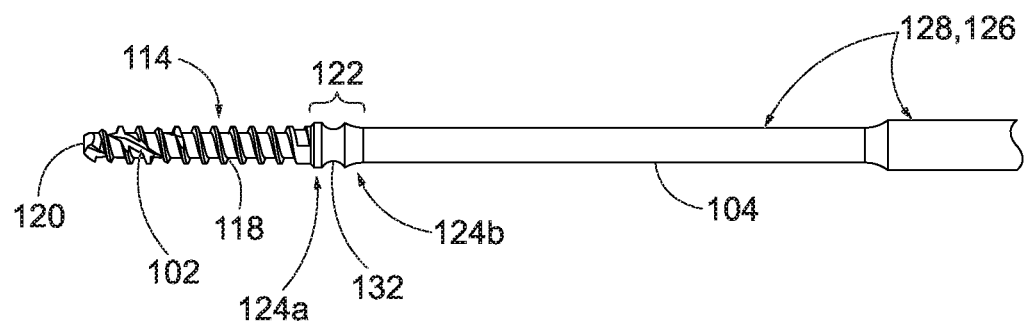
FIG. 2B is a detailed side view of a distal end of the locking screw device of FIG. 2A.

As shown in FIGS. 2A-2B, the locking screw device 101 may extend longitudinally from a proximal end 106 to a distal end 108 along Axis-I. In some embodiments, the locking screw device 101 may include a holding portion or a handle 112. The locking screw delivery mechanism 104 may include an elongate shaft 110, extending from a proximal end, where it attaches to or includes the handle 112, to a distal end where it is joined to the locking screw 102. The elongate shaft 110 of the delivery mechanism 104 may include a region 128 that tapers (at 130) to a flexible region 126, which may facilitate the locking screw 102 in detaching from the delivery mechanism 104, the details of which will be described in further detail below.

FIG. 2B, and others, shows a detailed side view of a distal portion of the locking screw device 101 of FIG. 1, according to certain embodiments. As shown, the locking screw 102 may comprise a tip 120, a helical ridge 114, and a groove 118. The locking screw 102 may screw into a facet joint implant (such as a facet screw) and a vertebra, to secure the implant in the joint and thus prevent the implant from backing out of the joint. The delivery mechanism 104 may be used to insert and secure the locking screw 102 to the vertebral bone. The locking screw device 101 may be configured such that, upon securing the locking screw 102 into the implant and the vertebra, the locking screw 102 may detach from the delivery mechanism 104. As such, the locking screw 102 may be inserted and secured into the vertebra and the facet joint implant.

Referring to FIGS. 2A and 2B, the locking screw 102 may be detachably connected to the delivery mechanism 104 at a breakable junction 122. The breakable junction may include a distal portion 124a and a proximal portion 124b that taper to form an arcuate shaped groove 132. The groove 132 may break upon experiencing a predetermined amount of force, the details of which will be described in detail below.

Figure 3:
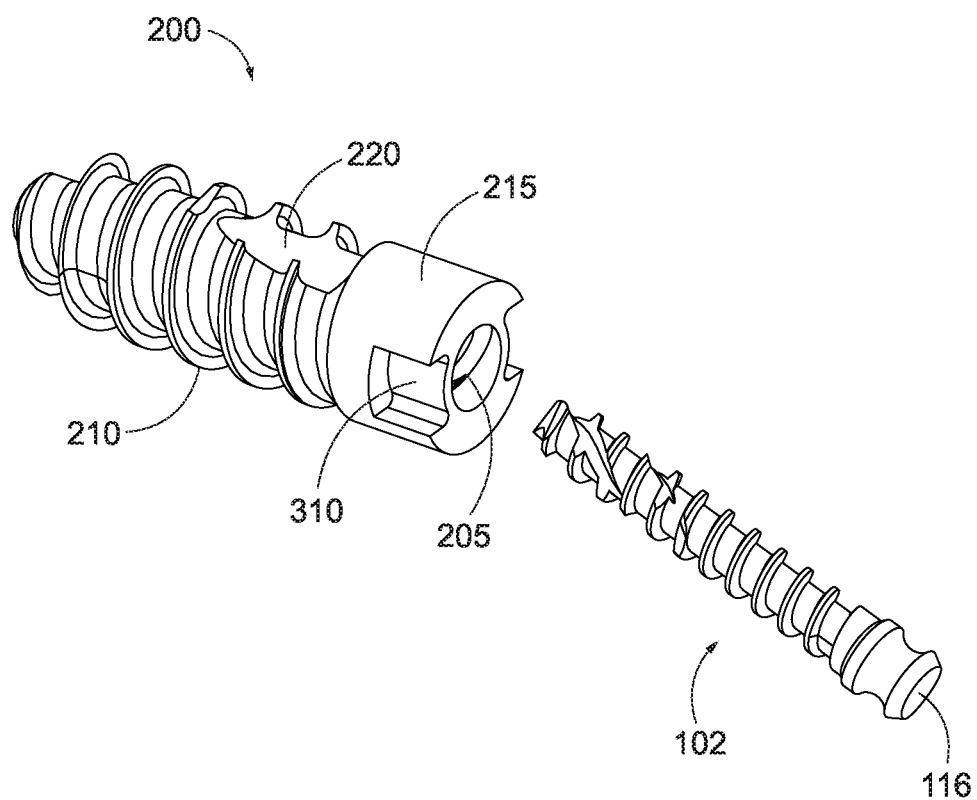
FIG. 3 is an exploded view of an implant and a locking screw according to some embodiments of FIG. 1A.
Figure 4:
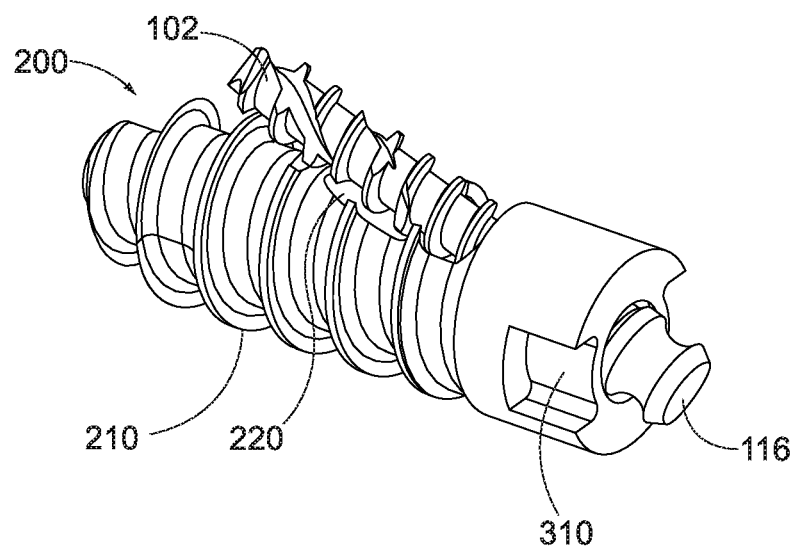
FIG. 4 is a perspective view and FIG. 5 is a cross-section view which depicts the implant and locking screw of FIG. 3 shown in a coupled state.
Figure 5:
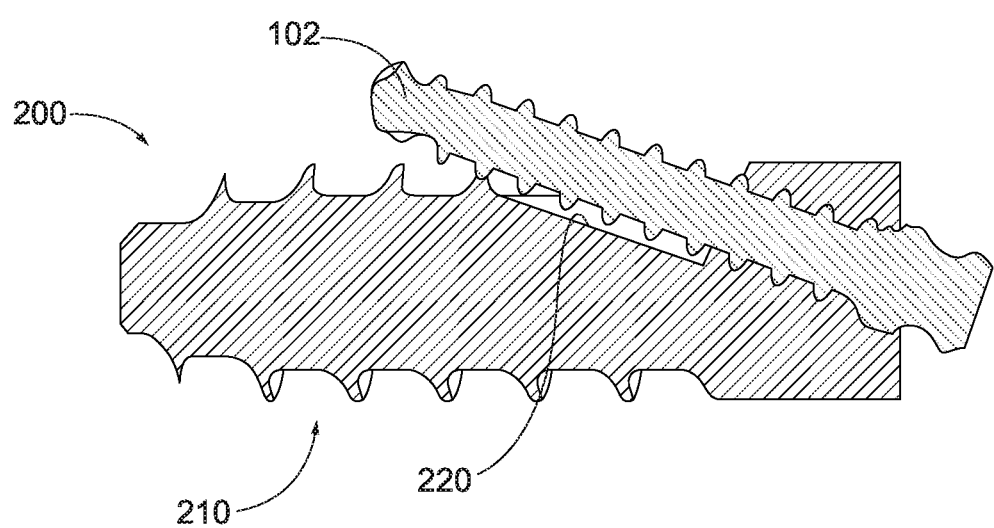

As can be understood from FIG. 1A and indicated in FIGS. 3, 4 and 5, upon the breakable junction 122 breaking, the locking screw 102 may detach from the delivery mechanism 104, so that a screw head 116 is exposed.

FIGS. 3, 4 and 5 show an exploded, perspective and cross-section view of the locking screw 102 inserted into a facet joint implant, such as facet screw 200. The depicted facet joint implant 200 is a facet screw, and in alternative embodiments the locking screw device 101 may be used to secure any suitable implant within a vertebral joint. In the depicted embodiment, the facet screw 200 may include a cylindrical body with external threads, a channel and, optionally, a washer 215. The cylindrical body 210 may include an opening 205 leading to the channel 220. The channel 220 may be located within a top wall so that the screw 102 may screw into the upper vertebra of a patient's facet joint to secure the implant 200 thereto. The channel 220 may include complementary threads configured to engage with the helical ridge 114 of the locking screw 102. Thus, when securing the locking screw 102 to the implant 200, a user may rotate the locking screw device 101 to cause the helical ridge 114 to mate with the complementary threads within the channel 220 so that the screw 102 progresses through the cavity 220. FIGS. 5A-5D show the screw 102 progressing through the opening 210 and out through the channel. When the locking screw 102 is sufficiently screwed into implant or facet screw 200 and vertebra to secure the implant or facet screw 200 to the vertebra, the screw 102 may detach from the delivery mechanism 104. FIGS. 4-5 show the locking screw 102 secured to the implant or facet screw 200 after the locking screw 102 has detached from the delivery mechanism 104.

Figure 6A:
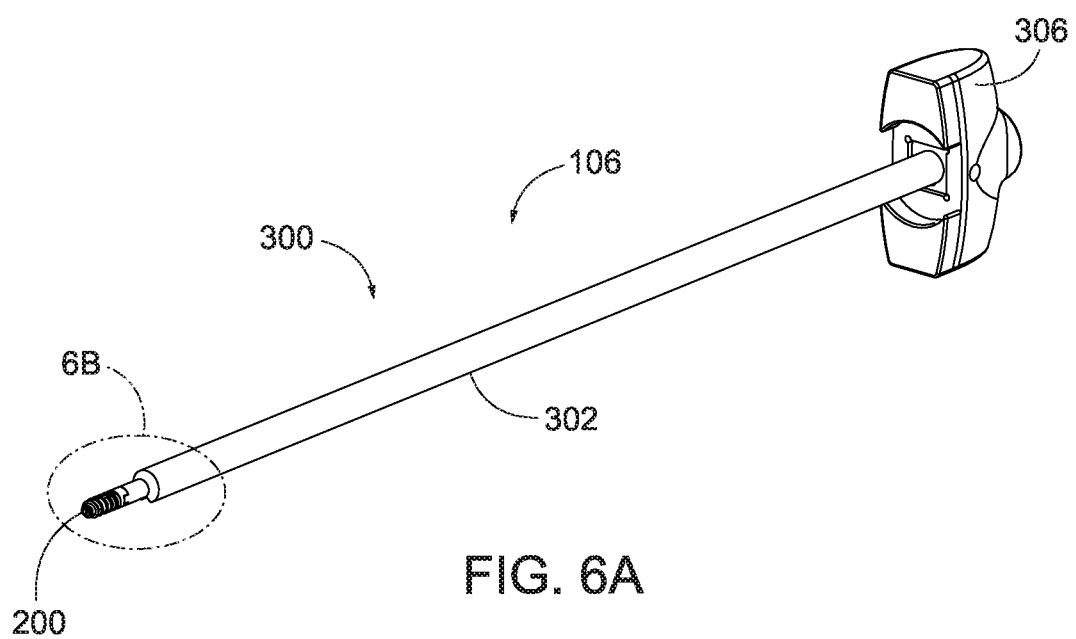
FIGS. 6A-6C depict perspective, partial and cross section views of the implant delivery device of FIG. 1A.
Figure 6B:
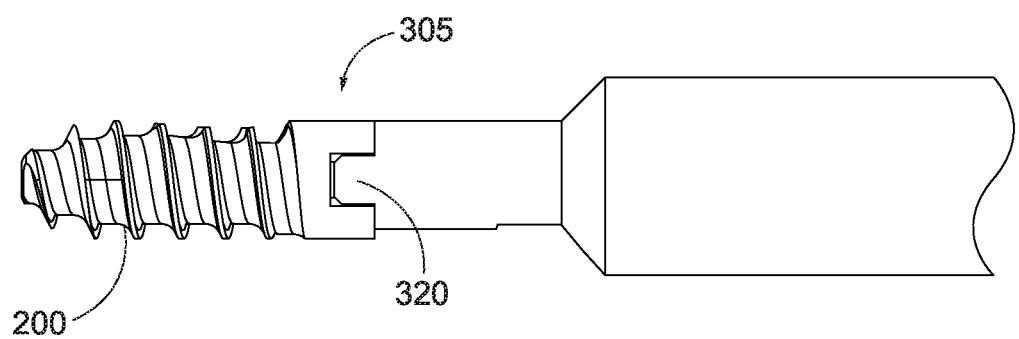

Now turning to FIGS. 6A-6B, the implant 200, such as facet screw 200, is delivered to the facet joint via an implant (or facet screw) delivery device 300, through which the locking screw and locking screw delivery mechanism is deployed. More particularly, the implant (or facet screw) delivery device 300 may be used with the locking screw device 101 and is configured to cause the locking screw 102 to detach from the delivery mechanism 104 upon the locking screw 102 becoming sufficiently secured to the implant or facet screw 200 and vertebra.

Figure 6C:
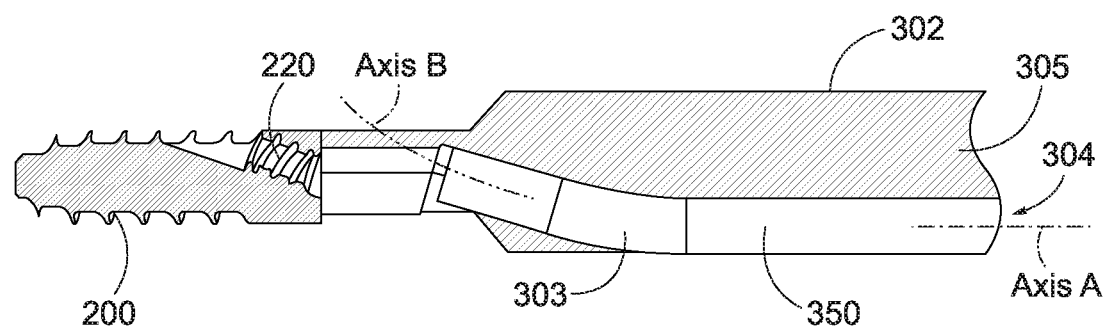

As shown in FIG. 6C, the implant delivery device 300 may include a shaft 302 with a lumen 304 extending therethrough. In some embodiments, the delivery device 300 may include a handle 306 for engaging with other components of a deployment system. The delivery device 300 may include an inner guide tube 350 extending within the lumen 304.

The inner guide tube 350 is configured to receive the locking screw device 101 and guide the locking screw 102 to the implant, such as facet screw 200. The distal end 305 of the implant delivery device 300 is engaged with the implant or facet screw 200. In one embodiment, the facet screw includes recesses 310 defined in the washer. The recesses are complementary to protrusions 320 at the distal portion of the implant delivery device 300.

Thus, as the locking screw device 101 is advanced through the inner guide tube 350, the locking screw 102 may exit the tube and engage the implant. A user may then continue to advance the locking screw 102 through the implant 200 by rotating the locking screw device 101, and thus cause the screw 102 to screw into the implant 200 and into the patient's vertebra. The inner guide tube 350 may include a proximal portion that extends longitudinally along Axis-A and a distal portion that extends along Axis-B, wherein the proximal portion and distal portion are joined at a bend 303. Axis-B may extend upward from Axis-A at an angle. As shown, the channel 220 of the facet joint implant 200 may extend at an angle. The angle of the bend, together with the angle of the channel, may be configured to cause the locking screw 102 to detach from the delivery mechanism 104 upon securing the implant 200 to a vertebra of a patient's facet joint. As the locking screw 102 is advanced through the inner guide tube 350, the bend 303 in the inner guide tube 350 may be configured to cause the flexible region of the delivery mechanism 104 to flex. When the locking screw 102 is screwed into the implant 200 and vertebra a predetermined amount (e.g., to fully secure the implant 200 into the vertebra), the locking screw 102 may become stabilized so that the flexing or bending force is concentrated at the breakable junction 122. As such, when a user further secures the screw 102, the force on the breakable junction reaches a threshold and causes the junction 122 to break, thus detaching the locking screw 102 from the delivery mechanism 104. Thus, the implant delivery device 300 may facilitate a user in securing the locking screw 102 into an implant 200 and vertebra a sufficient amount.

Figure 7A:
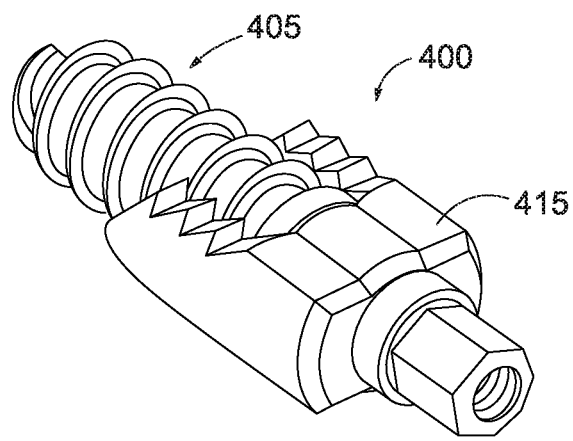
FIGS. 7A-7C depict perspective and exploded views of an implant that may be used with embodiments according to the present disclosure.
Figure 7B:
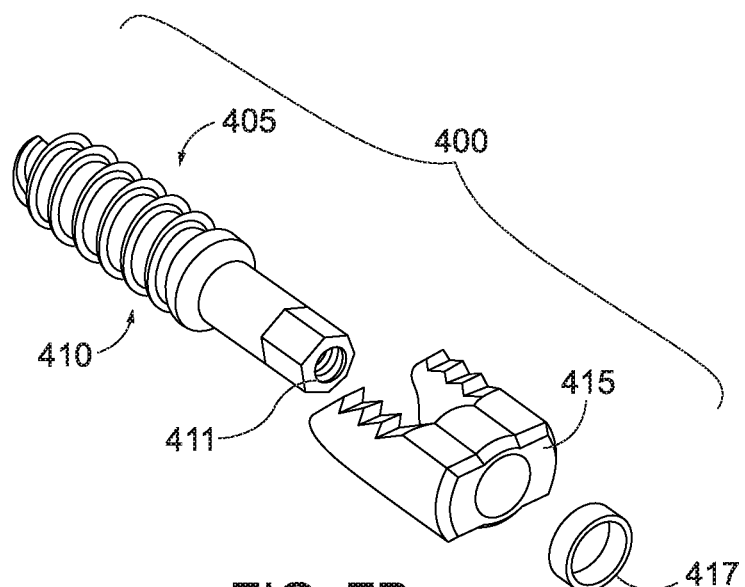
Figure 7C:
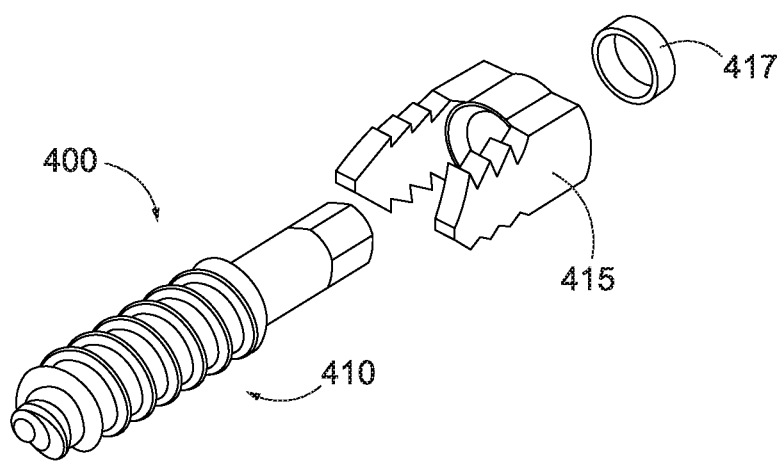

As described elsewhere herein, the implant 200 may be a facet screw. As shown in FIGS. 7A-7C, the facet screw assembly 400 may have some similar features to facet screw 200. For example, similar to facet screw 200, the assembly 400 may include a facet screw 405 that includes a cylindrical body 410 having an elongated shaft and external threads. In contrast to facet screw 200, the assembly 400 also includes washer 415, a lock ring 417, and optionally, a channel 420 for a screw. The washer 415 includes a base having an opening for engagement with the proximal end of the elongated shaft of the facet screw. The washer also includes one or more protrusions extending longitudinally from the base. In some embodiments, the protrusions have teeth extending therefrom. The locking ring is generally ring shaped. In one embodiment, the locking ring secures the washer to the proximal end of the facet screw.

Figure 8A:
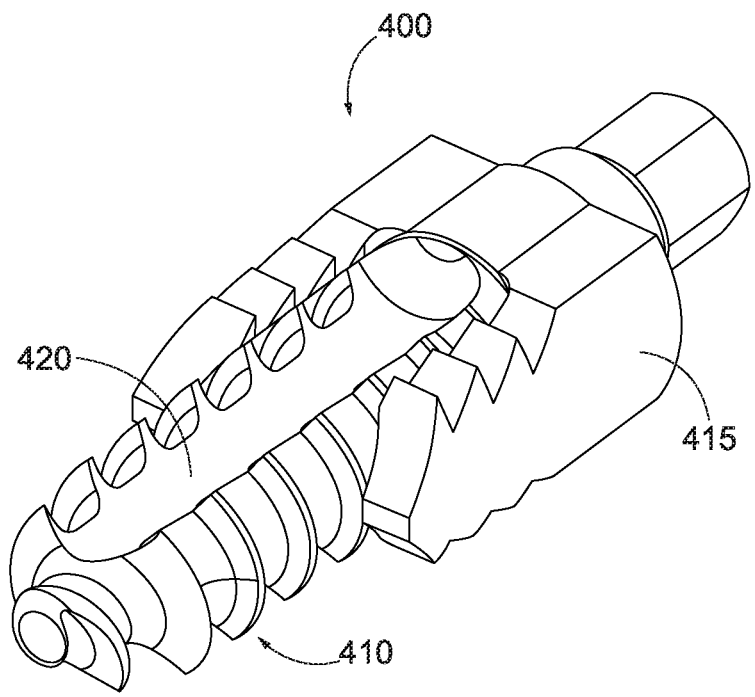
FIGS. 8A-8B depict perspective and rear views of an implant that may be used with embodiments according to the present disclosure.
Figure 8B:
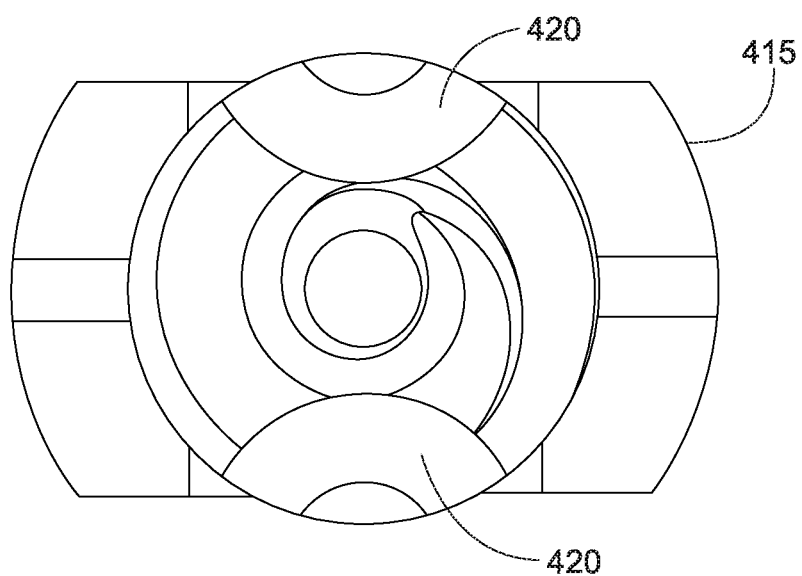

In another embodiment, as shown in FIGS. 8A-8B, the cylindrical body 210 or 410 may include channel features 420 along its axis. The channels 420 may be located diametrically opposed to each other so that it modifies the cross-sectional shape of the cylindrical body 210 or 410, as shown in FIG. 8B, such that the implant, once placed within the vertebrae, resists rotation or other unwanted migration.

Figure 9A:
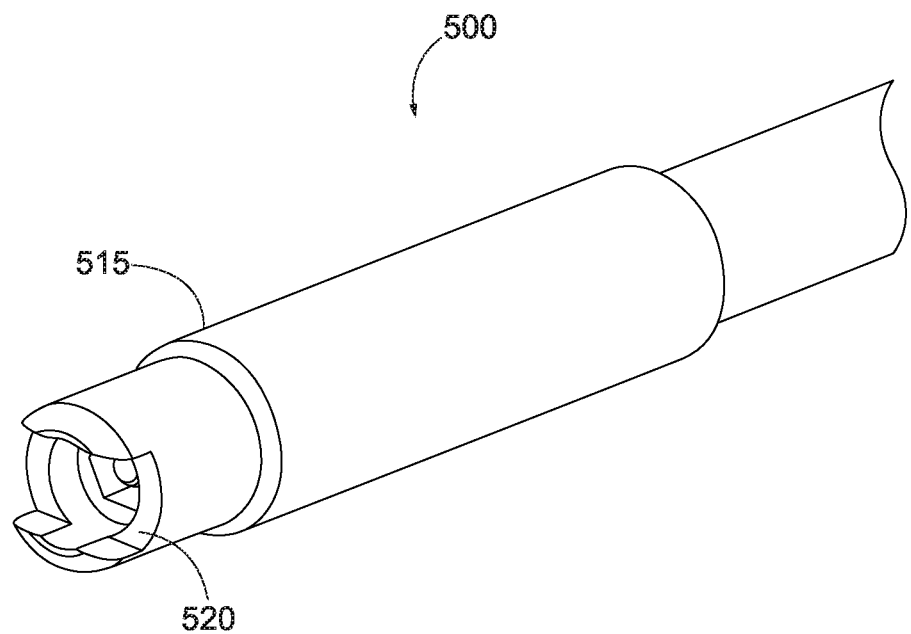
FIGS. 9A-9B are partial perspective and cross-section views of a delivery device for use with the implants of FIGS. 7A-8B, and others, according to certain embodiments.
Figure 9B:
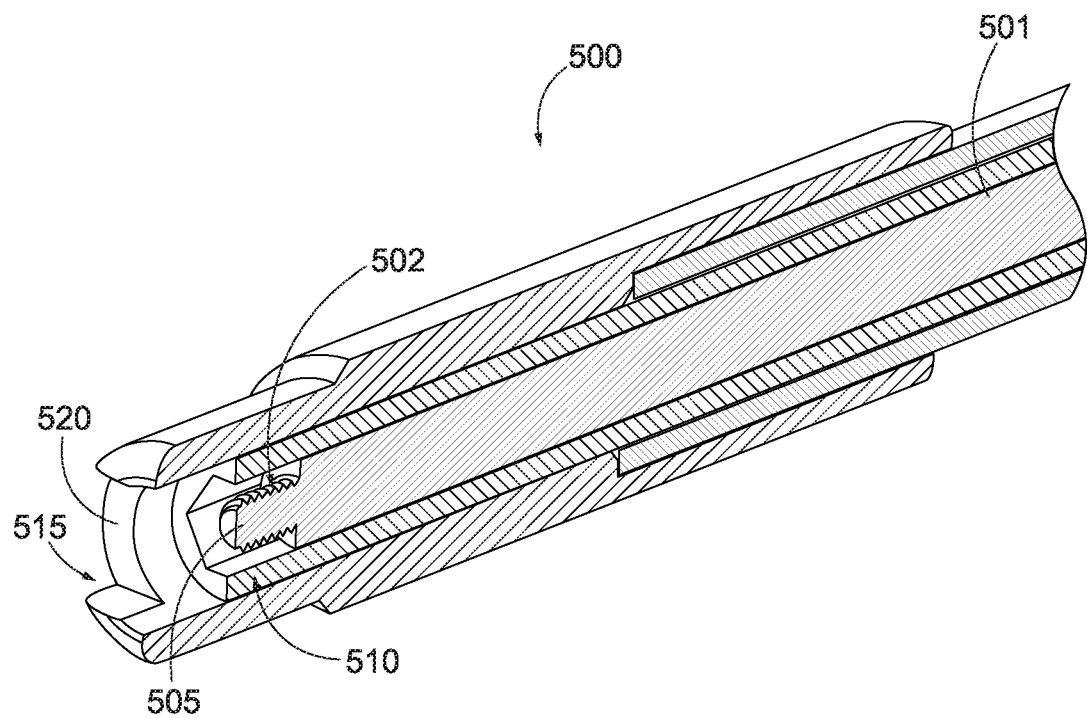

In some embodiments, the facet screw assembly 400 may be part of a system. The system may further include a delivery device 500, as shown in FIGS. 9A-9B. The delivery device 500 includes an actuator shaft 501 having a distal end 505 with threads 502 configured to receive at least a portion of the facet screw assembly. The device 500 may also include a central sleeve 510 defining a first longitudinally extending lumen. The central sleeve is configured to receive the actuator shaft. The device 500 also includes an outer sleeve 515 having one or more notches 520 at a distal end. The outer sleeve defines a second longitudinally extending lumen and is configured to receive the central sleeve. In some embodiments, the one or more notches of the outer sleeve engage at least a second portion of the facet screw assembly to aid in delivery of the facet screw assembly.

Figure 10A:
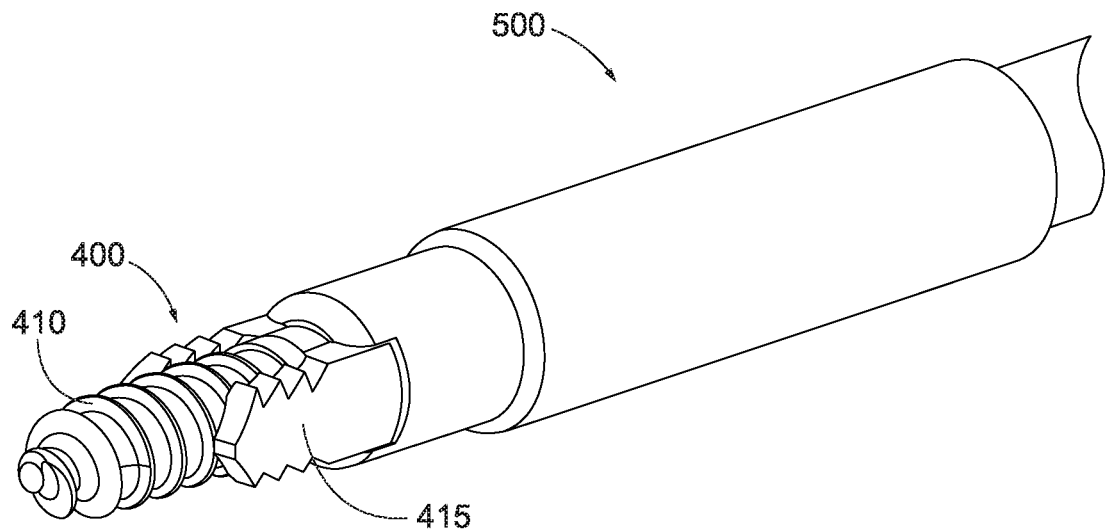
FIGS. 10A-10B are partial perspective and cross-section views of the delivery device of FIGS. 9A-9B, shown with an implant, according to certain embodiments.
Figure 10B:
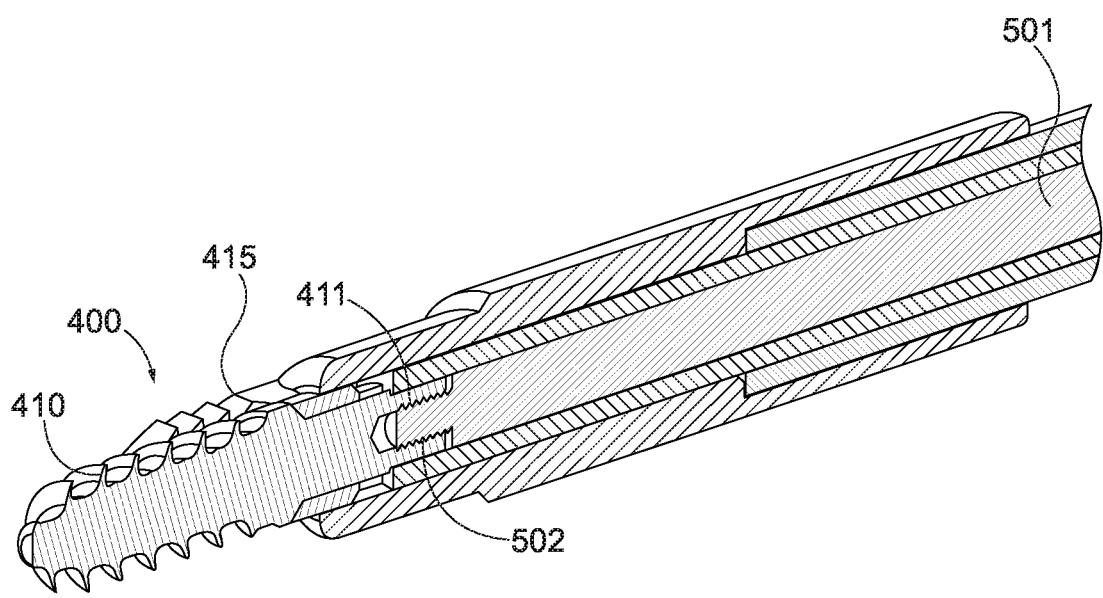
Figure 11A:
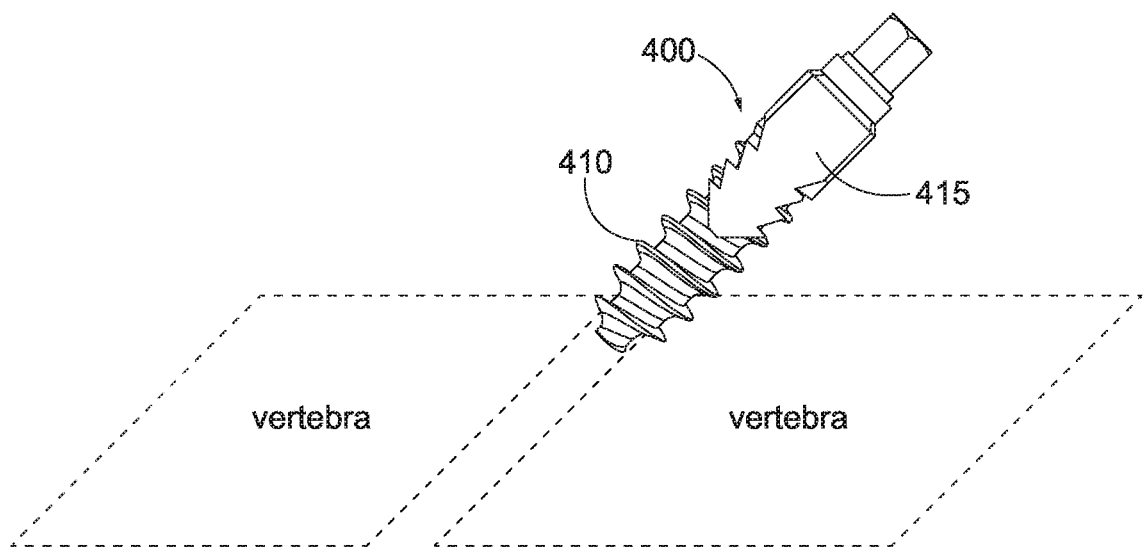
FIGS. 11A-11B are perspective, partial views of the implant and delivery device of FIGS. 9-10 when inserted in a facet joint for intra-facet placement, according to certain embodiments.
Figure 11B:
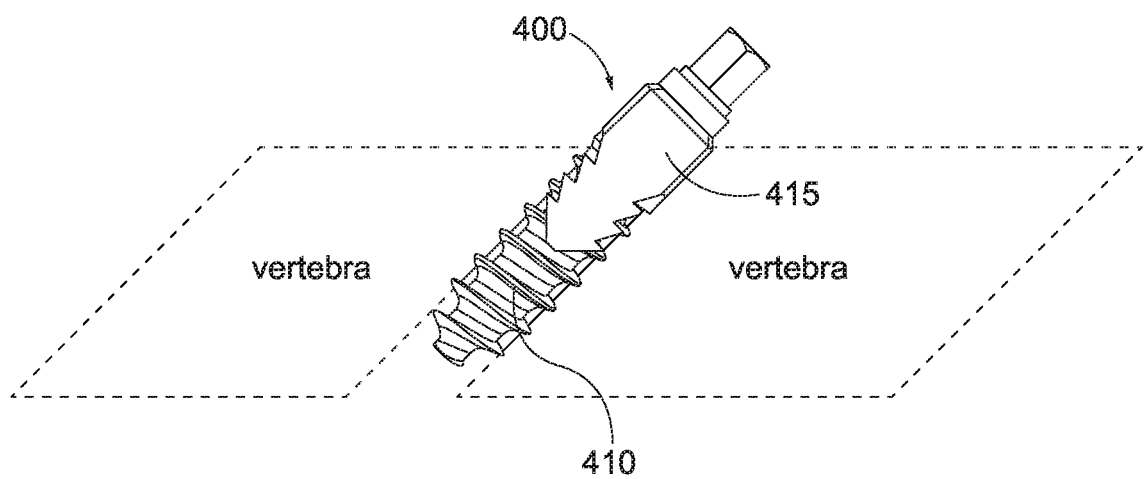
Figure 11C:
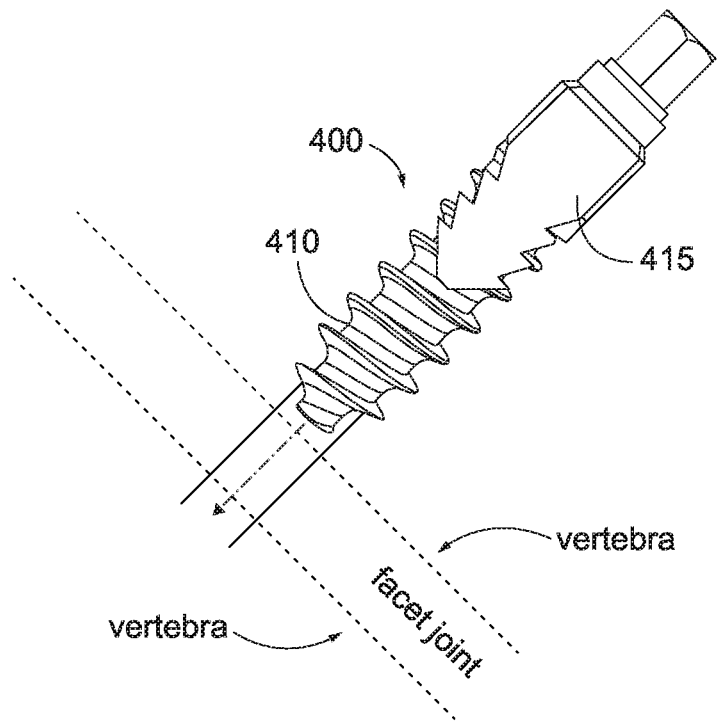
FIGS. 11C-11D are perspective, partial views of the implant and delivery device of FIGS. 9-10 when inserted in a facet joint for trans-facet placement, according to certain embodiments.
Figure 11D:
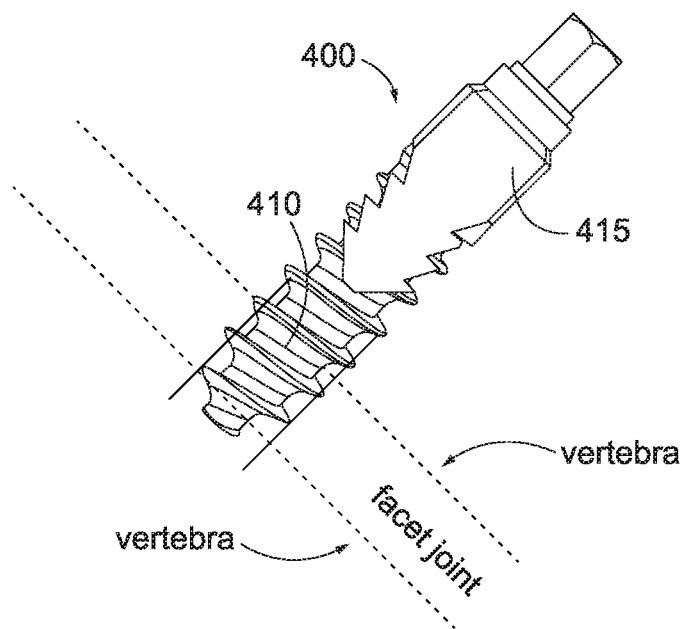
Figure 12A:
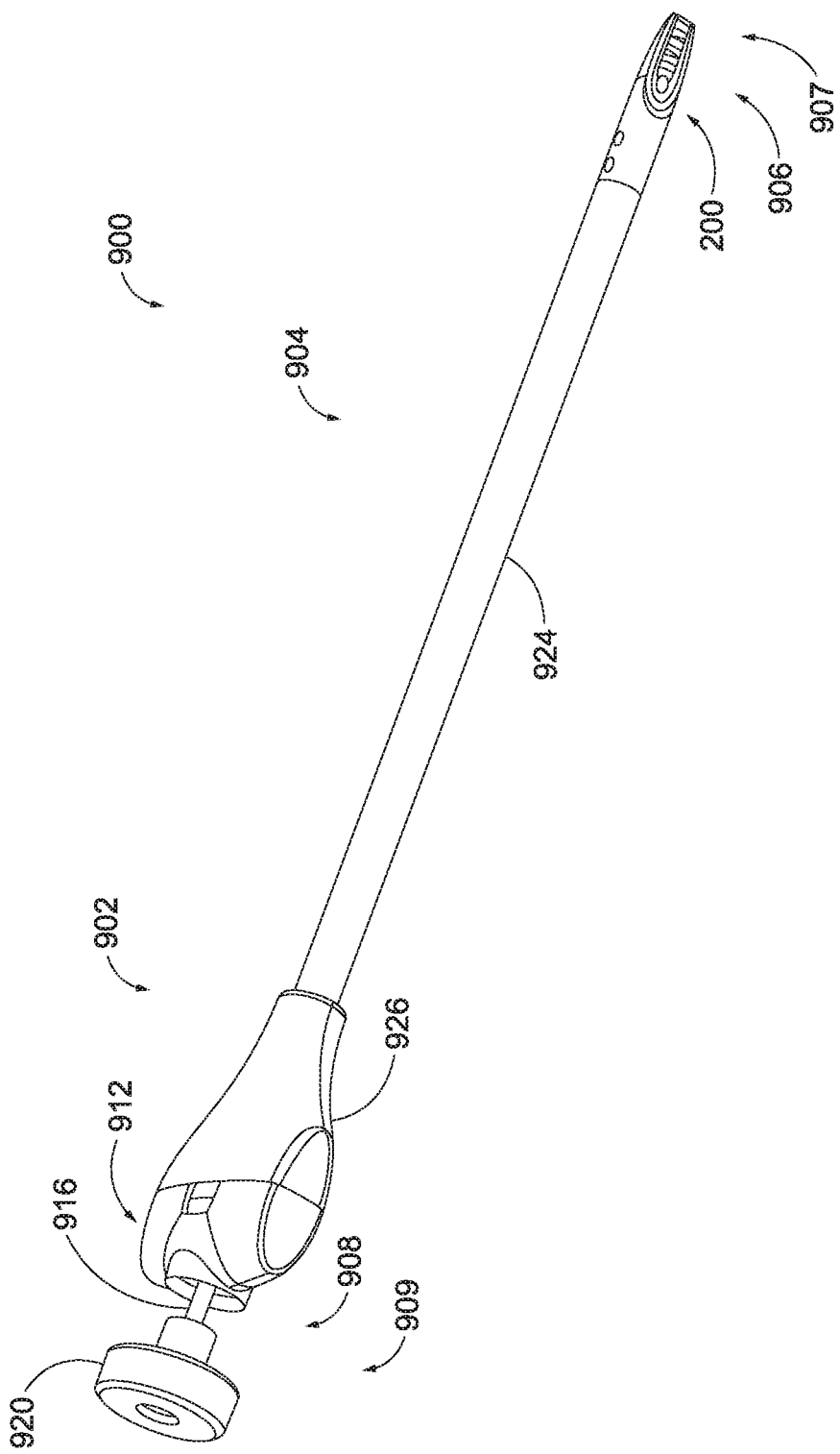
Figure 12B:
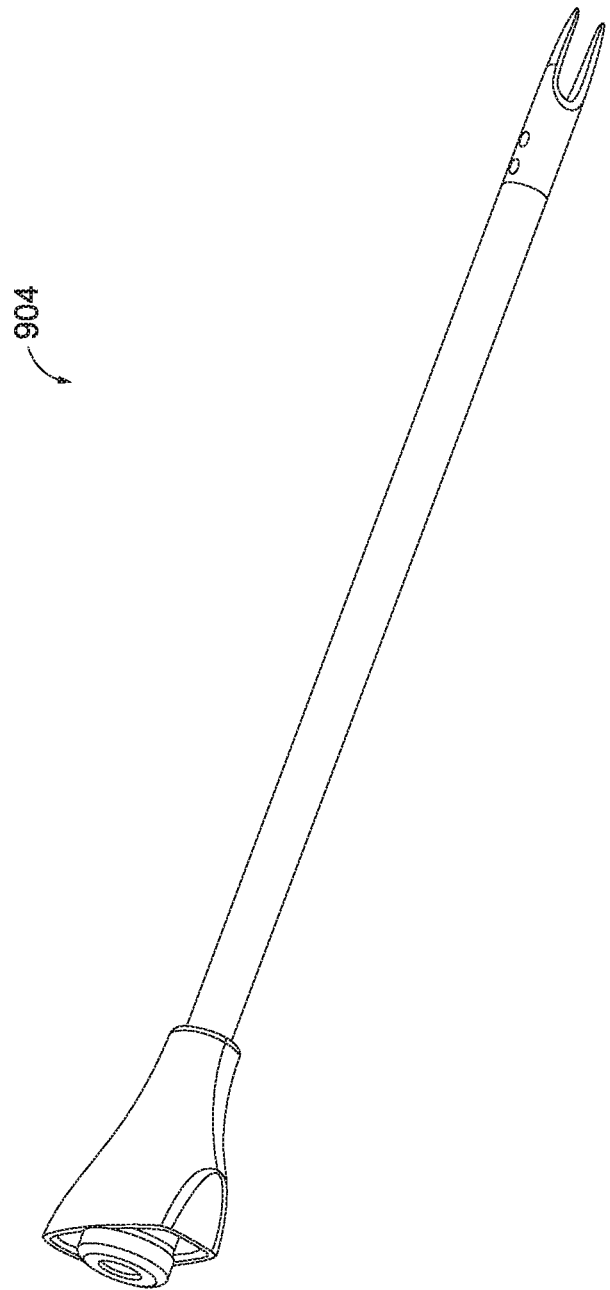
Figure 12D:
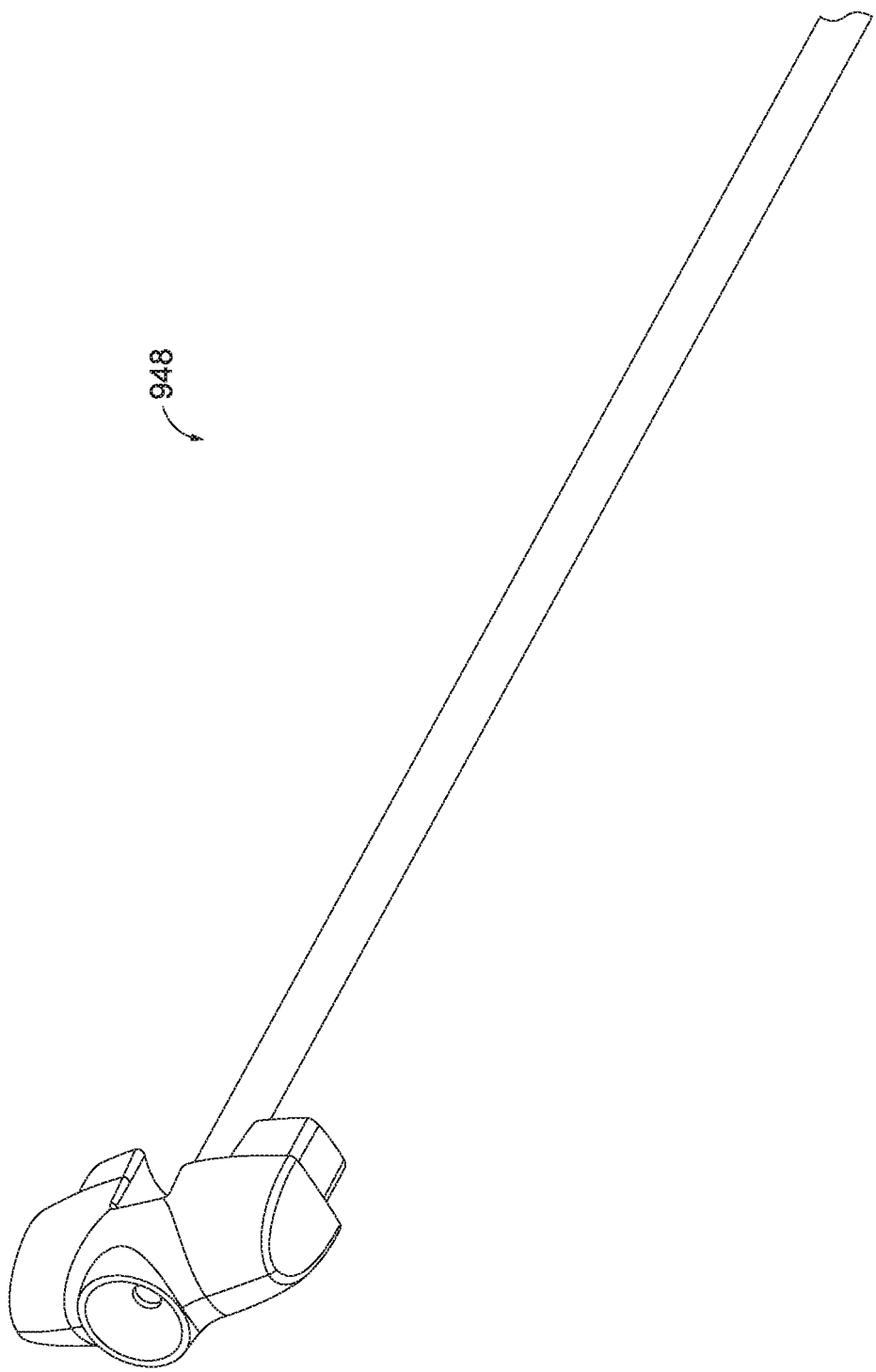
Figure 12E:
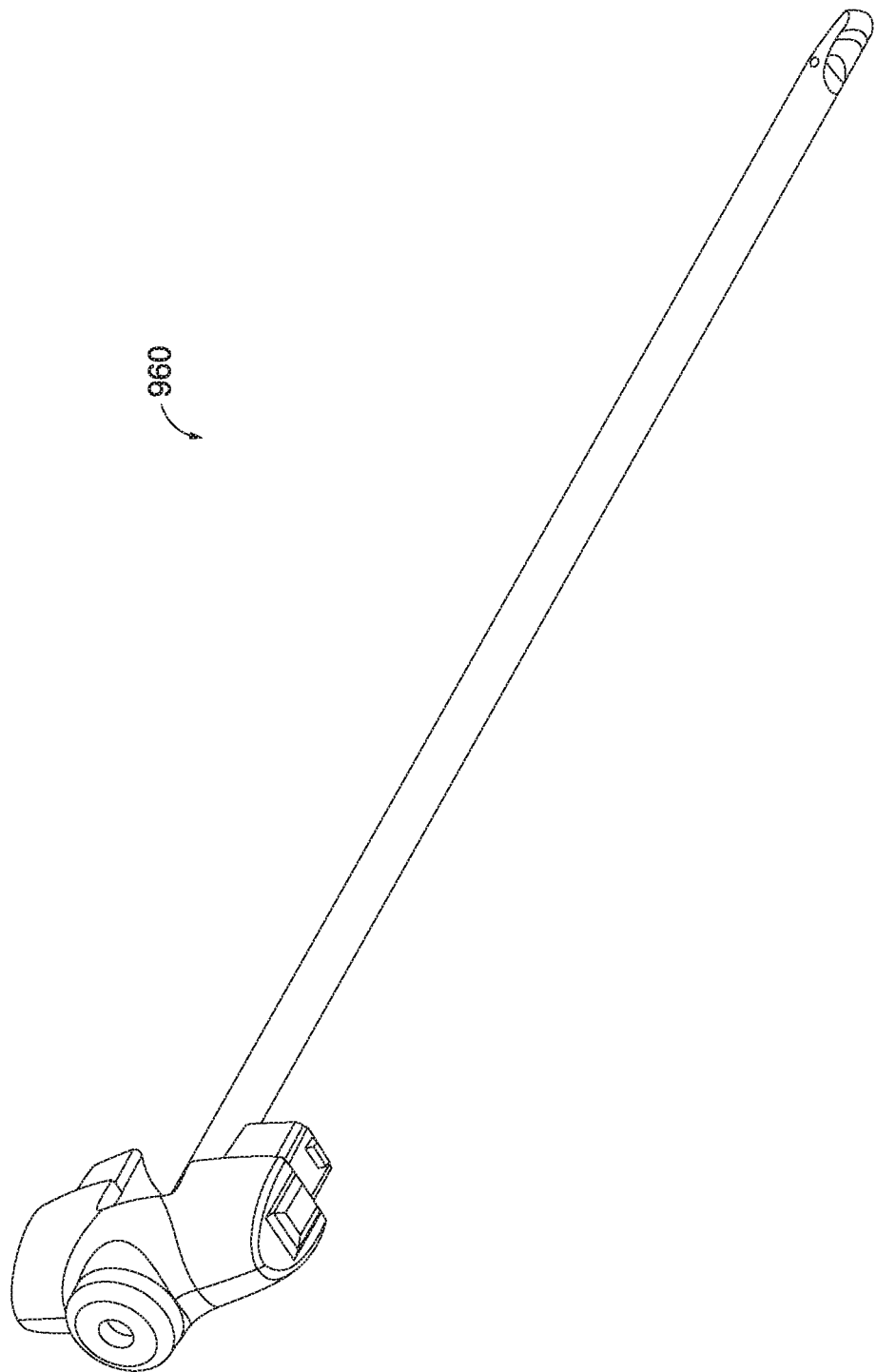

In some embodiments, the elongated shaft of the facet screw includes internal threads 411. The internal threads 411 engage with the threads 502 of the distal end 505 of the actuator shaft 501 of the delivery device, as shown in FIGS. 10A-10B. The washer 415 engages with the notches 520. The actuator shaft engages the facet screw assembly to advance the facet screw assembly to the facet joint. As indicated in FIGS. 11A-11B, the system is inserted into the narrowed facet joint (FIG. 11A) to expand the facet joint (FIG. 11B). The threads of the facet screw and the teeth of the washer engage with the vertebrae of the facet joint to secure in the joint and prevent backout. Alternatively, the facet screw assembly may be inserted in a trans-facet direction (see FIGS. 11C-11D) to fixate the facet joint without joint distraction.

Figure 13A:
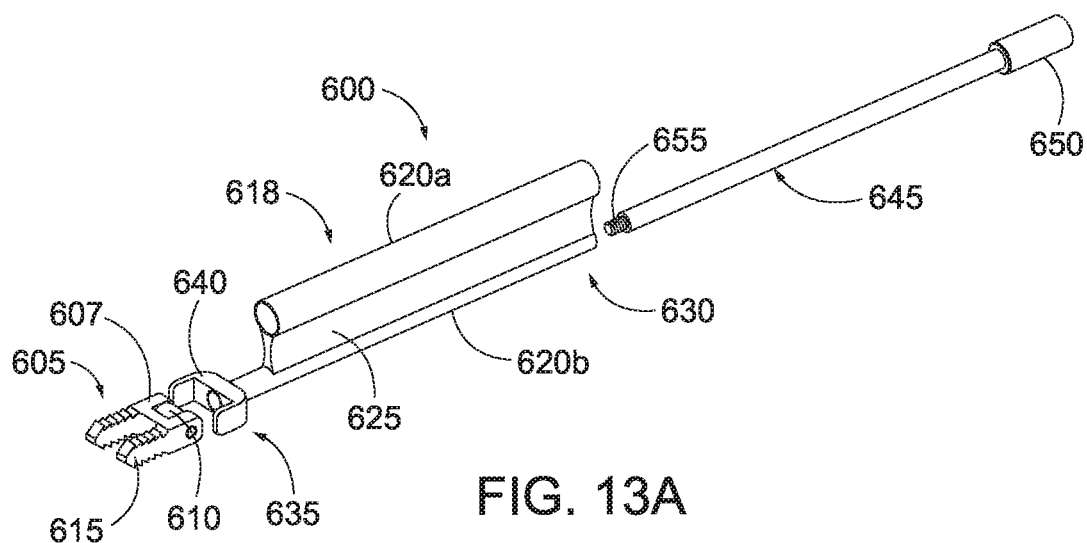
FIGS. 13A-13C depict various views of a delivery system and facet assembly, according to certain embodiments.
Figure 13B:
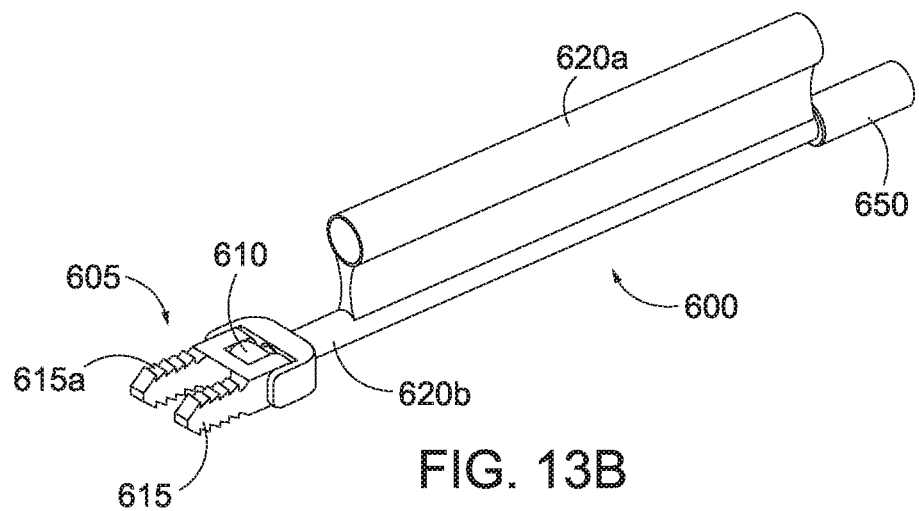

In some embodiments, the facet screw assembly and the delivery system associated with it are useful for a transfacet approach. In such embodiments, the facet screw assembly also comprises a facet screw and a washer (also referred to in these embodiments as a spacer), but the delivery system is different from other embodiments. Turning now to FIGS. 13A-13B, which illustrate portions of a delivery system and facet screw assembly, the delivery system 600 includes a delivery device 618 having one or more guide lumens 620. The delivery device may be an articulating delivery device. In embodiments with more than one guide lumen, the guide lumens 620 may be generally parallel or coplanar. As indicated in FIG. 13A, delivery device 618 comprises a first lumen 620a configured to receive a facet screw and a second lumen 620b configured to receive a rod associated with a washer or spacer. The first lumen is coupled to the second lumen by a connecting member 625 and extends less than the full length of the second lumen. In some embodiments, the length of the first lumen may be the same or similar to the length of the second lumen. The second lumen 620b extends longitudinally between a proximal portion 630 and distal portion 635. The distal portion 635 includes a spacer receiving member 640 having a base 645 and two arms or prongs 650 extending therefrom and configured to receive at least a portion of the spacer.

In some aspects, the delivery system 600 further comprises a rod 645 having a proximal portion with a knob 650 and a distal portion 655 for engagement with the spacer. The distal portion 655 may include threads.

Figure 14A:
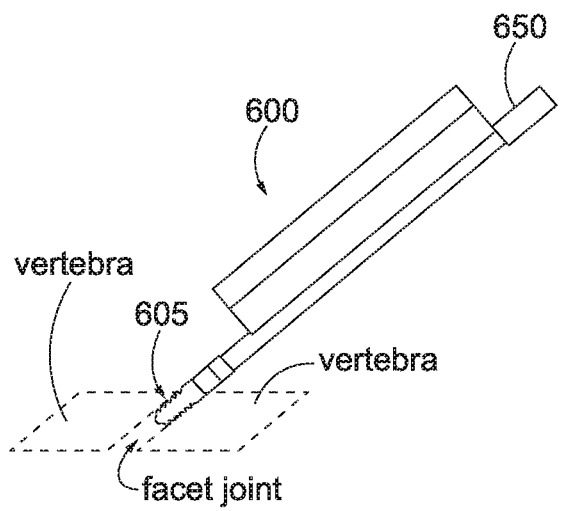
FIGS. 14A-14F depict the system and assembly of FIGS. 13A-13C in use.
Figure 14B:
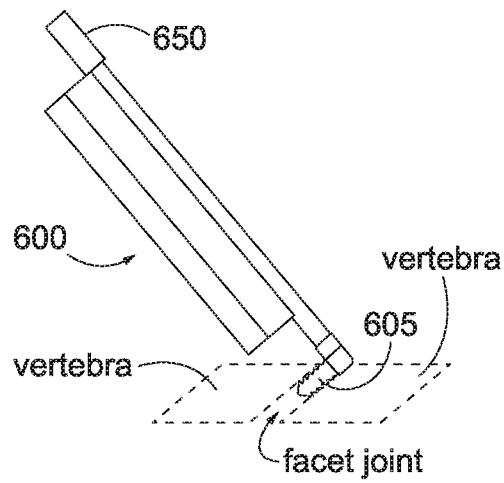

As depicted in FIGS. 13A-13B, the delivery system 600 is used with a component of the facet screw assembly, the washer or spacer 605 includes a base 607 having a rotatable member 610, such as a pin. As can be seen in FIG. 14F, the rotatable member 610 includes a rod opening 612 configured to receive the rod 640. The spacer 605 also includes one or more arms or protrusions 615 extending longitudinally from the base. In some embodiments, the protrusions have teeth 615a extending therefrom. In use, and as shown in later figures, the spacer 605, and more specifically the arms 615, help to anchor the facet screw of the facet screw assembly in the facet joint.

Figure 13C:
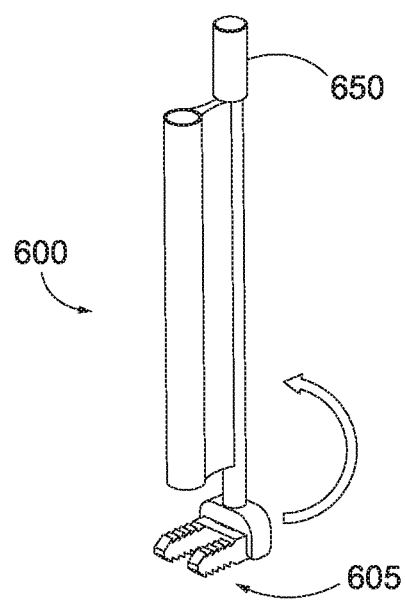
Figure 14C:
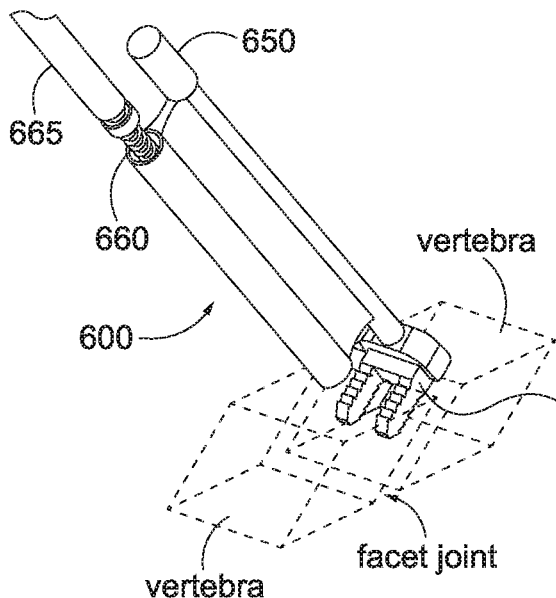

FIG. 13C illustrates how the delivery system 600 transitions from delivering the spacer 605 to delivering the facet screw (not shown here, but see FIG. 14C, et seq.). In use, and as shown in FIG. 14A and others, the second (or rod receiving lumen) 620b of the delivery device 618 and the spacer 605 are initially substantially planar for insertion into a facet joint. Once in position, the knob 650 is rotated thereby rotating the rod and engaging the rotation member 610 of the spacer 605 and unlocking or loosening the spacer. In doing so, the delivery system 600 may rotate approximately 90 degrees at which point the knob and rod are rotated again to engage the rotation member and tighten and lock the system 600 into position for receiving a facet screw. In this position, the rotated device acts as a trajectory guide for the facet screw and allows the screw to be placed across the facet joint in a transfacet approach.

Figure 14D:
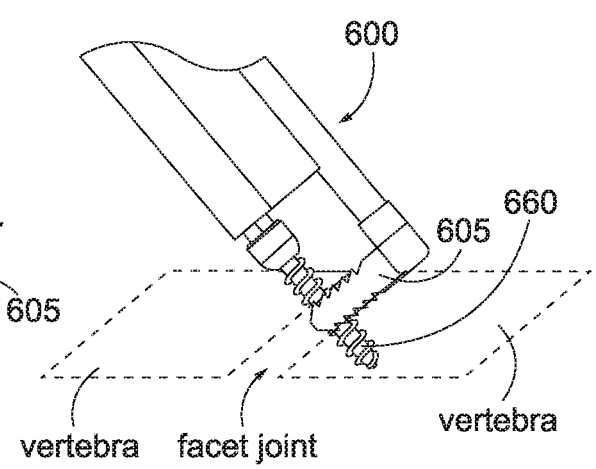
Figure 14E:
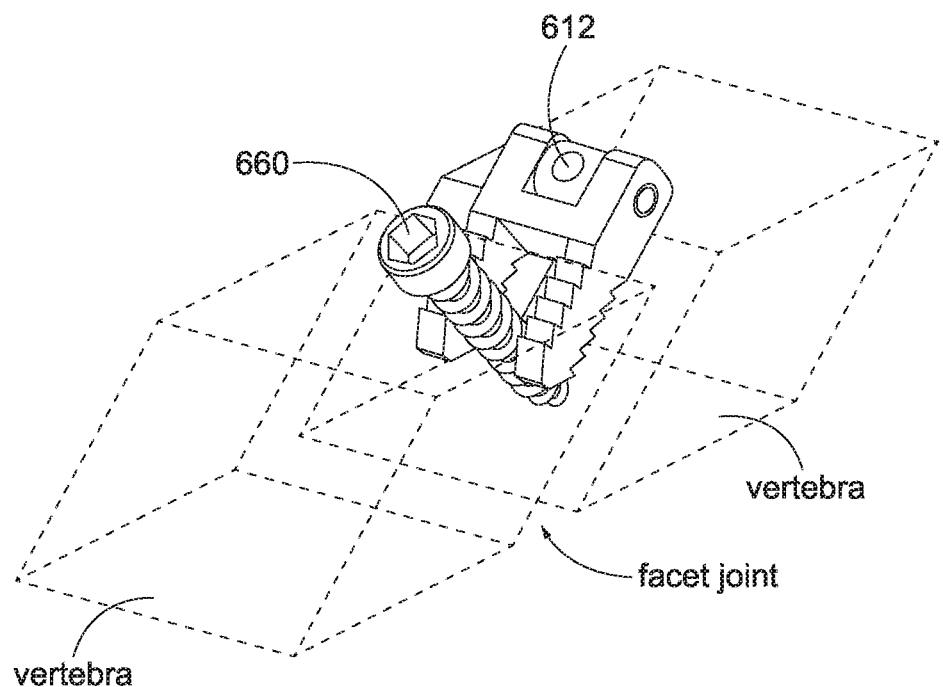
Figure 14F:
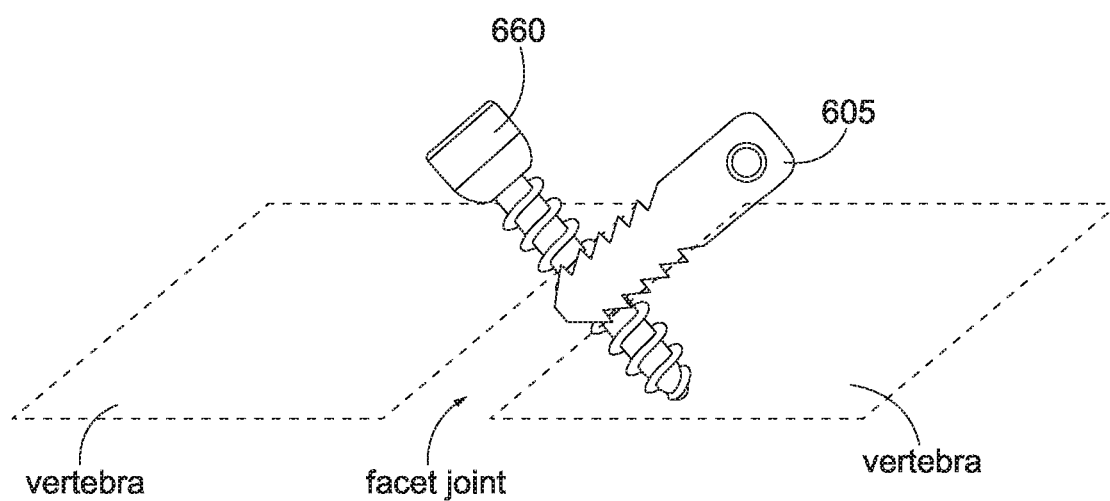

FIGS. 14A-14F illustrate a method of using the delivery system 600 with both components of the facet screw assembly—the washer or spacer 605 and the facet screw 660. In FIG. 14A, the method begins by inserting the spacer 605 into the facet joint with the delivery system 600 via a posterior approach. As shown in FIG. 14B, the delivery system 600 is then rotated 90 degrees as described with reference to FIG. 13C to put the spacer into the proper position to receive the facet screw. The facet screw 660, coupled to driver 665, is then inserted into the screw receiving lumen of the delivery device 618 (FIG. 14C) and across the facet joint (FIG. 14D). A pilot hole may be pre-drilled before the facet screw is inserted in the device 618. Once the facet screw is anchored in the facet joint, the driver 665 is detached from the facet screw and withdrawn. Then, knob 650 is rotated to disengage device 618 from spacer 605 (FIGS. 14E-14F). With the spacer deployed in the intra-facet joint and the facet screw deployed across the facet joint, the joint space is distracted while maintaining fixation with the spacer and the screw.

Turning now to FIGS. 15A-15F, in another embodiment of a system that may be used in a transfacet approach, the facet assembly 720 also comprises a facet screw and a washer (also referred to in these embodiments as a spacer), but the delivery system is different from other embodiments. As shown in FIGS. 15A-15D, the washer or spacer 700 comprises a first portion 705 having an intrafacet engagement portion 707 and a second portion 710 having a lateral mass engagement portion 712. Each of the first portion 705 and the second portion 710 includes a facet screw opening 715 configured to receive a facet screw 725. As indicated in FIGS. 15E-15F, the facet assembly also includes the facet screw 725, the screw comprising a head 730 and an elongated shaft 735 extending from the head. The shaft may include threads for additional fixation when placed across the facet joint. In use, when the screw is inserted in the spacer, the shaft passes through both facet screw openings 715 in each of the first and second portions of the spacer. The head of the screw, however, may be larger than the facet screw opening 715 in the first portion and may only engage a top surface of the first portion. In some embodiments, the head of the screw may have a smaller diameter than facet screw opening 715 such that when the screw is fully inserted, the screw head is flush or substantially flush with the top surface of the first portion. Optionally, the screw may be an anti-backout screw. The anti-backout screw may include an interference thread on the head of the screw that engages with a female thread on the opening 715. When the interference thread is engaged with the female thread, the screw is locked in position thereby hindering or preventing backout or unscrewing.

In this embodiment, and as shown in FIGS. 16A-16H, a delivery system 800 includes a delivery device 805 having one or more guide lumens 810, each guide lumen having a central longitudinal axis therethrough. In embodiments with more than one guide lumen, the guide lumens 810 may be generally parallel or coplanar. In some embodiments with more than one guide lumen, the guide lumens 810 may have parallel central longitudinal axes. As can be understood from FIGS. 16A-16F, delivery device 805 comprises a first lumen 810a configured to receive a facet screw and a second lumen 810b configured to receive a rod associated with a washer or spacer. The first lumen is coupled to the second lumen by a connecting member 815 and extends less than the full length of the second lumen. In some embodiments, the length of the first lumen may be the same or similar to the length of the second lumen. The second lumen 810b extends longitudinally between a proximal portion 820 and distal portion 825. The distal portion 825 includes a spacer receiving member 830 configured to receive at least a portion of the spacer.

In some aspects, the delivery system 800 further comprises a rod 840 having a proximal portion with a knob 845 and a distal portion 850 for engagement with the spacer. The distal portion 850 may include threads (not shown).

Figure 16A:
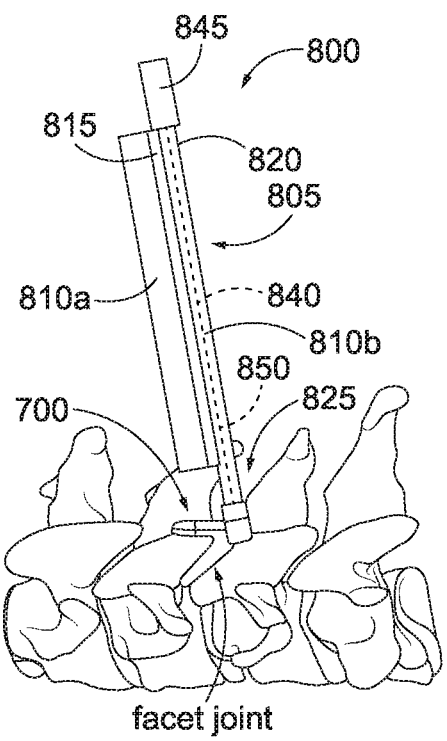
FIGS. 16A-16H depict a delivery system and use of the assembly of FIGS. 15A-15F in use.
Figure 16B:
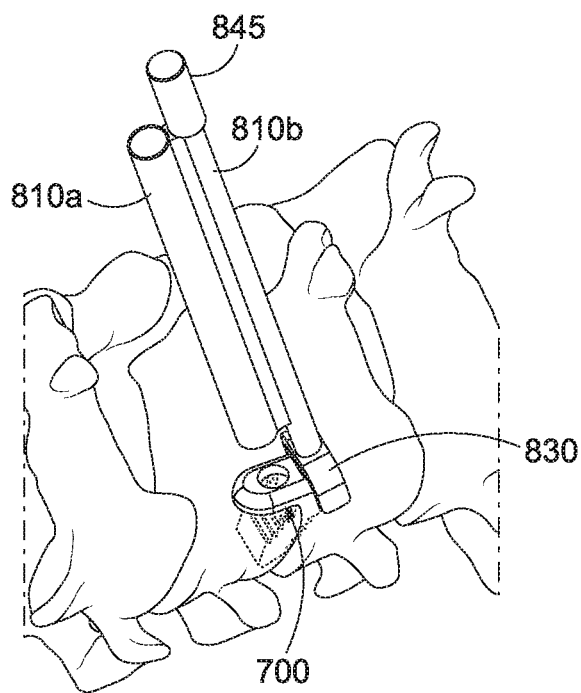
Figure 16C:
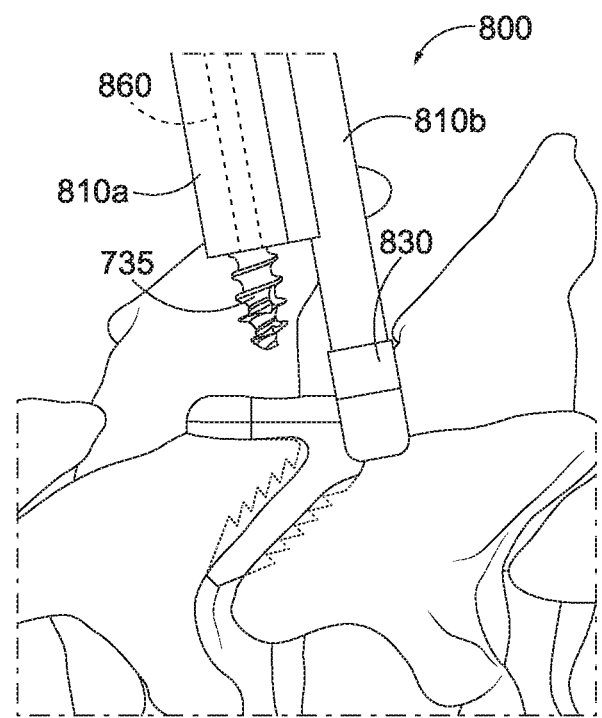

FIGS. 16A-16H illustrate a method of using the delivery system 800 with the facet screw assembly 720. In FIG. 16A, the method begins by inserting the spacer 700 into the facet joint with the delivery system 800 via a posterior approach.

Figure 16D:
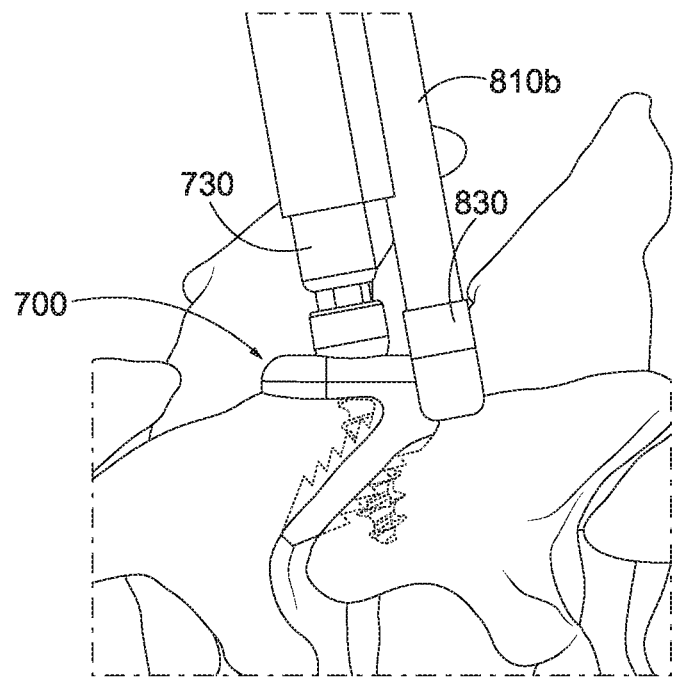
Figure 16E:
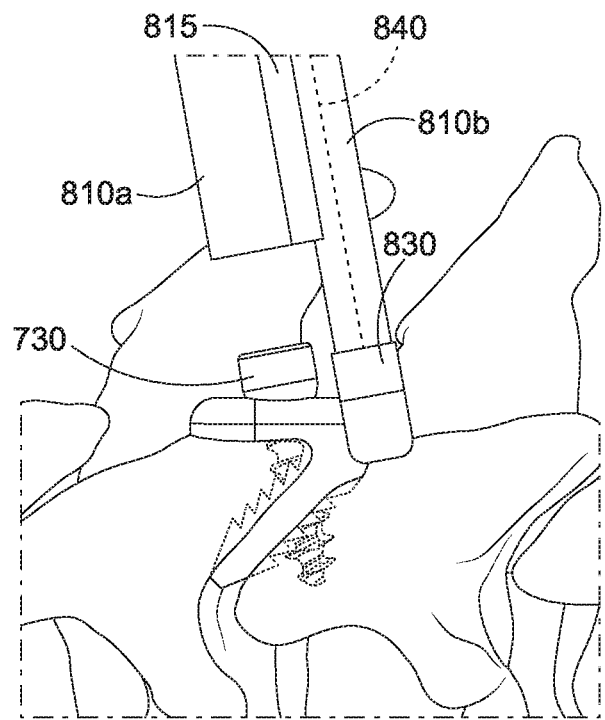
Figure 16F:
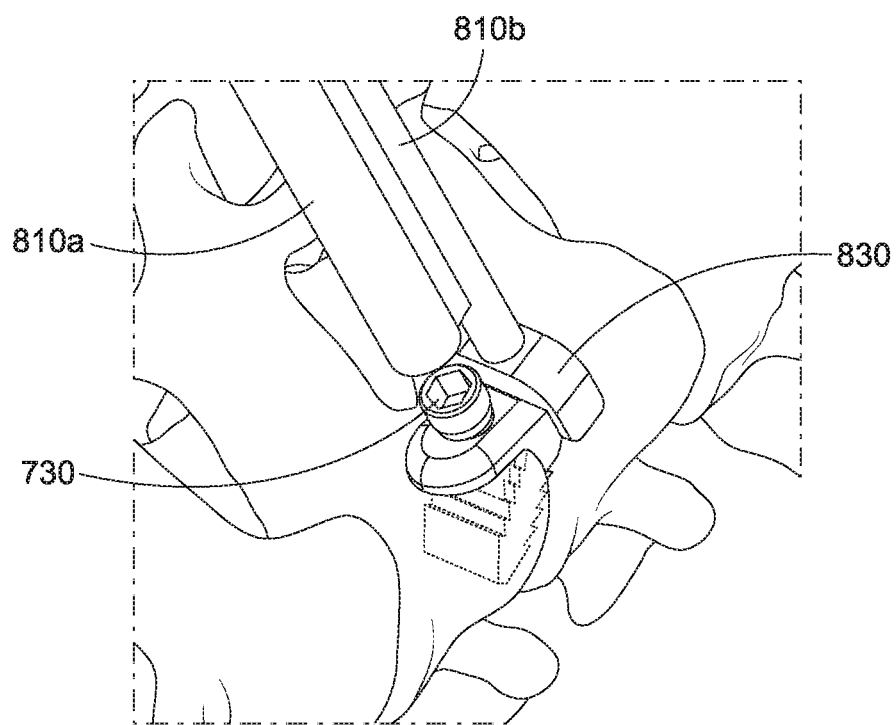
Figure 16G:
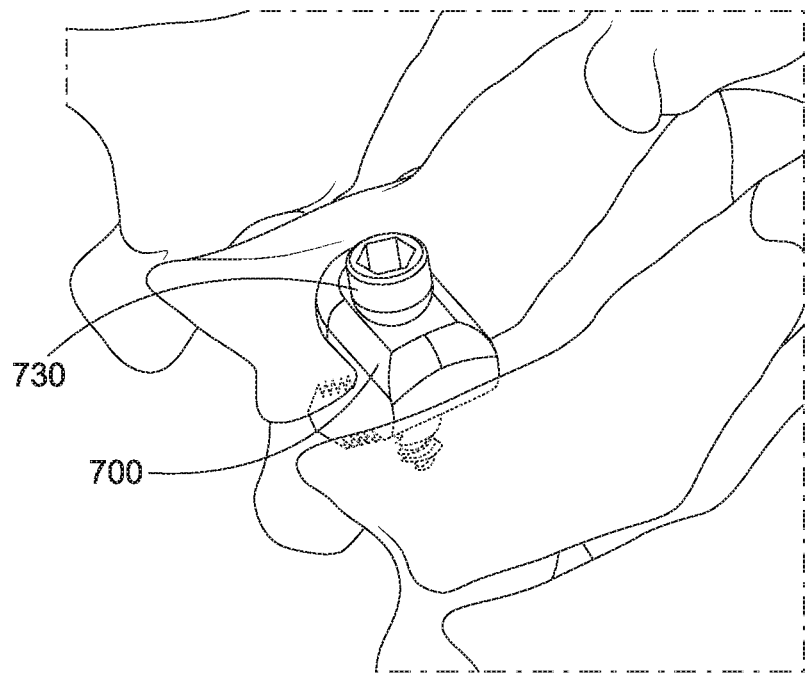
Figure 16H:
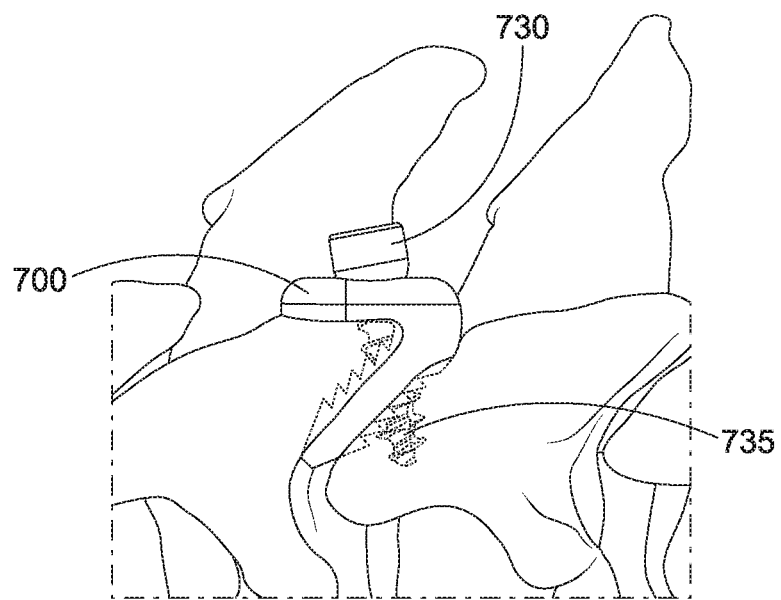

In this embodiment, the system does not articulate but rather is placed in a trajectory that is close to vertical relative to a horizontal spine (i.e. the patient is laying down). The facet screw 725, coupled to driver 860, is then inserted into the screw receiving lumen of the delivery device 805 (FIG. 16C), through the screw receiving openings in the spacer and across the facet joint (FIG. 16D). A pilot hole may be pre-drilled before the facet screw is inserted in the device 805. Once the facet screw is anchored in the facet joint, the driver 860 is detached from the facet screw and withdrawn. Then, knob 845 is rotated to disengage device 805 from spacer 700 (FIGS. 16E-16F). With a portion of the spacer deployed in the intra-facet joint and the other portion acting as a washer for the screw, the joint space is distracted while maintaining fixation with the spacer and the screw.

Turning now to FIGS. 12A-12G, the systems and devices disclosed herein may be used with a distraction system 900 configured to minimally invasively or percutaneously deliver implementations of the implant into a spinal facet joint space via, for example, a posterior approach. While the following discussion is made in terms of implant 200, it can be appreciated that certain aspects of distraction system 900 may also be used with the facet screw assemblies 400, 605, 660, 720 and others and related delivery devices or systems 500, 600, 800, and others.

In one implementation, the system 900 includes a delivery tool 902 and a guide tool 904, both of which extend from a respective leading distal end 906, 907 to a respective trailing proximal end 908, 909. As can be understood from FIGS. 12A-12G, the delivery tool 902 can be received in the lumen of the guide tool 904 to bring about the delivery of the implant 200 into the target spinal facet joint. The system 900 may further include a decorticator 936, an injector or push rod or actuator 948, a chisel 960, a place holding chisel 974, and a mallet 980.

The delivery system components depicted in FIGS. 12A-12G can be used to implant an implant 200 in a spinal facet joint that is the target of treatment. For example, in one embodiment, a percutaneous or minimally invasive incision is made in the posterior region of the neck to lead to the target facet joint. The access chisel 974 is routed through an incision, optionally under fluoroscopic guidance, until the tapered distal tip resides in the target facet joint and the chisel shaft extends out of the patient via the incision. With the access chisel so positioned, the outer decorticator can be grasped and distally routed over the access chisel such that the chisel shaft is received in the lumen that extends longitudinally through the outer decorticator. With the distal decorticating end of the outer decorticator abutting against one or more lateral masses adjacent the target facet joint, the outer decorticator can be rotated about the chisel shaft to decorticate the bone surfaces of the lateral masses adjacent the target facet joint. Once decortication of the lateral masses has been sufficiently achieved, the decorticator can be removed from about the chisel shaft and from the patient.

With the place holding or access chisel so positioned, the guide tool is grasped and distally routed over the chisel 974 such that the chisel shaft is received in the guide tool lumen that extends longitudinally through the guide tool shaft. The tapered forked distal end of the guide tool 904 is distally advanced through the incision and along the chisel shaft until the tapered forks of the guide tool 904 are positioned inside the target facet joint, the chisel tapered distal tip being located between the pair of forks of the guide tool distal end, the guide tool shaft extending out of the patient via the incision.

With the guide tool 904 so positioned, the place holding or access chisel 974 can be withdrawn out of the guide tool lumen and out of the patient, leaving the guide tool tapered forked distal end residing in the target facet joint and the guide tool shaft extending out of the patient. The decorticating chisel 960 can then be distally routed through the lumen of the guide tool 904 to place the tapered decorticating distal end of the chisel 960 between the guide tool forks located in the target facet joint space. The decorticating chisel 960 can then be displaced distal-proximal to cause the tapered decorticating distal end of the chisel 960 to remove the cartilage of the target facet joint space located between the guide tool forks and further decorticate any associated bone surfaces of the target facet joint space. Once the target facet joint space surfaces have been prepped with the decorticating chisel 960, the chisel 960 can be removed from the lumen of the guide tool 904 and the patient.

In some embodiments, the implant 200 may be coupled to, and supported off of, the distal end 906 of an implant delivery tool. Once the implant 200 is decoupled from the delivery tool and delivered or deposited into the facet joint space, the delivery tool can be withdrawn from the guide tool 904, which is left in place with its forked distal end occupying the facet joint space and the implant 200 being located between the forks of the guide tool 904.

When the delivery tool 902 is withdrawn from the guide tool 904, and the implant 200 is located as desired, a user may insert the implant delivery device 300 through the lumen of the guide tool 904 to deliver the locking screw 102 and thus anchor the implant 200 to the vertebra. For example, a user may insert the implant delivery device 300 through the lumen of the guide tool 904 such that the distal end of the inner guide tube 350 is proximate the facet implant, such as the facet screw 200. The user may insert the locking screw device 101 through a proximal end of the inner guide tube 350 and advance the locking screw device 101 through the proximal portion of the inner guide tube 350 along a first trajectory. The user may continue to advance the locking screw device 101 through the inner guide tube, and the bend within the guide tube may cause the flexible region 126 of the delivery mechanism 104 to flex. Thus, the locking screw 102 may exit the distal end of the inner guide tube 350 along a second trajectory so that the locking screw 102 is directed to the channel 220. When the locking screw 102 is within the channel 220, the user may rotate the locking screw device 101 to cause the locking screw 102 to advance through implant 200 and into the vertebra. The locking screw 102 may advance through the implant 200 and into the vertebra along a third trajectory. As the user further screws the screw 102 into the implant 200 and vertebra, the flexible region 126 further flexes and a load is concentrated at the breakable junction 122. When the user screws the screw 102 a sufficient amount to anchor the implant 200 to the vertebra, the breakable junction 122 may experience a predetermined load to cause the bone screw 102 to detach from the delivery mechanism 104. The process can then be repeated for another facet joint if needed.

In one embodiment, a system for delivering a facet screw assembly to a joint between a vertebra and an adjacent vertebra may include the facet screw assembly. The facet screw assembly includes a facet screw that interfaces with a washer that is deployed in the facet joint to distract or maintain the facet joint space thereby reducing or preventing radiculopathy. The washer may also be used as an additional anchoring point for the screw to reduce the likelihood of screw backout. The interface between the washer and the screw provides a fixed length for the screw to protrude beyond the facet joint and into bone which makes the placement of the screw predictable and minimizes bone breach and potential nerve or tissue damage to the patient.

In some embodiments, the instruments that interface with the screw and washer provide a way to place the facet screw assembly while minimizing the required tissue incision size typically seen in facet screw placement. The instruments also provide a way to decorticate the lateral mass to prepare for fusion. The instruments guide the facet screw at a fixed angle across the facet joint, eliminating the variability by doing it with other methods.

The embodiments of the current disclosure may be an improvement over traditional facet screws placed across the facet joint with a transfacet approach. The traditional transfacet approach compresses the facet joint, narrows the lateral foramen, and potentially induces spinal stenosis. In addition, the traditional approach does not decompress the nerve root. Another traditional method is the use of bone dowels, where the bone dowels are placed within the facet joint to expand and fuse the joint. However, this approach may require further instrumentation to fixate the joint and/or spine construct, to allow for fusion.

Figure 17A:
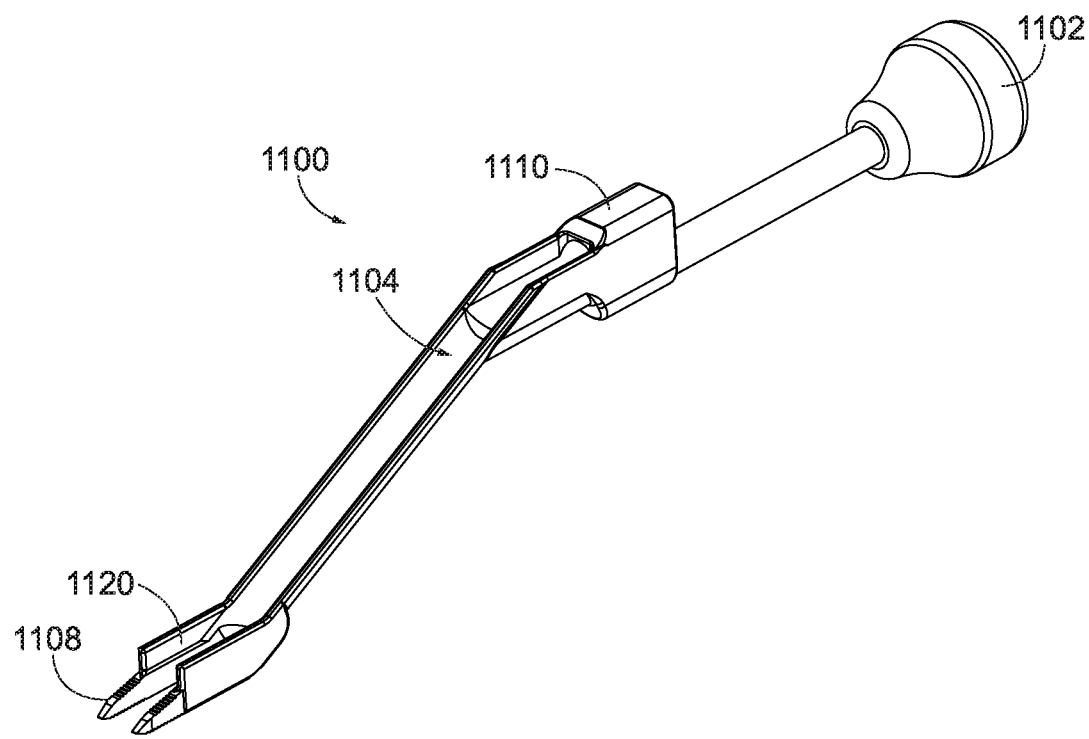
FIG. 17A is a perspective view of a facet access guide and an impact handle.
Figure 17B:
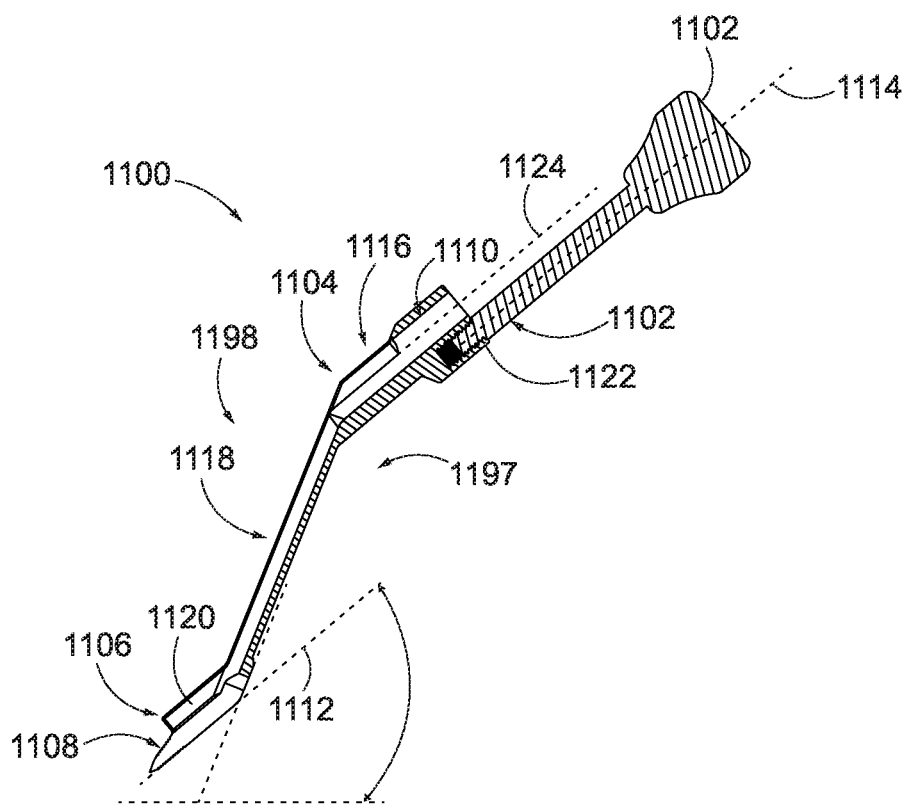
FIG. 17B is a cross-sectional view of the facet access guide and impact handle of FIG. 17A.

FIG. 17A is a perspective view of components of a facet screw assembly delivery system including a facet access guide 1100 and a detachably connected impact handle or handle 1102. While the handle 1102 is referred to as an impact handle, it can be appreciated that it is a handle with a portion having a wider surface area for grasping or hitting or driving an instrument in accordance with the present disclosure. FIG. 17B is a cross-sectional view of the facet access guide and handle of FIG. 17A. The facet access guide 1100 may be used in the delivery system and multiple tools may be configured to engage, such as slidably or rotatably engage with, various features of the facet access guide 1100 to deliver the facet screw assembly.

The facet access guide 1100 includes a posterior side 1198, an anterior side 1197, and a distal end formed as ramp 1120 including an intra-facet distractor 1108 and a stop or depth stop 1106. The facet access guide 1100 also includes a proximal end formed by an instrument guide handle portal 1110 and impact handle socket 1122. An instrument guide portal 1104 is positioned between the ramp 1120 and the combination of the instrument guide handle portal 1110 and impact handle socket 1122. The instrument guide portal 1104 includes an upper portion 1116 and a lower portion 1118. The upper portion 1116 is positioned adjacent the instrument guide handle portal 1110. The lower portion 1118 is adjacent the ramp 1120.

Referring to FIG. 17B, the instrument guide handle portal 1110 may be a lumen formed as a circle, square, triangular, oblong, tube or other shaped portal extending through the proximal end of the facet access guide 1100. The instrument guide handle portal 1110 includes an axis 1124 that is generally parallel to an axis 1114 that extends through the impact handle socket 1122. In some examples, the impact handle socket 1122 may be formed as a cavity within the proximal end of the facet access guide 1100.

The upper portion 1116 of the instrument guide portal 1104 may be generally coaxial with the axis 1124 of the instrument guide handle portal 1110. The upper portion 1116 may form an open lumen or channel, such as a generally half-cylindrical channel with an open side or a u-shaped channel, with an opening directed towards a posterior side 1198 of the facet access guide 1100. The upper portion 1116 is angled with respect to the lower portion 1118. The lower portion 1118 may also form a channel, such as generally half-cylindrical channel with an open side or a u-shaped channel, with an opening directed towards the posterior side 1198 of the facet access guide 1100.

Referring to FIG. 17B, the lower portion 1118 of the instrument guide portal 1104 may be angled with respect to the distal end of the facet access guide 1100. For example, a plane extending through the ramp 1120 may be parallel to the axis 1114 and axis 1124 of the proximal end. The angle of the lower portion 1118 of the instrument guide portal 1104 may help to minimize the tissue incision size due to the off-axis, multi-angle geometry of the facet access guide 1100.

At the end of the ramp 1120 may be the intra-facet distractor 1108. The intra-facet distractor 1108 may be used to distract a target facet joint to prepare the joint for insertion, coupling, or receipt of a facet screw assembly. The ramp 1120 and intra-facet distractor 1108 may form a fork like shape that may aid in preparation of the facet joint by partially or fully distracting the facet joint or at least anchoring the tool in the joint. A stop or depth stop 1106 may also be positioned at the end of the ramp 1120. In use, the depth stop 1106 may positively locate the intra-facet distractor 108 and prevent the intra-facet distractor 1108 from extending too far or being inserted to an undesired depth into the facet joint.

In some examples and in use, the angled or non-linear shape of the facet access guide 100 may reduce tissue incision size and/or instrument footprint for distracting a facet joint and inserting a facet screw assembly.

The delivery system of FIGS. 17A-17B may also include a detachable impact handle 1102. In use, and as shown in FIG. 17B, the impact handle 1102 may be detachably coupled to the facet access guide 1100 at the impact handle socket 1122. In some examples, the detachable coupling may be in the form of a threaded rod and socket assembly, such that the impact handle socket 1122 includes threads on an internal surface that may mate with external threads formed on an end of the impact handle 1102.

Figure 18B:
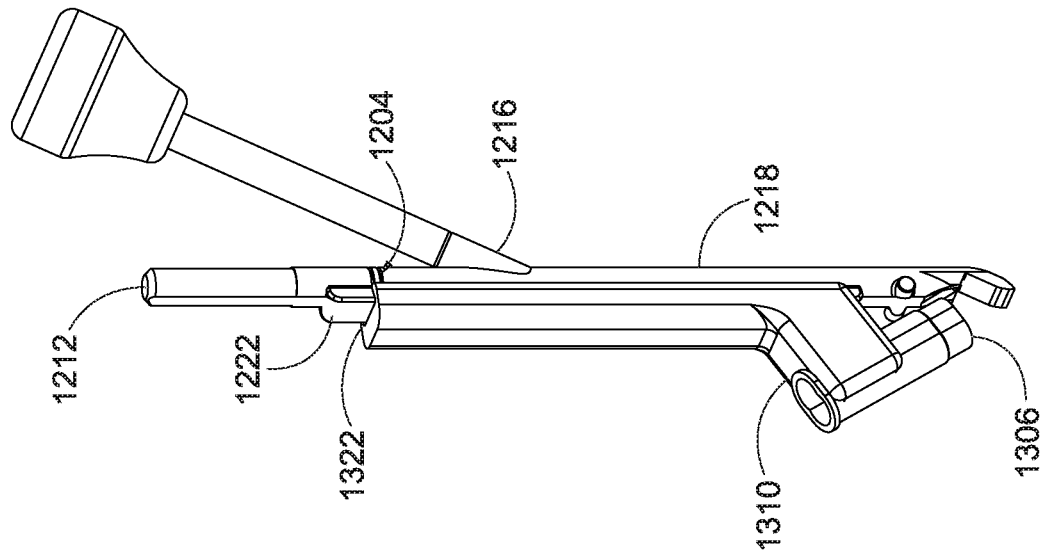
FIG. 18B is a perspective view of the washer sizer tool with the lateral mass decorticator guide of FIG. 18A in an alternate position.
Figure 18A:
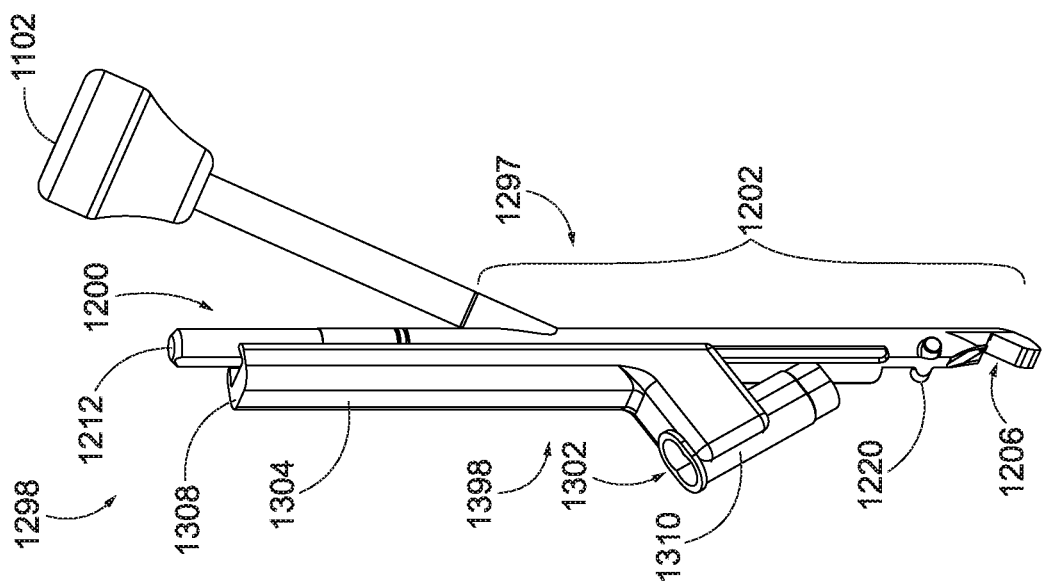
FIG. 18A is a perspective view of a washer sizer tool and a lateral mass decorticator guide in a first position.

FIG. 18A is a perspective view of a facet screw assembly delivery system that includes a washer sizer tool and a lateral mass decorticator guide in a first position. FIG. 18B is a perspective view of the washer sizer tool and the lateral mass decorticator guide of FIG. 18A in an alternate position.

The delivery system may also include a washer sizer tool 1200 and a lateral mass decorticator guide 1300. The washer sizer tool 1200 may include an anterior side 1297, a posterior side 1298, and an access guide interface 1202, which extends from a central portion of the washer sizer tool 1200 on the anterior side 1297 down to a distal end. The access guide interface 1202 may be shaped to engage, fit adjacent to or detachably couple with the instrument guide portal 1104 of the facet access guide 1100. For example, the access guide interface 1202 may be cylindrical or u-shaped to fit at least partially within and slide with respect to the posterior side 1198 of the instrument guide portal 1104 of the facet access guide 1100. The access guide interface 1202 may include an upper portion 1216 and a lower portion 1218. The lower portion 1218 may be generally coaxial with a washer sizer shaft 1212, which is positioned adjacent the upper portion 1216. The upper portion 1216 may be angled with respect to the lower portion 1218 and the washer sizer shaft 1212. The angle and shape of the upper portion 1216 is configured to align with the upper portion 1116 of the facet access guide 1100.

The upper portion 1216 may also include a threaded socket configured so that the washer sizer tool 1200 may be detachably coupled with the impact handle 1102 (as shown assembled in FIG. 18B). Positioned above the upper portion 1216 may be a shoulder. The shoulder may be used to help align the washer sizer tool 1200 with the facet access guide 1100.

At the distal end of the washer sizer tool 1200 is a joint spacer 1206. The joint spacer 1206 is shaped to be positioned and slide along the ramp 1120 and between the forks that form the intra-facet distractor 1108 on the posterior side 1198 of the facet access guide 1100. The joint spacer may include teeth extending from its sides to help position the joint spacer 1206 within the facet joint and to also help decorticate the facet joint in preparation for the installation of the facet screw assembly.

A dovetail feature 1222 may be formed on the posterior side 1298 of the washer sizer tool 1200. The dovetail feature 1222 may extend along at least half a length of the washer sizer tool 1200, and is configured to align with a corresponding dovetail feature on the lateral mass decorticator guide 1300. This may allow the lateral mass decorticator guide 1300 to be fixedly axially located with respect to the washer sizer tool 1200, but allows the lateral mass decorticator guide 1300 to be translated or slid up and down along the washer sizer tool 1200.

As shown in FIG. 18B, the washer sizer tool 1200 may also include a washer size indication or indicator, such as a washer size marker line 1204 positioned on or at least partially about the circumference of the washer sizer shaft 1212. The washer size marker line 1204 may be used in conjunction with the lateral mass decorticator guide 1300 to help a user determine the washer or spacer that is needed in the facet screw assembly.

The posterior side of the washer sizer tool 1200 may also include a pin 1220, or posts that extends away from, in a lateral medial direction, the general body of the washer sizer tool 1200 adjacent the joint spacer 1206. In use, the post or pin 1220 may align with the ramp 1120 of the facet access guide 1100 to help guide the washer sizer tool 1200 during the facet screw assembly installation procedure. For example, the pin may slide or ride against the edge of the ramp to help ensure alignment of the washer sizer tool 1200 with respect to the facet access guide 1100.

The lateral mass decorticator guide 1300 is also shown in FIGS. 18A-18B. The lateral mass decorticator guide 1300 may include a decorticator guide shaft 1304 extending from a proximal end 1308 towards a distal end of the lateral mass decorticator guide 1300. The distal end of the lateral mass decorticator guide 1300 may include a tool guide 1310 with a decorticator portal 1302 extending through it. The decorticator guide shaft 1304 is angled with respect to the axis of the decorticator portal 1302. A distal end of the tool guide 1310 is the lateral mass contacting surface 1306. The lateral mass contacting surface 1306 is used to contact the lateral mass of the vertebrae forming the target facet joint.

In some examples, the lateral mass decorticator guide 1300 includes a dovetail feature 1322 that extends from the anterior side 1397 of the lateral mass decorticator guide 1300 and is configured to slidably align or mate with the dovetail feature 1222 that extends from the posterior side of the washer sizer tool 1200. In use, the lateral mass decorticator guide 1300 may be translated or slide up and down the dovetail feature 1222 to help position the lateral mass decorticator guide 1300 in the desired location, and to indicate, using the washer size marker line 1204, which size facet screw assembly should be used.

In use, there is a distance or space 1312 formed between the lateral mass contacting surface 1306 of the lateral mass decorticator guide 1300 and the joint spacer 1206 of the washer sizer tool 1200. This distance or space 1312 helps determine the size of the facet screw assembly components, such as the length and size of the facet screw and the size of the washer implant 1400.

Figure 19:
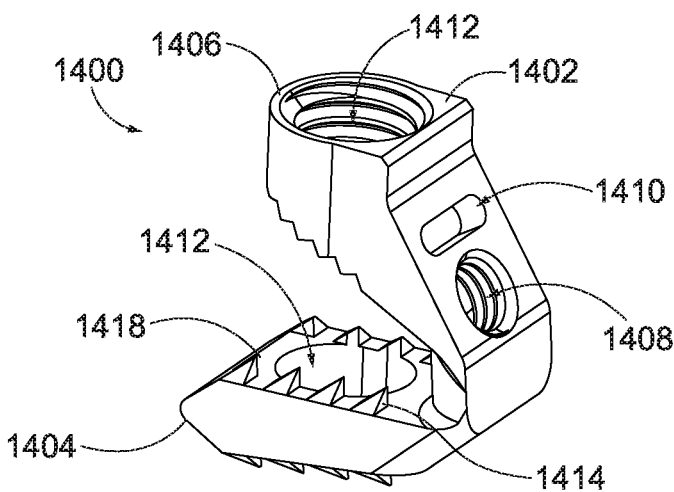
FIG. 19 is a perspective view of one example of a washer implant that may be used in accordance with the present disclosure.

FIG. 19 is a perspective view of a washer implant 1400 that may be used in a facet screw assembly delivery system. Other washer implants that may be used with the systems described herein include those described in U.S. Application No. 62/667,951 and U.S. Application No. 62/613,547, which are hereby incorporated by reference. The washer implant 1400 includes a first portion 1402 having a lateral mass engagement portion 1416 and a second portion 1404 having an intrafacet engagement portion 1418. Each of the first portion 1402 and second portion 1404 includes a facet screw opening 1412 configured to receive a facet screw. The facet screw opening 1412 in the first portion 1402 may include a threaded portion 1406, so that the head of a facet screw may fit at least partially within or flush within the first portion 1402. The threaded portion 1406 may have a machine type thread pitch, and is configured to engage with the threaded head of the facet screw. The threaded portion 1406 may not extend the full length of the facet screw opening 1412 in the first portion 1402, so that there is a shoulder 1420 near the bottom of the facet screw opening 1412 of the first portion 1402. This shoulder 1420 may help to prevent a facet screw from being rotated through the entire facet screw opening 1412 of the first portion 1402 and becoming decoupled or disengaged from the washer implant 1400.

The intrafacet engagement portion 1418 of the second portion 1404 may also include teeth 1414 extending from either side. The teeth may be used to engage the intrafacet surfaces of a first or primary and adjacent vertebra.

The washer implant 1400 may also include a coupling member or feature to couple the washer to an implant delivery tool. In some examples, the coupling member is a threaded aperture 1408 that extends through a portion of the washer implant 1400, such as extending through the intrafacet engagement portion 1418.

In some examples, positioned between the threaded aperture 408 and the facet screw opening 1412 of the first portion 1402 is a keyway 1410. In some examples, the keyway 1410 is a groove 1410. The groove 1410 may be shaped to align or fit with a feature, such as a tongue or key feature, of the washer implant delivery tool (see FIG. 20B) to help prevent the washer implant 1400 from undesirably rotating or moving with respect to the washer implant delivery tool 1600 during the delivery of the facet screw assembly.

Figures 20A, 20B:
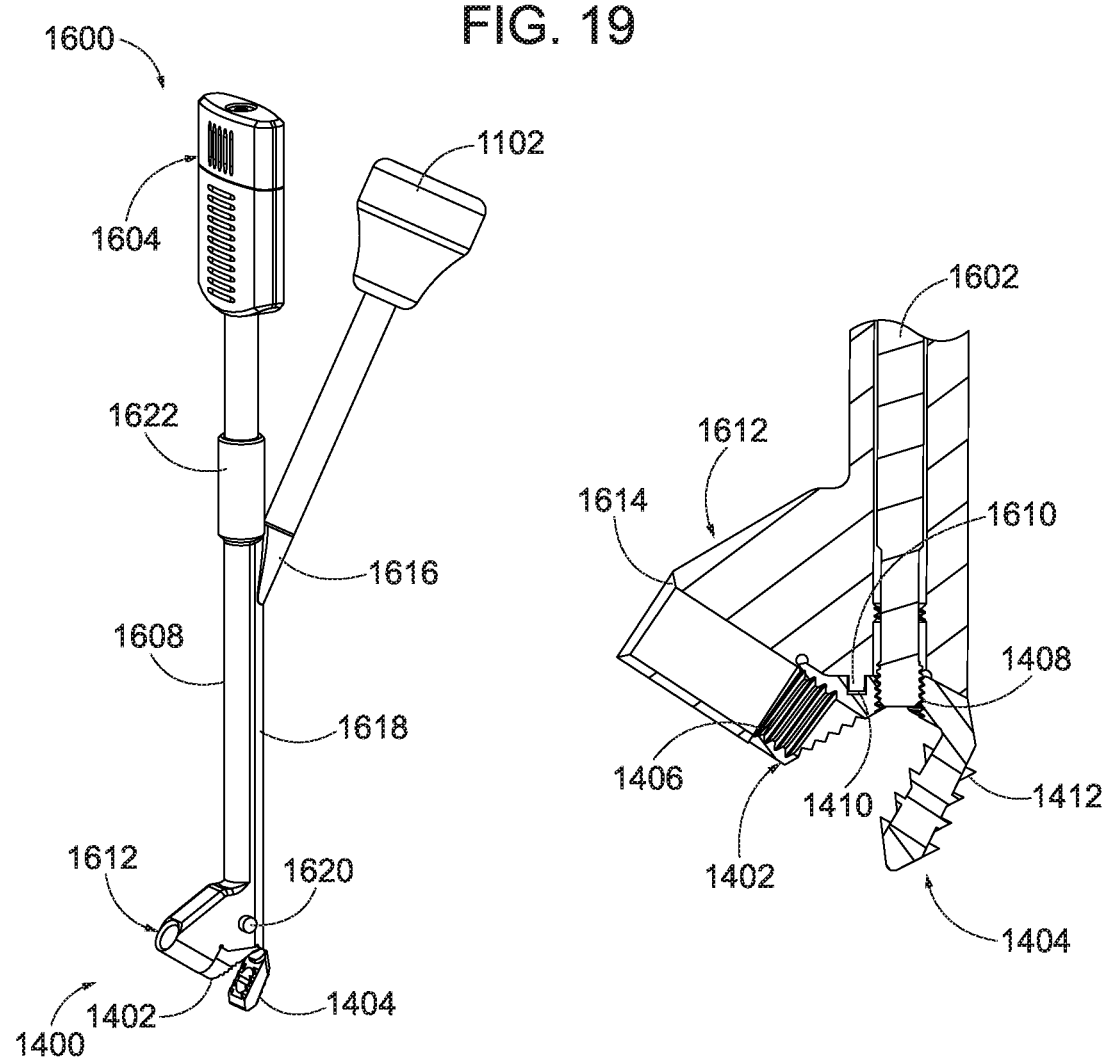
FIG. 20A is a perspective view of a washer implant delivery tool assembled with an impact handle and washer.
FIG. 20B is a cross-sectional view of a portion of the washer implant delivery tool and washer implant of FIG. 20A.

FIG. 20A is a perspective view of a facet screw assembly delivery system including a washer implant delivery tool assembled with an impact handle and a detachably connected washer implant. FIG. 20B is a cross-sectional view of a portion of the washer implant delivery tool and washer implant of FIG. 20A.

In some examples, the washer implant delivery tool 1600 includes a distal end with a facet screw guide 1612 and a proximal end with a washer release knob 1604. A shaft 1608 may extend between the facet screw guide 1612 and washer release knob 1604. Above the shaft and proximate to the washer release knob 1604 may be a shoulder 1622. In some examples, the shoulder 1622 may be cylindrically shaped and have a diameter that is larger than a diameter of the shaft 1608. In use, the shoulder 1622 may be used to align the washer implant delivery tool 1600 with the facet access guide 1100.

The shaft 1608 may include an upper portion 1616 and a lower portion 1618. Similar to the upper portion 1116 and lower portion 1118 of the facet access guide 1100, the upper portion 1616 and lower portion 1618 may be angled with respect to each other. The upper portion 1616 may be shaped to fit adjacent to or align with the posterior side of the upper portion 1116 of the facet access guide 1100. The lower portion 1618 may be shaped to fit adjacent to or align with the posterior side of the lower portion 1118 of the facet access guide 1100.

As can be understood from FIG. 20B, in some examples, an actuation rod 1602 may be coupled to the washer release knob 1604 on a proximal end of the actuation rod 1602. The actuation rod 1602 may be configured to be coupled to the threaded aperture 1408 of the washer implant 1400 on a distal end of the actuation rod 1602. In some examples, the distal end of the actuation rod 1602 may not be threaded, but may be keyed in an acceptable manner to engage a complementary-shaped keyway on the washer implant 1400 at a location similar to threaded aperture 1408.

The distal end of the washer implant delivery tool 1600 also includes a key feature 1610. In some examples, the key feature is a raised feature or a tongue 1610. In use, the tongue 1610 is configured to align with the keyway or groove 1410 of the washer implant 1400 to properly position the washer implant 1400 with the washer implant delivery tool 1600.

The distal end of the washer implant delivery tool 1600 also includes a facet screw guide 1612, including a facet screw portal 1614 extending through the facet screw guide 1612. The facet screw guide 1612 may be positioned at an angle with respect to the shaft 1608 and actuation rod 1602. When assembled with the washer implant 1400, the facet screw portal 1614 may be generally coaxial with the facet screw opening 1412 of the first portion 1402 and second portion 1404 of the washer implant 1400.

A post or pin 1620 may extend away from the facet screw guide 1612, in a lateral medial direction. The pin 1620 of washer implant delivery tool 1600 may be similar to the pin 1220 of washer sizer tool 1200. The pin 1620 may be used to align or locate the washer implant delivery tool 1600 with respect to the facet access guide 1100 when assembled or coupled together to deliver the facet screw assembly.

Figure 21:
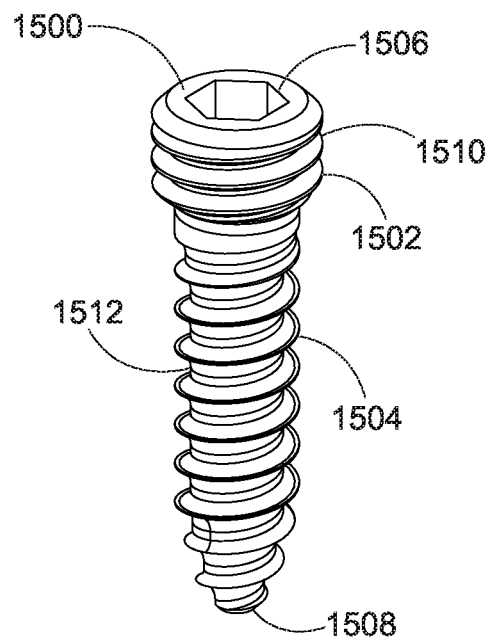
FIG. 21 is a perspective view of a facet screw.

FIG. 21 is a perspective view of an embodiment of a facet screw that may be used in various embodiments of a facet screw assembly delivery system. The facet screw 1500 may include a head 1510 having external threads and a cylindrical body extending away from the head 1510 with an elongated shaft 1512 and additional external threads. In an example, the facet screw 1500 is not a set screw, and a diameter of the head 1510 may be larger in size than a diameter of the elongated shaft 1512. The external threads on the head 1510 may differ from those on the elongated shaft 1512. For example, the head 1510 may include a washer interface 1502 and the elongated shaft 1512 may include a facet joint interface 1504. For example, the washer interface 1502 includes machine threads on an outside or outer circumference of the head 1510 and the facet joint interface 1504 includes screw threads that extend to the end 1508. The elongated shaft 1512 may taper from a larger diameter adjacent the head 1510 to a small diameter at the end 1508. The threads of the elongated shaft 1512 may be formed so that the elongated shaft 1512 is self-tapping to engage the lateral mass of the vertebrae.

The head 1510 may also include a tool connector feature 1506, for example a keyway or being keyed to accept a hex, star, cross, or other type of tool key to rotate or manipulate the position of the facet screw 1500.

Figure 22A:
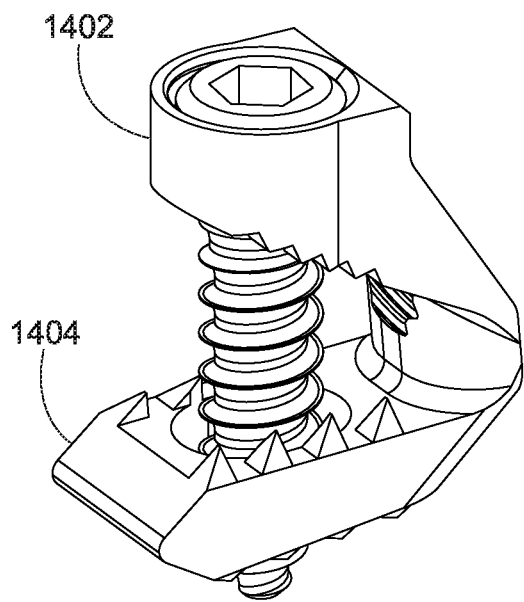
FIG. 22A is a perspective view of a facet screw assembly.
Figure 22B:
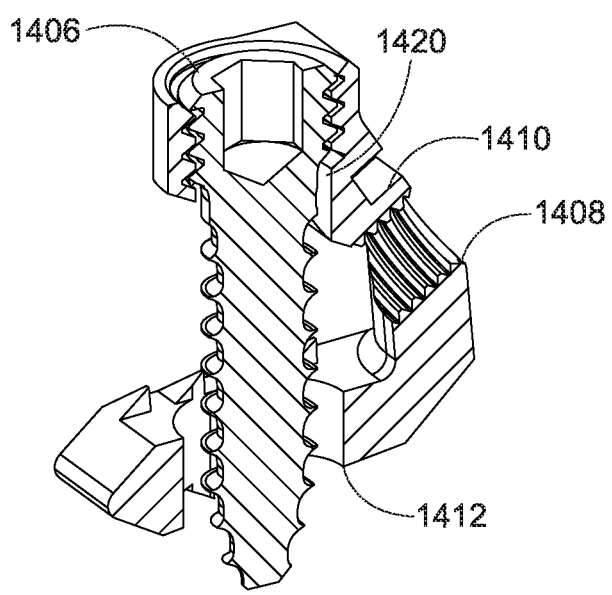
FIG. 22B is a cross-sectional view of the facet screw assembly of FIG. 22A.
Figure 22C:
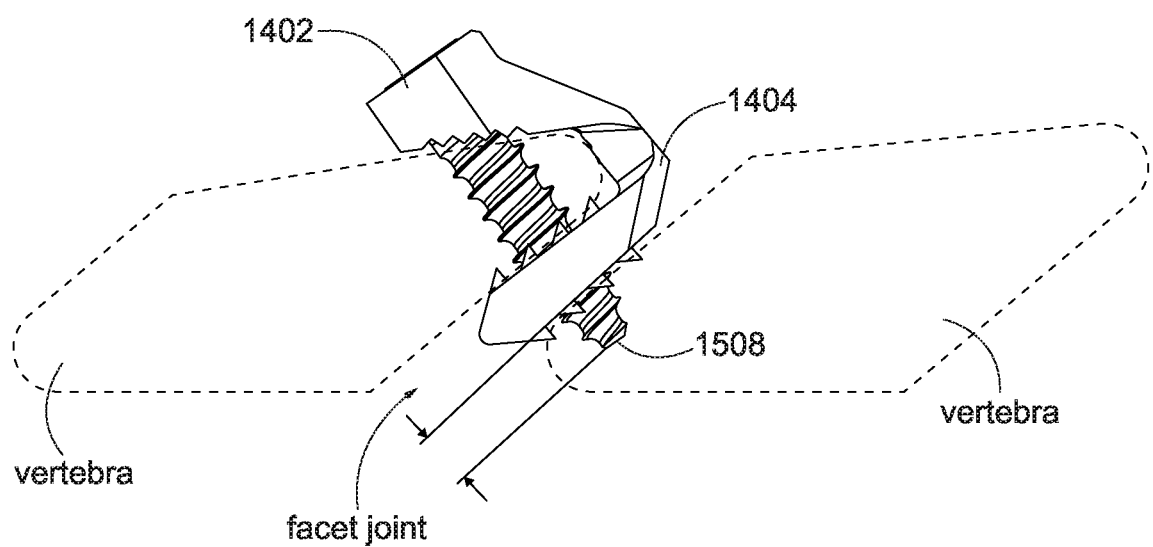
FIG. 22C is a cross-sectional view of the washer or spacer positioned with respect to a facet joint.

FIG. 22A is a perspective view of a facet screw assembly that may be used with a facet screw assembly delivery system, with a facet screw assembled with a washer implant 1400. FIG. 22B is a cross-sectional view of the facet screw and washer of FIG. 22A. FIG. 22C is a cross-sectional view of the washer positioned over the lateral mass of a first vertebrae and into the facet joint. In FIG. 22C, the facet screw extends through the lateral mass, through the facet joint, and into the adjacent vertebrae. In use, when the screw is inserted into the washer or spacer, the facet screw shaft passes through both facet screw openings 1412 in each of the first and second portions of the spacer. The threaded head 1510 of the facet screw 1500 engages with the threaded portion 1406 of the facet screw opening 1412 in the first portion 1402 of the spacer 1400. The threaded facet joint interface 1504 of the facet screw 1500 engages and extends through the lateral mass of a first vertebrae, extends through the facet screw opening 1412 of the second portion 1404 of the washer implant 1400, and then extends through the intrafacet surface and, into an adjacent vertebrae. As the facet screw 1500 is inserted, the engagement of the threaded head 1510 with the threaded portion 1406 of the washer implant 1400, in combination with the engagement of the threaded elongated shaft 1512, work to create a compressive effect across the facet joint to fix the first and adjacent vertebrae. This compressive effect may also help to prevent the facet screw from backing out or separating from the spacer 1400.

As shown in FIG. 22C, the overall length of the facet screw 1500 in combination with the size of washer implant 1400 controls the depth at which the end 1508 of the facet screw 1500 extends into the adjacent vertebrae. In this manner, the protrusion length across the facet joint is known and can be used as a safety feature to minimize bone breach.

FIGS. 23-26B shows the process and progression of delivering a facet screw assembly using the described facet screw assembly delivery system components.

Figure 23:
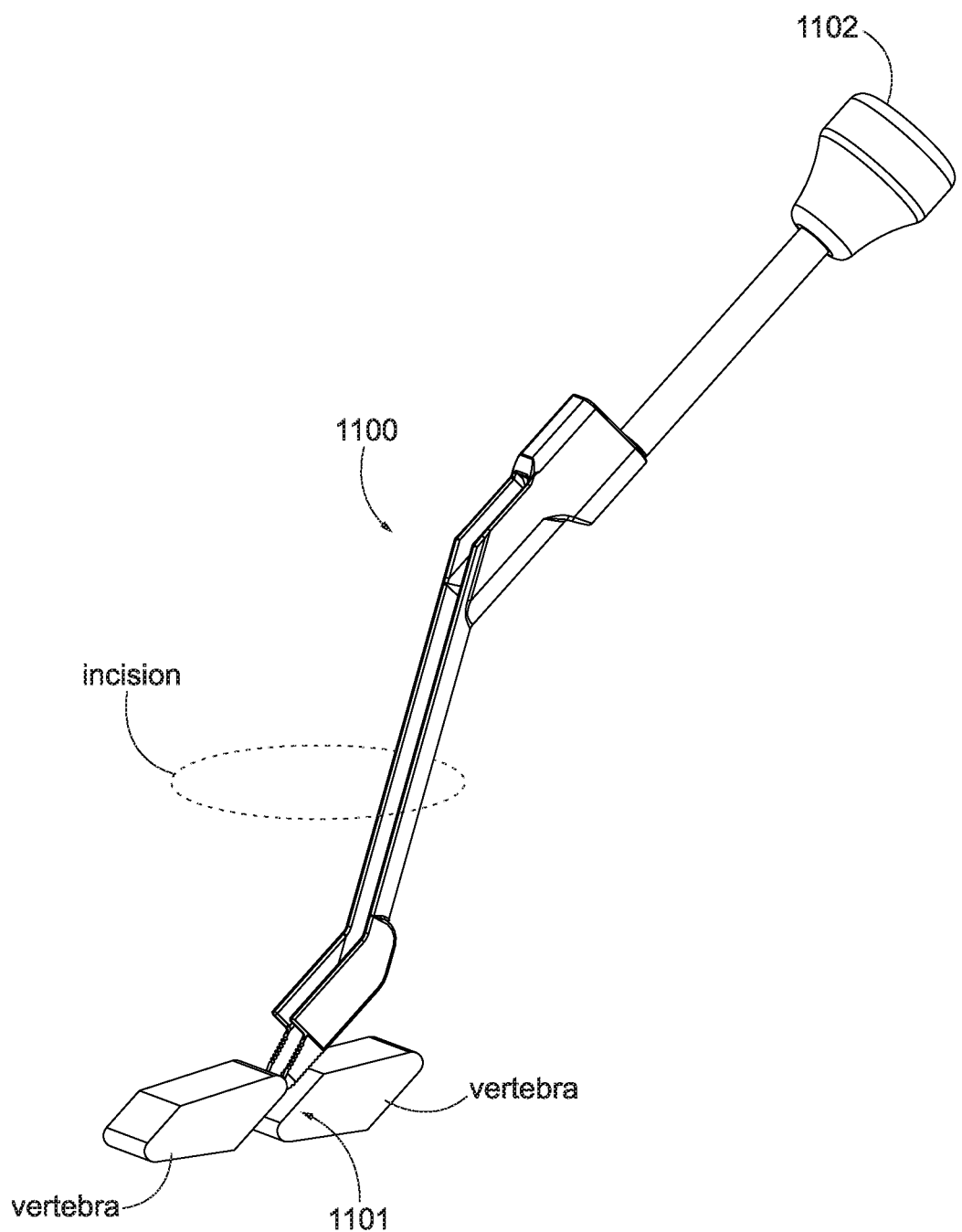
FIG. 23 is a perspective view of the facet access guide positioned adjacent a facet joint.

FIG. 23 is a perspective view of the facet access guide 1100 positioned adjacent a facet joint. The facet access guide 1100 may be positioned so that the intra-facet distractor 1108 begins to extend into the facet joint 1101. To distract the facet joint with the intra-facet distractor 1108, the impact handle 1102 is impacted or tamped. The force on the impact handle 1102 is transmitted to the intra-facet distractor 1108, which helps to drive the facet access guide 1100 correctly into the facet joint at a proper angle and maximizes the transfer of force from the impact handle 1102 to the facet access guide 1100. The angle of the lower portion 1118 of the instrument guide portal 1104 helps minimize the tissue incision size due to the off-axis, multi-angle geometry of the facet access guide 1100. As the intra-facet distractor 1108 distracts the facet joint 1101, the depth stop 1106 may engage with the lateral mass of the vertebra to help prevent the intra-facet distractor 1108 from extending too far into or from being over inserted into the facet joint 1101.

Once the facet access guide 1100 is positioned properly with respect to the facet joint 1101, a user will separate or remove the impact handle 1102 from the facet access guide 1100. The user may then removably and/or slidably engage or assemble the washer sizer tool 1200 with the facet access guide 1100, so that the access guide interface 1202 of the washer sizer tool 1200 aligns with the instrument guide portal 1104 of the facet access guide 1100. A user may then remove or decouple the impact handle 1102 from impact handle connection 1107 of the facet access guide 1100 (see FIG. 24A). The user may then removably or detachably couple the impact handle 1102 to the upper portion 216 (see FIG. 18A) of the washer sizer tool 1200, with the distal end of the impact handle 1102 extending through the instrument guide handle portal 1110.

Figure 24A:
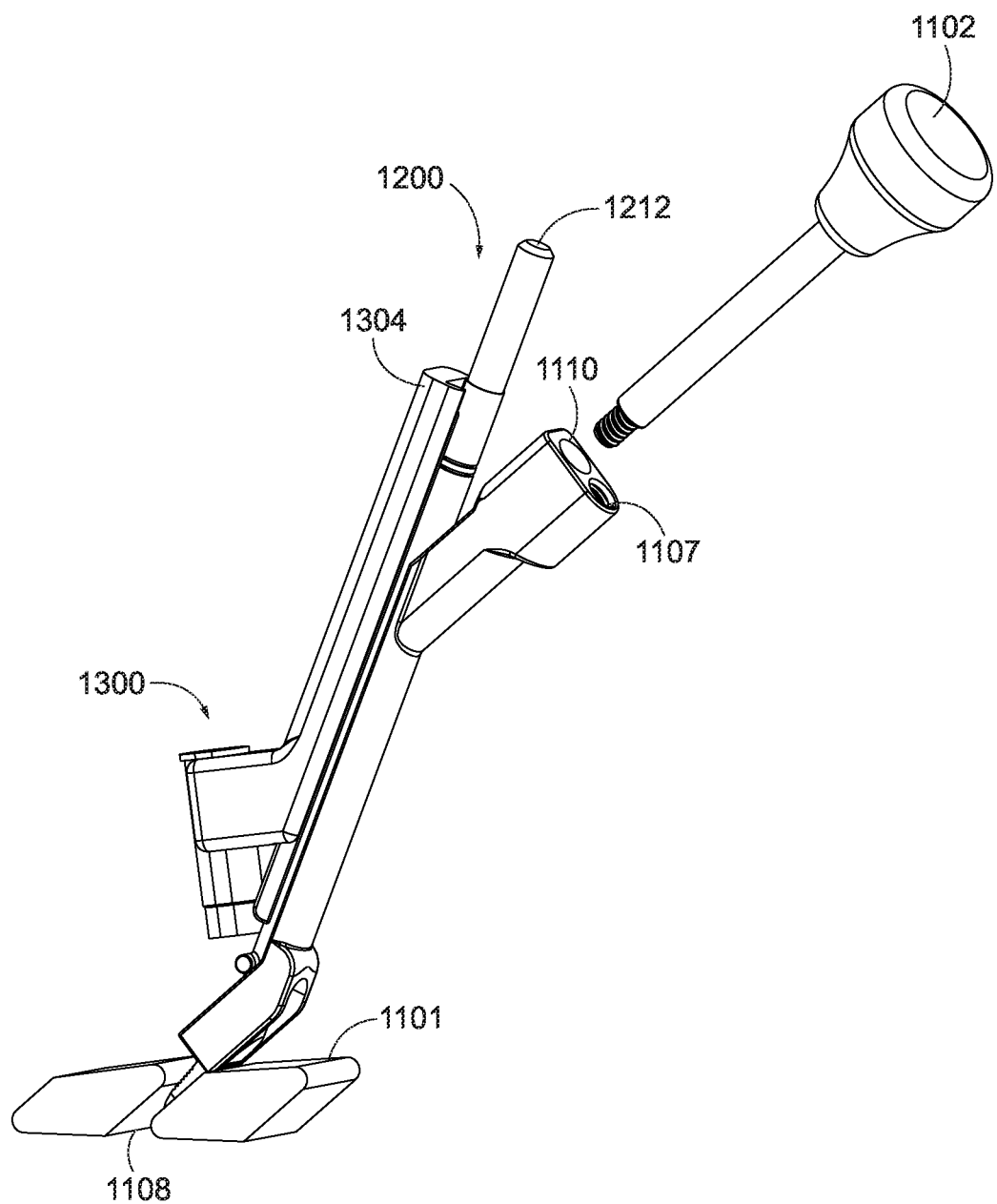
FIG. 24A is a perspective view of the facet access guide positioned adjacent the facet joint and further assembled with the lateral mass decorticator guide and washer sizer tool.
Figure 24C:
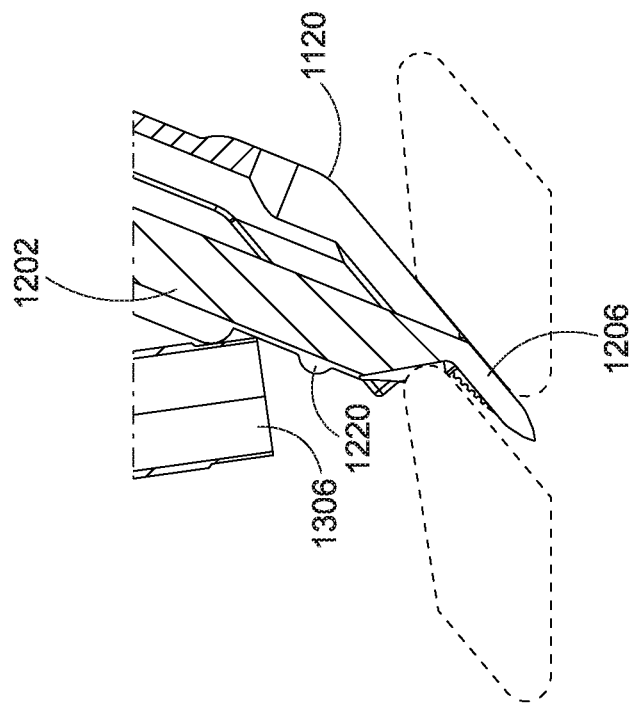
FIG. 24C is an enlarged cross-sectional view of the assembly of FIG. 24B.
Figure 24B:
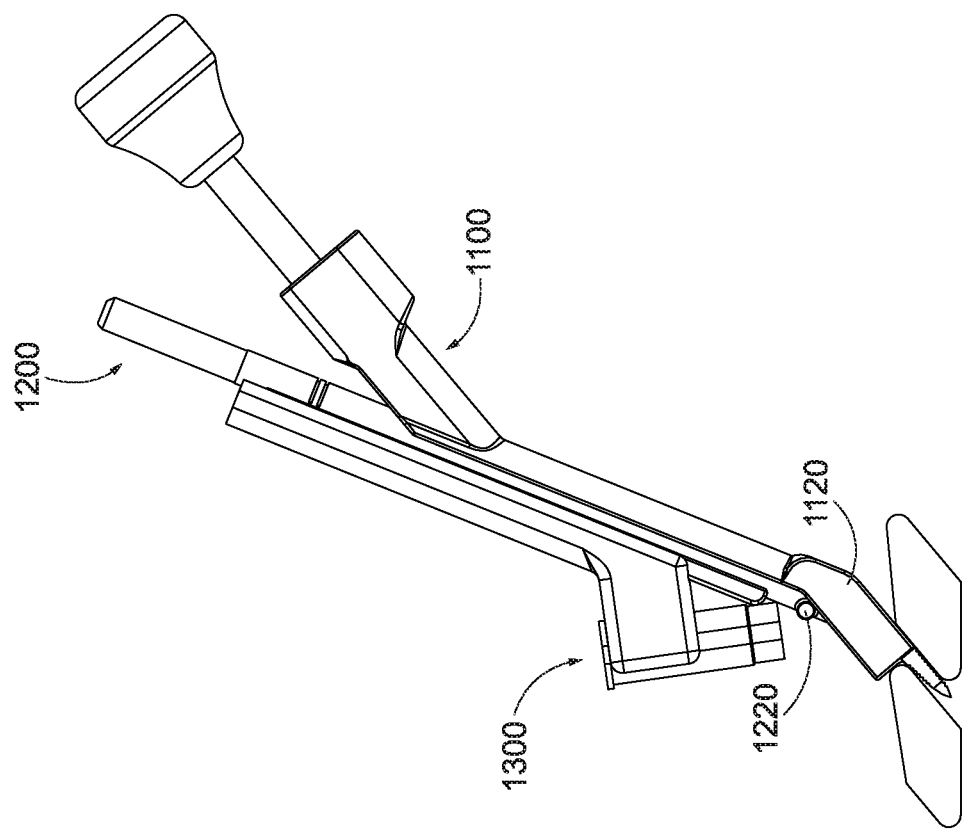
FIG. 24B is a side view of the assembly of FIG. 24A.

FIG. 24A is a perspective view of the facet access guide positioned adjacent the facet joint and further assembled with the lateral mass decorticator guide and washer sizer tool. FIG. 24B is a side view of the assembly of FIG. 24A, with the impact handle 1102 detachably coupled to the upper portion 1216 of the washer sizer tool 1200. FIG. 24C is an enlarged cross-sectional view of the assembly of FIG. 24B.

After the washer sizer tool 1200 is initially assembled with the facet access guide 1100, the joint spacer 1206 may not be in the desired or proper positon within the facet joint. To move or adjust the position of the washer sizer tool 1200 so that the joint spacer 1206 is moved into position, a user would tamp or impact the impact handle 1102 coupled to the washer sizer tool 1200. The impact force on the impact handle 1102 would move or force the washer sizer tool 200 downwards with respect to the facet access guide 1100. The connection of the impact handle 1102 to the upper portion 1216 would provide alignment support for the washer sizer tool 200 with respect to the facet access guide 1100, and the pin 1220 would engage the ramp 1120 to provide further alignment and support. The trajectory of washer sizer tool 1200 is guided by the impact handle 1102 shaft and the instrument guide handle portal 1110, as well as the ramp 1120 and the pin 1220. With this, the distal end of the joint spacer 1206 may be properly placed in the facet joint.

Next, a user may determine the appropriate size facet screw assembly components, such as the washer implant 1400 and facet screw 1500, to use for the procedure.

Figure 24D:
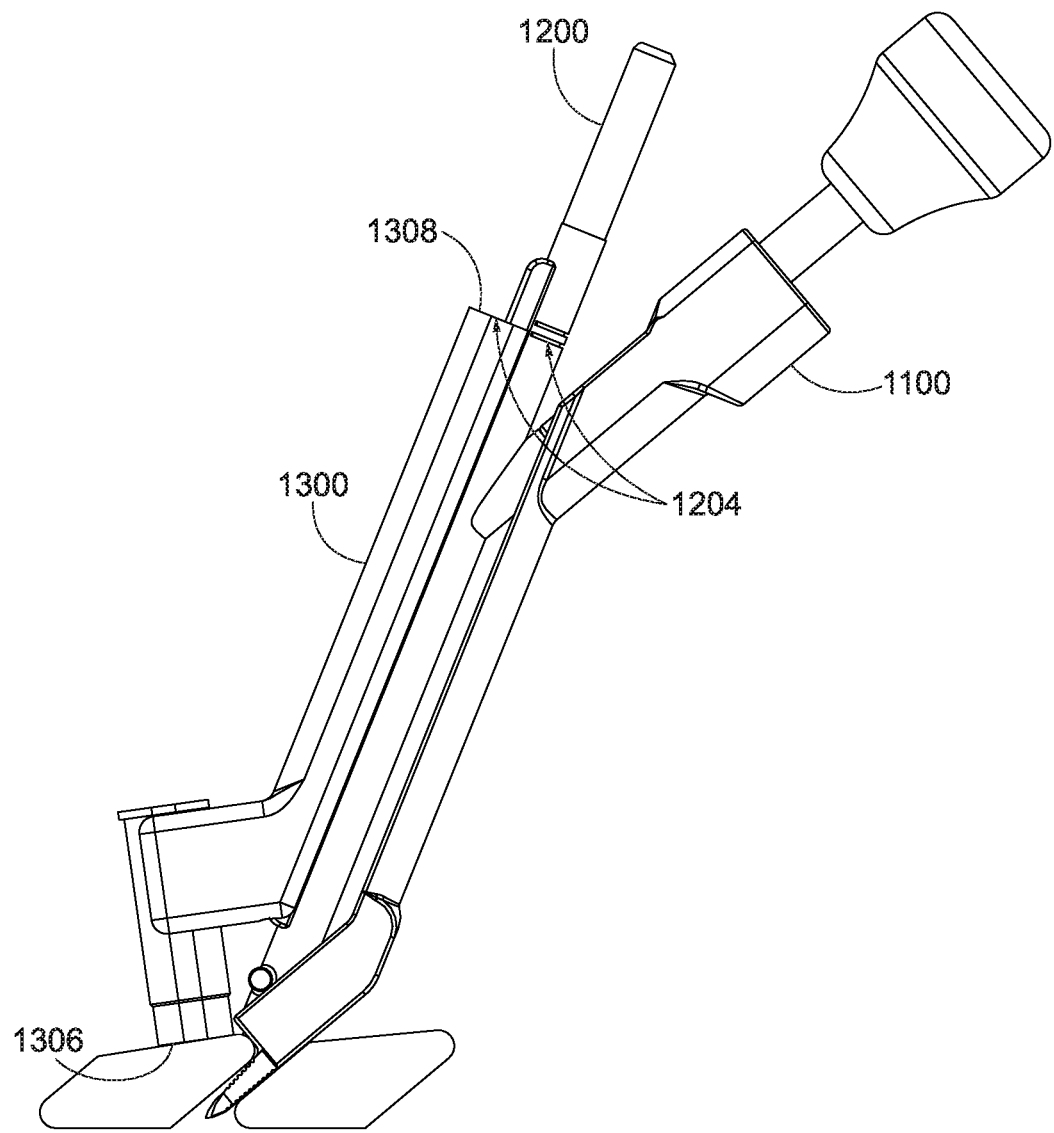
FIG. 24D is a side view of the assembly of FIG. 24B with the lateral mass decorticator guide positioned in an alternate position adjacent the lateral mass.

FIG. 24D is a side view of the assembly of FIG. 24B with the lateral mass decorticator guide positioned in an alternate position adjacent the lateral mass. Once the distal end of the joint spacer 1206 is properly positioned, the user may slidably adjust the position of the lateral mass decorticator guide 1300 with respect to the washer sizer tool 1200. The user will slide the distal end of the lateral mass decorticator guide 1300 towards the facet joint until the lateral mass contacting surface 1306 contacts the lateral mass of the first vertebrae. Once the lateral mass contacting surface 1306 contacts the lateral mass, the user may inspect the washer size marker line 1204 of the washer sizer tool 1200 with respect to the proximal end 1308 of the lateral mass decorticator guide 1300. The alignment of the proximal end 308 with the washer size marker line 1204 helps measure the thickness of the lateral mass and can provide a determination or instruction to a user about what size facet screw assembly components, such as a washer implant 1400 and facet screw 1500, to use.

Figure 24E:
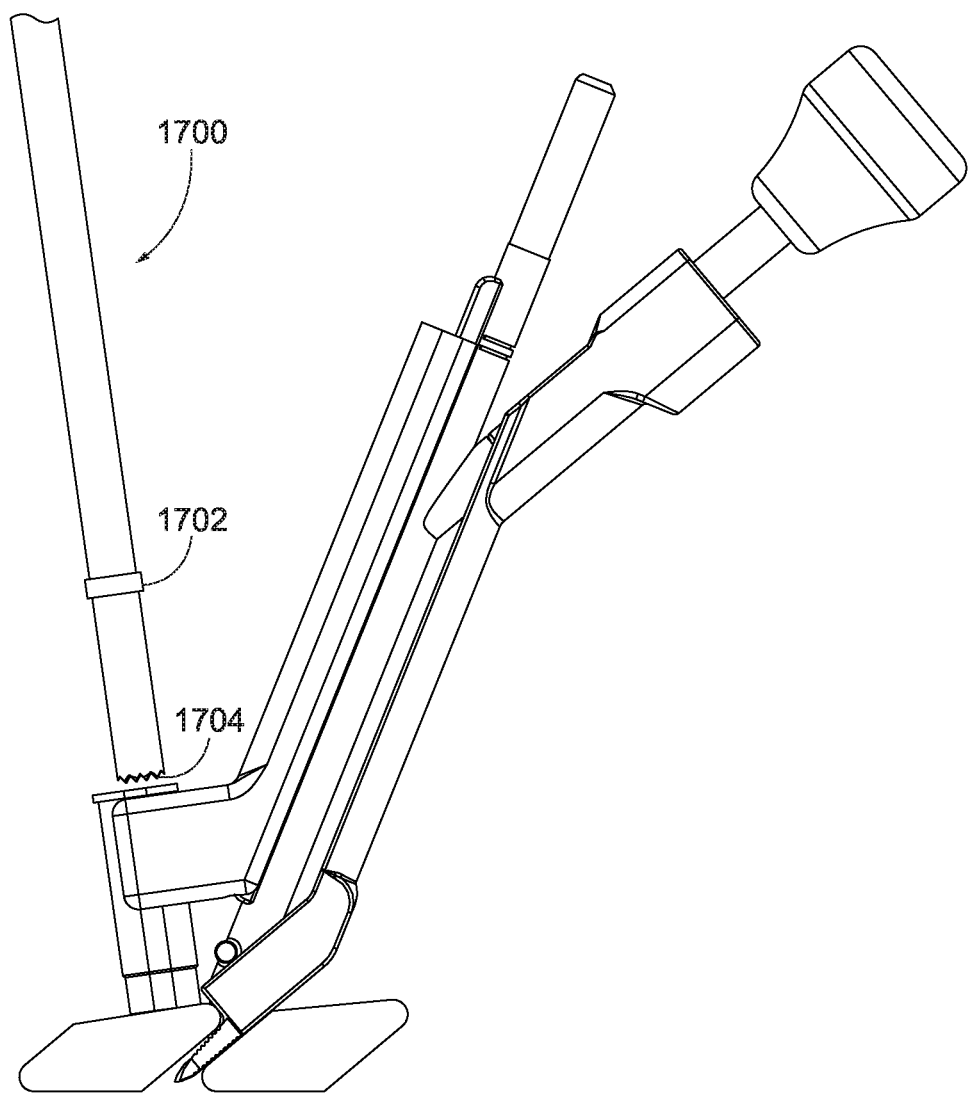
FIG. 24E is a side view of the assembly of FIG. 24D with a decorticator instrument.

In some instances, the lateral mass may be an uneven or contoured bone surface (i.e. bumpy, wavy, or generally not flat), and a user may want to flatten or even out the surface to help to size the washer implant 1400 appropriately. In some instances, the lateral mass may be generally flat, but the user may wish to decorticate the surface to help stimulate and improve bone growth around the area of the facet screw assembly. FIG. 24E is a side view of the assembly of FIG. 24D with a decorticator instrument. When the lateral mass contacting surface 1306 of the lateral mass decorticator guide 1300 is positioned adjacent the lateral mass, such as in FIG. 24E, a user may then insert or place a distal end of a decorticator instrument 1700 down through the decorticator portal 1302 of the lateral mass decorticator guide 1300. The decorticator instrument 1700 may include a shoulder or raised lip 1702 that helps to control the depth that the distal end of the decorticator instrument 1700 may be moved to. For example, the shoulder or raised lip 1702 may act as a hard stop to prevent the over-decortication of the lateral mass. The decortication of the lateral mass may help flatten or otherwise refine the bony surface to the shape of the washer implant 1400.

Once the combination of the washer sizer tool 1200 and lateral mass decorticator guide 1300 have been used to determine the appropriately sized facet screw assembly components, a user may then detach the impact handle 1102 from the washer sizer tool 1200, and remove the washer sizer tool 1200 and lateral mass decorticator guide 1300.

Figure 25A:
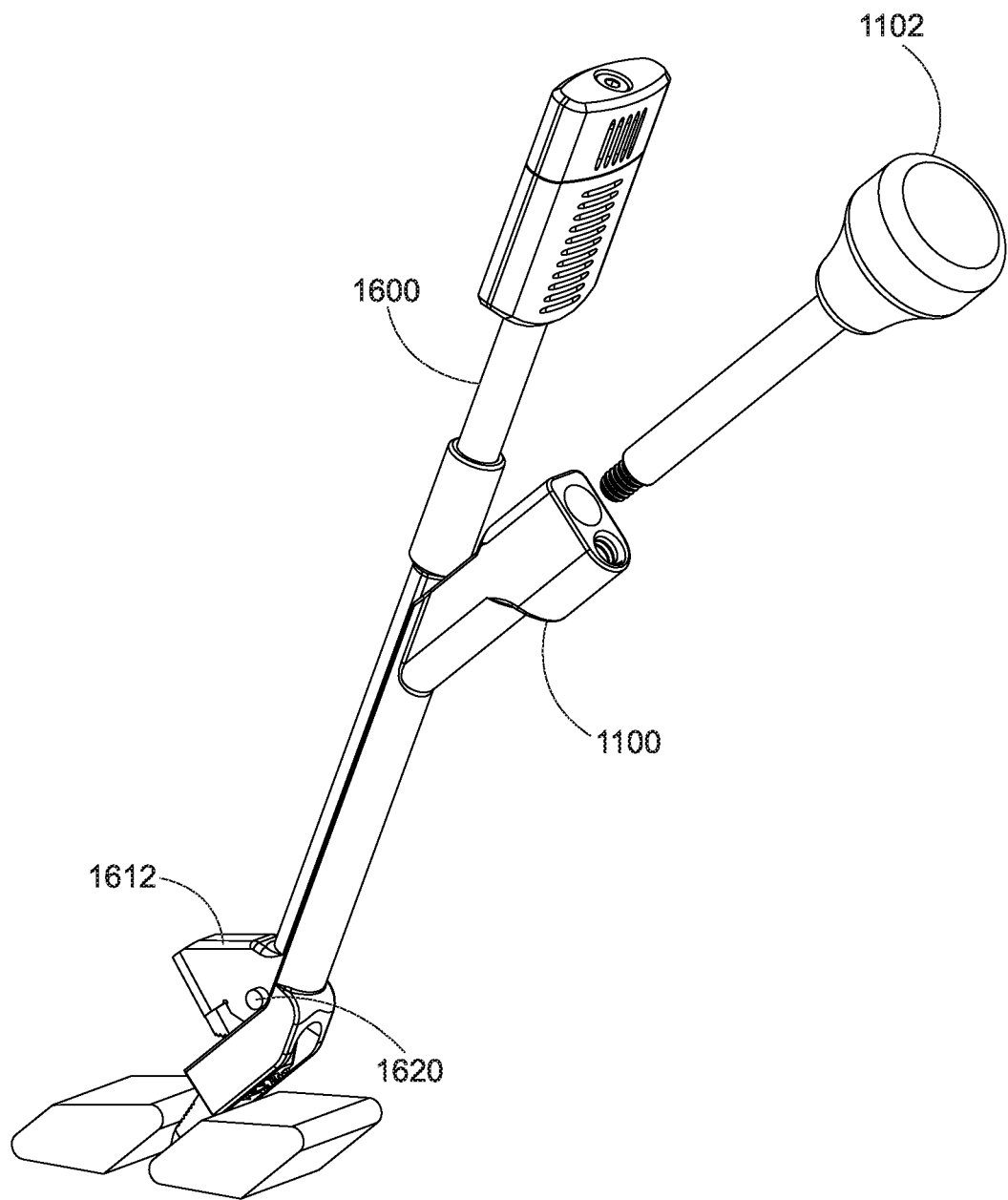
FIG. 25A is a perspective view of the facet access guide assembled with a washer implant delivery tool and washer positioned in a first position.
Figure 25B:
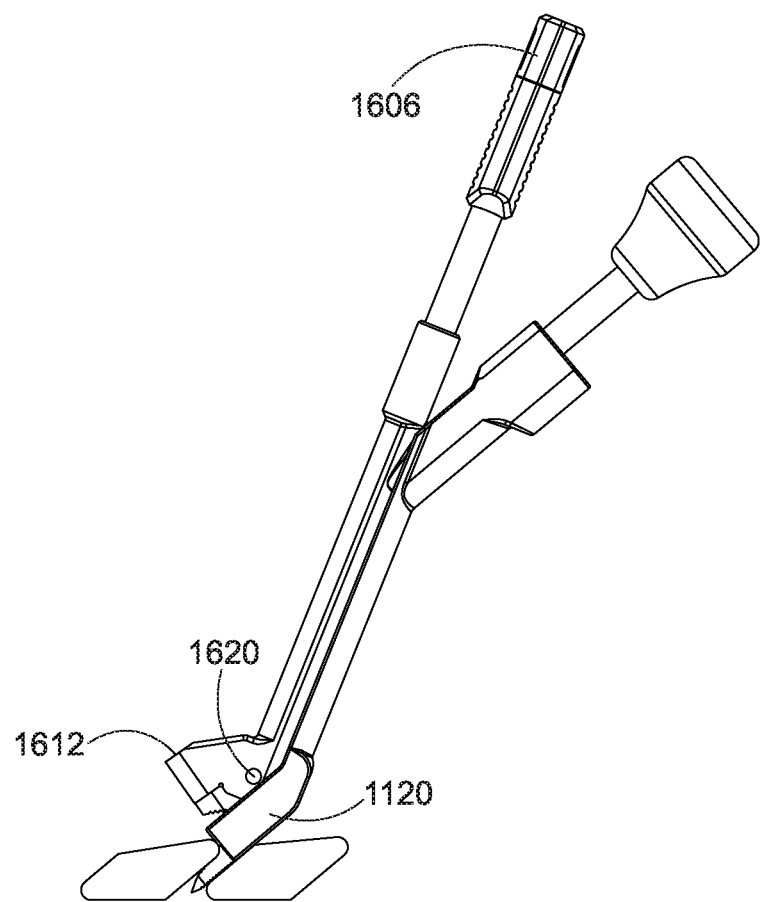
FIG. 25B is a side view of the tool assembly of FIG. 25A.

FIG. 25A is a perspective view of the facet access guide assembled with a washer implant delivery tool and washer implant positioned in a first position. FIG. 25B is a side view of the tool assembly of FIG. 25A. A user will then attach the appropriately sized washer implant 1400 to the actuation rod 1602 of the washer implant delivery tool 1600. The user will then slidably engage or assemble the washer implant delivery tool 1600 with the facet access guide 1100. To do this, the user will align the upper portion 616 of the washer implant delivery tool 1600 with the upper portion 116 of the facet access guide 1100, align the lower portion 1618 of the washer implant delivery tool 1600 with the lower portion 1118 of the facet access guide 1100, and then insert the impact handle 1102 through the instrument guide handle portal 1110 and reattach it to the washer implant delivery tool 1600 at the upper portion 1616 of the washer implant delivery tool 1600.

The user will then impact the handle to advance the washer implant 1400 over the lateral mass of the first or primary vertebrae and into the facet joint. The instrument trajectory is guided by the shaft of the impact handle 1102 through the instrument guide handle portal 1110 and by the ramp 1120 and the pin 1620 of the washer implant delivery tool 1600.

Figure 25C:
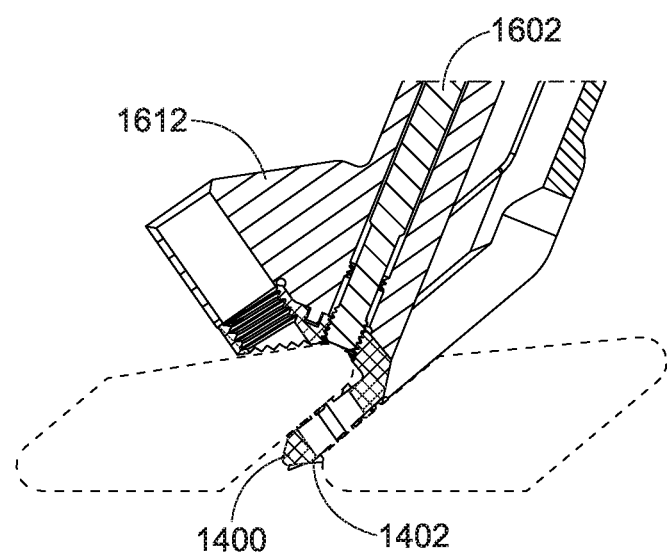
FIG. 25C is an enlarged cross-sectional view of the tool assembly of FIG. 25B with the washer implant delivery tool and washer positioned in the facet joint.
Figure 25D:
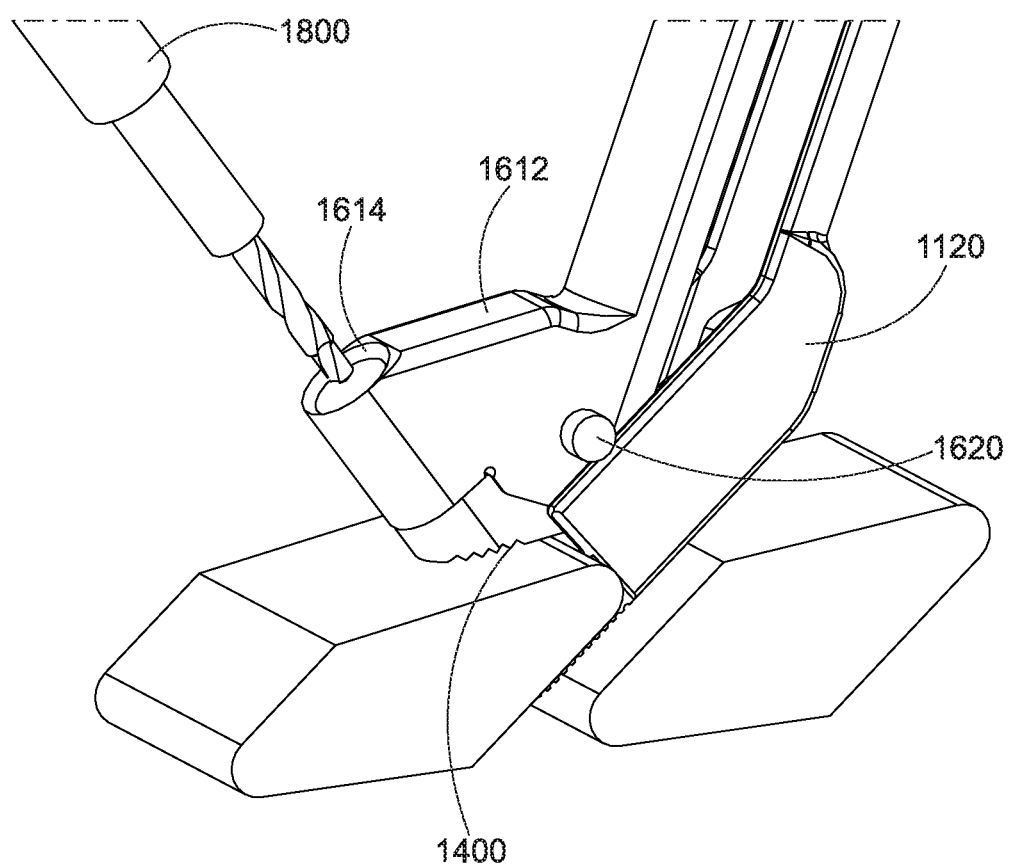
FIG. 25D is a perspective view of the tool assembly of FIG. 25C with a drill positioned adjacent a facet screw portal of the washer implant delivery tool.

FIG. 25C is an enlarged cross-sectional view of the tool assembly of FIG. 25B with the washer implant delivery tool and washer implant 1400 positioned in a placed position, with the lateral mass engagement portion 1416 of the washer implant 1400 adjacent the lateral mass and the intrafacet engagement portion 1418 positioned within the facet joint. FIG. 25D is a perspective view of the tool assembly of FIG. 25C with a drill positioned adjacent the facet screw portal of the washer implant delivery tool. Once the washer implant 1400 is placed so that the intrafacet engagement portion 1418 is positioned within the facet joint, a user may use a drill 1800 to create a pilot hole across the facet joint for the facet screw. The trajectory of the drill is guided by the facet screw portal 1614 of the facet screw guide 1612 of the washer implant delivery tool 1600.

Figure 26A:
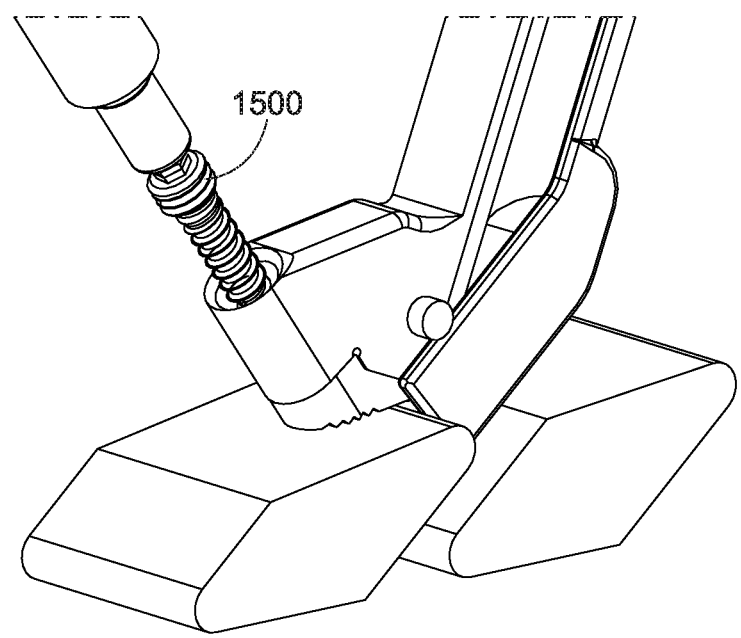
FIG. 26A is a perspective view of the washer implant delivery tool and washer positioned within the facet joint with a facet screw adjacent the lateral mass.
Figure 26B:
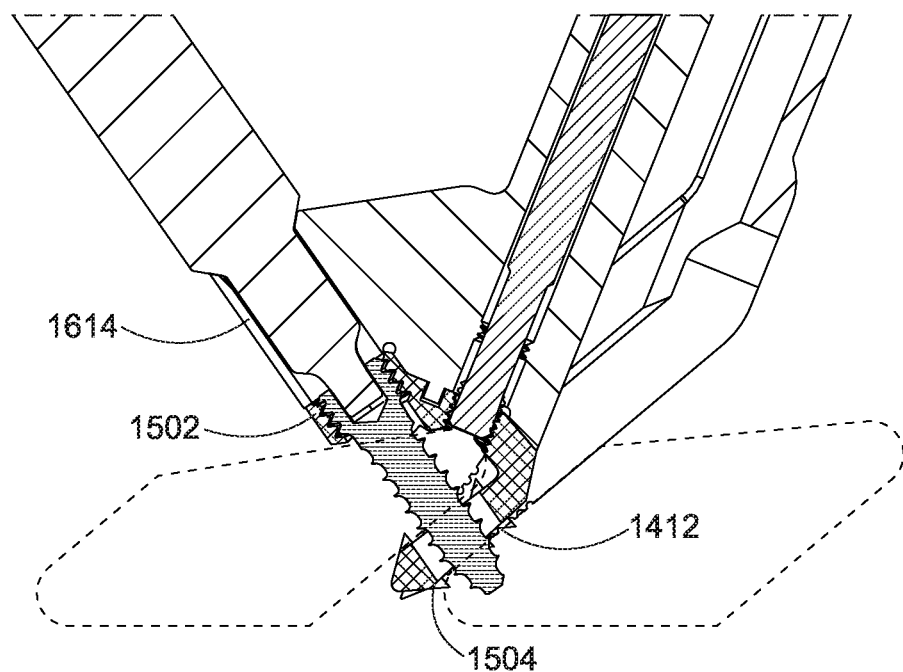
FIG. 26B is a cross-sectional view of the washer implant delivery tool and washer positioned in the placed position with a facet screw positioned to extend through the facet joint.

FIG. 26A is a perspective view of the washer implant delivery tool and washer implant. FIG. 26B is a cross-sectional view of the washer implant delivery tool and washer implant with a facet screw positioned to extend through the facet joint.

Once the pilot hole is drilled, the user may then insert the appropriately sized facet screw 1500 through the facet screw portal 1614 and advance the screw 1500 there through. The facet screw portal 1614 guides the facet screw 1500 to the proper fixed angle trajectory across the washer implant 1400 and the facet joint. The tightening of the head 1510 of the facet screw 1500 with the threaded portion 1406 of first portion 1402 of the washer implant 1400 in combination with the threaded elongated shaft 1512 engaging with the first or primary vertebra helps to compress the facet joint.

To release the washer implant 1400 from the actuation rod 1602 of the washer implant delivery tool 1600, a user will remove the drill bit from the facet screw portal 1614. The user will then rotatably engage the washer release knob

1604, thereby rotating the actuation rod 1602. As the washer release knob 1604 is rotated, the distal end of the actuation rod 1602 will disengage or unscrew from the threaded aperture 1408 of the washer implant 1400. Once the actuation rod 1602 is disengaged, a user may remove both the washer implant delivery tool 1600 and the facet access guide 1100 from the surgical space, and the washer implant 1400 will remain in place. The process can then be repeated for another facet joint if needed.

In some examples, a method of delivering a facet screw assembly to a facet joint using a facet screw assembly delivery system may include placing a facet access guide, such as or similar to facet access guide 1100, into the facet joint. The method may include detachably or removably coupling a washer sizer tool, such as or similar to washer sizer tool 1200, with the facet access guide. In some examples, the washer sizer tool may be slidably coupled with the facet access guide. An impact handle may then be disconnected from the facet access guide and detachably coupled to the washer sizer tool. The impact handle may then be impact to position the washer sizer tool in an appropriate location with respect to the facet joint.

The method may also include coupling a lateral mass decorticator guide, such as or similar to lateral mass decorticator guide 1300, with the washer sizer tool. The lateral mass decorticator guide may be slid down a shaft of the washer sizer tool to be positioned adjacent or contact a lateral mass of the facet joint.

The method may include advancing a decorticator through a tool guide of the lateral mass decorticator guide and decorticating the lateral mass.

The method may include measuring, by the alignment of the lateral mass decorticator guide and the washer sizer tool, a recommended facet screw assembly size for the facet joint. In some examples, the facet screw assembly may include components that are the same or similar to the facet screw 1500 and washer 1400.

The method may include decoupling the lateral mass decorticator guide and washer sizer tool from the facet access guide. The method may then include selecting a washer size and coupling the washer to a washer implant delivery tool. The washer implant delivery tool may then be slidably coupled to the facet access guide, and the impact handle may be coupled to the washer implant delivery tool. The washer implant delivery tool may then be impacted to position the washer into the facet joint.

The method may then include drilling a pilot hole across the facet joint for the facet screw.

The method may then include advancing a facet screw through the pilot hole and placing the facet screw across the facet joint. The method may include tightening the screw onto the washer and compressing the facet joint.

The method may then include decoupling the washer implant delivery tool from the facet screw assembly. The method may then include removing the washer implant delivery tool and facet access guide from the facet joint.

Figure 27:
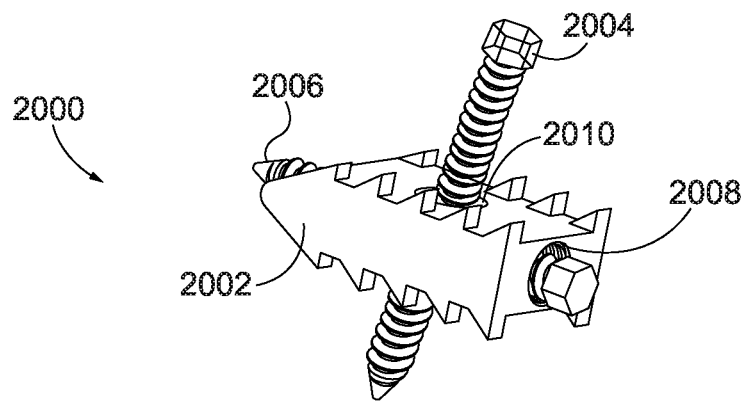
FIGS. 27-29B depict views of an implant that may be used with embodiments according to the present disclosure.
Figure 28:
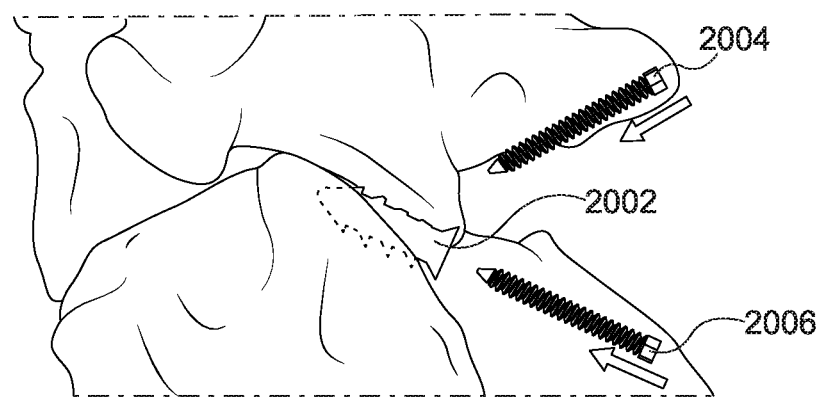
Figure 29A:
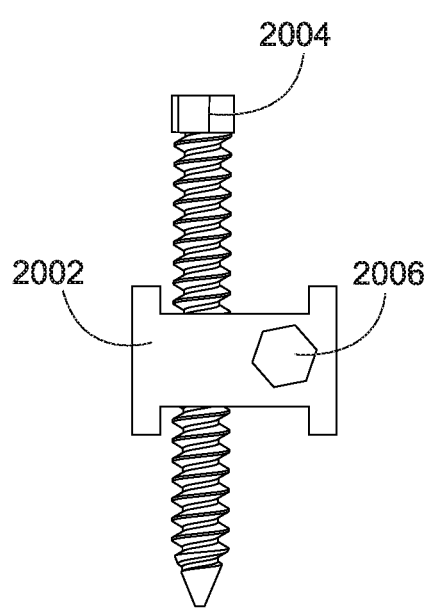
Figure 29B:
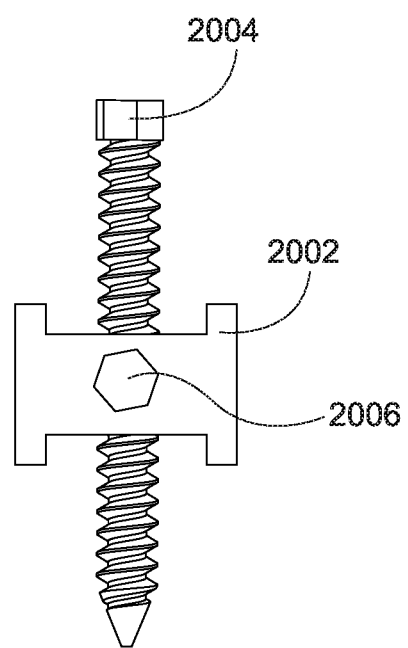
Figure 30:
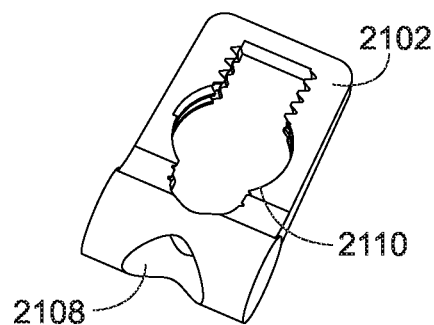
FIGS. 30-32B depict views of an implant that may be used with embodiments according to the present disclosure.
Figure 31A:
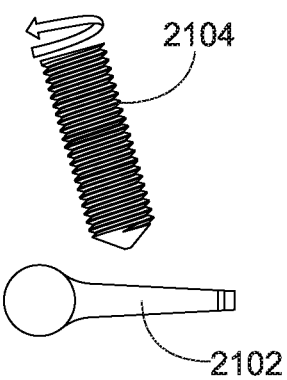
Figure 31B:
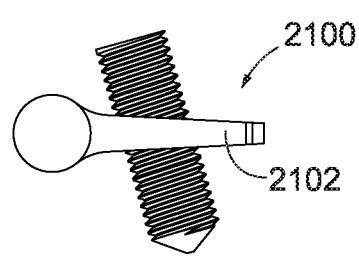
Figure 31C:
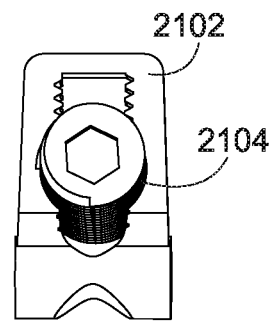
Figure 32A:
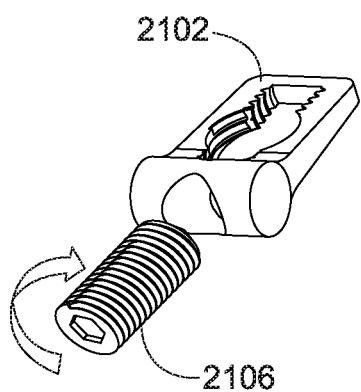
Figure 32B:
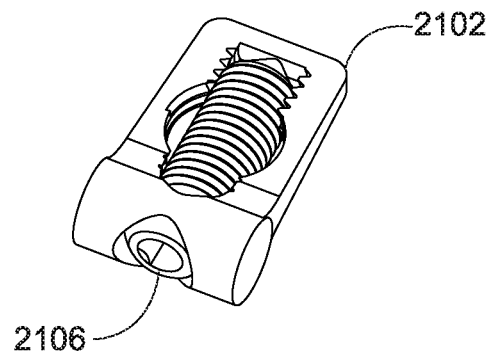
Figure 33:
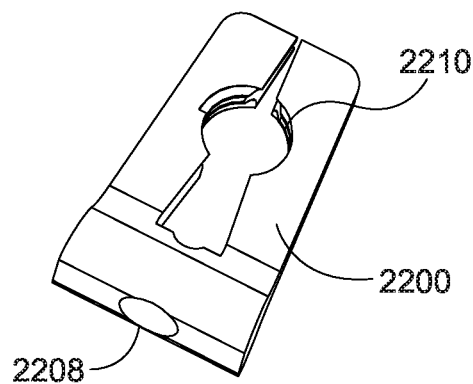
FIGS. 33-35B depict views of an implant that may be used with embodiments according to the present disclosure.
Figure 34A:
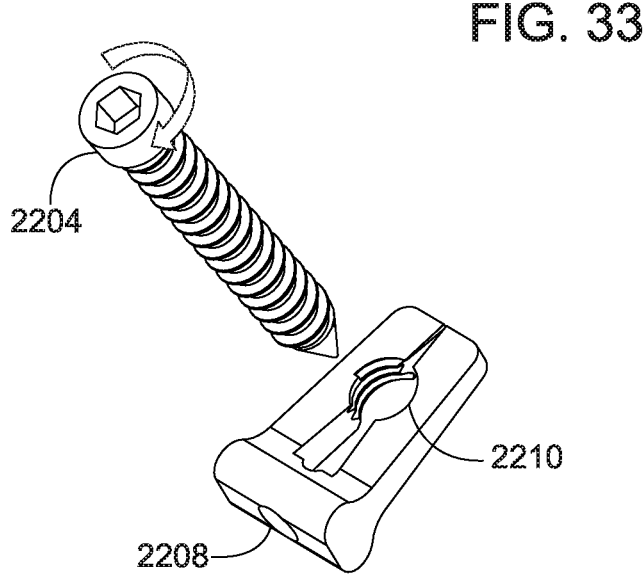
Figure 34B:
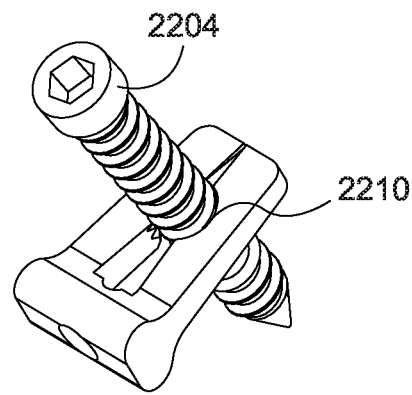

FIGS. 27-29B depict views of an implant that may be used with embodiments according to the present disclosure. FIG. 27 is an isometric view of the implant, and FIG. 28 is a view of the implant within the facet joint space between adjacent vertebra. The implant 2000 may include a washer 2002, a trans-facet screw 2004, and an intra-facet screw 2006. The washer 2002 may include two threaded apertures and the washer may have a generally constant thickness from a first end to a second end. An intra-facet threaded aperture 2008 extending through a length of or along a longitudinal axis of the washer 2002 includes internal threads that correspond to the external threads of the intra-facet screw 2006. A trans-facet aperture 2010 extending through a width of or along a transverse axis of the washer 2002 has internal threads that correspond to the external threads of the trans-facet screw 2004. When in use, the washer 2002 is inserted into a facet joint space and allows for modular compatibility for placement of the intra-facet screw 2006 and/or the placement of the trans-facet screw 2004. As shown in FIGS. 29A and 29B, the positioning of the threaded apertures 2008, 2010 allow for either a combination of the two screws (intra-facet screw 2006 and trans-facet screw 2004 in FIG. 29A), or a single screw placement (either an intra-facet screw 2006 or a trans-facet screw 2004 in FIG. 29B.)

FIGS. 30-32B depict views of an implant that may be used with embodiments according to the present disclosure. The implant 2100 of FIGS. 30-32B may be similar to the implant 2000 of FIGS. 27-29B, with intra-facet threaded aperture 2108 and a trans-facet threaded aperture 2110. A washer 2102 may have a reduced thickness, with the height of the washer at a first end being larger or greater than the height of a second end of the washer along the length of the intra-facet threaded aperture 2108. The reduced thickness of the washer 2102 may allow for more intra-facet and trans-facet screw engagement. The washer may include one or more teeth on the top and bottom surfaces to provided retention of the intra-facet surfaces of the facet joint.

In some embodiments, the diameter of the trans-facet threaded aperture 2108 and corresponding trans-facet screw 2104 (FIGS. 31A-31C) is larger or greater than the intra-facet threaded aperture 2110 and corresponding intra-facet screw 2106 (FIGS. 32A-32B) to allow thread engagement for both screws.

Figure 35A:
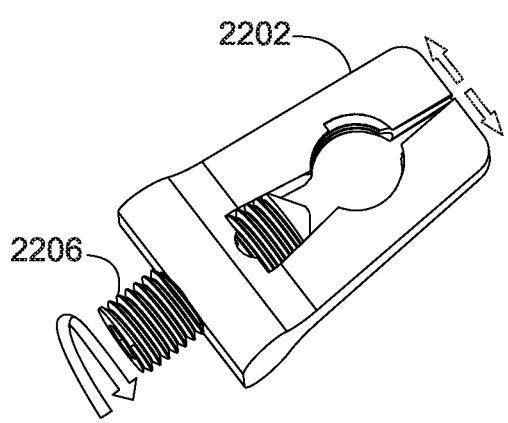
Figure 35B:
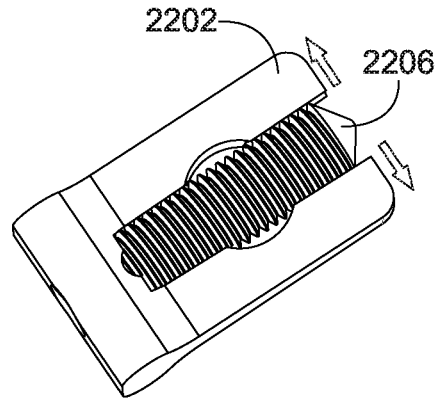

FIGS. 33-35B depict views of an implant that may be used with embodiments according to the present disclosure. The implant 2200 of FIGS. 33-35B may be similar to the implant 2000, 2100 of FIGS. 27-32B, with intra-facet threaded aperture 2208 and a trans-facet threaded aperture 2210. As shown in FIGS. 35A, 35B, a second end of the washer 2202 may expand in a width-direction as the intra-facet screw 2206 is inserted. The expanding washer 2202 may allow the diameter of the trans-facet screw 2204 (FIGS. 34A-34B) to be reduced in relation to the diameter of the intra-facet screw 2206 (FIGS. 35A-35B). The washer may include one or more teeth on the top and bottom surfaces (such as the teeth shown on the washer of FIG. 36) to provide retention of the washer at the intra-facet surfaces within the facet joint.

Figure 36:
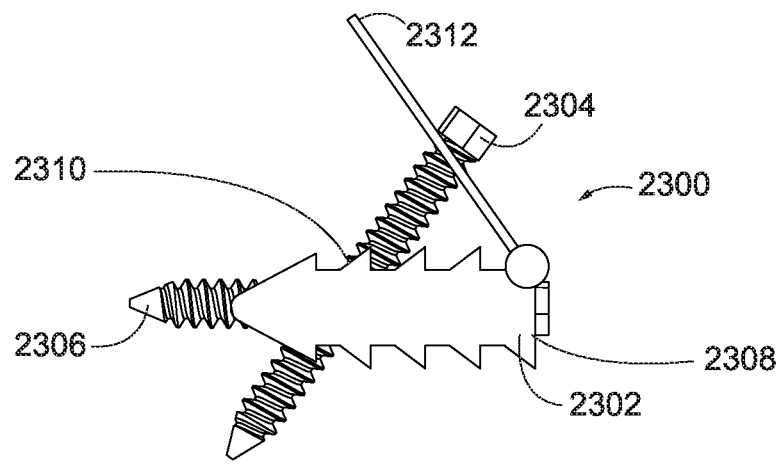
FIGS. 36-37D depict views of an implant that may be used with embodiments according to the present disclosure.
Figure 37A:
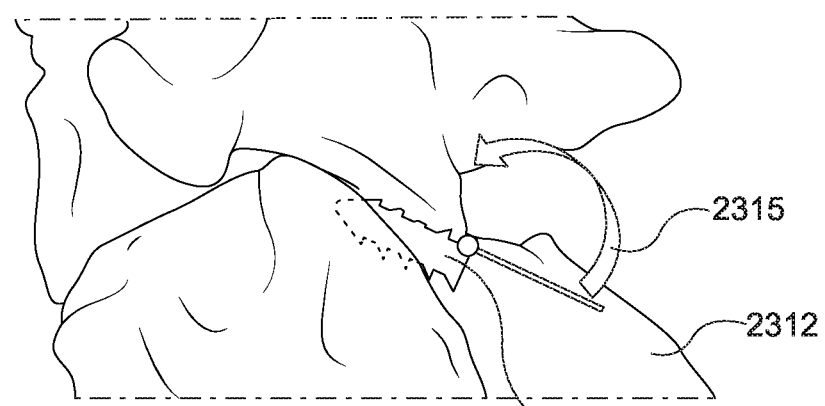
Figure 37B:
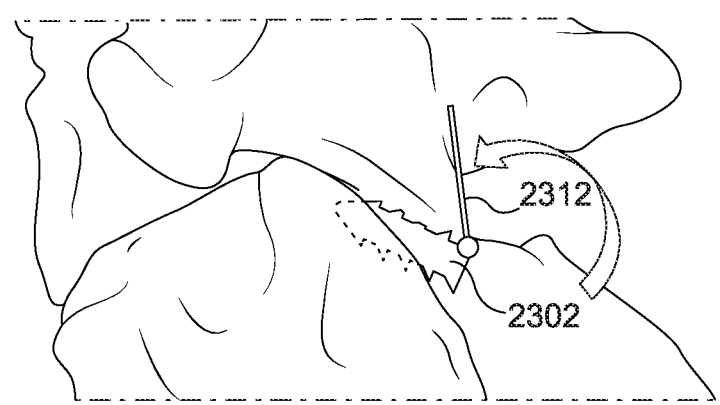
Figure 37C:
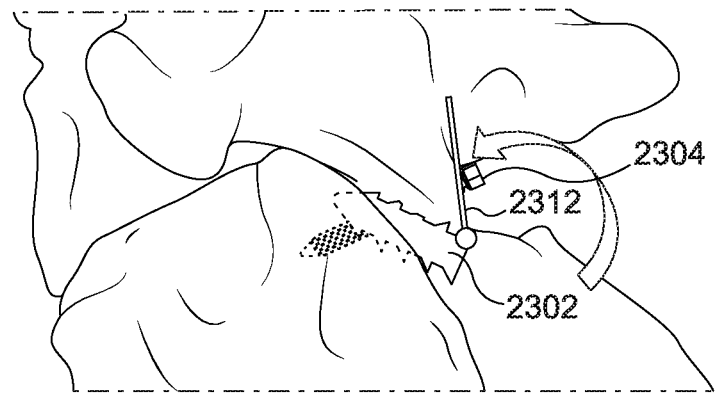
Figure 37D:
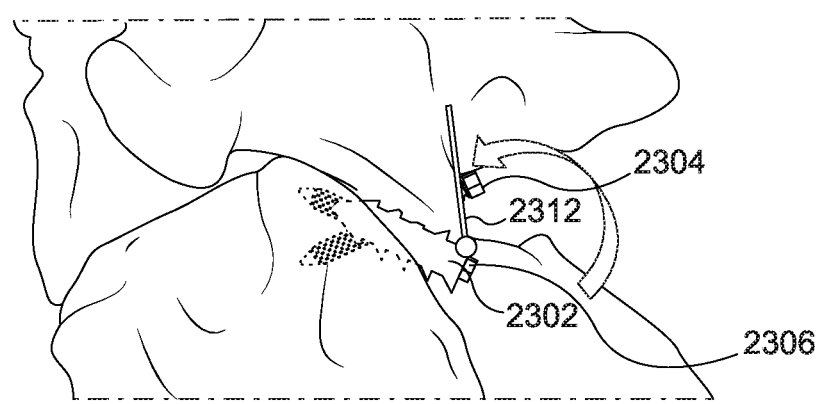

FIGS. 36-37D depict views of an implant that may be used with embodiments according to the present disclosure. The implant 2300 of FIGS. 36-37D may be similar to the implant 2000 of FIGS. 27-29B, with intra-facet threaded aperture 2308 and a trans-facet threaded aperture 2310. The implant 2300 may also include a pivoting plate 2312 which may be rotatably coupled to the first end of the washer 2302. The pivoting plate may include a trans-facet aperture that allows the trans-facet screw 2304 to be inserted through a portion of the pivoting plate 2312. The trans-facet aperture in the pivoting plate 2312 may be threaded or a thru-hole. The pivoting plate 2312 may pivot about the first end of the washer 2302. The plate 2312 may provide trans-facet screw alignment assistance of the trans-facet screw 2304 to the washer 2302. As shown in FIG. 37A, the washer 2302 may be inserted in the facet joint space. The plate 2312 may then be pivoted in the direction of arrow 2315 so that it contacts the lateral mass of the adjacent vertebra, as shown in FIG. 37B. As shown in FIG. 37C, the trans-facet screw 2304 may then be inserted through the trans-facet aperture of the pivoting plate, through the lateral mass of the adjacent vertebra, through the intrafacet surface of the adjacent vertebra, through the washer 2302, through the intrafacet surface of the vertebra, and into the lateral mass of the vertebra. As shown in FIG. 37D, the intra-facet screw 2306 may then be inserted through the washer 2302. In some examples, the trans-facet screw 2304 includes a head that may be positioned against the pivoting plate 2312 when the trans-facet screw 2304 is deployed across the facet joint to further compress the pivoting plate 2312 against the lateral mass of the adjacent vertebra.

FIGS. 38A-38E depict views of an implant and delivery device that may be used with embodiments according to the present disclosure. The implant may include the washer 2302, the intra-facet screw 2306, and the trans-facet screw 2304. The delivery device 2320 may include a washer guide tube 2350 and an intra-facet inserter 2352, an additional screw guide tube 2356 and trans-facet screw inserter 2354, and an alignment tool 2358.

Figure 38A:
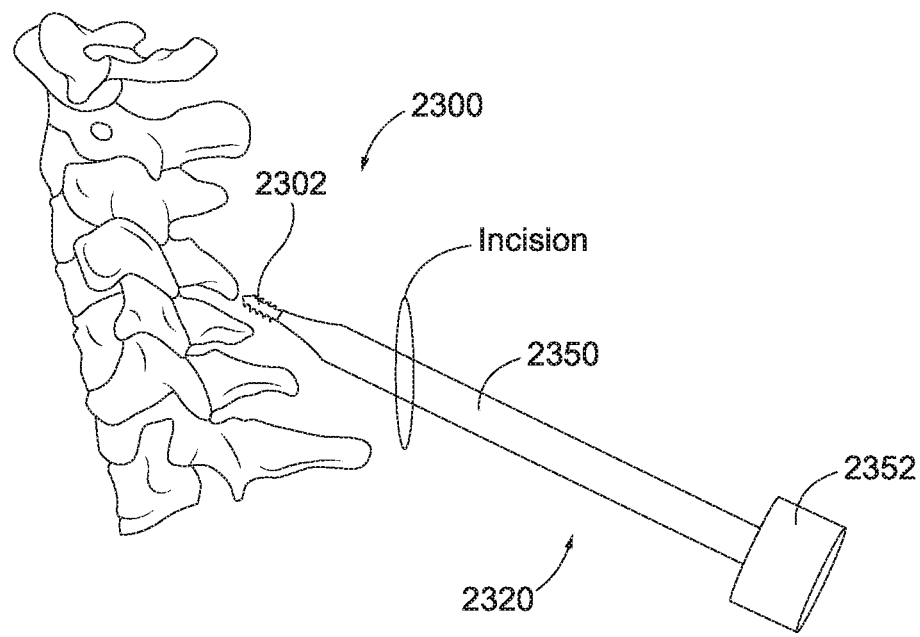
FIGS. 38A-38E depict views of an implant and delivery device that may be used with embodiments according to the present disclosure.
Figure 38B:
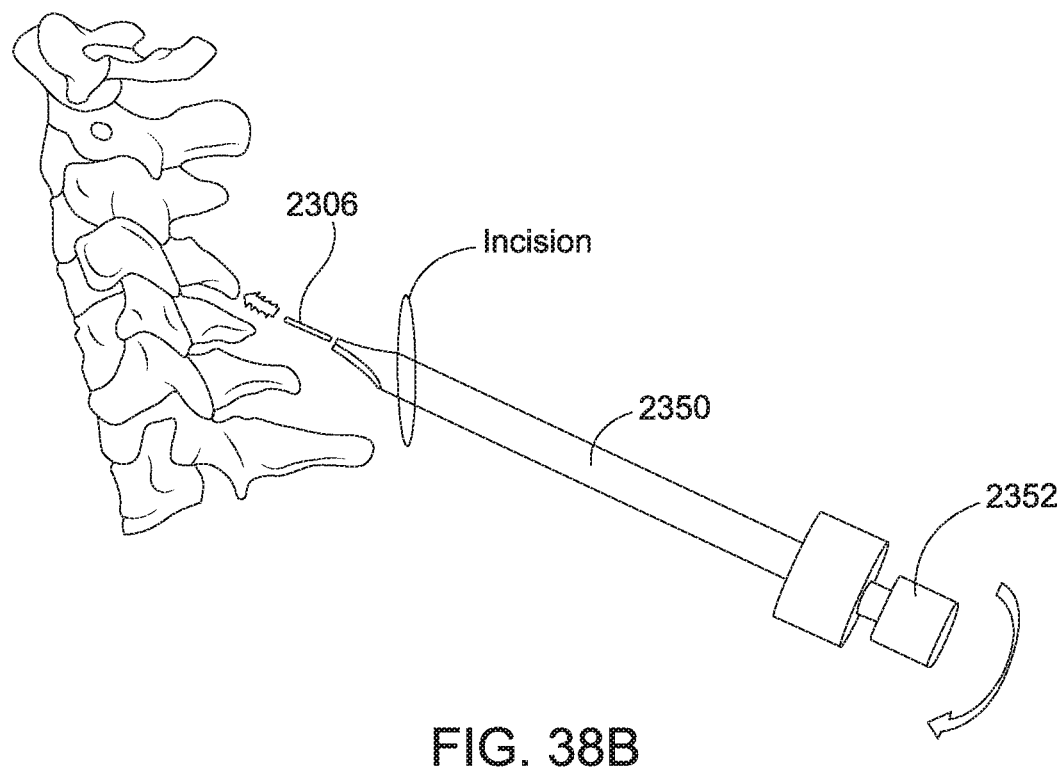
Figure 38C:
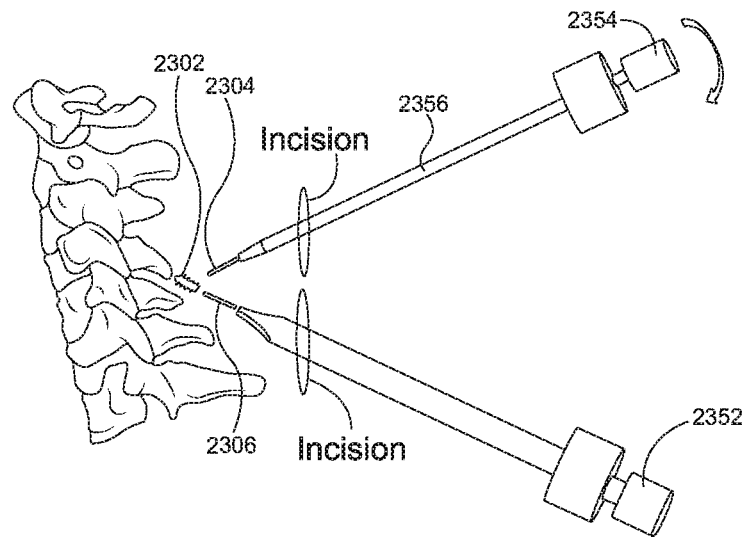
Figure 38D:
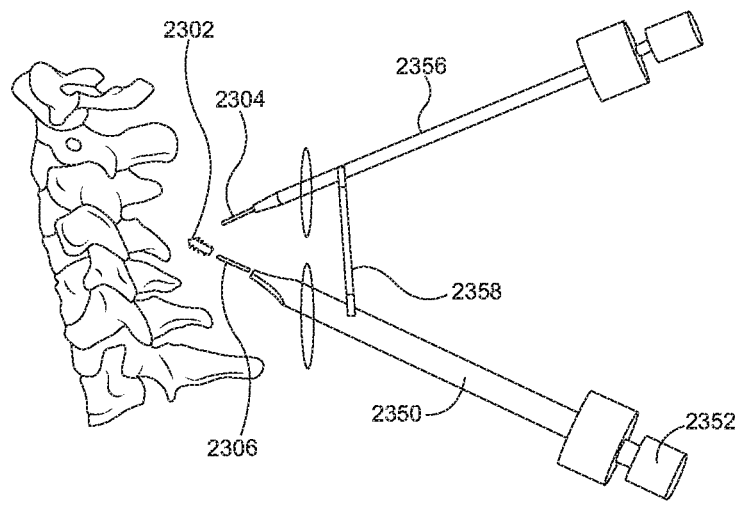
Figure 38E:
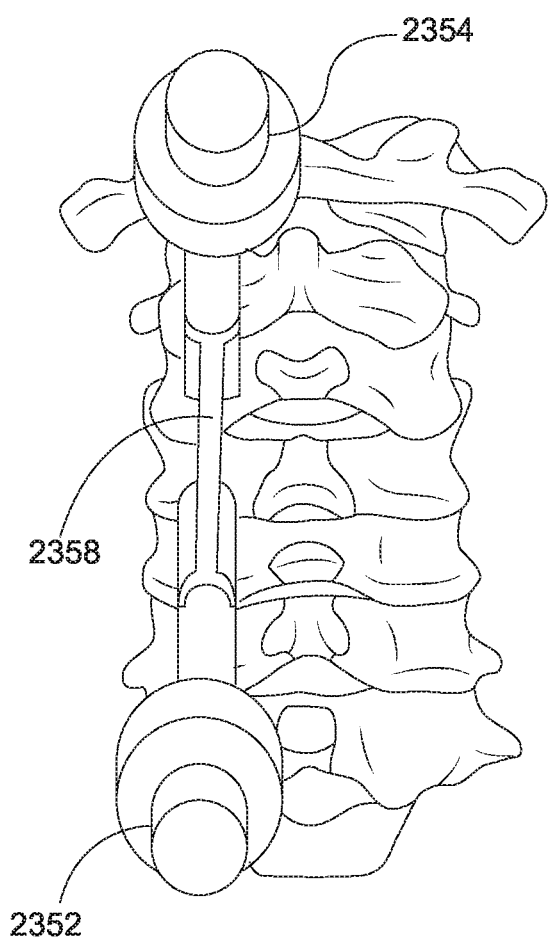

As shown in FIG. 38A, an incision may be made and the washer 2302 will be inserted through the incision and into the facet joint via the guide tube 2350. In FIGS. 38A-38E, the washer depicted outside the facet joint to allow for better visualization of the insertion process. As shown in FIG. 38B, the intra-facet screw 2306 may be inserted through the washer guide tube 2350 and driven into the washer 2302 via rotation of the intra-facet inserter 2352. As shown in FIG. 38C, the trans-facet screw 2304 may be inserted through a separate incision and through the lateral mass of an adjacent vertebra and driven into the washer 2302. The trans-facet screw 2304 may be driven through the washer 2302 and into the lateral mass via rotation of the trans-facet screw inserter 2354 in the screw guide tube 2356. As shown in FIG. 38E, in some examples, an alignment tool 2358 can be attached or coupled to the screw guide tube 2356 and the washer guide tube 2350 to help vertically align the trans-facet screw 2304, the intra-facet screw 2306, and the washer 2302. Once the screws are placed, the delivery device 2320 is removed, leaving the washer 2302, the intra-facet screw 2306, and trans-facet screw 2304 placed in the facet joint space.

FIGS. 39A-41D depict views of an implant and delivery device that may be used with embodiments according to the present disclosure. The implant 2400 is shown in an exploded view (FIG. 39A), a view depicting a first configuration (FIG. 39B), and a view depicting a deployed configuration or position (FIG. 39C). FIGS. 40A-40D show views of the implant 2400 in an assembled view (FIG. 40A), a view in a semi-deployed position or configuration (FIG. 40B), a view in a fully deployed position or configuration (FIG. 40C), and a cross-sectional view of the assembled view (FIG. 40D), respectively.

In some examples the implant 2400 includes a facet screw 2402, an expandable spacer 2404, and a compression nut 2406. As shown in FIGS. 39A and 40D, the facet screw may include a first end 2410 that is keyed to align with a keyway or socket feature on a driver 2412, and a tapered threaded end 2408 opposite the first end 2410. Located along the shaft of the screw 2402, between the first end 2410 and the tapered threaded end 2408, may be a threaded portion 2414.

When assembled, the expandable spacer 2404 may be coupled to the facet screw 2402 as to help prevent rotational movement of the spacer relative to the screw 2402. In some examples, the spacer 2404 may be welded or keyed to the screw 2402. The expandable spacer 2404 may be generally cylinder shaped or cylindrical, with an inner diameter that is larger or greater than the shaft diameter of the facet screw 2402. This may allow the spacer 2404 to slide along the shaft of the facet screw 2402 and abut the threaded end 2408, such as in the configuration shown in FIGS. 39B and 40A.

Figure 41C:
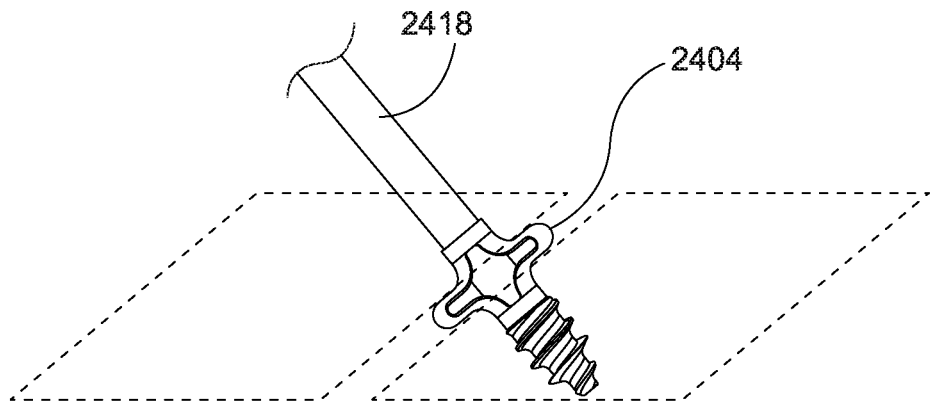
Figure 41D:
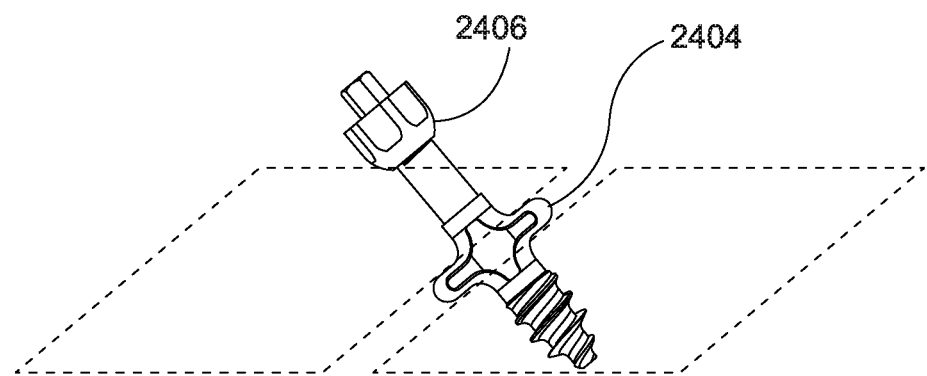

In use, such as in the deployed position or configuration shown in FIGS. 39C and 41C-41D, the spacer 2404 may be compressed and expanded outward from a central axis or central longitudinal axis of the spacer. Once deployed, the internal threads of the compression nut 2406 may be coupled to the threaded portion 2414 of the screw 2402 to fix the screw 2402 across the facet joint.

In use, as shown in FIG. 40D, the threaded screw holder 2412 is inserted through a lumen or portal in a guide tube 2418. The expandable sleeve 2404 is positioned about the shaft of the screw 2402. The facet screw 2402 may then be detachably coupled at end 2410 to the threaded screw holder 2412. In some examples, the end 2410 includes an internal threaded end configured to engage the threads of the threaded screw holder. The screw 2402 may then be inserted in a trans-facet direction into the facet joint, as shown in FIG. 41A. The outer sleeve 2418 is then deployed to compress the spacer 2404. The spacer 2404 expands partially (FIG. 41B) and then fully (FIG. 41C) to help distract the joint and maintain the distracted position. The threaded screw holder 2412 is then disengaged from the screw 2402, and the outer sleeve 2418 and threaded screw holder 2412 are removed. As shown in FIG. 41D, the compression nut 2406 is then threadably coupled to the screw 2402 to fixate the screw 2402 across the facet joint.

Figure 42A:
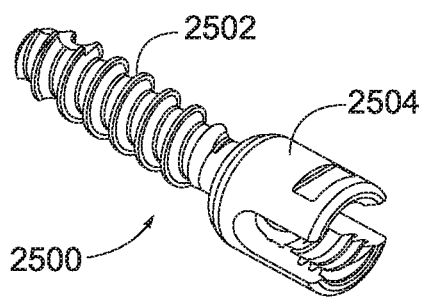
FIGS. 42A-42B depict views of an implant that may be used with embodiments according to the present disclosure
Figure 42B:
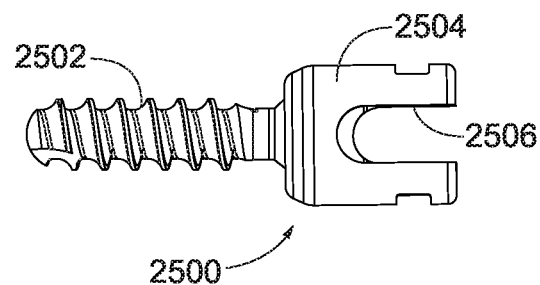

FIGS. 42A-42B depict views of an implant that may be used with embodiments according to the present disclosure. FIGS. 42A and 42B are an isometric and side view of an implant 2500. In some examples, the implant 2500 includes a screw 2505 and a head 2504. The head 2504 may be formed as a polyaxial head structure, such as a captured ball joint, and may be designed to accept a posterior fixation rod (see 2508 in FIG. 43A), such as in a notch 2506.

Figure 43A:
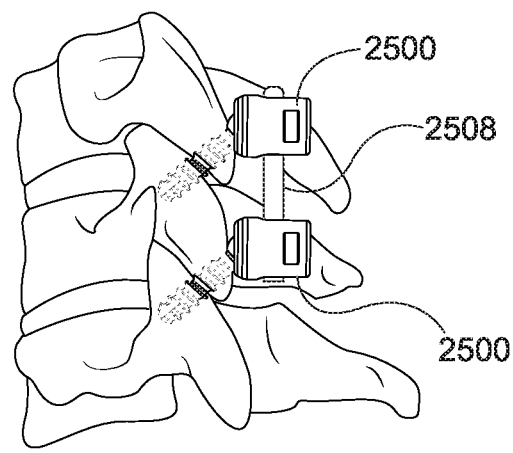
FIGS. 43A-43B depict views of the implant of FIGS. 42A-42B in use in a trans-facet deployment.
Figure 43B:
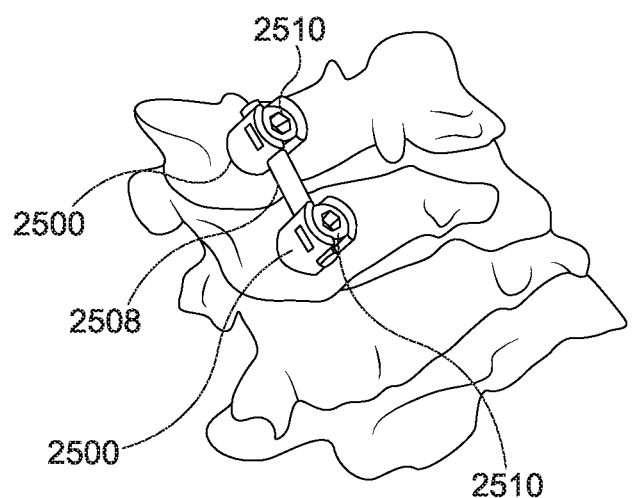

FIGS. 43A-43B depict views of the implant of FIGS. 42A-42B in use in a trans-facet deployment. FIG. 43A is a side view of two deployed implants, while FIG. 43B is a perspective view of FIG. 43A. In use, in some examples, after initial preparation of the surgical site to expose the target area, a pilot hole is drilled with a trajectory that spans the two vertebral bodies across the facet joint. Once the implant 2500 is deployed across the facet joint, the polyaxial head 2504 can be rotated such that the rod receiving feature 2506 is in line with the spinal axis. A second implant 2500 may now be deployed across the adjacent facet joint. The heads 2504 of each implant 2500 may then be connected at their respective notches 2506 with an appropriately sized rod component 2508. The rod 2508 is then held in place via a set screw 2510 (FIG. 43B), which also locks the polyaxial head 2504 in the desired position. In use, multiple implants 2500 may be placed in adjacent vertebra, and then connected or coupled with a rod of appropriate length.

Figure 44A:
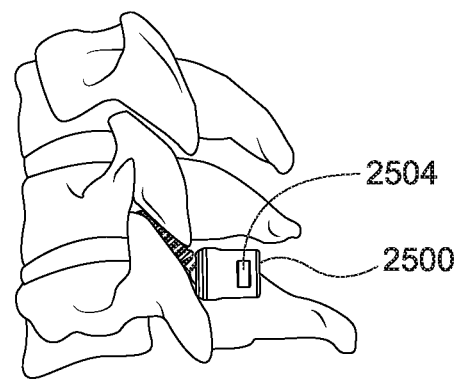
FIGS. 44A-44E depict views of the implant of FIGS. 42A-42B in use in an intra-facet deployment.
Figure 44B:
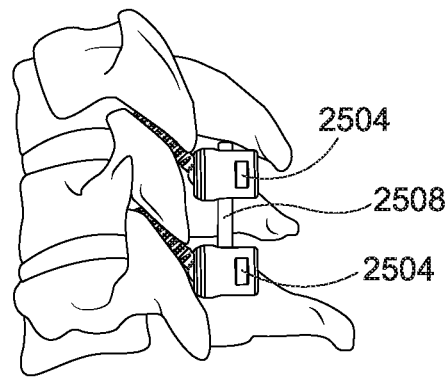
Figure 44C:
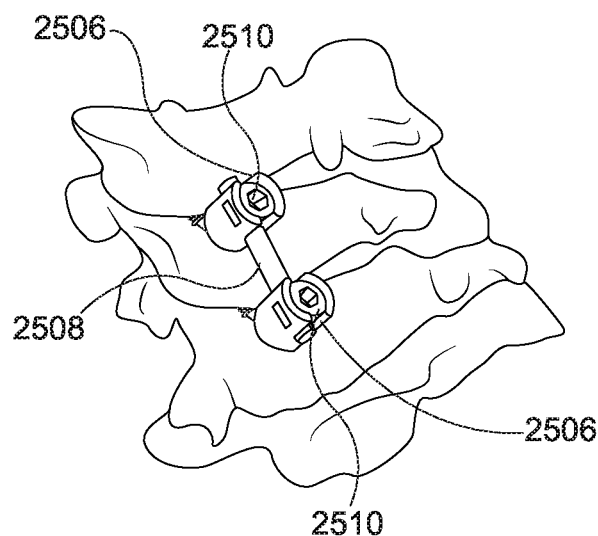

FIGS. 44A-44E depict views of the implant of FIGS. 42A-42B in use in an intra-facet deployment. FIG. 44A is a side view of a single deployed implant. FIG. 42B is a side view of two deployed implants. FIG. 44C is a perspective view of FIG. 44B. After initial preparation of the surgical site to expose the target area, the implant 2500 is deployed with a trajectory that is parallel to the facet joint opening, with the shaft of the screw 2502 driven in between the two bone surfaces of the facet joint. Once deployed into the facet joint, the polyaxial head 2504 can be rotated such that the rod receiving feature 2506 is in line with the spinal axis, as shown in FIG. 44A. A second implant 2500 may now be deployed with a trajectory that is parallel to the adjacent facet joint opening. The heads 2504 of each implant 2500 may then be connected at their respective notches 2506 with an appropriately sized rod component 2508. The rod 2508 is then held in place via a set screw 2510, which also locks the polyaxial head 2504 in the desired position. In use, multiple implants 2500 may be placed in adjacent vertebra, and then connected or coupled with a rod of appropriate length.

Figure 44D:
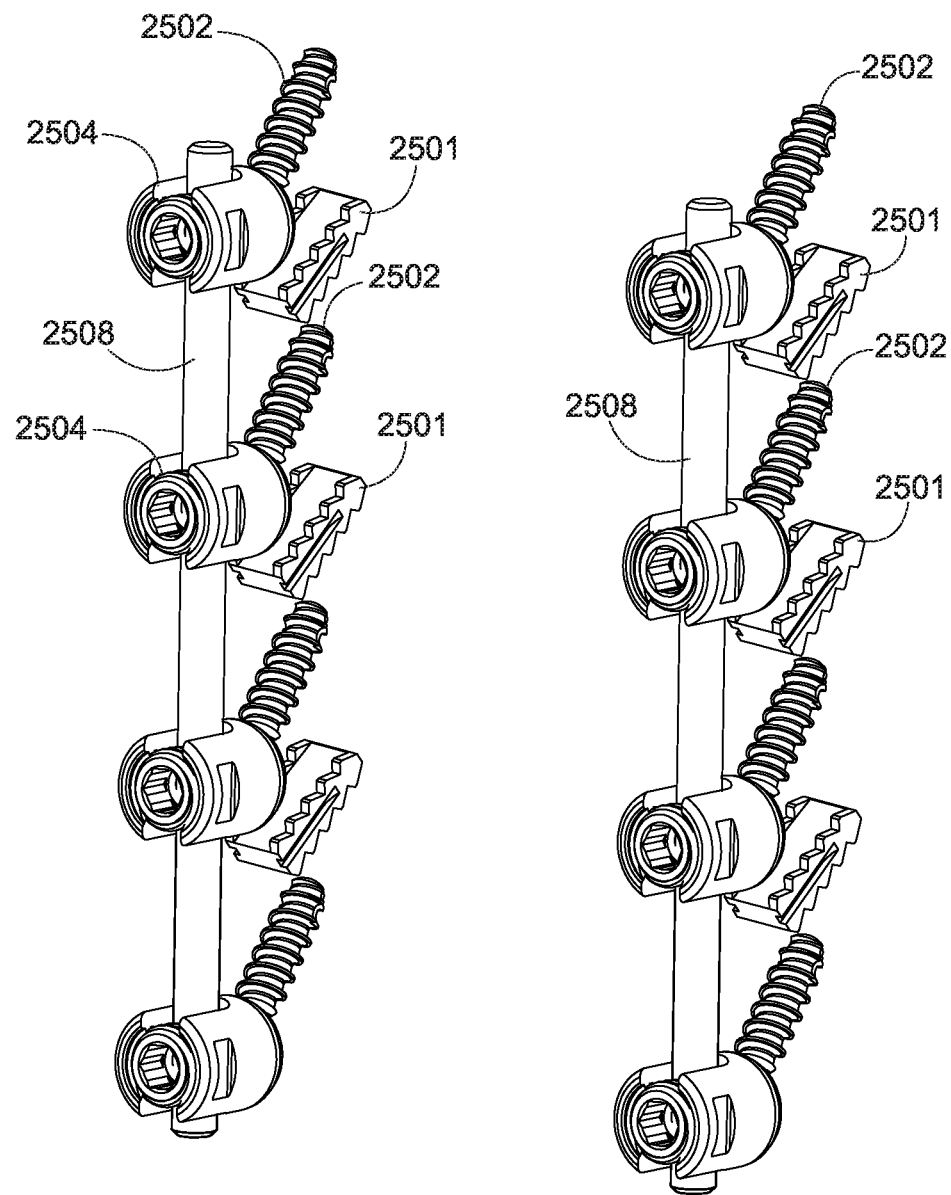
Figure 44E:
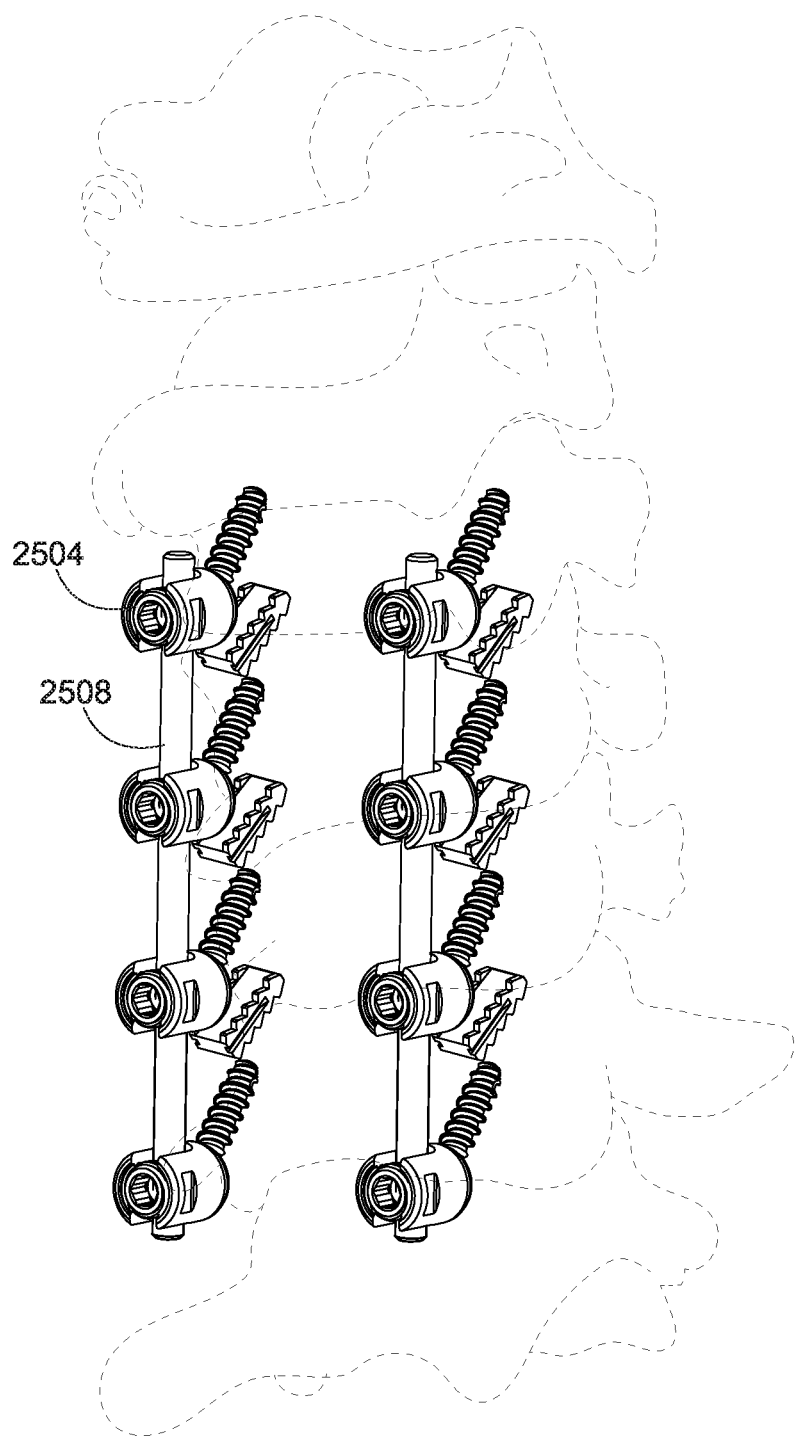

FIGS. 44D and 44E depict views of the implant of FIGS. 42A-42C in use in an intra-facet deployment. FIG. 44D is a perspective view of implants 2500 connected by rods 2508, and FIG. 44E is a perspective view of FIG. 44D as deployed in a spine. The assembly of FIGS. 44D-44E may also include a cage implant 2501. When deployed, each cage implant 2501 may be deployed in an intra-facet manner, in between the two bone surfaces of the facet joint, adjacent to implants 2500. A similar assembly may be used for a next series of adjacent vertebra and facet joint. In some examples, a similar assembly may be used on the left and right sides of each vertebra.

FIGS. 45A-49C depict views of an implant and delivery device that may be used with embodiments according to the present disclosure.

Figure 45A:
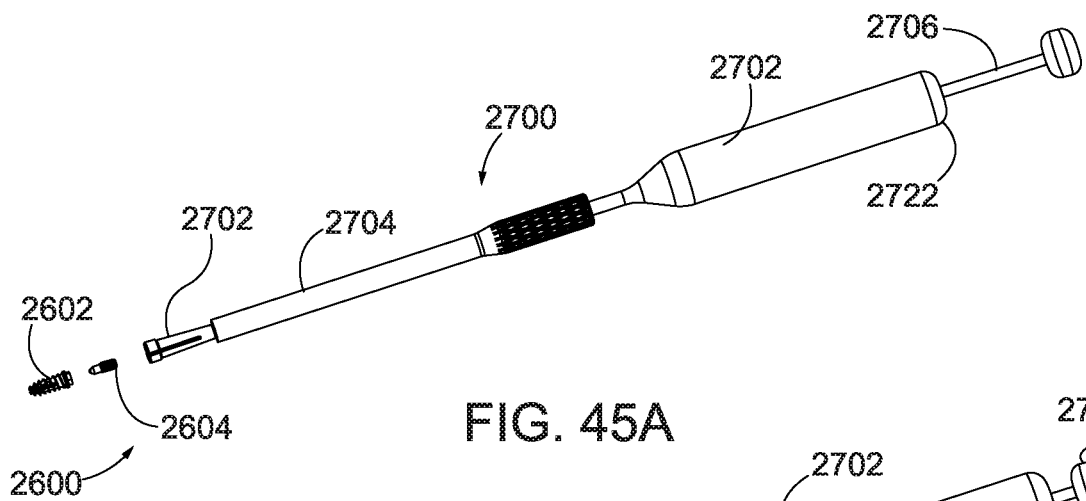
FIGS. 45A-49C depict views of an implant and delivery device that may be used with embodiments according to the present disclosure.
Figure 45B:
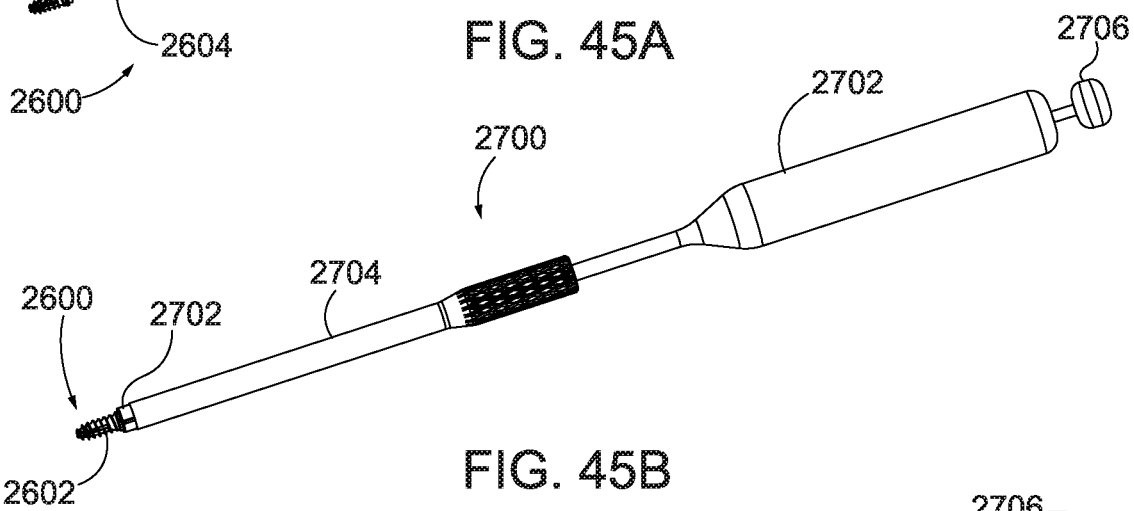
Figure 45C:
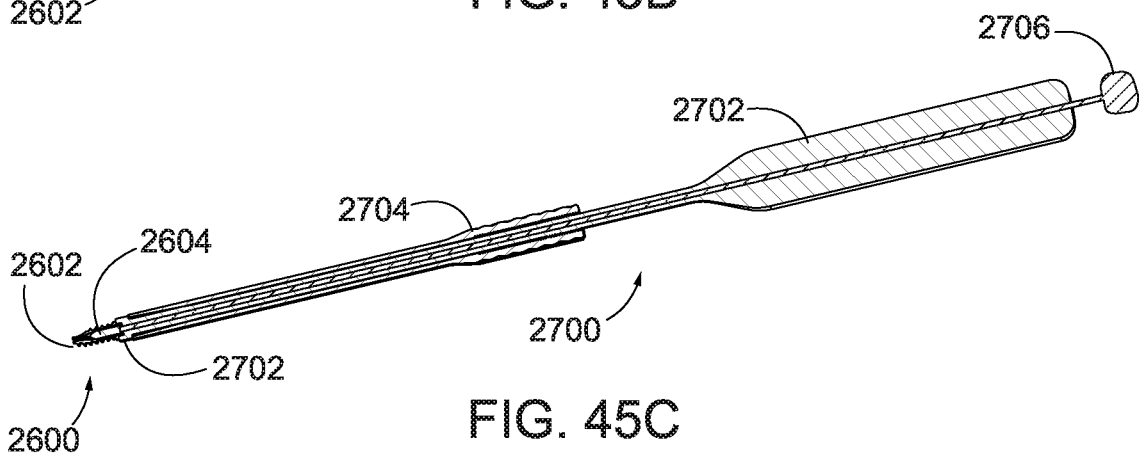
Figure 45D:
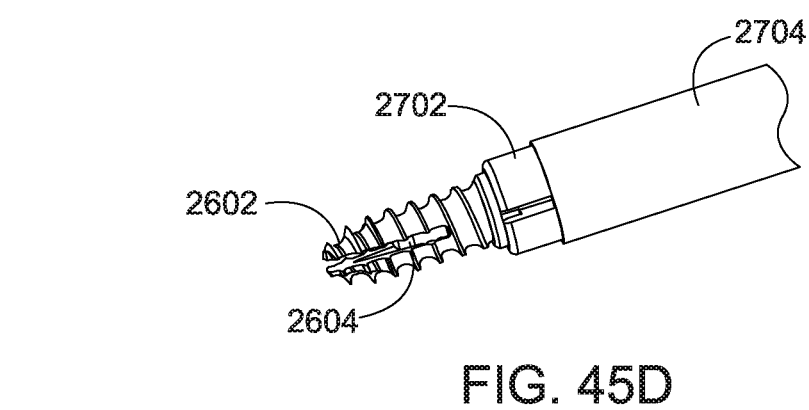

FIGS. 45A-45F includes views of an implant 2600 and delivery device 2700. In some examples, the implant 2600 includes a screw 2602 and a screw expander 2604. The delivery device 2700 may include a screw driver 2702, a screw driver locking collar 2704, and a screw expander driver 2706. FIG. 45A is an exploded view of the implant 2600 and delivery device 2700. FIG. 45B is a perspective view of the implant 2600 and delivery device 2700, and FIG. 45C is a cross-sectional view of FIG. 45B. FIG. 45D is an enlarged view of a portion of FIG. 45B, with FIG. 45E a cross-sectional view of FIG. 45D. FIG. 45F is a semi-expanded view of the implant 2600 and delivery device 2700 of FIG. 45B with the screw driver locking collar 2704 minimized.

As shown in FIG. 45C, in an assembled position, the screw expander 2604 is positioned within the screw 2602. The screw expander driver 2706 fits within a lumen of the screw driver 2702. A portion of the screw driver 2702 fits within a lumen of the screw driver locking collar 2704.

As shown in FIG. 45E, the screw expander driver 2706 includes a first end 2612, a shaft 2626, and a second end 2616. In an assembled position, the second end 2728 of screw expander driver 2706 engages the first end 2612 of the screw expander 2604. An end 2718 of the screw driver 2702 engages with the screw 2602.

Details of the screw 2602 and screw expander 2604 are shown in FIGS. 45E-46E. FIGS. 46A-46B are side and cross-sectional views of the implant 2600. FIG. 46C is a side view of the implant 2600 in a splayed configuration. As shown in FIG. 45E, screw expander 2604 includes external threads 2620 that extend from the first end 2610 and about a portion of the shaft 2626. The second end 2616 of screw expander 2604 is tapered, and the portion of the shaft 2626 adjacent the second end 2616 is smooth, with an external diameter that is smaller than the outer-diameter of the external threads 2620.

As shown in FIGS. 45E-46C, the screw 2602 includes a first end 2610 and a second end 2614. The first end 2610 includes a key feature 2618 (FIGS. 45E and 46D), such as a hex feature. The screw 2602 is hollow and/or has a lumen 2628 extending through its center. The lumen 2628 has a taper 2630 that expands as it extends from adjacent the second end 2614 towards first end 2610. The lumen 2628 also includes internal threads 2622 extending from the first end 2610 towards the taper 2630. The internal threads 2622 are shaped to receive and engage the external threads 2620 of screw expander 2604. The screw 2602 includes external threads 2624 which extend from adjacent the first end 2610 and towards the second end 2614. Adjacent the second end 2614 of the screw 2602, the outer diameter and external threads 2624 taper. A slot 2608 extends from the second end 2614 towards the first end 2610, extending through the taper 2630 and a portion of the internal threads 2622 and external threads 2624.

Figure 46D:
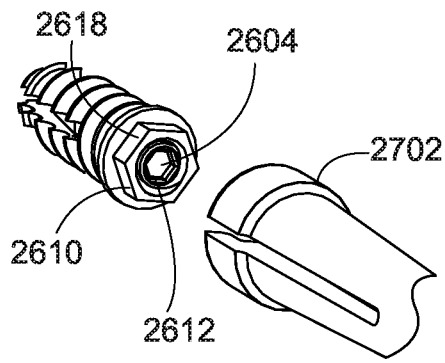
Figure 46E:
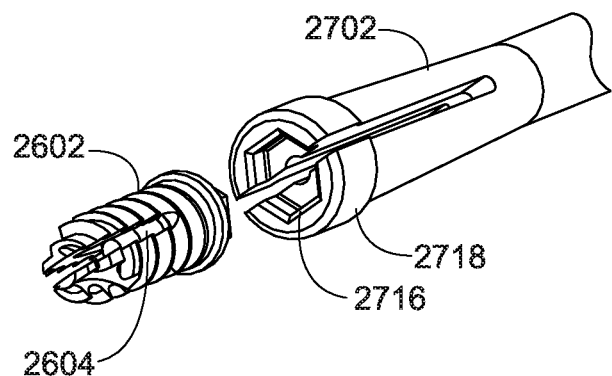
Figure 47A:
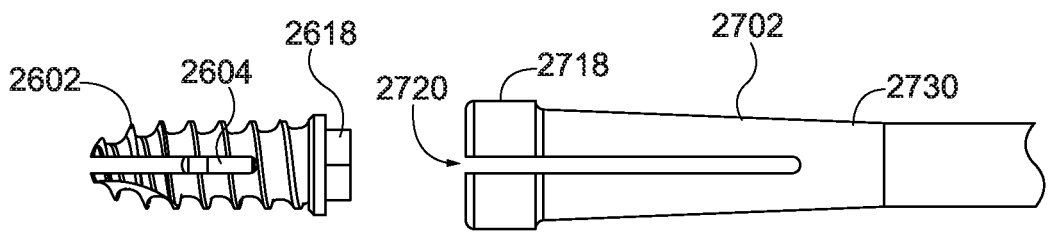
Figure 47B:
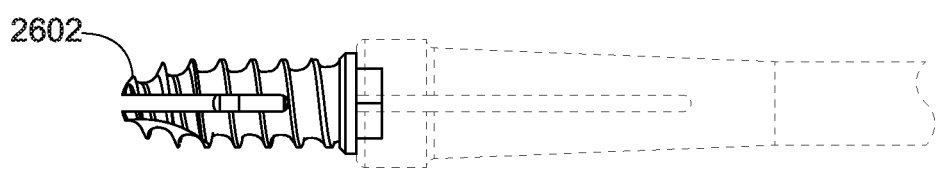

Details of the engagement between the implant 2600 and the screw driver 2702 are shown in FIGS. 46D-47B. FIGS. 46D and 46E are front and rear perspective views of the implant 2600 and a second end 2718 of the screw driver 2702. FIGS. 47A and 47B are exploded and assembled cross-sections views of the implant 2600 and the second end 2718 of the screw driver 2702, with the end of the screw driver 2702 shown in dash in FIG. 47B. The first end 2610 of the screw 2602 includes the key 2618, such as an external hex feature or shape. The second end 2718 of the screw driver 2702 includes a keyway 2716, such as an internal hex feature. In use, the keyway 2716 may be used to engage with the key 2618. The key 2618 and keyway 2716 may help orient the screw 2602 to the screw driver 2702 and to transfer any rotational force and/or movement from the screw driver 2702 to the screw 2602. In an initial state or first configuration, the second end 2718 of the screw driver 2702 has enough clearance to accept a first end of the screw assembly 2600, such as the first end 2610 of the screw 2602.

As is also shown in FIGS. 47A-B, the screw driver 2702 includes a taper 2730 adjacent the second end 2718. A slot 2720 extends from the second end 2718 and through a majority of the taper 2730.

Figure 48A:
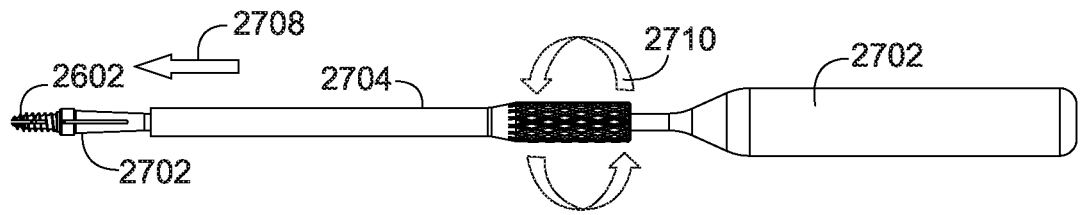
Figure 48B:
Figure 48C:
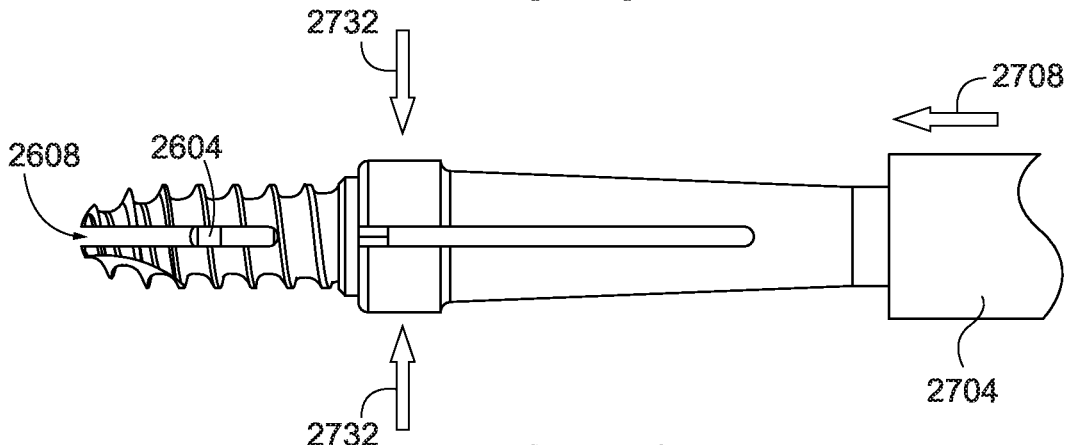
Figure 48D:
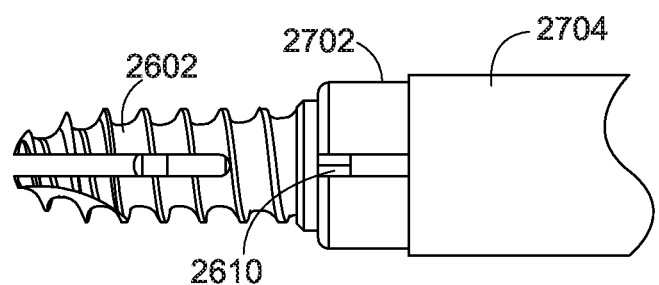
Figure 49A:
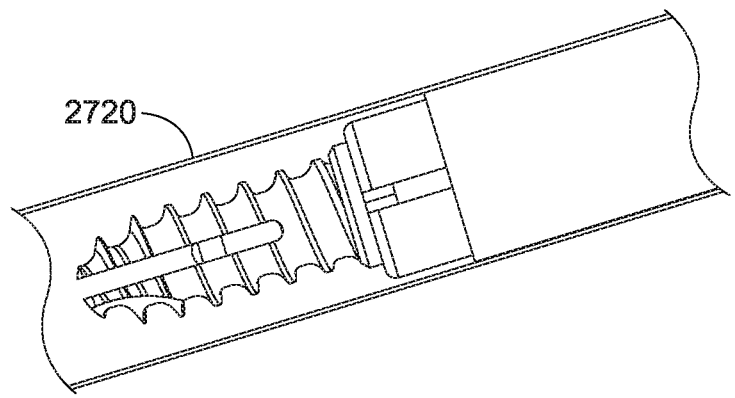
Figure 49B:
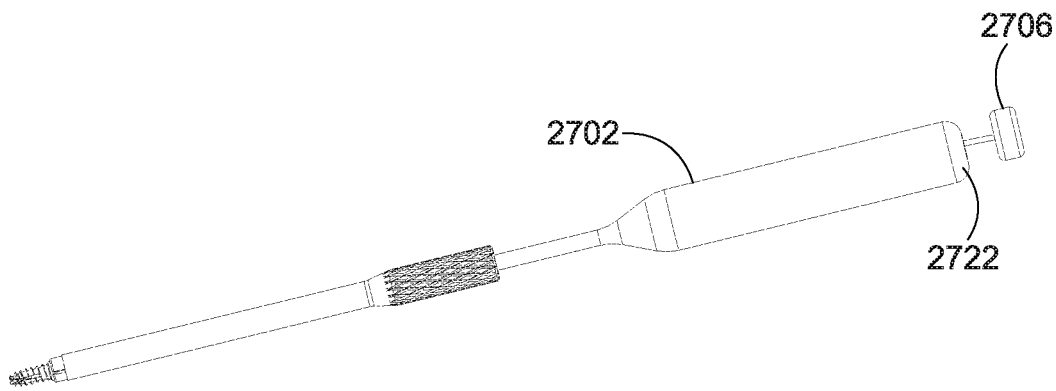
Figure 49C:
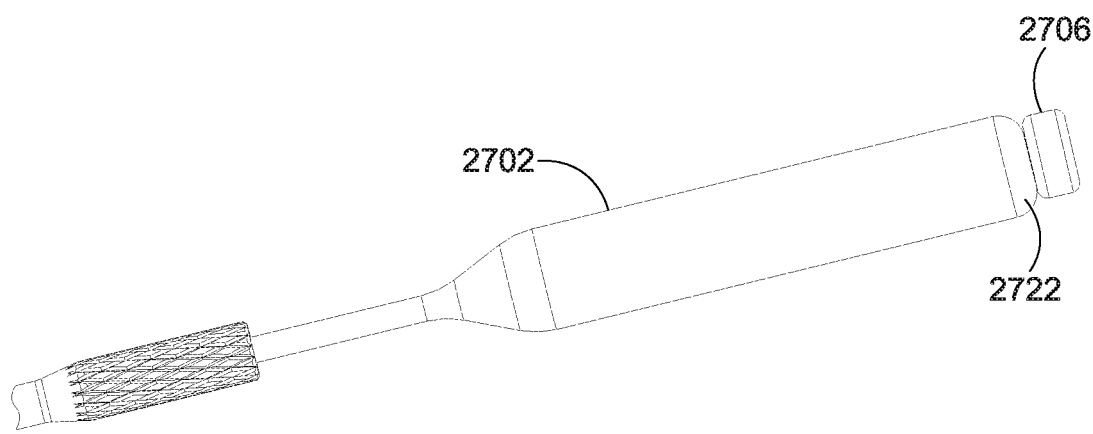

FIGS. 48A-49C depict how the implant 2600 and delivery tool 2700 are engaged in use. FIG. 48A is a side view of the implant 2600 and the driver assembly 2700 without the screw expander driver 2706 shown. FIG. 48B is an enlarged, cross-sectional view of the components of FIG. 48A. FIG. 48C is an enlarged view of the implant 2600 and end of the drive assembly 2700 in a first configuration. FIG. 48D is an enlarged view of the implant 2600 and end of the drive assembly 2700 in a secured configuration. FIG. 49A is a perspective view of the implant 2600 and second end of the driver assembly 2700 positioned within a guide tube 2720. FIGS. 49B and 49C are views of the driver assembly 2700 with the expander driver 2706 shown when the implant is in the secured position (FIG. 49B) and when the implant is in the deployed position (FIG. 49C).

As shown in FIG. 48B, the screw driver locking collar 2704 includes internal threads 2712 adjacent a first end 2726. The screw driver 2702 includes external threads 2714 extending about a portion of the shaft of the screw driver 2702. In use, the screw 2602 is secured to the screw driver 2702 by rotating the locking collar 2704 clockwise, in direction of arrow 2710 (FIG. 48A). As the locking collar 2704 is rotated, the second end 2724 of the collar 2704 advances toward the second end 2718 of the screw driver 2702 in the direction of arrow 2708 with the aid of the external threads 2714 and internal threads 2712 on both the driver and collar.

As shown in FIG. 48C, the screw driver locking collar 2704 forces the second end 2718 of the screw driver 2702 to compress (in direction of arrows 2732) as the locking collar 2704 contacts the tapered neck 2730 of the screw driver 2702. The slot 2720 on the screw driver 2702 allows the second end 2718 of the screw driver 2702 to compress about the first end 2610 of the screw 2602 and firmly secure the implant 2600 with the delivery tool delivery tool 2700. The implant 2600 is fully locked or secured with the delivery tool 2700 when the screw driver locking collar 2704 butts up against or abuts the second end 2718 of the screw driver screw driver 2702.

In use, an incision is made in the posterior spine, such as the cervical, thoracic, and/or lumbar spine and manual dissection performed down to the surgical area, such as a cervical, thoracic, and/or lumbar facet joints. In an intra-facet scenario, the facet joint is accessed with an access chisel and a guide tube is placed. The surgical site is prepared using an awl and chisel rasp. As can be understood from FIGS. 49A-C, and others, once the surgical site has been prepped, the assembled implant 2600 and delivery tool 2700 are placed down the guide tube to implant the implant 2600. The screw driver 2702 is rotated clockwise with a pushing force to implant the implant 2600. The threads 2624 on the screw 2602 and downward pressure placed on the delivery tool 2700 and transferred to the implant 2600 advances the implant 2600 into the facet joint space. Once the implant 2600 is placed at the proper location, the screw expander driver 2706 is placed into the cannula of the screw driver 2702. The screw expander driver 2706 mates with the first end 2612 of the screw expander 2604. A clockwise rotation is applied to the screw expander driver 2706 to advance the screw expander 2604 forward with respect to the screw 2602. The threads 2620 on the screw expander 2604 engage with the internal threads 2622 on the screw 2602 and allow the screw expander 2604 to advance forward with respect to screw 2602. As the screw expander 2604 advances forward, the second end 2616 of the screw expander 2604 forces the screw 2602 to splay open (see FIG. 46C). The screw expander 2604 is fully deployed when the screw expander driver 2706 knob bottoms out on the first end 2722 of the screw driver screw driver 2702, as shown in FIG. 49C. The screw expander driver 2706 is removed by pulling the screw driver 2702 straight out from the delivery tool 2700. The implant 2600 is released from the screw driver 2702 by rotating the screw driver locking collar 2704 counter clockwise.

Figure 50A:
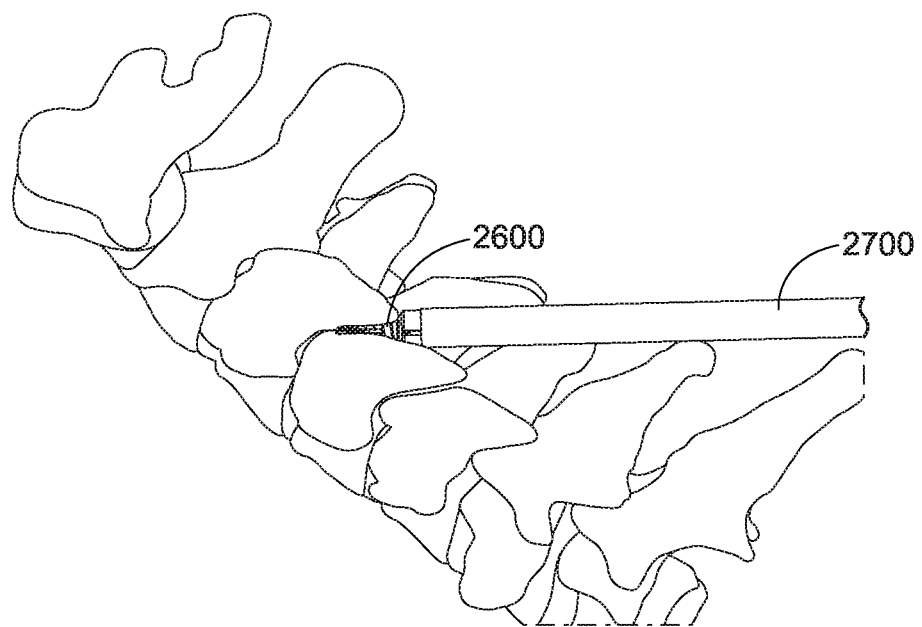
Figure 50B:
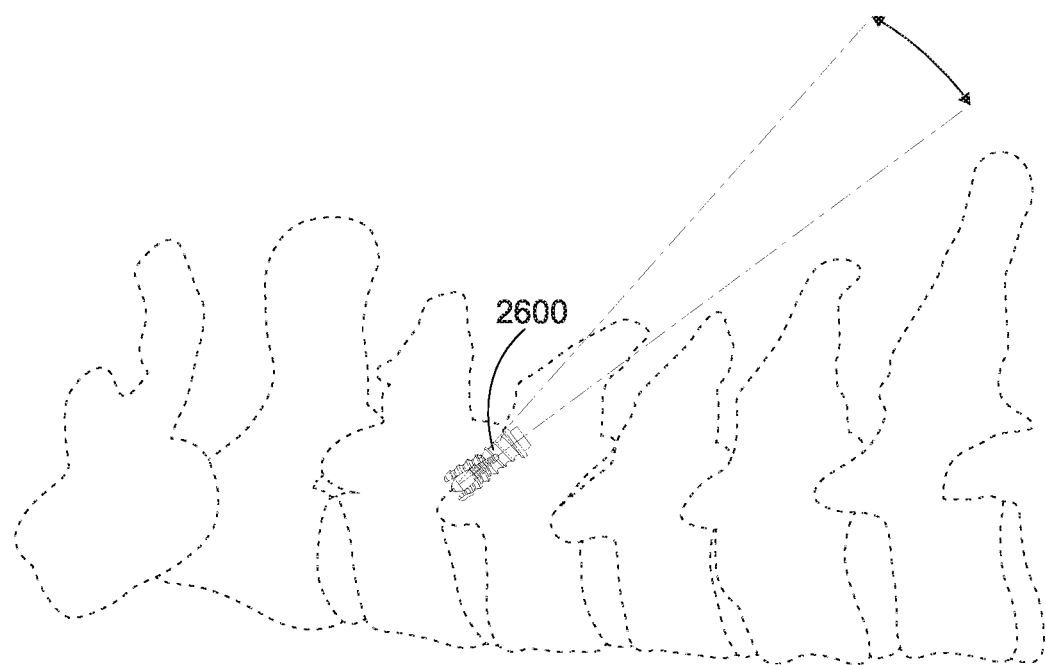

FIGS. 50A-50C depict views of the implant and delivery tool of FIGS. 45A-49C in use in an intra-facet deployment. As shown in FIG. 50B, the split screw design of implant 2600 may provide a lordotic angle to the implant 2600 when placed into the facet joint. The amount of lordosis can be adjusted by how far the screw expander 2604 is advanced forward within the screw 2602. The more the screw expander 2604 is positioned forward, the more lordosis or splay the screw 2602 will have. In some examples, this application is suited for lordotic correction.

Figure 51C:
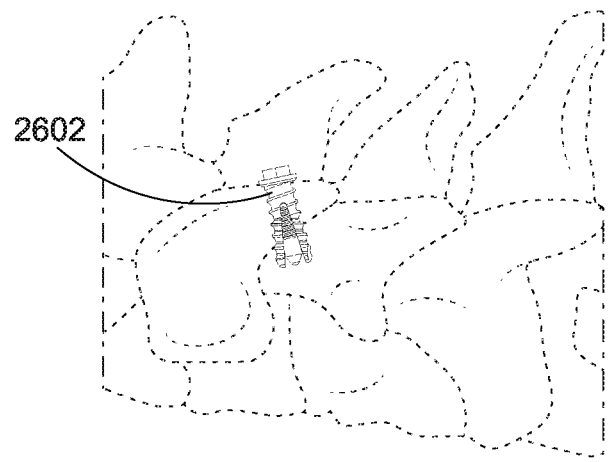

FIGS. 51A-51C depict views of the implant and delivery tool of FIGS. 45A-49C in use in a trans-facet deployment. In a trans-facet scenario, the implant 2600 is preloaded onto the screw driver 2702 as described with reference to FIGS. 45A-48D. The implant 2600 is then implanted into the facet joint by rotating the screw driver 2702 clockwise and applying force on the screw driver 2702 as the screw 2702 is driven in. The screw is expanded in a similar manner as described in FIGS. 45A-49C. FIG. 51C shows the screw 2602 fully implanted and deployed or expanded. The expansion of the screw 2602 creates more interference between screw 2602 and facet body which provide additional "locking" in the bone in a trans-facet scenario.

FIGS. 52A-53E depict views of an implant 2800 and delivery device 2900 that may be used with embodiments according to the present disclosure. In some examples, the implant 2800 includes a screw 2802 and a retracting ball expander 2804. FIGS. 53A-53E depict various views and configurations of the implant 2800. FIGS. 53A-B are side and perspective views of the implant 2800. FIG. 53C is a cross-sectional view of the implant 2800 of FIG. 53A. FIGS. 53D and 53E are cross-sectional and side views of the implant 2800 in an expanded or splayed configuration.

Figure 52A:
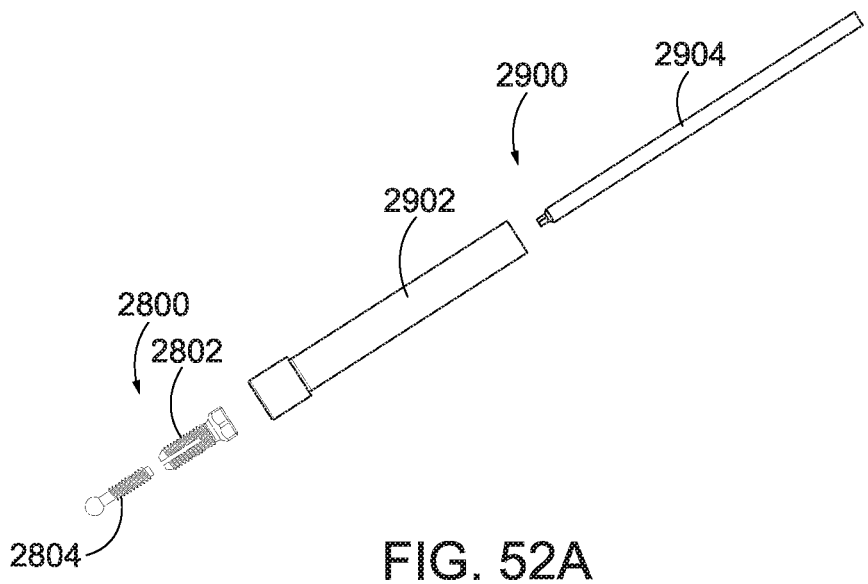
Figure 52B:
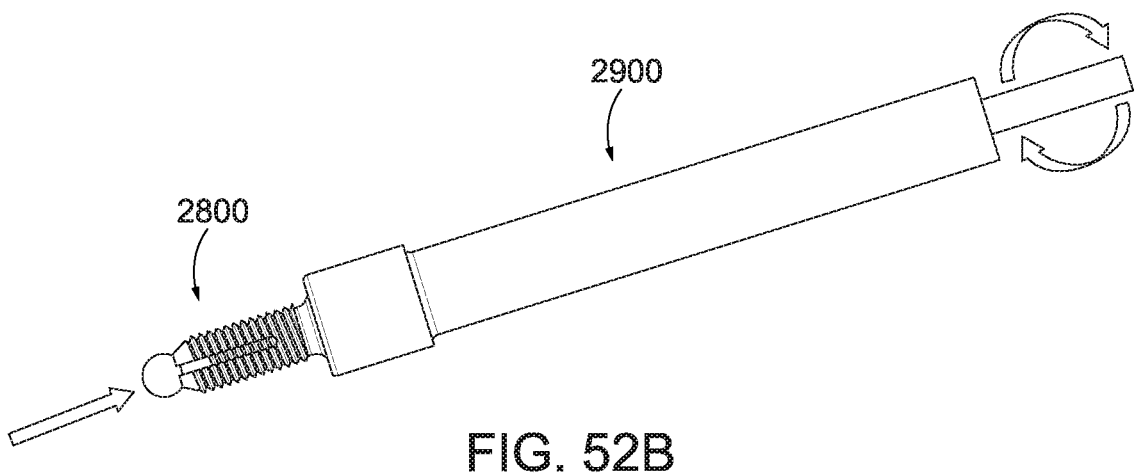

FIG. 52A is an exploded view of the implant 2800 of FIGS. 53A-53E and delivery device 2900. The delivery device 2900 includes a screw driver 2902 and a retracting ball expander driver 2904. The implant 2800 and delivery device 2900 may include similar features to the implant 2600 and delivery device 2700. Similar to screw 2602, the screw 2802 may include a hex or keying feature at its first end 2810 and a slot 2808 to allow the second end 2814 of the screw 2802 to be expanded or splayed in a deployed position. Similar to the expander 2604, the retracting ball expander driver 2804 may include a hex or keying feature on its first end 2812. In some examples, unlike the expander 2604, the retracting ball expander driver 2804 may include a ball or enlarged portion on its second end 2816. In some examples, unlike the screw driver 2702, the screw driver 2902 may use a friction fit to hold or position the screw 2802 with respect to the delivery device 2900.

Figure 54A:
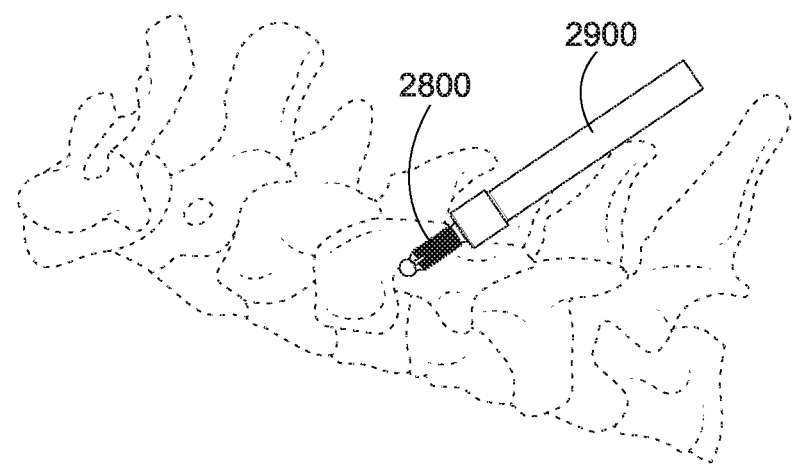
FIGS. 54A-54C depict views of the implant and delivery tool of FIGS. 51A-52E in use in an intra-facet deployment.
Figure 54B:
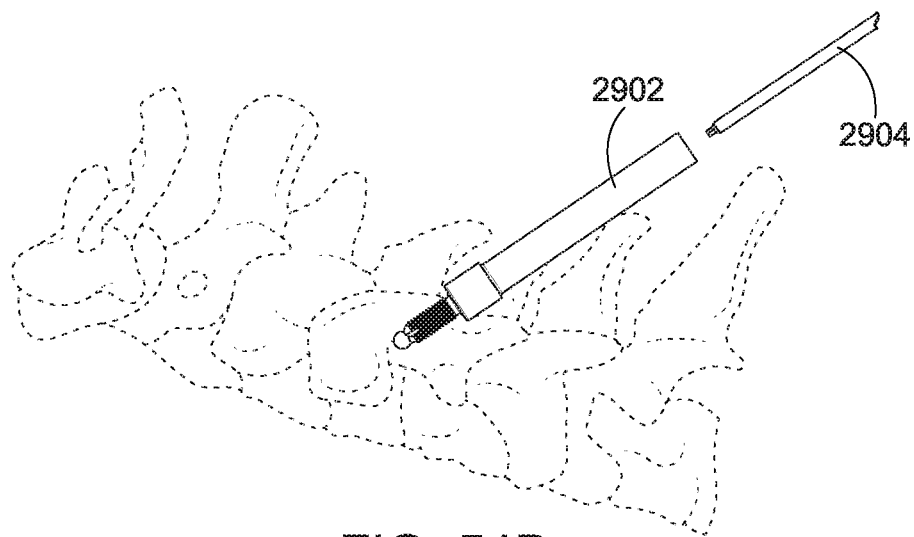
Figure 54C:
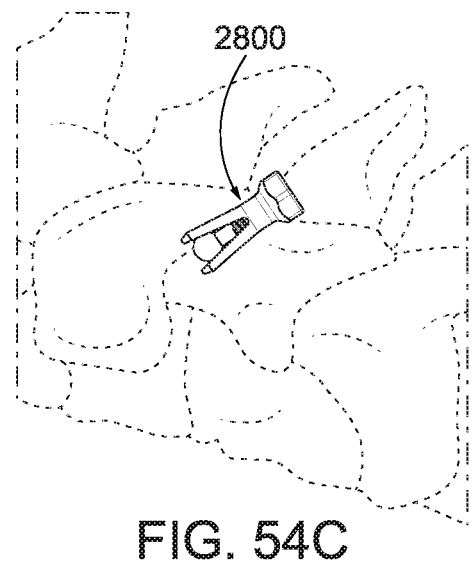

FIGS. 54A-54C depict views of the implant and delivery tool of FIGS. 52A-53E in use in an intra-facet deployment. In use, the implant 2800 is loaded onto the screw driver 2902. Once the surgical site is prepped, the implant 2800 is installed in its correct position. In an intra-facet scenario, the implant 2800 is implanted into the facet as shown using the screw driver 2902 with a clockwise rotation and pushing force. Once the implant 2800 is in the proper location, the retracting ball expander driver 2904 is placed down the screw driver 2902 cannula, as shown in FIG. 54B. The retracting ball expander driver 2904 mates with the retracting ball expander 2804. The ball expander driver is engaged, such as by rotating counter clockwise, to retract the ball end 2816 into the screw 2802. As the ball expander 2804 retracts, the expander 2804 forces the second end 2814 of the screw to 2802 splay open, as shown in FIGS. 53D-E. (The screw 2802 in the splayed position or configuration of FIGS. 53D-E is shown without threads.) In an intra-facet scenario, the splayed screw 2802 provides lordotic correction. The further the retracting ball expander 2804 is retracted with respect to the screw 2802, the more lordosis or splay the screw 2802 has.

Figure 55A:
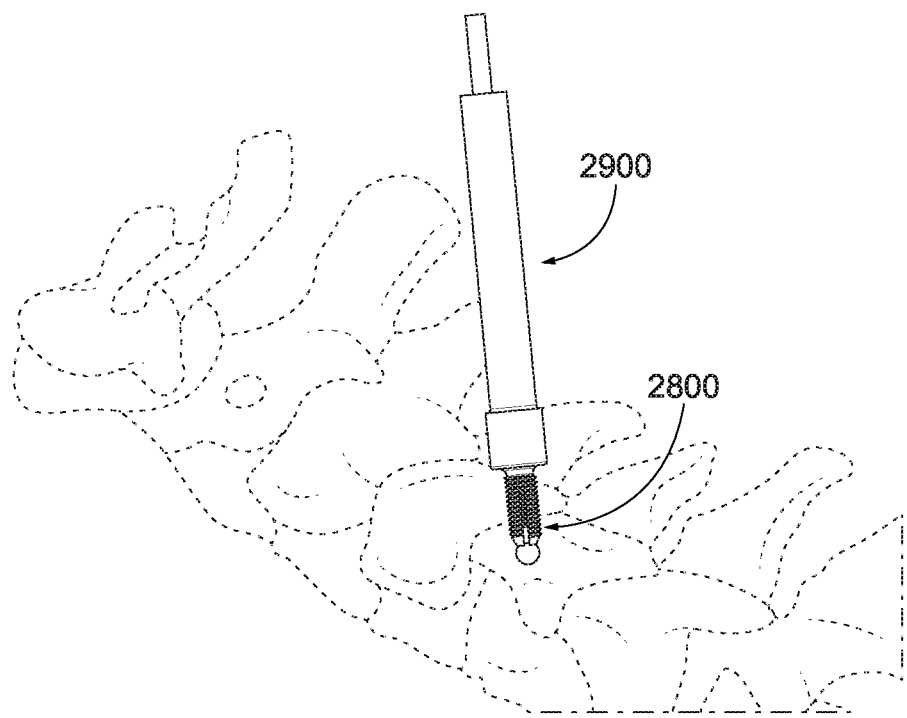
FIGS. 55A-55B depict views of the implant and delivery tool of FIGS. 51A-52E in use in a trans-facet deployment.
Figure 55B:
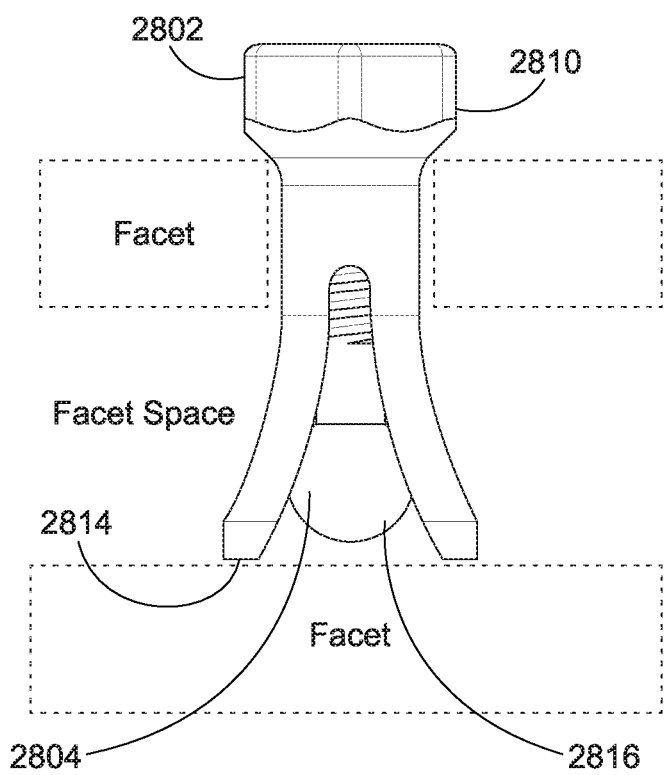

FIGS. 55A-55B depict views of the implant and delivery tool of FIGS. 52A-53E in use in a trans-facet deployment. In a trans-facet scenario, the implant 2800 is loaded onto the screw driver 2902 as described with respect to FIGS. 52A-54C and implanted into the facet as shown in FIG. 55A. Expansion of the screw 2802 is similar to the procedure described in FIGS. 52A-54C. In the trans-facet scenario, the screw 2802 is presumed to not breach the next facet. The tip 2814 of the screw 2802 remains within the facet joint space. As the ball expander 2804 is retracted, the screw 2802 splays open and the splay prevents screw back out and provides additional "locking" into the bone.

Figure 56A:
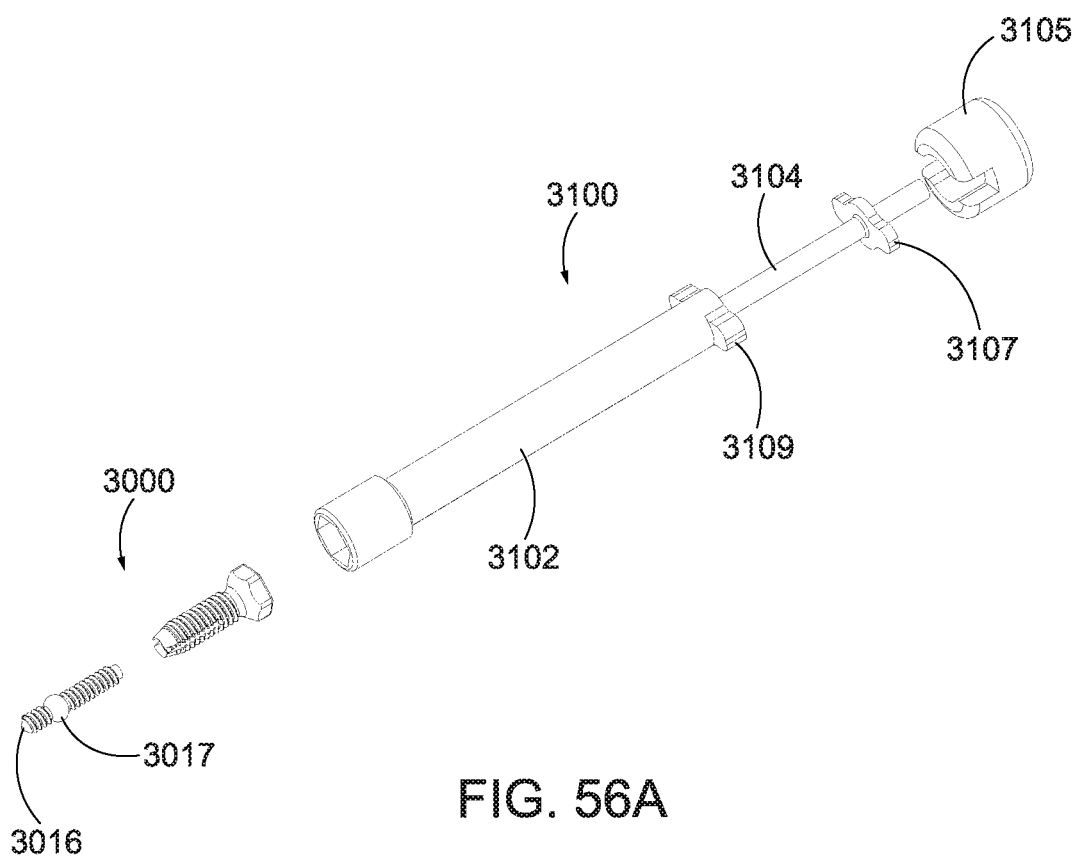
FIGS. 56A-57C depict views of an implant and delivery device that may be used with embodiments according to the present disclosure.
Figure 56B:
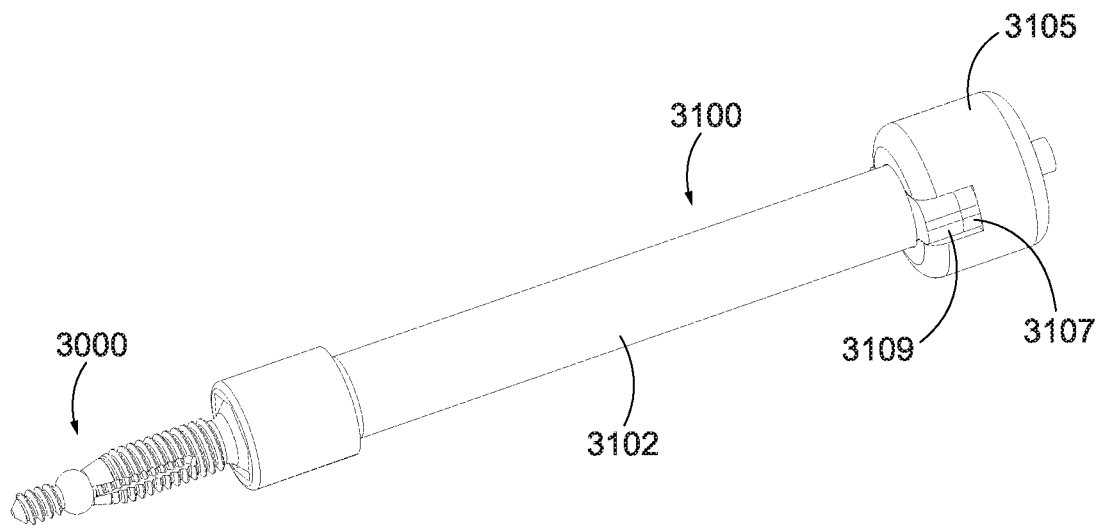
Figure 56C:
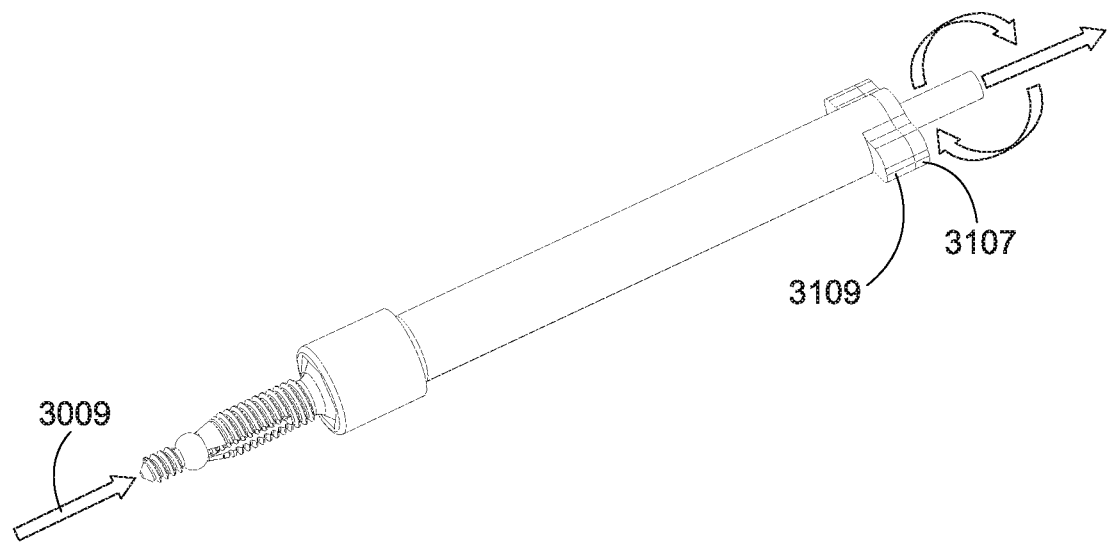
Figure 57A:
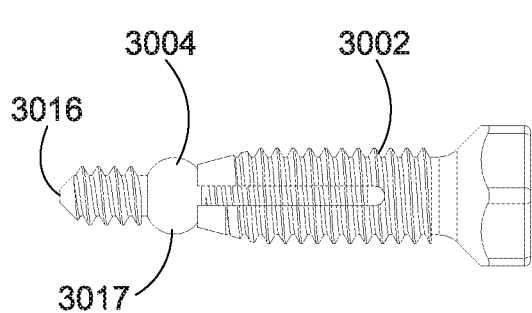
Figure 57B:
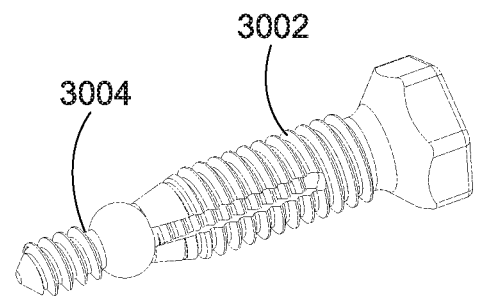
Figure 57C:
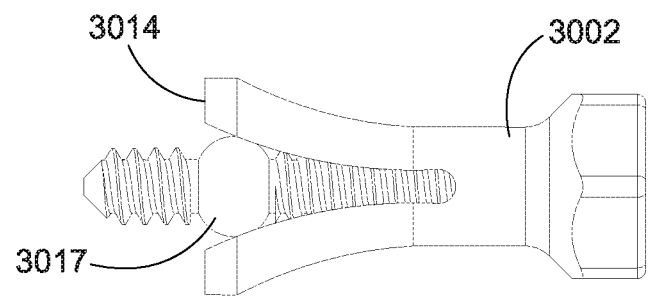

FIGS. 56A-57C depict views of an implant 3000 and delivery device 3100 that may be used with embodiments according to the present disclosure. FIGS. 56A and 56B are exploded and perspective views of the implant 3000 and delivery device 3100, and FIG. 56C is a perspective view of FIG. 56B with a locking collar 3105 minimized. FIGS. 57A-57B are side and perspective views of the implant 3000 in an unexpanded configuration. FIG. 57C is a side view of the implant 3000 is an expanded or deployed configuration. The implant 3000 may be similar to the implant 2800, with, for example, a difference being that a ball expander portion 3017 is not positioned at an end 3016 of the expander 3004, but adjacent the end 3016 of the expander 3004 so that threaded portions of the expander 3004 extend from both side of the ball expander portion 3017. The delivery device 3100 may be similar to the delivery device 2900, with, in some examples, a difference being that the delivery device 3100 may also include a locking collar 3105 (FIGS. 56A-B) that engages with a locking feature or tabs 3107 of the expander driver 3104, which also engage with a locking feature or tabs 3109 of the screw driver 3102. In use, the locking collar 3105 keeps the screw driver 3102 and screw expander driver 3104 from rotating in opposite direction as the implant 3000 is driven.

In some examples, the same implantation technique for intra-facet and trans-facet may be used with the implant 3000 and delivery device 3100. Similar to the implant 2800 and delivery device 2900, the implant 3000 is loaded onto the screw driver 3102. In the assembly of implant 3000 and delivery device 3100, a friction fit may be used as a holding mechanism for the screw 3002. In some embodiments, the same screw holding mechanism described with respect to implant 2600 and delivery device 2700 could be applied.

Once the screw 3002 of the implant 3000 is properly implanted, the locking collar 3105 is removed from the screw driver 3102, as shown in FIG. 56C. The screw expander driver 3104 is rotated counter clockwise to retract the ball 3017 in the direction of arrow 3009 in FIG. 56. The retraction of the ball 3017 splays open the screw 3002 and may provide lordosis when implanted in an intra-facet scenario and provides additional locking in a trans-facet application.

Figure 58A:
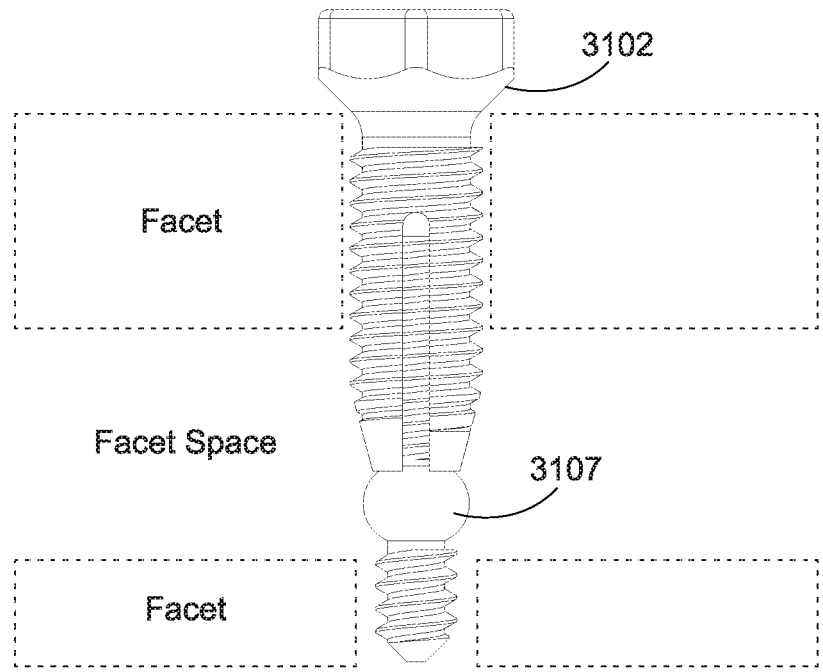
FIGS. 58A-58B depicts views of the implant and delivery device of FIGS. 56A-57C in use in a trans-facet deployment.
Figure 58B:
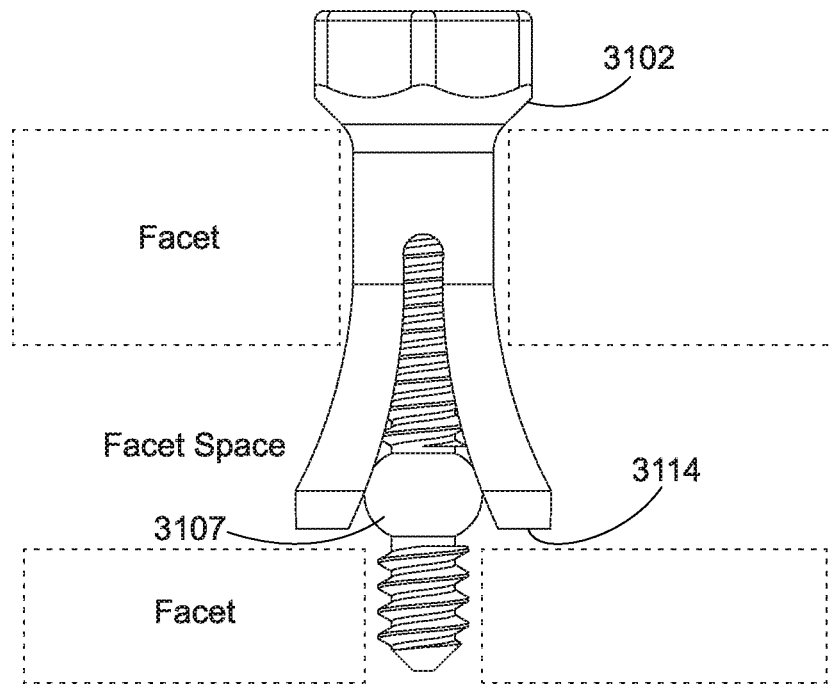

FIGS. 58A-58B depicts views of the implant 3000 and delivery device 3100 of FIGS. 55A-56C in use in a trans-facet deployment. In a trans-facet application, the screw 3002 is to be driven into both facets, as shown in FIGS. 58A-58B. The ball 3017 remains in the facet joint space. The screw 3002 being driven into both facet bodies provides additional anchoring of the screw construct. The splayed end 3107 of the screw 3002 provides further locking of the screw construct, as shown in FIG. 58B.

Figure 59A:
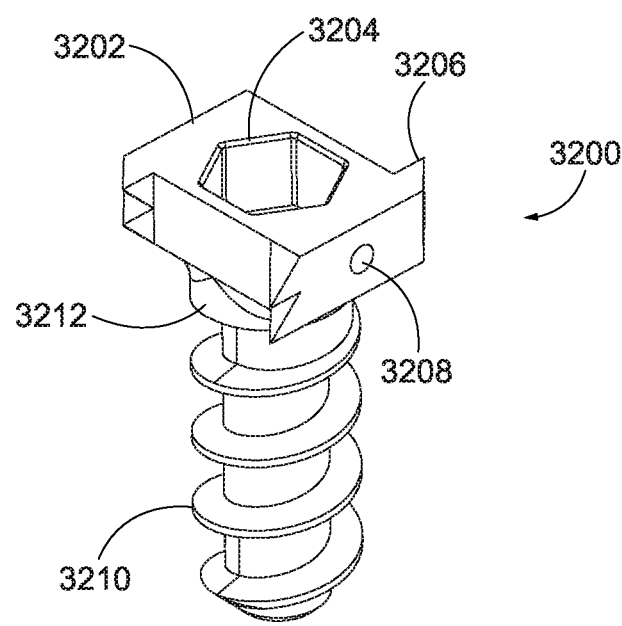
FIGS. 59A-60D depict views of an implant and delivery device that may be used with embodiments according to the present disclosure.
Figure 59B:
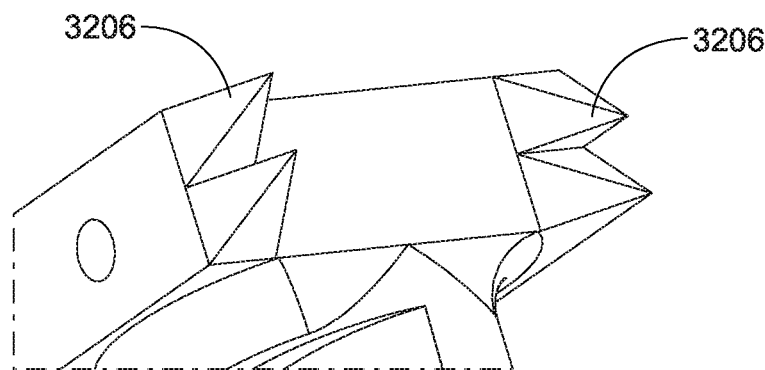

FIGS. 59A-60D depict views of an implant 3200 and delivery device 3300 that may be used with embodiments according to the present disclosure. FIG. 59A is a perspective view of the implant 3200, and FIG. 59B is an enlarged view of the head portion of the implant 3200 of FIG. 59A. In some examples, the implant 3200 is a screw, with a rectangular head 3202 including a keyway feature 3204, such as a hex head socket. An outer circumference of the head 3202 may include teeth 3206 that may be used to anchor, grip, or engage bone. In some examples, the teeth 3206 may be generally positioned on two sides of the rectangular head, with alternating teeth angles. A holding indentation 3208 or keyway feature may also be positioned on two side of the head 3202. The implant 3200 may also include a screw body with self-tapping threads 3210.

Figure 60A:
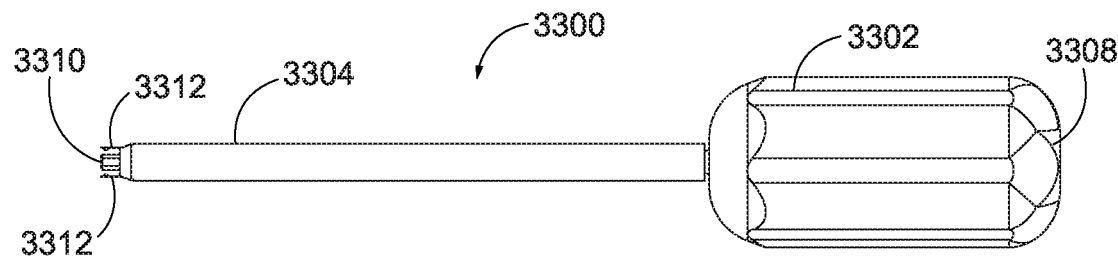
Figure 60B:
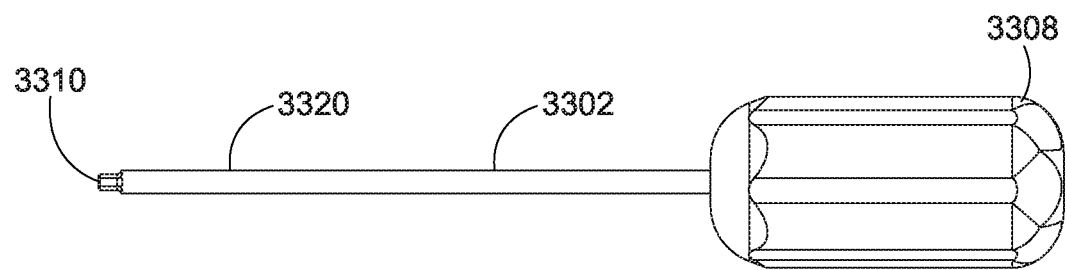
Figure 60C:
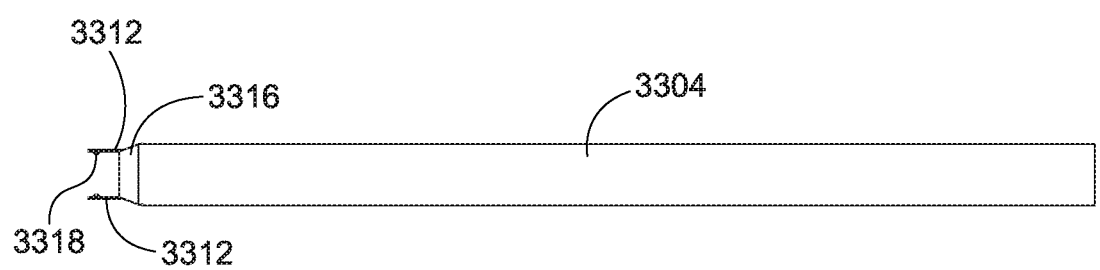
Figure 60D:
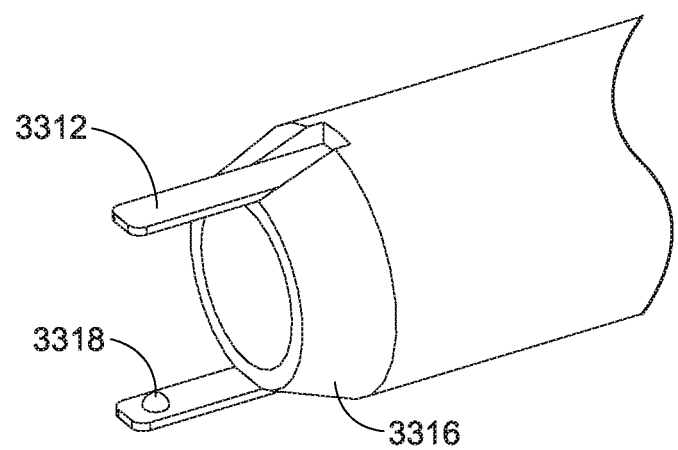

FIGS. 60A-60D are views of the delivery device 3300 that may be used to deliver implant 3200 to a surgical site. FIG. 60A is a side view of the fully assembled delivery device 3300. FIG. 60B is a side view of the hex driver assembly 3302. FIG. 60C is a side view of the end portion of a screw holder 3304. FIG. 60D is a perspective view of the end of the screw holder 3304 of FIG. 60C. In some examples, the delivery device 3300 may include two subassemblies—a driver 3302 (see FIG. 60B) and holder 3304 (see FIG. 60C-60D). As shown in FIG. 60B, the driver 3302 may include a shaft 3320, with handle 3308 on one end, and the other end formed into a key 3310, such as a hex head shape.

As shown in FIGS. 60C-60D, the holder 3304 may include a hollow shaft body 3314 with a tapered end 3316 and arms 3312 extending from the tapered end 3316. The shaft body 3314 may have an inner diameter that is larger than an outer diameter of the driver shaft 3320, so that the driver shaft 3320 may be inserted through or positioned within the lumen of the holder body 3314.

As shown in FIG. 60C, an inner surface of the end of each arm 3312 may include a raised feature, such as a detent 3318. In some examples, the detents 3318 are hemispherical shaped. Each arm 3312 may be secured to the body 3314, such as by welding or screw attachment. In use, the detents 3318 interface with the indentations 3208 of the implant 3200.

Figure 61A:
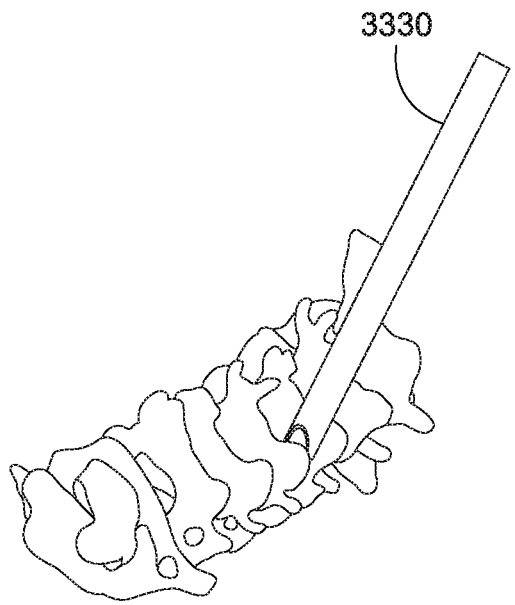
FIGS. 61A-62G depict views of the implant and delivery tool of FIGS. 59A-60D in use in an intra-facet deployment.
Figure 61B:
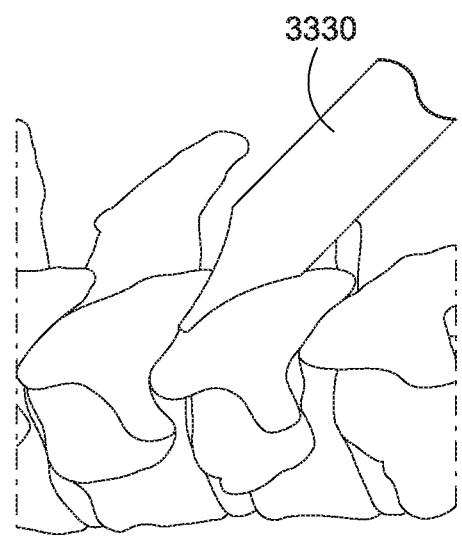
Figure 61C:
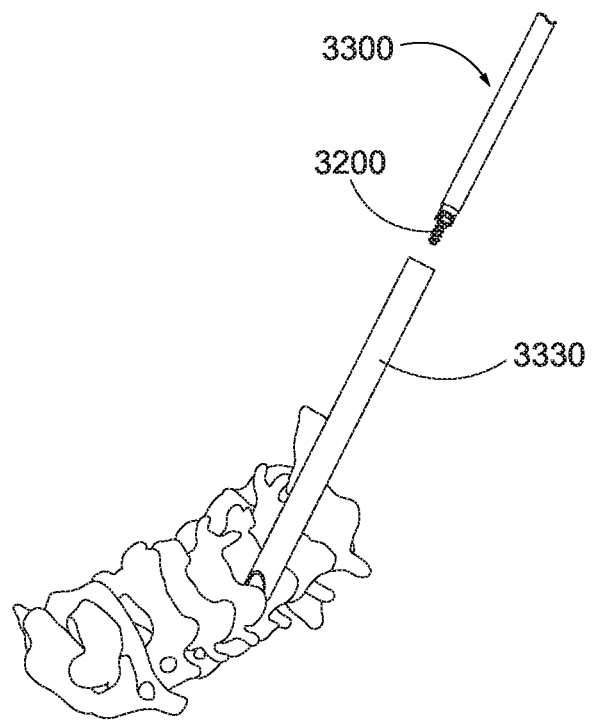
Figure 61D:
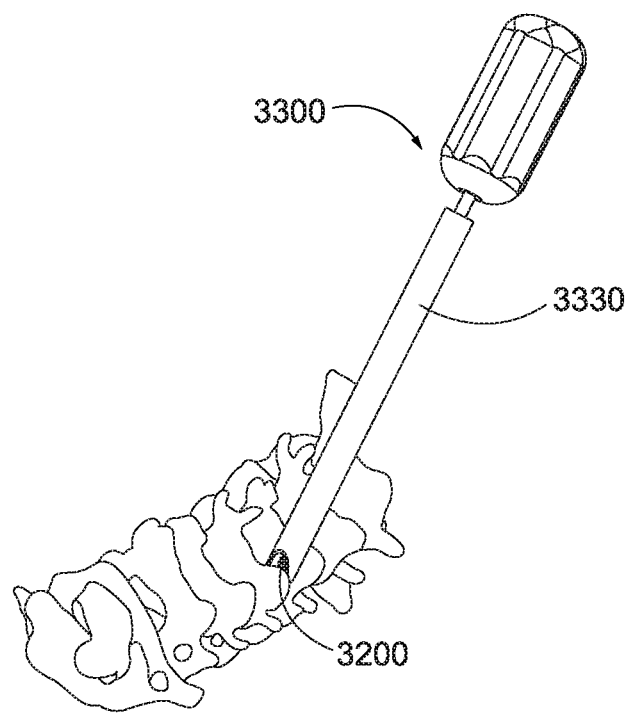
Figures 61E, 61F:
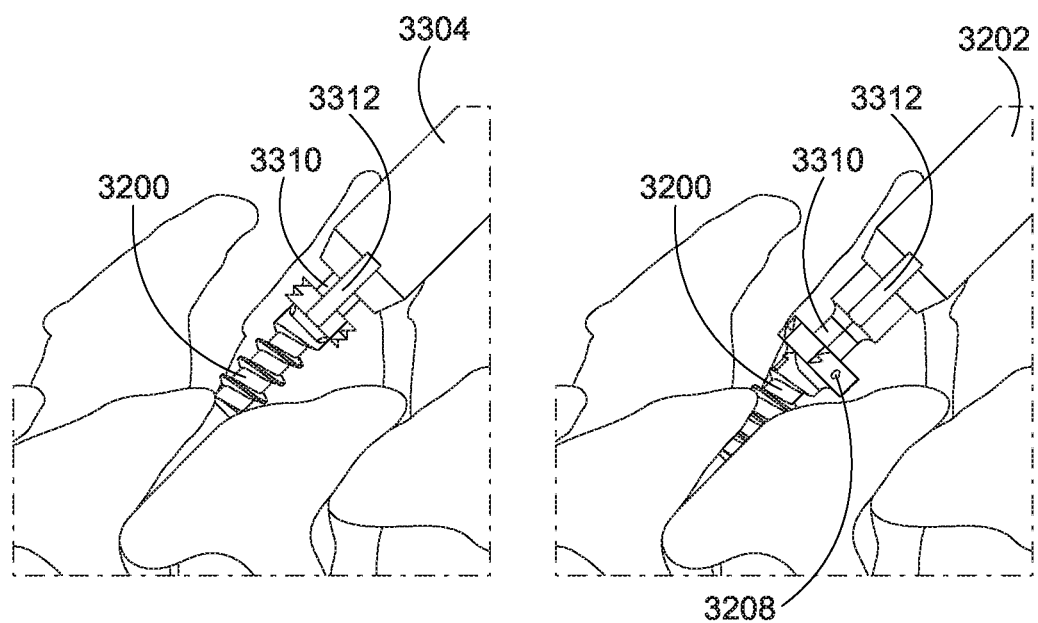

FIGS. 61A-62G depict views of the implant 3200 and delivery tool 3300 of FIGS. 59A-60D in use in an intra-facet deployment. In use, an incision is made in the posterior spine, such as the cervical, thoracic, and/or lumbar spine and access tube 3330 is inserted to anchor into spinal joint, such as a cervical, thoracic, and/or lumbar facet joint as shown in FIGS. 61A-61B. As shown in FIGS. 61C-61D, the delivery device 3300 with the attached implant 3200 is inserted through the access tube 3330 until implant 3200 contacts the spinal joint. FIGS. 61E-61F show the implant advancement and release from the delivery instrument 3300 without the guide tube 3330 shown. A user will then apply pressure and rotate the driver handle 3308 clockwise to advance implant 3200 into the spinal joint until driver handle 3308 abuts the access tube 3330. The tabs or arms 3312, which help to hold or couple the implant via the engagement of the detents 3318 with the holding indentations 3208, will flex open naturally, disengaging the detents 3318 from the indentations 3208, to allow the implant 3200 to be released from the arms 3312 and the holder 3304, as shown in FIG. 61F.

Figure 62A:
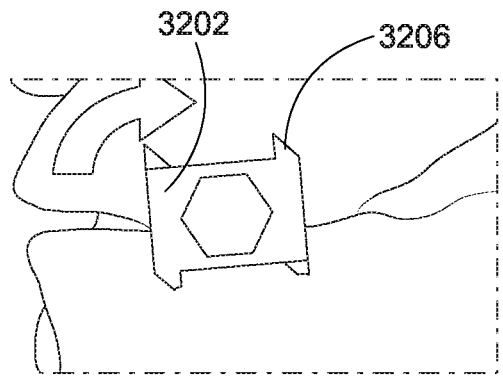
Figure 62B:
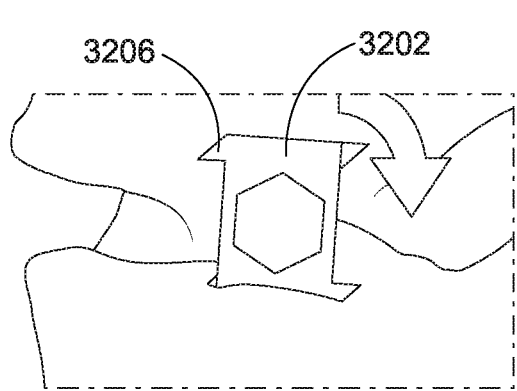
Figure 62C:
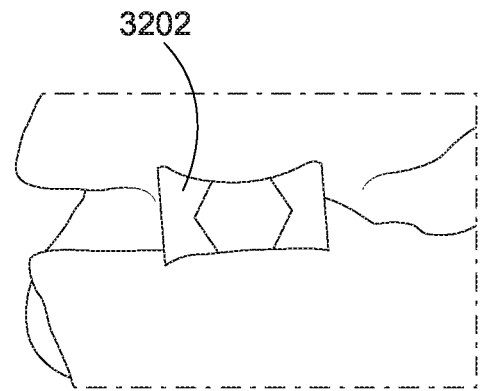
Figure 62D:
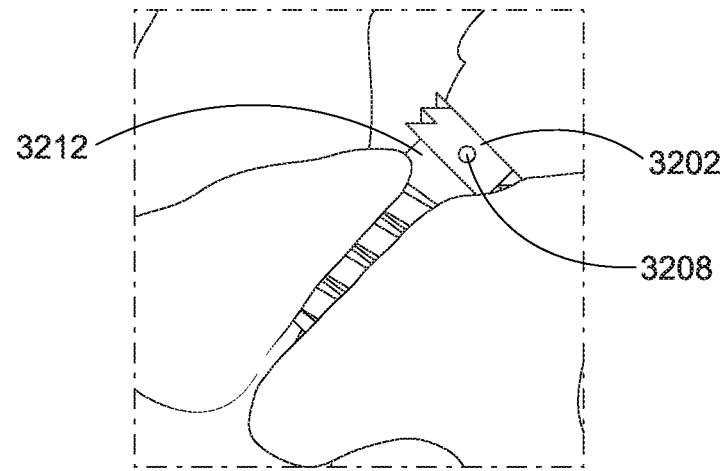
Figure 62E:
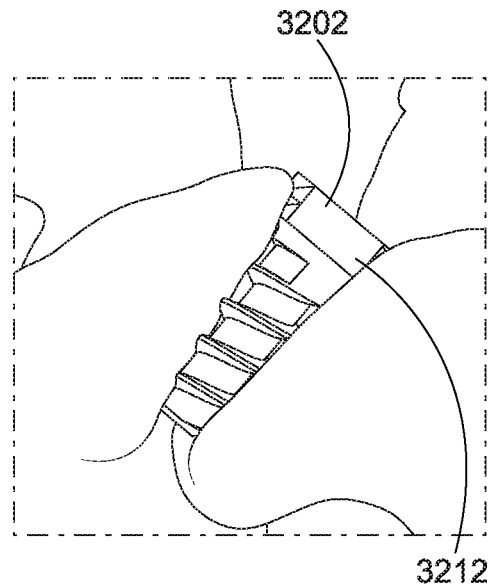
Figure 62F:
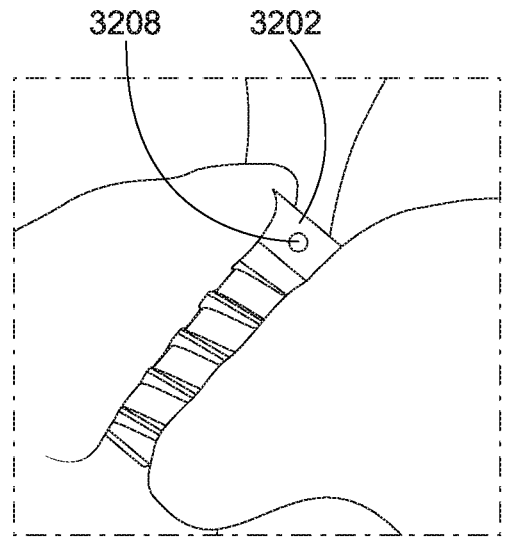
Figure 62G:
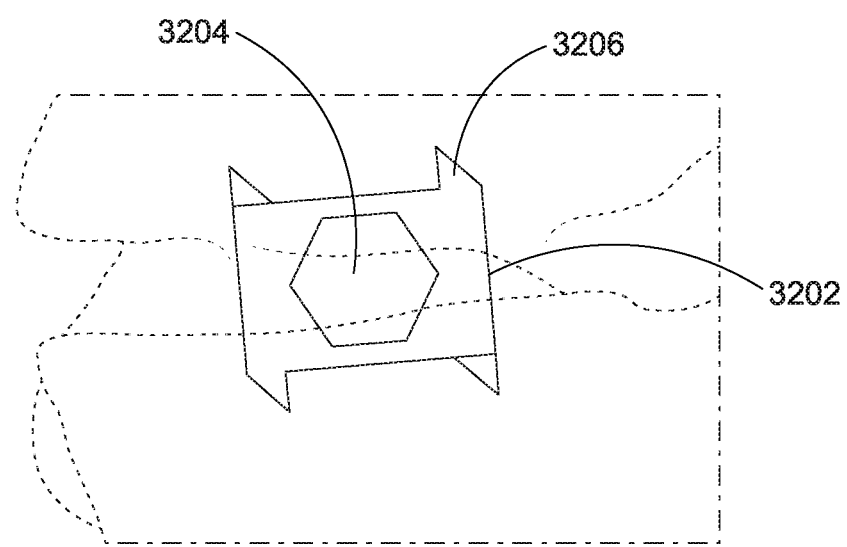

FIGS. 62A-C are top views showing the sequence of inserting the implant 3200 by the clockwise rotation of the implant. FIGS. 62D-F are side views of the sequence of FIGS. 62A-62C. When the head 3202 contacts the facet joint, the neck radius 3212 opens the facet joint to allow at least a portion of the head 3202 to enter. As shown in FIG. 62G, the angle of teeth 3206 allow clockwise rotation of the implant 3200 but helps prevent backout and advancement of the implant 3200 when anchored in bone. Once the head of the implant 3200 is anchored into the spinal joint, the access tube 3330 and delivery device 3300 are removed from the incision site.

All relative and directional references (including: upper, lower, upward, downward, left, right, leftward, rightward, top, bottom, side, above, below, front, middle, back, vertical, horizontal, and so forth) are given by way of example to aid the reader's understanding of the particular embodiments described herein. They should not be read to be requirements or limitations, particularly as to the position, orientation, or use unless specifically set forth in the claims. Connection references (e.g., attached, coupled, connected, joined, and the like) are to be construed broadly and may include intermediate members between a connection of elements and relative movement between elements. As such, connection references do not necessarily infer that two elements are directly connected and in fixed relation to each other unless specifically set forth in the claims.

Those skilled in the art will appreciate that the presently disclosed embodiments teach by way of example and not by limitation. Therefore, the matter contained in the above description or shown in the accompanying drawings should be interpreted as illustrative and not in a limiting sense. Thus, it is intended that the scope of the present disclosure should not be limited by the particular embodiments described above. Changes in detail or structure may be made without departing from the spirit of the invention as defined in the appended claims. In methodologies directly or indirectly set forth herein, various steps and operations are described in one possible order of operation, but those skilled in the art will recognize that steps and operations may be rearranged, replaced, or eliminated without necessarily departing from the spirit and scope of the present invention as claimed below.

What is claimed is:

1. A facet screw assembly delivery system comprising:
a facet screw assembly;
a facet access guide;
a washer sizer tool configured to removably engage with the facet access guide;
a lateral mass decorticator guide configured to slidably and removably engage with the washer size tool;
a washer implant delivery tool configured to removably engage with the facet access guide and detachably couple to the facet screw assembly; and
an impact handle configured to detachably couple to the facet access guide, the washer sizer tool, and the washer implant delivery tool,
wherein the facet access guide comprises:
a proximal end including an instrument guide handle portal that is parallel to an impact handle socket;
a ramped distal end including an intra-facet distractor and depth stop adjacent the intra-facet distractor; and
an instrument guide portal formed an open channel and extending between the proximal end and the distal end.

2. The facet screw assembly of claim 1, wherein the facet screw assembly comprises:
a facet screw having an elongated shaft with a proximal end and a distal end;
a washer implant comprising:
a lateral mass engagement portion;
an intrafacet engagement portion;
a facet screw opening extending through the lateral mass engagement portion and the intrafacet engagement portion, the facet screw opening configured to accept the distal end of the facet screw;
a keyway configured to align with a keyed feature on the washer implant delivery tool to maintain a position of the washer implant during delivery; and
a coupling member configured to detachably couple the washer implant to the washer implant delivery tool.

3. The facet screw assembly of claim 1, wherein the washer sizer tool comprises:
an access guide interface configured to engage with the facet access guide;
a joint spacer positioned at a distal end of the washer size tool, the joint spacer angled with respect to a central portion of the washer sizer tool;
a pin positioned adjacent the joint spacer and configured to engage with the facet access guide;
an alignment feature extending from a posterior side of the washer sizer tool and configured to slidably engage with the lateral mass decorticator guide; and
a washer size marker configured to provide a user with information regarding a recommended size of the facet screw assembly.

4. The facet screw assembly of claim 1, wherein the washer implant delivery tool comprises:
a shaft;
a rotatable washer release knob adjacent a proximal end of the shaft;
an actuation rod coupled to the rotatable washer release knob and extending through at least a portion of the shaft, the actuation rod including a distal end configured to engage the facet screw assembly;
a facet screw guide positioned at an angle with respect to the shaft and including a facet screw portal extending through the facet screw guide; and
a key feature configured to align with a keyway feature on the facet screw assembly to maintain a position of the face screw assembly during delivery.

5. A system for delivering a facet screw assembly to a joint between a vertebra and an adjacent vertebra, the system comprising:
a facet screw assembly;
a delivery device comprising:
a facet access guide;
a washer implant delivery tool configured to removably engage with the facet access guide and detachably couple to the facet screw assembly; and
an impact handle configured to detachably connect to the facet access guide and the washer implant delivery tool,
wherein the facet access guide comprises:
a proximal end including an instrument guide handle portal that is parallel to an impact handle socket;
a ramped distal end including an intra-facet distractor and depth stop adjacent the intra-facet distractor; and
an instrument guide portal formed an open channel and extending between the proximal end and the distal end.

6. The system of claim 5, the facet screw assembly comprising:
a facet screw having an elongated shaft with a proximal end and a distal end;
a washer implant comprising:
a lateral mass engagement portion;
an intrafacet engagement portion;
a facet screw opening extending through the lateral mass engagement portion and the intrafacet engagement portion, the facet screw opening configured to accept the distal end of the facet screw;
a keyway configured to align with a keyed feature on the washer implant delivery tool to maintain a position of the washer implant during delivery; and
a coupling member configured to detachably couple the washer implant to the washer implant delivery tool.

7. The system of claim 5, further comprising a washer sizer tool, the washer sizer tool comprising:
an access guide interface configured to engage with a facet access guide;
a joint spacer positioned at a distal end of the washer size tool, the joint spacer angled with respect to a central portion of the washer sizer tool;
a pin positioned adjacent the joint spacer and configured to engage with the facet access guide;
an alignment feature extending from a posterior side of the washer sizer tool and configured to slidably engage with a lateral mass decorticator guide; and
a washer size marker configured to provide a user with information regarding a recommended size of a facet screw assembly.

8. The system of claim 5, the washer implant delivery tool comprising:
a shaft;
a rotatable washer release knob adjacent a proximal end of the shaft;

an actuation rod coupled to the rotatable washer release knob and extending through at least a portion of the shaft, the actuation rod including a distal end configured to engage a facet screw assembly;

a facet screw guide positioned at an angle with respect to the shaft and including a facet screw portal extending through the facet screw guide; and a key feature configured to align with a keyway feature on the facet screw assembly to maintain a position of the facet screw assembly during delivery.

9. The system of claim 5, wherein the facet access guide is angled and/or non-linear in shape.

10. The system of claim 5, the facet screw assembly comprising:

a trans-facet screw having an elongated shaft with a proximal portion and a distal portion;

an intra-facet screw having an elongated shaft with a proximal portion and a distal portion;

a washer comprising
an intra-facet threaded aperture extending through a length of or along a longitudinal axis of the washer; and
a trans-facet aperture extending through a width of or along a transverse axis of the washer;
wherein when assembled, the trans-facet screw is positioned within the trans-facet aperture and the intra-facet screw is positioned within the intra-facet aperture, and the washer is configured to be positioned in a facet joint.

11. The system of claim 5, the facet screw assembly comprising:

a screw;

a washer comprising:
an intra-facet threaded aperture extending through a length of or along a longitudinal axis of the washer; and
a trans-facet aperture extending through a width of or along a transverse axis of the washer;
wherein when assembled, the screw is positioned within one of the trans-facet aperture and the intra-facet aperture, and the washer is configured to be positioned in a facet joint.

12. The system of claim 11, wherein the screw is a trans-facet screw and when assembled, the trans-facet screw is positioned in the trans-facet aperture.

13. The system of claim 11, wherein the screw is an intra-facet screw and when assembled, the intra-facet screw is positioned in the intra-facet aperture.

* * * * *